US008211828B2

(12) United States Patent
Dietz et al.

(10) Patent No.: US 8,211,828 B2
(45) Date of Patent: Jul. 3, 2012

(54) FUNGICIDAL MIXTURES OF 1-METHYLPYRAZOL-4-YLCARBOXANILIDES AND AZOLOPYRIMIDINYLAMINES

(75) Inventors: Jochen Dietz, Mannheim (DE); Ulrich Schoefl, Bruehl (DE); Egon Haden, Kleinniedesheim (DE)

(73) Assignee: BASF SE, Ludwigshafen (DE)

( * ) Notice: Subject to any disclaimer, the term of this patent is extended or adjusted under 35 U.S.C. 154(b) by 406 days.

(21) Appl. No.: 12/522,209

(22) PCT Filed: Jan. 17, 2008

(86) PCT No.: PCT/EP2008/050494
§ 371 (c)(1),
(2), (4) Date: Jul. 6, 2009

(87) PCT Pub. No.: WO2008/087182
PCT Pub. Date: Jul. 24, 2008

(65) Prior Publication Data
US 2009/0318291 A1 Dec. 24, 2009

(30) Foreign Application Priority Data
Jan. 19, 2007 (EP) .................... 07100851

(51) Int. Cl.
A01N 43/56 (2006.01)
A01N 43/54 (2006.01)
A01N 43/90 (2006.01)
A01P 3/00 (2006.01)

(52) U.S. Cl. ............... 504/100; 514/406; 514/259.3; 514/259.31

(58) Field of Classification Search .................. 504/100; 514/406, 259.3, 259.31
See application file for complete search history.

(56) References Cited

U.S. PATENT DOCUMENTS

| | | | |
|---|---|---|---|
| 3,060,084 A | 10/1962 | Littler | |
| 3,299,566 A | 1/1967 | MacMullen | |
| 3,920,442 A | 11/1975 | Albert et al. | |
| 4,144,050 A | 3/1979 | Frensch et al. | |
| 4,172,714 A | 10/1979 | Albert | |
| 4,822,779 A | 4/1989 | Hwang et al. | |
| 4,845,106 A | 7/1989 | Shiokawa et al. | |
| 5,013,659 A | 5/1991 | Bedbrook et al. | |
| 5,180,587 A | 1/1993 | Moore | |
| 5,208,030 A | 5/1993 | Hoy et al. | |
| 5,232,701 A | 8/1993 | Ogawa et al. | |
| 6,221,890 B1 | 4/2001 | Hatakoshi | |
| 6,277,856 B1* | 8/2001 | Cotter et al. ............ | 514/259.31 |
| 6,335,357 B1 | 1/2002 | Okui et al. | |
| 2008/0076785 A1* | 3/2008 | Blettner et al. .......... | 514/259.31 |
| 2008/0125445 A1 | 5/2008 | Schafer et al. | |
| 2008/0153707 A1 | 6/2008 | Gewehr et al. | |
| 2008/0171657 A1 | 7/2008 | Schafer et al. | |
| 2008/0188493 A1 | 8/2008 | Schaefer et al. | |
| 2008/0188494 A1* | 8/2008 | Dietz et al. .............. | 514/259.31 |
| 2008/0200480 A1 | 8/2008 | Dietz et al. | |
| 2008/0207455 A1 | 8/2008 | Schafer et al. | |
| 2008/0221130 A1 | 9/2008 | Dietz et al. | |
| 2008/0227796 A1* | 9/2008 | Wagner et al. .......... | 514/259.31 |
| 2008/0262000 A1 | 10/2008 | Schafer et al. | |
| 2008/0293798 A1 | 11/2008 | Dietz et al. | |
| 2009/0156398 A1 | 6/2009 | Dietz et al. | |
| 2009/0264289 A1 | 10/2009 | Dietz et al. | |
| 2010/0160311 A1 | 6/2010 | Dietz et al. | |

FOREIGN PATENT DOCUMENTS

CA 2 084 140 6/1993
(Continued)

OTHER PUBLICATIONS

International Search Report completed Nov. 3, 2008, in International Application No. PCT/EP2008/050494, filed Jan. 17, 2008.

(Continued)

Primary Examiner — John Pak
(74) Attorney, Agent, or Firm — Brinks Hofer Gilson & Lione

(57) ABSTRACT

Fungicidal mixtures comprising as active components:
1) at least one 1-methylpyrazol-4-ylcarboxanilide of the formula I

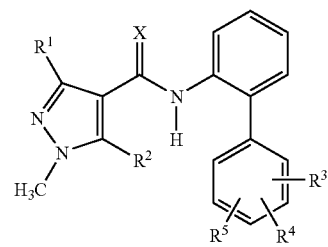

in which the substituents are defined according to the description
and
2) at least one azolopyrimidinylamine of the formula II

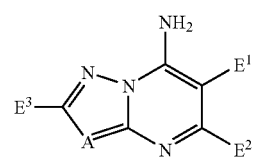

in which the substituents are defined according to the description
in a synergistically effective amount.
Methods for controlling harmful fungi using mixtures of the compound I and compound II and also the use of the compound I and the compound II for preparing such mixtures, and compositions comprising such mixtures.

16 Claims, No Drawings

FOREIGN PATENT DOCUMENTS

| | | |
|---|---|---|
| CN | 101028009 | 9/2007 |
| EP | 0 071 792 | 2/1983 |
| EP | 0 141 317 | 5/1985 |
| EP | 142 924 | 5/1985 |
| EP | 193 259 | 9/1986 |
| EP | 242 236 | 10/1987 |
| EP | 242 246 | 10/1987 |
| EP | 257 993 | 3/1988 |
| EP | 454621 | 10/1991 |
| EP | 462 456 | 12/1991 |
| EP | 0 545 834 | 6/1993 |
| EP | 707 445 | 4/1996 |
| EP | 1 952 690 | 8/2008 |
| GB | 2095558 | 10/1982 |
| JP | 10-109913 | 4/1998 |
| JP | 2002193709 | 7/2002 |
| WO | WO 91/13546 | 9/1991 |
| WO | WO 91/13972 | 9/1991 |
| WO | WO 91/19806 | 12/1991 |
| WO | WO 92/00377 | 1/1992 |
| WO | WO 92/11376 | 7/1992 |
| WO | WO 92/14827 | 9/1992 |
| WO | WO 98/28277 | 7/1998 |
| WO | WO 98/28279 | 7/1998 |
| WO | WO 98/45274 | 10/1998 |
| WO | WO 98/50422 | 11/1998 |
| WO | WO 00/29426 | 5/2000 |
| WO | WO 00/58442 | 10/2000 |
| WO | WO 01/00614 | 1/2001 |
| WO | WO 02/091824 | 11/2002 |
| WO | WO 03/007717 | 1/2003 |
| WO | WO 03/007718 | 1/2003 |
| WO | WO 03/009687 | 2/2003 |
| WO | WO 2004/080180 | 9/2004 |
| WO | WO 2005/087771 | 9/2005 |
| WO | WO 2005/087772 | 9/2005 |
| WO | WO 2005/087773 | 9/2005 |
| WO | WO 2006/087325 | 8/2006 |
| WO | WO 2006/087343 | 8/2006 |
| WO | WO 2006/092411 | 9/2006 |
| WO | WO 2006/092412 | 9/2006 |
| WO | WO 2006/092413 | 9/2006 |
| WO | WO 2006/092414 | 9/2006 |
| WO | WO 2006/092428 | 9/2006 |
| WO | WO 2007/000462 | 1/2007 |
| WO | WO 2007/003540 | 1/2007 |
| WO | WO 2007/012598 | 2/2007 |
| WO | WO 2007/012599 | 2/2007 |
| WO | WO 2007/012600 | 2/2007 |
| WO | WO 2007/017416 | 2/2007 |
| WO | WO 2008/092759 | 8/2008 |
| WO | WO 2009/037242 | 3/2009 |

OTHER PUBLICATIONS

English language translation of the International Preliminary Report on Patentability from corresponding International Application No. PCT/EP2008/050494, (Aug. 4, 2009).

Colby, S.R., "Calculating Synergistic and Antagonistic Responses of Herbicide Combinations", Weeds, Jan. 1967, p. 20-22, vol. 15, No. 1.

Kim, J-H. et al., "Aerobic soil metabolism of flupyrazofos," Pestic. Sci., 1998, 54, 237-243.

Zhang, A. et al., "Insect nicotinic acetylcholine receptor: Conserved neonicotinoid specificity of [$^3$H] imidacloprid binding site," Journal of Neurochemistry, 2000, 75:3, 1294-1303.

Database WPI Week 200821, Thompson Scientific, London, GB; AN 2008-C79838 "Agricultural chemical compounded by hexaconazole and *Bacillus subtilis*" XP002482265.

Derwent Abstract 1993-184519 (1993); abstracting EP 545834.

Office Action dated Jan. 31, 2012, from U.S. Appl. No. 12/523,793, filed Jul. 20, 2009.

Pike, K.S. et al. "Compatibility of imidacloprid with fungicides as a seed treatment control of Russian Wheat Aphid (Homoptera Aphididae) and Effect on Germination, Growth, and Yield of Wheat and Barley", Journal of Economic Entomology, Apr. 1993, p. 586-593, vol. 86, No. 2.

Webster's New World Dictionary, 2$^{nd}$ College ed., The World Publishing Co., NY, 1972 p. 1127.

* cited by examiner

FUNGICIDAL MIXTURES OF 1-METHYLPYRAZOL-4-YLCARBOXANILIDES AND AZOLOPYRIMIDINYLAMINES

This application is a National Stage application of International Application No. PCT/EP2008/050494 filed Jan. 17, 2008, the entire contents of which is hereby incorporated herein by reference. This application also claims the benefit under 35 U.S.C. §119 of European Patent Application No. 07100851.0 filed Jan. 19, 2007, the entire contents of which is hereby incorporated herein by reference.

The present invention relates to fungicidal mixtures comprising:
A) at least one 1-methylpyrazol-4-ylcarboxanilide of the formula I

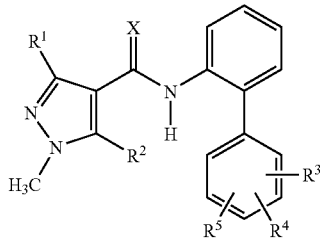

in which the substituents have the following meanings:
X is oxygen or sulfur;
$R^1$ is $C_1$-$C_4$-alkyl or $C_1$-$C_4$-haloalkyl;
$R^2$ is hydrogen or halogen;
$R^3$, $R^4$ and $R^5$ independently of one another are cyano, nitro, halogen, $C_1$-$C_4$-alkyl, $C_1$-$C_4$-haloalkyl, $C_1$-$C_4$-alkoxy, $C_1$-$C_4$-haloalkoxy or $C_1$-$C_4$-alkylthio;
and
B) at least one azolopyrimidinylamine of the formula II

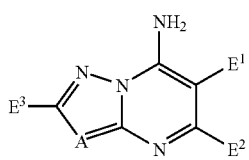

in which the substituents have the following meaning:
$E^1$ is $C_3$-$C_{12}$-alkyl, $C_2$-$C_{12}$-alkenyl, $C_5$-$C_{12}$-alkoxyalkyl, $C_3$-$C_6$-cycloalkyl, phenyl or phenyl-$C_1$-$C_4$-alkyl;
$E^2$ $C_1$-$C_{12}$-alkyl, $C_2$-$C_{12}$-alkenyl, $C_1$-$C_4$-haloalkyl or $C_1$-$C_4$-alkoxy-$C_1$-$C_4$-alkyl;
where the aliphatic chains in $E^1$ and/or $E^2$ may be substituted by one to four identical or different groups $R^a$:
$R^a$ is halogen, cyano, hydroxyl, mercapto, $C_1$-$C_{10}$-alkyl, $C_1$-$C_{10}$-haloalkyl, $C_3$-$C_8$-cycloalkyl, $C_2$-$C_{10}$-alkenyl, $C_2$-$C_{10}$-alkynyl, $C_1$-$C_6$-alkoxy, $C_1$-$C_6$-alkylthio, $C_1$-$C_6$-alkoxy-$C_1$-$C_6$-alkyl or $NR^AR^B$;
$R^A$, $R^B$ independently of one another are hydrogen or $C_1$-$C_6$-alkyl; where the cyclic groups in $E^1$ and/or $R^a$ may be substituted by one to four groups $R^b$:
$R^b$ is halogen, cyano, hydroxyl, mercapto, nitro, $NR^AR^B$, $C_1$-$C_{10}$-alkyl, $C_1$-$C_6$-haloalkyl, $C_2$-$C_6$-alkenyl, $C_2$-$C_6$-alkynyl or $C_1$-$C_6$-alkoxy;
$E^3$ is hydrogen, halogen, cyano, $NR^AR^B$, hydroxyl, mercapto, $C_1$-$C_6$-alkyl, $C_1$-$C_6$-haloalkyl, $C_3$-$C_8$-cycloalkyl, $C_1$-$C_6$-alkoxy, $C_1$-$C_6$-alkylthio, $C_3$-$C_8$-cycloalkoxy, $C_3$-$C_8$-cycloalkylthio, carboxyl, formyl, $C_1$-$C_{10}$-alkylcarbonyl, $C_1$-$C_{10}$-alkoxycarbonyl, $C_2$-$C_{10}$-alkenyloxycarbonyl, $C_2$-$C_{10}$-alkynyloxycarbonyl, phenyl, phenoxy, phenylthio, benzyloxy, benzylthio or $C_1$-$C_6$-alkyl-$S(O)_m$—;
m is 0, 1 or 2;
A is CH or N;
in a synergistically effective amount.

Moreover, the invention relates to a process for controlling harmful fungi using a mixture comprising at least one compound I and at least one compound II, to a process for preparing such mixtures and to compositions and seed comprising these mixtures.

The 1-methylpyrazol-4-ylcarboxanilides of the formula I, referred to above as component A, and their action against harmful fungi, and also their preparation, are known from WO 06/087343 and PCT/EP2006/064907 and the literature cited therein, or they can be prepared in the manner described therein.

Mixtures of compounds of the formula I with other active compounds are described in a general manner in PCT/EP2006/064907.

The azolopyrimidin-7-ylamines of the formula II, referred to above as component B, and their action against harmful fungi, and also their preparation, are known from PCT/EP2006/064463 and the literature cited therein, or they can be prepared in the manner described therein.

Mixtures of compounds of the formula II with other active compounds are described in a general manner in PCT/EP2006/064463.

It was an object to increase further the fungicidal activity of the known compounds of the formula I or the formula II, in particular at low application rates. With a view to reducing the application rates and broadening the activity spectrum of the compounds of the formulae I and II, it was therefore an object of the present invention to provide mixtures having, at a reduced total amount of active compounds applied, an improved activity against harmful fungi, in particular for certain indications.

We have found that this object is achieved by the mixtures defined at the outset comprising the compounds of the formulae I and II. Moreover, we have found that simultaneous, that is joint or separate, application of at least one compound I and at least one compound II, or at least one compound I and at least one compound II applied in succession, allows a superadditive control of harmful fungi that is better than with the individual compounds (synergistic mixtures).

In the definitions of the symbols given in the formulae above, collective terms are used which are generally representative for the substituents below:

In the context of the present invention, terms of the form $C_a$-$C_b$ refer to chemical compounds or substituents having a certain number of carbon atoms. The number of carbon atoms can be chosen from the entire range of a to b, including a and b; a is at least 1 and b is always greater than a. The chemical compounds or substituents are further specified by terms of the form $C_a$-$C_b$-V. Here, V denotes a class of chemical compounds or a class of substituents, for example alkyl compounds or alkyl substituents.

halogen: fluorine, chlorine, bromine or iodine;
alkyl: saturated, straight-chain or branched hydrocarbon radicals having 1 to 4, 1 to 6, 1 to 10, 1 to 12 or 3 to 12 carbon atoms, for example $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl: straight-chain or branched alkyl radicals having 1 to 4, 1 to 6 or 1 to 10 carbon atoms (as mentioned above), where some or all of the hydrogen atoms in these radicals may be replaced by halogen atoms as mentioned above: in particular $C_1$-$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl;

alkenyl: unsaturated straight-chain or branched hydrocarbon radicals having 2 to 6, 2 to 10 or 2 to 12 carbon atoms and one or two double bonds in any position, for example $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl or 1-ethyl-2-methyl-2-propenyl;

alkynyl: straight-chain or branched hydrocarbon radicals having 2 to 6 or 2 to 10 carbon atoms and one or two triple bonds in any position, for example $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl or 1-ethyl-1-methyl-2-propynyl;

cycloalkyl: mono- or bicyclic saturated hydrocarbon radicals having 3 to 6 or 3 to 8 carbon ring members, for example $C_3$-$C_8$-cycloalkyl, such as cyclopropyl, cyclobutyl, cyclopentyl, cyclohexyl, cycloheptyl or cyclooctyl;

cycloalkoxy: mono- or bicyclic saturated hydrocarbon radicals which are attached via an oxygen atom (—O—);

cycloalkylthio: mono- or bicyclic, saturated hydrocarbon radicals which are attached via a sulfur atom (—S—);

alkylthio: saturated, straight-chain or branched hydrocarbon radicals which are attached via a sulfur atom (—S—);

alkylcarbonyl: straight-chain or branched alkyl radicals which have 1 to 10 carbon atoms and are attached via a carbonyl group (—CO—);

alkoxy: straight-chain or branched alkyl radicals which are attached via an oxygen atom (—O—);

alkoxyalkyl: straight-chain or branched alkoxy radicals which are attached to an alkyl radical;

haloalkoxy: straight-chain or branched alkoxy radicals, where some or all of the hydrogen atoms in these radicals may be replaced by halogen;

alkoxycarbonyl: alkoxy radicals which have 1 to 10 carbon atoms and are attached via a carbonyl group (—CO—);

alkenyloxycarbonyl: alkenyl radicals which are attached via an oxygen atom (—O—) to a carbonyl group (—CO—);

alkynyloxycarbonyl: alkynyl radicals which are attached via an oxygen atom (—O—) to a carbonyl group (—CO—);

phenylalkyl: a phenyl group which is attached via saturated, straight-chain or branched alkyl radicals.

With a view to the fungicidal mixtures according to the invention comprising the compounds of the formulae I and II, to methods for controlling phytopathogenic harmful fungi, to seed comprising fungicidal mixtures, to fungicidal mixtures and to processes for preparing these compositions, particular preference is given to the following meanings of the substituents, in each case on their own or in combination:

One embodiment of the formula I relates to those compounds in which X is oxygen.

A further embodiment of the formula I relates to those compounds in which X is sulfur.

For the mixtures according to the invention, preference is given to compounds of the formula I in which $R^1$ is methyl or halomethyl, such as $CH_3$, $CHF_2$, $CH_2F$, $CF_3$, $CHFC_1$ or $CF_2Cl$, in particular $CHF_2$ or $CF_3$.

Preference is furthermore given to compounds I in which $R^2$ is hydrogen, fluorine or chlorine, in particular hydrogen.

Furthermore, preference is given to those compounds I in which $R^3$ is halogen, $C_1$-$C_4$-alkyl, $C_1$-$C_4$-haloalkyl, $C_1$-$C_4$-alkoxy, $C_1$-$C_4$-haloalkoxy or $C_1$-$C_4$-alkylthio, preferably halogen, methyl, halomethyl, methoxy, halomethoxy or methylthio, in particular F, Cl, $CH_3$, $CF_3$, $OCH_3$, $OCHF_2$, $OCF_3$ or $SCH_3$, particularly preferably fluorine.

Moreover, preference is given to those compounds I in which $R^4$ is halogen, in particular fluorine.

Preference is furthermore given to those compounds I in which $R^5$ is halogen, in particular fluorine.

In addition, preference is given to compounds of the formula I listed in Table 1 below:

TABLE 1

Compounds I where X = oxygen

| No. | $R^1$ | $R^2$ | $R^3$ | $R^4$ | $R^5$ |
|---|---|---|---|---|---|
| 1-1 | $CH_3$ | H | 2-F | 3-F | 4-F |
| 1-2 | $CH_3$ | H | 2-F | 3-F | 5-F |
| 1-3 | $CH_3$ | H | 2-F | 4-F | 5-F |
| 1-4 | $CH_3$ | H | 2-F | 4-F | 6-F |
| 1-5 | $CH_3$ | H | 3-F | 4-F | 5-F |
| 1-6 | $CH_3$ | H | 3-F | 5-F | 6-F |

TABLE 1-continued

Compounds I where X = oxygen

| No. | R¹ | R² | R³ | R⁴ | R⁵ |
|---|---|---|---|---|---|
| 1-7 | CH₂F | H | 2-F | 3-F | 4-F |
| 1-8 | CH₂F | H | 2-F | 3-F | 5-F |
| 1-9 | CH₂F | H | 2-F | 4-F | 5-F |
| 1-10 | CH₂F | H | 2-F | 4-F | 6-F |
| 1-11 | CH₂F | H | 3-F | 4-F | 5-F |
| 1-12 | CH₂F | H | 3-F | 5-F | 6-F |
| 1-13 | CHF₂ | H | 2-F | 3-F | 4-F |
| 1-14 | CHF₂ | H | 2-F | 3-F | 5-F |
| 1-15 | CHF₂ | H | 2-F | 4-F | 5-F |
| 1-16 | CHF₂ | H | 2-F | 4-F | 6-F |
| 1-17 | CHF₂ | H | 3-F | 4-F | 5-F |
| 1-18 | CHF₂ | H | 3-F | 5-F | 6-F |
| 1-19 | CF₃ | H | 2-F | 3-F | 4-F |
| 1-20 | CF₃ | H | 2-F | 3-F | 5-F |
| 1-21 | CF₃ | H | 2-F | 4-F | 5-F |
| 1-22 | CF₃ | H | 2-F | 4-F | 6-F |
| 1-23 | CF₃ | H | 3-F | 4-F | 5-F |
| 1-24 | CF₃ | H | 3-F | 5-F | 6-F |
| 1-25 | CHFCl | H | 2-F | 3-F | 4-F |
| 1-26 | CHFCl | H | 2-F | 3-F | 5-F |
| 1-27 | CHFCl | H | 2-F | 4-F | 5-F |
| 1-28 | CHFCl | H | 2-F | 4-F | 6-F |
| 1-29 | CHFCl | H | 3-F | 4-F | 5-F |
| 1-30 | CHFCl | H | 3-F | 5-F | 6-F |
| 1-31 | CF₂Cl | H | 2-F | 3-F | 4-F |
| 1-32 | CF₂Cl | H | 2-F | 3-F | 5-F |
| 1-33 | CF₂Cl | H | 2-F | 4-F | 5-F |
| 1-34 | CF₂Cl | H | 2-F | 4-F | 6-F |
| 1-35 | CF₂Cl | H | 3-F | 4-F | 5-F |
| 1-36 | CF₂Cl | H | 3-F | 5-F | 6-F |
| 1-37 | CH₃ | F | 2-F | 3-F | 4-F |
| 1-38 | CH₃ | F | 2-F | 3-F | 5-F |
| 1-39 | CH₃ | F | 2-F | 4-F | 5-F |
| 1-40 | CH₃ | F | 2-F | 4-F | 6-F |
| 1-41 | CH₃ | F | 3-F | 4-F | 5-F |
| 1-42 | CH₃ | F | 3-F | 5-F | 6-F |
| 1-43 | CH₂F | F | 2-F | 3-F | 4-F |
| 1-44 | CH₂F | F | 2-F | 3-F | 5-F |
| 1-45 | CH₂F | F | 2-F | 4-F | 5-F |
| 1-46 | CH₂F | F | 2-F | 4-F | 6-F |
| 1-47 | CH₂F | F | 3-F | 4-F | 5-F |
| 1-48 | CH₂F | F | 3-F | 5-F | 6-F |
| 1-49 | CHF₂ | F | 2-F | 3-F | 4-F |
| 1-50 | CHF₂ | F | 2-F | 3-F | 5-F |
| 1-51 | CHF₂ | F | 2-F | 4-F | 5-F |
| 1-52 | CHF₂ | F | 2-F | 4-F | 6-F |
| 1-53 | CHF₂ | F | 3-F | 4-F | 5-F |
| 1-54 | CHF₂ | F | 3-F | 5-F | 6-F |
| 1-55 | CF₃ | F | 2-F | 3-F | 4-F |
| 1-56 | CF₃ | F | 2-F | 3-F | 5-F |
| 1-57 | CF₃ | F | 2-F | 4-F | 5-F |
| 1-58 | CF₃ | F | 2-F | 4-F | 6-F |
| 1-59 | CF₃ | F | 3-F | 4-F | 5-F |
| 1-60 | CF₃ | F | 3-F | 5-F | 6-F |
| 1-61 | CHFCl | F | 2-F | 3-F | 4-F |
| 1-62 | CHFCl | F | 2-F | 3-F | 5-F |
| 1-63 | CHFCl | F | 2-F | 4-F | 5-F |
| 1-64 | CHFCl | F | 2-F | 4-F | 6-F |
| 1-65 | CHFCl | F | 3-F | 4-F | 5-F |
| 1-66 | CHFCl | F | 3-F | 5-F | 6-F |
| 1-67 | CF₂Cl | F | 2-F | 3-F | 4-F |
| 1-68 | CF₂Cl | F | 2-F | 3-F | 5-F |
| 1-69 | CF₂Cl | F | 2-F | 4-F | 5-F |
| 1-70 | CF₂Cl | F | 2-F | 4-F | 6-F |
| 1-71 | CF₂Cl | F | 3-F | 4-F | 5-F |
| 1-72 | CF₂Cl | F | 3-F | 5-F | 6-F |
| 1-73 | CH₃ | Cl | 2-F | 3-F | 4-F |
| 1-74 | CH₃ | Cl | 2-F | 3-F | 5-F |
| 1-75 | CH₃ | Cl | 2-F | 4-F | 5-F |
| 1-76 | CH₃ | Cl | 2-F | 4-F | 6-F |
| 1-77 | CH₃ | Cl | 3-F | 4-F | 5-F |
| 1-78 | CH₃ | Cl | 3-F | 5-F | 6-F |
| 1-79 | CH₂F | Cl | 2-F | 3-F | 4-F |
| 1-80 | CH₂F | Cl | 2-F | 3-F | 5-F |
| 1-81 | CH₂F | Cl | 2-F | 4-F | 5-F |
| 1-82 | CH₂F | Cl | 2-F | 4-F | 6-F |
| 1-83 | CH₂F | Cl | 3-F | 4-F | 5-F |
| 1-84 | CH₂F | Cl | 3-F | 5-F | 6-F |
| 1-85 | CHF₂ | Cl | 2-F | 3-F | 4-F |
| 1-86 | CHF₂ | Cl | 2-F | 3-F | 5-F |
| 1-87 | CHF₂ | Cl | 2-F | 4-F | 5-F |
| 1-88 | CHF₂ | Cl | 2-F | 4-F | 6-F |
| 1-89 | CHF₂ | Cl | 3-F | 4-F | 5-F |
| 1-90 | CHF₂ | Cl | 3-F | 5-F | 6-F |
| 1-91 | CF₃ | Cl | 2-F | 3-F | 4-F |
| 1-92 | CF₃ | Cl | 2-F | 3-F | 5-F |
| 1-93 | CF₃ | Cl | 2-F | 4-F | 5-F |
| 1-94 | CF₃ | Cl | 2-F | 4-F | 6-F |
| 1-95 | CF₃ | Cl | 3-F | 4-F | 5-F |
| 1-96 | CF₃ | Cl | 3-F | 5-F | 6-F |
| 1-97 | CHFCl | Cl | 2-F | 3-F | 4-F |
| 1-98 | CHFCl | Cl | 2-F | 3-F | 5-F |
| 1-99 | CHFCl | Cl | 2-F | 4-F | 5-F |
| 1-100 | CHFCl | Cl | 2-F | 4-F | 6-F |
| 1-101 | CHFCl | Cl | 3-F | 4-F | 5-F |
| 1-102 | CHFCl | Cl | 3-F | 5-F | 6-F |
| 1-103 | CF₂Cl | Cl | 2-F | 3-F | 4-F |
| 1-104 | CF₂Cl | Cl | 2-F | 3-F | 5-F |
| 1-105 | CF₂Cl | Cl | 2-F | 4-F | 5-F |
| 1-106 | CF₂Cl | Cl | 2-F | 4-F | 6-F |
| 1-107 | CF₂Cl | Cl | 3-F | 4-F | 5-F |
| 1-108 | CF₂Cl | Cl | 3-F | 5-F | 6-F |

Preference is furthermore given to compounds of the formula I in which X=O, R¹=CF₃ and R²=H and in which the variables R³ to R⁵ are defined as for formula I. They correspond to the formula Ia

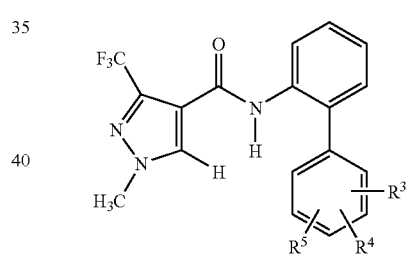

Ia

Preferred compounds 1a are listed in Table 2 (compounds 2-1 to 2-1029). Furthermore, particular preference is given to the compounds of the formulae Ib to If, in particular:
  the compounds Ib-1 to Ib-1029 which differ from the corresponding compounds 2-1 to 2-1029 in that R² is fluorine:

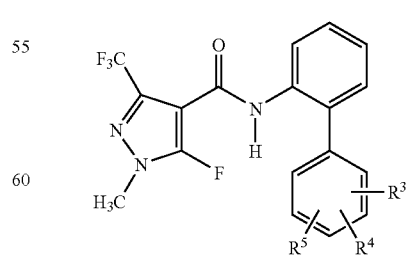

Ib the compounds Ic-1 to Ic-1029 which differ from the corresponding compounds 2-1 to 2-1029 in that R² is chlorine:

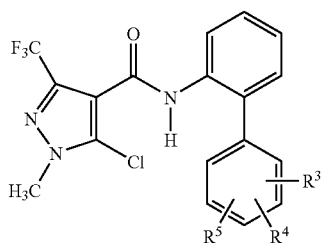

Ic the compounds Id-1 to Id-1029 which differ from the corresponding compounds 2-1 to 2-1029 in that R¹ is difluoromethyl:

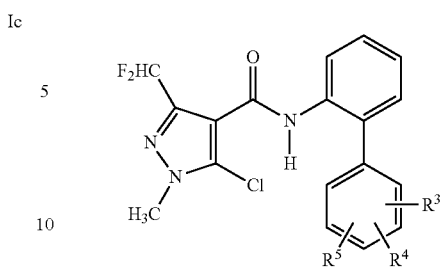

If the compounds Ig-1 to Ig-1029 which differ from the corresponding compounds 2-1 to 2-1029 in that R¹ is fluoromethyl:

Id

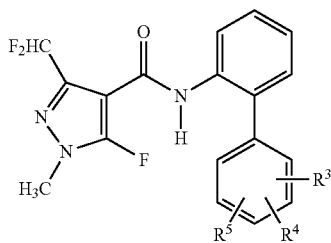

| Compound | m.p. [° C.] |
|---|---|
| Id-344 | 156-158 |
| Id-687 | 122-125 |
| Id-739 | 120-122 |
| Id-741 | 150-152 | the compounds Ie-1 to Ie-1029 which differ from the corresponding compounds 2-1 to 2-1029 in that R¹ is difluoromethyl and R² is fluorine:

Ie

Ig

| Compound | m.p. [° C.] |
|---|---|
| Ig-1 | 126-129 |
| Ig-344 | 152-156 | the compounds Ih-1 to Ih-1029 which differ from the corresponding compounds Il-1 to Il-1029 in that R¹ is $CF_2Cl$:

Ih

| Compound | m.p. [° C.] |
|---|---|
| Ih-344 | 158-161 | the compounds If-1 to If-1029 which differ from the corresponding compounds 2-1 to 2-1029 in that R¹ is difluoromethyl and R² is chlorine:

the compounds Ij-1 to Ij-1029 which differ from the corresponding compounds 2-1 to 2-1029 in that R¹ is chlorofluoromethyl:

TABLE 2

(Formulae Ia to Ij)

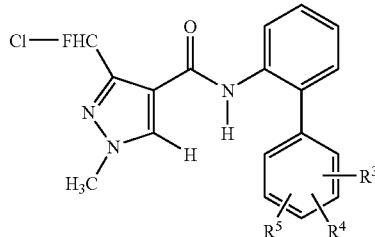

Ij

| Compound | m.p. [° C.] |
|---|---|
| Ij-344 | 154-157 |

| No. | R¹ | R² | R³ | R⁴ | R⁵ |
|---|---|---|---|---|---|
| 2-1 | CF₃ | H | 2-F | 3-F | 4-F |
| 2-2 | CF₃ | H | 2-F | 3-Cl | 4-F |
| 2-3 | CF₃ | H | 2-F | 3-CN | 4-F |
| 2-4 | CF₃ | H | 2-F | 3-CH₃ | 4-F |
| 2-5 | CF₃ | H | 2-F | 3-CF₃ | 4-F |
| 2-6 | CF₃ | H | 2-F | 3-OCH₃ | 4-F |
| 2-7 | CF₃ | H | 2-F | 3-OCF₃ | 4-F |
| 2-8 | CF₃ | H | 2-Cl | 3-F | 4-F |
| 2-9 | CF₃ | H | 2-Cl | 3-Cl | 4-F |
| 2-10 | CF₃ | H | 2-Cl | 3-CN | 4-F |
| 2-11 | CF₃ | H | 2-Cl | 3-CH₃ | 4-F |
| 2-12 | CF₃ | H | 2-Cl | 3-CF₃ | 4-F |
| 2-13 | CF₃ | H | 2-Cl | 3-OCH₃ | 4-F |
| 2-14 | CF₃ | H | 2-Cl | 3-OCF₃ | 4-F |
| 2-15 | CF₃ | H | 2-CN | 3-F | 4-F |
| 2-16 | CF₃ | H | 2-CN | 3-Cl | 4-F |
| 2-17 | CF₃ | H | 2-CN | 3-CN | 4-F |
| 2-18 | CF₃ | H | 2-CN | 3-CH₃ | 4-F |
| 2-19 | CF₃ | H | 2-CN | 3-CF₃ | 4-F |
| 2-20 | CF₃ | H | 2-CN | 3-OCH₃ | 4-F |
| 2-21 | CF₃ | H | 2-CN | 3-OCF₃ | 4-F |
| 2-22 | CF₃ | H | 2-CH₃ | 3-F | 4-F |
| 2-23 | CF₃ | H | 2-CH₃ | 3-Cl | 4-F |
| 2-24 | CF₃ | H | 2-CH₃ | 3-CN | 4-F |
| 2-25 | CF₃ | H | 2-CH₃ | 3-CH₃ | 4-F |
| 2-26 | CF₃ | H | 2-CH₃ | 3-CF₃ | 4-F |
| 2-27 | CF₃ | H | 2-CH₃ | 3-OCH₃ | 4-F |
| 2-28 | CF₃ | H | 2-CH₃ | 3-OCF₃ | 4-F |
| 2-29 | CF₃ | H | 2-CF₃ | 3-F | 4-F |
| 2-30 | CF₃ | H | 2-CF₃ | 3-Cl | 4-F |
| 2-31 | CF₃ | H | 2-CF₃ | 3-CN | 4-F |
| 2-32 | CF₃ | H | 2-CF₃ | 3-CH₃ | 4-F |
| 2-33 | CF₃ | H | 2-CF₃ | 3-CF₃ | 4-F |
| 2-34 | CF₃ | H | 2-CF₃ | 3-OCH₃ | 4-F |
| 2-35 | CF₃ | H | 2-CF₃ | 3-OCF₃ | 4-F |
| 2-36 | CF₃ | H | 2-OCH₃ | 3-F | 4-F |
| 2-37 | CF₃ | H | 2-OCH₃ | 3-Cl | 4-F |
| 2-38 | CF₃ | H | 2-OCH₃ | 3-CN | 4-F |
| 2-39 | CF₃ | H | 2-OCH₃ | 3-CH₃ | 4-F |
| 2-40 | CF₃ | H | 2-OCH₃ | 3-CF₃ | 4-F |
| 2-41 | CF₃ | H | 2-OCH₃ | 3-OCH₃ | 4-F |
| 2-42 | CF₃ | H | 2-OCH₃ | 3-OCF₃ | 4-F |
| 2-43 | CF₃ | H | 2-OCF₃ | 3-F | 4-F |
| 2-44 | CF₃ | H | 2-OCF₃ | 3-Cl | 4-F |
| 2-45 | CF₃ | H | 2-OCF₃ | 3-CN | 4-F |
| 2-46 | CF₃ | H | 2-OCF₃ | 3-CH₃ | 4-F |
| 2-47 | CF₃ | H | 2-OCF₃ | 3-CF₃ | 4-F |
| 2-48 | CF₃ | H | 2-OCF₃ | 3-OCH₃ | 4-F |
| 2-49 | CF₃ | H | 2-OCF₃ | 3-OCF₃ | 4-F |
| 2-50 | CF₃ | H | 2-F | 3-F | 4-Cl |
| 2-51 | CF₃ | H | 2-F | 3-Cl | 4-Cl |
| 2-52 | CF₃ | H | 2-F | 3-CN | 4-Cl |
| 2-53 | CF₃ | H | 2-F | 3-CH₃ | 4-Cl |
| 2-54 | CF₃ | H | 2-F | 3-CF₃ | 4-Cl |
| 2-55 | CF₃ | H | 2-F | 3-OCH₃ | 4-Cl |
| 2-56 | CF₃ | H | 2-F | 3-OCF₃ | 4-Cl |
| 2-57 | CF₃ | H | 2-Cl | 3-F | 4-Cl |
| 2-58 | CF₃ | H | 2-Cl | 3-Cl | 4-Cl |
| 2-59 | CF₃ | H | 2-Cl | 3-CN | 4-Cl |
| 2-60 | CF₃ | H | 2-Cl | 3-CH₃ | 4-Cl |
| 2-61 | CF₃ | H | 2-Cl | 3-CF₃ | 4-Cl |
| 2-62 | CF₃ | H | 2-Cl | 3-OCH₃ | 4-Cl |
| 2-63 | CF₃ | H | 2-Cl | 3-OCF₃ | 4-Cl |
| 2-64 | CF₃ | H | 2-CN | 3-F | 4-Cl |
| 2-65 | CF₃ | H | 2-CN | 3-Cl | 4-Cl |
| 2-66 | CF₃ | H | 2-CN | 3-CN | 4-Cl |
| 2-67 | CF₃ | H | 2-CN | 3-CH₃ | 4-Cl |
| 2-68 | CF₃ | H | 2-CN | 3-CF₃ | 4-Cl |
| 2-69 | CF₃ | H | 2-CN | 3-OCH₃ | 4-Cl |
| 2-70 | CF₃ | H | 2-CN | 3-OCF₃ | 4-Cl |
| 2-71 | CF₃ | H | 2-CH₃ | 3-F | 4-Cl |
| 2-72 | CF₃ | H | 2-CH₃ | 3-Cl | 4-Cl |
| 2-73 | CF₃ | H | 2-CH₃ | 3-CN | 4-Cl |
| 2-74 | CF₃ | H | 2-CH₃ | 3-CH₃ | 4-Cl |
| 2-75 | CF₃ | H | 2-CH₃ | 3-CF₃ | 4-Cl |
| 2-76 | CF₃ | H | 2-CH₃ | 3-OCH₃ | 4-Cl |
| 2-77 | CF₃ | H | 2-CH₃ | 3-OCF₃ | 4-Cl |
| 2-78 | CF₃ | H | 2-CF₃ | 3-F | 4-Cl |
| 2-79 | CF₃ | H | 2-CF₃ | 3-Cl | 4-Cl |
| 2-80 | CF₃ | H | 2-CF₃ | 3-CN | 4-Cl |
| 2-81 | CF₃ | H | 2-CF₃ | 3-CH₃ | 4-Cl |
| 2-82 | CF₃ | H | 2-CF₃ | 3-CF₃ | 4-Cl |
| 2-83 | CF₃ | H | 2-CF₃ | 3-OCH₃ | 4-Cl |
| 2-84 | CF₃ | H | 2-CF₃ | 3-OCF₃ | 4-Cl |
| 2-85 | CF₃ | H | 2-OCH₃ | 3-F | 4-Cl |
| 2-86 | CF₃ | H | 2-OCH₃ | 3-Cl | 4-Cl |
| 2-87 | CF₃ | H | 2-OCH₃ | 3-CN | 4-Cl |
| 2-88 | CF₃ | H | 2-OCH₃ | 3-CH₃ | 4-Cl |
| 2-89 | CF₃ | H | 2-OCH₃ | 3-CF₃ | 4-Cl |
| 2-90 | CF₃ | H | 2-OCH₃ | 3-OCH₃ | 4-Cl |
| 2-91 | CF₃ | H | 2-OCH₃ | 3-OCF₃ | 4-Cl |
| 2-92 | CF₃ | H | 2-OCF₃ | 3-F | 4-Cl |
| 2-93 | CF₃ | H | 2-OCF₃ | 3-Cl | 4-Cl |
| 2-94 | CF₃ | H | 2-OCF₃ | 3-CN | 4-Cl |
| 2-95 | CF₃ | H | 2-OCF₃ | 3-CH₃ | 4-Cl |
| 2-96 | CF₃ | H | 2-OCF₃ | 3-CF₃ | 4-Cl |
| 2-97 | CF₃ | H | 2-OCF₃ | 3-OCH₃ | 4-Cl |
| 2-98 | CF₃ | H | 2-OCF₃ | 3-OCF₃ | 4-Cl |
| 2-99 | CF₃ | H | 2-F | 3-F | 4-CN |
| 2-100 | CF₃ | H | 2-F | 3-Cl | 4-CN |
| 2-101 | CF₃ | H | 2-F | 3-CN | 4-CN |
| 2-102 | CF₃ | H | 2-F | 3-CH₃ | 4-CN |
| 2-103 | CF₃ | H | 2-F | 3-CF₃ | 4-CN |
| 2-104 | CF₃ | H | 2-F | 3-OCH₃ | 4-CN |
| 2-105 | CF₃ | H | 2-F | 3-OCF₃ | 4-CN |
| 2-106 | CF₃ | H | 2-Cl | 3-F | 4-CN |
| 2-107 | CF₃ | H | 2-Cl | 3-Cl | 4-CN |
| 2-108 | CF₃ | H | 2-Cl | 3-CN | 4-CN |
| 2-109 | CF₃ | H | 2-Cl | 3-CH₃ | 4-CN |
| 2-110 | CF₃ | H | 2-Cl | 3-CF₃ | 4-CN |
| 2-111 | CF₃ | H | 2-Cl | 3-OCH₃ | 4-CN |
| 2-112 | CF₃ | H | 2-Cl | 3-OCF₃ | 4-CN |
| 2-113 | CF₃ | H | 2-CN | 3-F | 4-CN |
| 2-114 | CF₃ | H | 2-CN | 3-Cl | 4-CN |
| 2-115 | CF₃ | H | 2-CN | 3-CN | 4-CN |
| 2-116 | CF₃ | H | 2-CN | 3-CH₃ | 4-CN |

TABLE 2-continued (Formulae Ia to Ij)

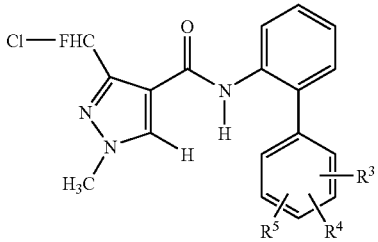

Ij

| Compound | m.p. [° C.] |
|---|---|
| Ij-344 | 154-157 |

| No. | R¹ | R² | R³ | R⁴ | R⁵ |
|---|---|---|---|---|---|
| 2-117 | CF₃ | H | 2-CN | 3-CF₃ | 4-CN |
| 2-118 | CF₃ | H | 2-CN | 3-OCH₃ | 4-CN |
| 2-119 | CF₃ | H | 2-CN | 3-OCF₃ | 4-CN |
| 2-120 | CF₃ | H | 2-CH₃ | 3-F | 4-CN |
| 2-121 | CF₃ | H | 2-CH₃ | 3-Cl | 4-CN |
| 2-122 | CF₃ | H | 2-CH₃ | 3-CN | 4-CN |
| 2-123 | CF₃ | H | 2-CH₃ | 3-CH₃ | 4-CN |
| 2-124 | CF₃ | H | 2-CH₃ | 3-CF₃ | 4-CN |
| 2-125 | CF₃ | H | 2-CH₃ | 3-OCH₃ | 4-CN |
| 2-126 | CF₃ | H | 2-CH₃ | 3-OCF₃ | 4-CN |
| 2-127 | CF₃ | H | 2-CF₃ | 3-F | 4-CN |
| 2-128 | CF₃ | H | 2-CF₃ | 3-Cl | 4-CN |
| 2-129 | CF₃ | H | 2-CF₃ | 3-CN | 4-CN |
| 2-130 | CF₃ | H | 2-CF₃ | 3-CH₃ | 4-CN |
| 2-131 | CF₃ | H | 2-CF₃ | 3-CF₃ | 4-CN |
| 2-132 | CF₃ | H | 2-CF₃ | 3-OCH₃ | 4-CN |
| 2-133 | CF₃ | H | 2-CF₃ | 3-OCF₃ | 4-CN |
| 2-134 | CF₃ | H | 2-OCH₃ | 3-F | 4-CN |
| 2-135 | CF₃ | H | 2-OCH₃ | 3-Cl | 4-CN |
| 2-136 | CF₃ | H | 2-OCH₃ | 3-CN | 4-CN |
| 2-137 | CF₃ | H | 2-OCH₃ | 3-CH₃ | 4-CN |
| 2-138 | CF₃ | H | 2-OCH₃ | 3-CF₃ | 4-CN |
| 2-139 | CF₃ | H | 2-OCH₃ | 3-OCH₃ | 4-CN |
| 2-140 | CF₃ | H | 2-OCH₃ | 3-OCF₃ | 4-CN |
| 2-141 | CF₃ | H | 2-OCF₃ | 3-F | 4-CN |
| 2-142 | CF₃ | H | 2-OCF₃ | 3-Cl | 4-CN |
| 2-143 | CF₃ | H | 2-OCF₃ | 3-CN | 4-CN |
| 2-144 | CF₃ | H | 2-OCF₃ | 3-CH₃ | 4-CN |
| 2-145 | CF₃ | H | 2-OCF₃ | 3-CF₃ | 4-CN |
| 2-146 | CF₃ | H | 2-OCF₃ | 3-OCH₃ | 4-CN |
| 2-147 | CF₃ | H | 2-OCF₃ | 3-OCF₃ | 4-CN |
| 2-148 | CF₃ | H | 2-F | 3-F | 4-CH₃ |
| 2-149 | CF₃ | H | 2-F | 3-Cl | 4-CH₃ |
| 2-150 | CF₃ | H | 2-F | 3-CN | 4-CH₃ |
| 2-151 | CF₃ | H | 2-F | 3-CH₃ | 4-CH₃ |
| 2-152 | CF₃ | H | 2-F | 3-CF₃ | 4-CH₃ |
| 2-153 | CF₃ | H | 2-F | 3-OCH₃ | 4-CH₃ |
| 2-154 | CF₃ | H | 2-F | 3-OCF₃ | 4-CH₃ |
| 2-155 | CF₃ | H | 2-Cl | 3-F | 4-CH₃ |
| 2-156 | CF₃ | H | 2-Cl | 3-Cl | 4-CH₃ |
| 2-157 | CF₃ | H | 2-Cl | 3-CN | 4-CH₃ |
| 2-158 | CF₃ | H | 2-Cl | 3-CH₃ | 4-CH₃ |
| 2-159 | CF₃ | H | 2-Cl | 3-CF₃ | 4-CH₃ |
| 2-160 | CF₃ | H | 2-Cl | 3-OCH₃ | 4-CH₃ |
| 2-161 | CF₃ | H | 2-Cl | 3-OCF₃ | 4-CH₃ |
| 2-162 | CF₃ | H | 2-CN | 3-F | 4-CH₃ |
| 2-163 | CF₃ | H | 2-CN | 3-Cl | 4-CH₃ |
| 2-164 | CF₃ | H | 2-CN | 3-CN | 4-CH₃ |
| 2-165 | CF₃ | H | 2-CN | 3-CH₃ | 4-CH₃ |
| 2-166 | CF₃ | H | 2-CN | 3-CF₃ | 4-CH₃ |
| 2-167 | CF₃ | H | 2-CN | 3-OCH₃ | 4-CH₃ |
| 2-168 | CF₃ | H | 2-CN | 3-OCF₃ | 4-CH₃ |
| 2-169 | CF₃ | H | 2-CH₃ | 3-F | 4-CH₃ |
| 2-170 | CF₃ | H | 2-CH₃ | 3-Cl | 4-CH₃ |
| 2-171 | CF₃ | H | 2-CH₃ | 3-CN | 4-CH₃ |
| 2-172 | CF₃ | H | 2-CH₃ | 3-CH₃ | 4-CH₃ |
| 2-173 | CF₃ | H | 2-CH₃ | 3-CF₃ | 4-CH₃ |
| 2-174 | CF₃ | H | 2-CH₃ | 3-OCH₃ | 4-CH₃ |

TABLE 2-continued (Formulae Ia to Ij)

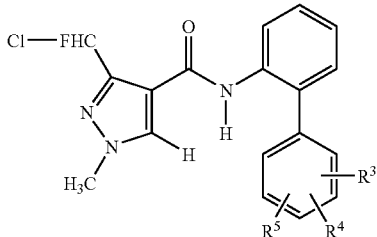

Ij

| Compound | m.p. [° C.] |
|---|---|
| Ij-344 | 154-157 |

| No. | R¹ | R² | R³ | R⁴ | R⁵ |
|---|---|---|---|---|---|
| 2-175 | CF₃ | H | 2-CH₃ | 3-OCF₃ | 4-CH₃ |
| 2-176 | CF₃ | H | 2-CF₃ | 3-F | 4-CH₃ |
| 2-177 | CF₃ | H | 2-CF₃ | 3-Cl | 4-CH₃ |
| 2-178 | CF₃ | H | 2-CF₃ | 3-CN | 4-CH₃ |
| 2-179 | CF₃ | H | 2-CF₃ | 3-CH₃ | 4-CH₃ |
| 2-180 | CF₃ | H | 2-CF₃ | 3-CF₃ | 4-CH₃ |
| 2-181 | CF₃ | H | 2-CF₃ | 3-OCH₃ | 4-CH₃ |
| 2-182 | CF₃ | H | 2-CF₃ | 3-OCF₃ | 4-CH₃ |
| 2-183 | CF₃ | H | 2-OCH₃ | 3-F | 4-CH₃ |
| 2-184 | CF₃ | H | 2-OCH₃ | 3-Cl | 4-CH₃ |
| 2-185 | CF₃ | H | 2-OCH₃ | 3-CN | 4-CH₃ |
| 2-186 | CF₃ | H | 2-OCH₃ | 3-CH₃ | 4-CH₃ |
| 2-187 | CF₃ | H | 2-OCH₃ | 3-CF₃ | 4-CH₃ |
| 2-188 | CF₃ | H | 2-OCH₃ | 3-OCH₃ | 4-CH₃ |
| 2-189 | CF₃ | H | 2-OCH₃ | 3-OCF₃ | 4-CH₃ |
| 2-190 | CF₃ | H | 2-OCF₃ | 3-F | 4-CH₃ |
| 2-191 | CF₃ | H | 2-OCF₃ | 3-Cl | 4-CH₃ |
| 2-192 | CF₃ | H | 2-OCF₃ | 3-CN | 4-CH₃ |
| 2-193 | CF₃ | H | 2-OCF₃ | 3-CH₃ | 4-CH₃ |
| 2-194 | CF₃ | H | 2-OCF₃ | 3-CF₃ | 4-CH₃ |
| 2-195 | CF₃ | H | 2-OCF₃ | 3-OCH₃ | 4-CH₃ |
| 2-196 | CF₃ | H | 2-OCF₃ | 3-OCF₃ | 4-CH₃ |
| 2-197 | CF₃ | H | 2-F | 3-F | 4-CF3 |
| 2-198 | CF₃ | H | 2-F | 3-Cl | 4-CF3 |
| 2-199 | CF₃ | H | 2-F | 3-CN | 4-CF3 |
| 2-200 | CF₃ | H | 2-F | 3-CH₃ | 4-CF3 |
| 2-201 | CF₃ | H | 2-F | 3-CF₃ | 4-CF3 |
| 2-202 | CF₃ | H | 2-F | 3-OCH₃ | 4-CF3 |
| 2-203 | CF₃ | H | 2-F | 3-OCF₃ | 4-CF3 |
| 2-204 | CF₃ | H | 2-Cl | 3-F | 4-CF₃ |
| 2-205 | CF₃ | H | 2-Cl | 3-Cl | 4-CF₃ |
| 2-206 | CF₃ | H | 2-Cl | 3-CN | 4-CF₃ |
| 2-207 | CF₃ | H | 2-Cl | 3-CH₃ | 4-CF₃ |
| 2-208 | CF₃ | H | 2-Cl | 3-CF₃ | 4-CF₃ |
| 2-209 | CF₃ | H | 2-Cl | 3-OCH₃ | 4-CF₃ |
| 2-210 | CF₃ | H | 2-Cl | 3-OCF₃ | 4-CF₃ |
| 2-211 | CF₃ | H | 2-CN | 3-F | 4-CF₃ |
| 2-212 | CF₃ | H | 2-CN | 3-Cl | 4-CF₃ |
| 2-213 | CF₃ | H | 2-CN | 3-CN | 4-CF₃ |
| 2-214 | CF₃ | H | 2-CN | 3-CH₃ | 4-CF₃ |
| 2-215 | CF₃ | H | 2-CN | 3-CF₃ | 4-CF₃ |
| 2-216 | CF₃ | H | 2-CN | 3-OCH₃ | 4-CF₃ |
| 2-217 | CF₃ | H | 2-CN | 3-OCF₃ | 4-CF₃ |
| 2-218 | CF₃ | H | 2-CH₃ | 3-F | 4-CF₃ |
| 2-219 | CF₃ | H | 2-CH₃ | 3-Cl | 4-CF₃ |
| 2-220 | CF₃ | H | 2-CH₃ | 3-CN | 4-CF₃ |
| 2-221 | CF₃ | H | 2-CH₃ | 3-CH₃ | 4-CF₃ |
| 2-222 | CF₃ | H | 2-CH₃ | 3-CF₃ | 4-CF₃ |
| 2-223 | CF₃ | H | 2-CH₃ | 3-OCH₃ | 4-CF₃ |
| 2-224 | CF₃ | H | 2-CH₃ | 3-OCF₃ | 4-CF₃ |
| 2-225 | CF₃ | H | 2-CF₃ | 3-F | 4-CF₃ |
| 2-226 | CF₃ | H | 2-CF₃ | 3-Cl | 4-CF₃ |
| 2-227 | CF₃ | H | 2-CF₃ | 3-CN | 4-CF₃ |
| 2-228 | CF₃ | H | 2-CF₃ | 3-CH₃ | 4-CF₃ |
| 2-229 | CF₃ | H | 2-CF₃ | 3-CF₃ | 4-CF₃ |
| 2-230 | CF₃ | H | 2-CF₃ | 3-OCH₃ | 4-CF₃ |
| 2-231 | CF₃ | H | 2-CF₃ | 3-OCF₃ | 4-CF₃ |
| 2-232 | CF₃ | H | 2-OCH₃ | 3-F | 4-CF3 |

TABLE 2-continued (Formulae Ia to Ij)

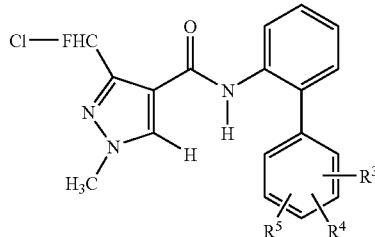

Ij

| Compound | m.p. [° C.] |
|---|---|
| Ij-344 | 154-157 |

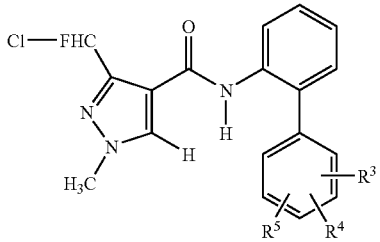

Ij

| Compound | m.p. [° C.] |
|---|---|
| Ij-344 | 154-157 |

| No. | R¹ | R² | R³ | R⁴ | R⁵ |
|---|---|---|---|---|---|
| 2-233 | CF₃ | H | 2-OCH₃ | 3-Cl | 4-CF₃ |
| 2-234 | CF₃ | H | 2-OCH₃ | 3-CN | 4-CF₃ |
| 2-235 | CF₃ | H | 2-OCH₃ | 3-CH₃ | 4-CF₃ |
| 2-236 | CF₃ | H | 2-OCH₃ | 3-CF₃ | 4-CF₃ |
| 2-237 | CF₃ | H | 2-OCH₃ | 3-OCH₃ | 4-CF₃ |
| 2-238 | CF₃ | H | 2-OCH₃ | 3-OCF₃ | 4-CF₃ |
| 2-239 | CF₃ | H | 2-OCF₃ | 3-F | 4-CF₃ |
| 2-240 | CF₃ | H | 2-OCF₃ | 3-Cl | 4-CF₃ |
| 2-241 | CF₃ | H | 2-OCF₃ | 3-CN | 4-CF₃ |
| 2-242 | CF₃ | H | 2-OCF₃ | 3-CH₃ | 4-CF₃ |
| 2-243 | CF₃ | H | 2-OCF₃ | 3-CF₃ | 4-CF₃ |
| 2-244 | CF₃ | H | 2-OCF₃ | 3-OCH₃ | 4-CF₃ |
| 2-245 | CF₃ | H | 2-OCF₃ | 3-OCF₃ | 4-CF₃ |
| 2-246 | CF₃ | H | 2-F | 3-F | 4-OCH₃ |
| 2-247 | CF₃ | H | 2-F | 3-Cl | 4-OCH₃ |
| 2-248 | CF₃ | H | 2-F | 3-CN | 4-OCH₃ |
| 2-249 | CF₃ | H | 2-F | 3-CH₃ | 4-OCH₃ |
| 2-250 | CF₃ | H | 2-F | 3-CF₃ | 4-OCH₃ |
| 2-251 | CF₃ | H | 2-F | 3-OCH₃ | 4-OCH₃ |
| 2-252 | CF₃ | H | 2-F | 3-OCF₃ | 4-OCH₃ |
| 2-253 | CF₃ | H | 2-Cl | 3-F | 4-OCH₃ |
| 2-254 | CF₃ | H | 2-Cl | 3-Cl | 4-OCH₃ |
| 2-255 | CF₃ | H | 2-Cl | 3-CN | 4-OCH₃ |
| 2-256 | CF₃ | H | 2-Cl | 3-CH₃ | 4-OCH₃ |
| 2-257 | CF₃ | H | 2-Cl | 3-CF₃ | 4-OCH₃ |
| 2-258 | CF₃ | H | 2-Cl | 3-OCH₃ | 4-OCH₃ |
| 2-259 | CF₃ | H | 2-Cl | 3-OCF₃ | 4-OCH₃ |
| 2-260 | CF₃ | H | 2-CN | 3-F | 4-OCH₃ |
| 2-261 | CF₃ | H | 2-CN | 3-Cl | 4-OCH₃ |
| 2-262 | CF₃ | H | 2-CN | 3-CN | 4-OCH₃ |
| 2-263 | CF₃ | H | 2-CN | 3-CH₃ | 4-OCH₃ |
| 2-264 | CF₃ | H | 2-CN | 3-CF₃ | 4-OCH₃ |
| 2-265 | CF₃ | H | 2-CN | 3-OCH₃ | 4-OCH₃ |
| 2-266 | CF₃ | H | 2-CN | 3-OCF₃ | 4-OCH₃ |
| 2-267 | CF₃ | H | 2-CH₃ | 3-F | 4-OCH₃ |
| 2-268 | CF₃ | H | 2-CH₃ | 3-Cl | 4-OCH₃ |
| 2-269 | CF₃ | H | 2-CH₃ | 3-CN | 4-OCH₃ |
| 2-270 | CF₃ | H | 2-CH₃ | 3-CH₃ | 4-OCH₃ |
| 2-271 | CF₃ | H | 2-CH₃ | 3-CF₃ | 4-OCH₃ |
| 2-272 | CF₃ | H | 2-CH₃ | 3-OCH₃ | 4-OCH₃ |
| 2-273 | CF₃ | H | 2-CH₃ | 3-OCF₃ | 4-OCH₃ |
| 2-274 | CF₃ | H | 2-CF₃ | 3-F | 4-OCH₃ |
| 2-275 | CF₃ | H | 2-CF₃ | 3-Cl | 4-OCH₃ |
| 2-276 | CF₃ | H | 2-CF₃ | 3-CN | 4-OCH₃ |
| 2-277 | CF₃ | H | 2-CF₃ | 3-CH₃ | 4-OCH₃ |
| 2-278 | CF₃ | H | 2-CF₃ | 3-CF₃ | 4-OCH₃ |
| 2-279 | CF₃ | H | 2-CF₃ | 3-OCH₃ | 4-OCH₃ |
| 2-280 | CF₃ | H | 2-CF₃ | 3-OCF₃ | 4-OCH₃ |
| 2-281 | CF₃ | H | 2-OCH₃ | 3-F | 4-OCH₃ |
| 2-282 | CF₃ | H | 2-OCH₃ | 3-Cl | 4-OCH₃ |
| 2-283 | CF₃ | H | 2-OCH₃ | 3-CN | 4-OCH₃ |
| 2-284 | CF₃ | H | 2-OCH₃ | 3-CH₃ | 4-OCH₃ |
| 2-285 | CF₃ | H | 2-OCH₃ | 3-CF₃ | 4-OCH₃ |
| 2-286 | CF₃ | H | 2-OCH₃ | 3-OCH₃ | 4-OCH₃ |
| 2-287 | CF₃ | H | 2-OCH₃ | 3-OCF₃ | 4-OCH₃ |
| 2-288 | CF₃ | H | 2-OCF₃ | 3-F | 4-OCH₃ |
| 2-289 | CF₃ | H | 2-OCF₃ | 3-Cl | 4-OCH₃ |
| 2-290 | CF₃ | H | 2-OCF₃ | 3-CN | 4-OCH₃ |
| 2-291 | CF₃ | H | 2-OCF₃ | 3-CH₃ | 4-OCH₃ |
| 2-292 | CF₃ | H | 2-OCF₃ | 3-CF₃ | 4-OCH₃ |
| 2-293 | CF₃ | H | 2-OCF₃ | 3-OCH₃ | 4-OCH₃ |
| 2-294 | CF₃ | H | 2-OCF₃ | 3-OCF₃ | 4-OCH₃ |
| 2-295 | CF₃ | H | 2-F | 3-F | 4-OCF₃ |
| 2-296 | CF₃ | H | 2-F | 3-Cl | 4-OCF₃ |
| 2-297 | CF₃ | H | 2-F | 3-CN | 4-OCF₃ |
| 2-298 | CF₃ | H | 2-F | 3-CH₃ | 4-OCF₃ |
| 2-299 | CF₃ | H | 2-F | 3-CF₃ | 4-OCF₃ |
| 2-300 | CF₃ | H | 2-F | 3-OCH₃ | 4-OCF₃ |
| 2-301 | CF₃ | H | 2-F | 3-OCF₃ | 4-OCF₃ |
| 2-302 | CF₃ | H | 2-Cl | 3-F | 4-OCF₃ |
| 2-303 | CF₃ | H | 2-Cl | 3-Cl | 4-OCF₃ |
| 2-304 | CF₃ | H | 2-Cl | 3-CN | 4-OCF₃ |
| 2-305 | CF₃ | H | 2-Cl | 3-CH₃ | 4-OCF₃ |
| 2-306 | CF₃ | H | 2-Cl | 3-CF₃ | 4-OCF₃ |
| 2-307 | CF₃ | H | 2-Cl | 3-OCH₃ | 4-OCF₃ |
| 2-308 | CF₃ | H | 2-Cl | 3-OCF₃ | 4-OCF₃ |
| 2-309 | CF₃ | H | 2-CN | 3-F | 4-OCF₃ |
| 2-310 | CF₃ | H | 2-CN | 3-Cl | 4-OCF₃ |
| 2-311 | CF₃ | H | 2-CN | 3-CN | 4-OCF₃ |
| 2-312 | CF₃ | H | 2-CN | 3-CH₃ | 4-OCF₃ |
| 2-313 | CF₃ | H | 2-CN | 3-CF₃ | 4-OCF₃ |
| 2-314 | CF₃ | H | 2-CN | 3-OCH₃ | 4-OCF₃ |
| 2-315 | CF₃ | H | 2-CN | 3-OCF₃ | 4-OCF₃ |
| 2-316 | CF₃ | H | 2-CH₃ | 3-F | 4-OCF₃ |
| 2-317 | CF₃ | H | 2-CH₃ | 3-Cl | 4-OCF₃ |
| 2-318 | CF₃ | H | 2-CH₃ | 3-CN | 4-OCF₃ |
| 2-319 | CF₃ | H | 2-CH₃ | 3-CH₃ | 4-OCF₃ |
| 2-320 | CF₃ | H | 2-CH₃ | 3-CF₃ | 4-OCF₃ |
| 2-321 | CF₃ | H | 2-CH₃ | 3-OCH₃ | 4-OCF₃ |
| 2-322 | CF₃ | H | 2-CH₃ | 3-OCF₃ | 4-OCF₃ |
| 2-323 | CF₃ | H | 2-CF₃ | 3-F | 4-OCF₃ |
| 2-324 | CF₃ | H | 2-CF₃ | 3-Cl | 4-OCF₃ |
| 2-325 | CF₃ | H | 2-CF₃ | 3-CN | 4-OCF₃ |
| 2-326 | CF₃ | H | 2-CF₃ | 3-CH₃ | 4-OCF₃ |
| 2-327 | CF₃ | H | 2-CF₃ | 3-CF₃ | 4-OCF₃ |
| 2-328 | CF₃ | H | 2-CF₃ | 3-OCH₃ | 4-OCF₃ |
| 2-329 | CF₃ | H | 2-CF₃ | 3-OCF₃ | 4-OCF₃ |
| 2-330 | CF₃ | H | 2-OCH₃ | 3-F | 4-OCF₃ |
| 2-331 | CF₃ | H | 2-OCH₃ | 3-Cl | 4-OCF₃ |
| 2-332 | CF₃ | H | 2-OCH₃ | 3-CN | 4-OCF₃ |
| 2-333 | CF₃ | H | 2-OCH₃ | 3-CH₃ | 4-OCF₃ |
| 2-334 | CF₃ | H | 2-OCH₃ | 3-CF₃ | 4-OCF₃ |
| 2-335 | CF₃ | H | 2-OCH₃ | 3-OCH₃ | 4-OCF₃ |
| 2-336 | CF₃ | H | 2-OCH₃ | 3-OCF₃ | 4-OCF₃ |
| 2-337 | CF₃ | H | 2-OCF₃ | 3-F | 4-OCF₃ |
| 2-338 | CF₃ | H | 2-OCF₃ | 3-Cl | 4-OCF₃ |
| 2-339 | CF₃ | H | 2-OCF₃ | 3-CN | 4-OCF₃ |
| 2-340 | CF₃ | H | 2-OCF₃ | 3-CH₃ | 4-OCF₃ |
| 2-341 | CF₃ | H | 2-OCF₃ | 3-CF₃ | 4-OCF₃ |
| 2-342 | CF₃ | H | 2-OCF₃ | 3-OCH₃ | 4-OCF₃ |
| 2-343 | CF₃ | H | 2-OCF₃ | 3-OCF₃ | 4-OCF₃ |
| 2-344 | CF₃ | H | 3-F | 4-F | 5-F |
| 2-345 | CF₃ | H | 3-Cl | 4-F | 5-F |
| 2-346 | CF₃ | H | 3-CN | 4-F | 5-F |
| 2-347 | CF₃ | H | 3-CH₃ | 4-F | 5-F |
| 2-348 | CF₃ | H | 3-CF₃ | 4-F | 5-F |

TABLE 2-continued (Formulae Ia to Ij)

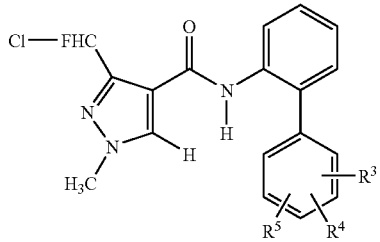

Ij

| Compound | m.p. [° C.] |
|---|---|
| Ij-344 | 154-157 |

| No. | R¹ | R² | R³ | R⁴ | R⁵ |
|---|---|---|---|---|---|
| 2-349 | CF₃ | H | 3-OCH₃ | 4-F | 5-F |
| 2-350 | CF₃ | H | 3-OCF₃ | 4-F | 5-F |
| 2-351 | CF₃ | H | 3-F | 4-F | 5-Cl |
| 2-352 | CF₃ | H | 3-Cl | 4-F | 5-Cl |
| 2-353 | CF₃ | H | 3-CN | 4-F | 5-Cl |
| 2-354 | CF₃ | H | 3-CH₃ | 4-F | 5-Cl |
| 2-355 | CF₃ | H | 3-CF₃ | 4-F | 5-Cl |
| 2-356 | CF₃ | H | 3-OCH₃ | 4-F | 5-Cl |
| 2-357 | CF₃ | H | 3-OCF₃ | 4-F | 5-Cl |
| 2-358 | CF₃ | H | 3-F | 4-F | 5-CN |
| 2-359 | CF₃ | H | 3-Cl | 4-F | 5-CN |
| 2-360 | CF₃ | H | 3-CN | 4-F | 5-CN |
| 2-361 | CF₃ | H | 3-CH₃ | 4-F | 5-CN |
| 2-362 | CF₃ | H | 3-CF₃ | 4-F | 5-CN |
| 2-363 | CF₃ | H | 3-OCH₃ | 4-F | 5-CN |
| 2-364 | CF₃ | H | 3-OCF₃ | 4-F | 5-CN |
| 2-365 | CF₃ | H | 3-F | 4-F | 5-CH₃ |
| 2-366 | CF₃ | H | 3-Cl | 4-F | 5-CH₃ |
| 2-367 | CF₃ | H | 3-CN | 4-F | 5-CH₃ |
| 2-368 | CF₃ | H | 3-CH₃ | 4-F | 5-CH₃ |
| 2-369 | CF₃ | H | 3-CF₃ | 4-F | 5-CH₃ |
| 2-370 | CF₃ | H | 3-OCH₃ | 4-F | 5-CH₃ |
| 2-371 | CF₃ | H | 3-OCF₃ | 4-F | 5-CH₃ |
| 2-372 | CF₃ | H | 3-F | 4-F | 5-CF₃ |
| 2-373 | CF₃ | H | 3-Cl | 4-F | 5-CF₃ |
| 2-374 | CF₃ | H | 3-CN | 4-F | 5-CF₃ |
| 2-375 | CF₃ | H | 3-CH₃ | 4-F | 5-CF₃ |
| 2-376 | CF₃ | H | 3-CF₃ | 4-F | 5-CF₃ |
| 2-377 | CF₃ | H | 3-OCH₃ | 4-F | 5-CF₃ |
| 2-378 | CF₃ | H | 3-OCF₃ | 4-F | 5-CF₃ |
| 2-379 | CF₃ | H | 3-F | 4-F | 5-OCH₃ |
| 2-380 | CF₃ | H | 3-Cl | 4-F | 5-OCH₃ |
| 2-381 | CF₃ | H | 3-CN | 4-F | 5-OCH₃ |
| 2-382 | CF₃ | H | 3-CH₃ | 4-F | 5-OCH₃ |
| 2-383 | CF₃ | H | 3-CF₃ | 4-F | 5-OCH₃ |
| 2-384 | CF₃ | H | 3-OCH₃ | 4-F | 5-OCH₃ |
| 2-385 | CF₃ | H | 3-OCF₃ | 4-F | 5-OCH₃ |
| 2-386 | CF₃ | H | 3-F | 4-F | 5-OCF₃ |
| 2-387 | CF₃ | H | 3-Cl | 4-F | 5-OCF₃ |
| 2-388 | CF₃ | H | 3-CN | 4-F | 5-OCF₃ |
| 2-389 | CF₃ | H | 3-CH₃ | 4-F | 5-OCF₃ |
| 2-390 | CF₃ | H | 3-CF₃ | 4-F | 5-OCF₃ |
| 2-391 | CF₃ | H | 3-OCH₃ | 4-F | 5-OCF₃ |
| 2-392 | CF₃ | H | 3-OCF₃ | 4-F | 5-OCF₃ |
| 2-393 | CF₃ | H | 3-F | 4-Cl | 5-F |
| 2-394 | CF₃ | H | 3-Cl | 4-Cl | 5-F |
| 2-395 | CF₃ | H | 3-CN | 4-Cl | 5-F |
| 2-396 | CF₃ | H | 3-CH₃ | 4-Cl | 5-F |
| 2-397 | CF₃ | H | 3-CF₃ | 4-Cl | 5-F |
| 2-398 | CF₃ | H | 3-OCH₃ | 4-Cl | 5-F |
| 2-399 | CF₃ | H | 3-OCF₃ | 4-Cl | 5-F |
| 2-400 | CF₃ | H | 3-F | 4-Cl | 5-Cl |
| 2-401 | CF₃ | H | 3-Cl | 4-Cl | 5-Cl |
| 2-402 | CF₃ | H | 3-CN | 4-Cl | 5-Cl |
| 2-403 | CF₃ | H | 3-CH₃ | 4-Cl | 5-Cl |
| 2-404 | CF₃ | H | 3-CF₃ | 4-Cl | 5-Cl |
| 2-405 | CF₃ | H | 3-OCH₃ | 4-Cl | 5-Cl |
| 2-406 | CF₃ | H | 3-OCF₃ | 4-Cl | 5-Cl |
| 2-407 | CF₃ | H | 3-F | 4-Cl | 5-CN |
| 2-408 | CF₃ | H | 3-Cl | 4-Cl | 5-CN |
| 2-409 | CF₃ | H | 3-CN | 4-Cl | 5-CN |
| 2-410 | CF₃ | H | 3-CH₃ | 4-Cl | 5-CN |
| 2-411 | CF₃ | H | 3-CF₃ | 4-Cl | 5-CN |
| 2-412 | CF₃ | H | 3-OCH₃ | 4-Cl | 5-CN |
| 2-413 | CF₃ | H | 3-OCF₃ | 4-Cl | 5-CN |
| 2-414 | CF₃ | H | 3-F | 4-Cl | 5-CH₃ |
| 2-415 | CF₃ | H | 3-Cl | 4-Cl | 5-CH₃ |
| 2-416 | CF₃ | H | 3-CN | 4-Cl | 5-CH₃ |
| 2-417 | CF₃ | H | 3-CH₃ | 4-Cl | 5-CH₃ |
| 2-418 | CF₃ | H | 3-CF₃ | 4-Cl | 5-CH₃ |
| 2-419 | CF₃ | H | 3-OCH₃ | 4-Cl | 5-CH₃ |
| 2-420 | CF₃ | H | 3-OCF₃ | 4-Cl | 5-CH₃ |
| 2-421 | CF₃ | H | 3-F | 4-Cl | 5-CF₃ |
| 2-422 | CF₃ | H | 3-Cl | 4-Cl | 5-CF₃ |
| 2-423 | CF₃ | H | 3-CN | 4-Cl | 5-CF₃ |
| 2-424 | CF₃ | H | 3-CH₃ | 4-Cl | 5-CF₃ |
| 2-425 | CF₃ | H | 3-CF₃ | 4-Cl | 5-CF₃ |
| 2-426 | CF₃ | H | 3-OCH₃ | 4-Cl | 5-CF₃ |
| 2-427 | CF₃ | H | 3-OCF₃ | 4-Cl | 5-CF₃ |
| 2-428 | CF₃ | H | 3-F | 4-Cl | 5-OCH₃ |
| 2-429 | CF₃ | H | 3-Cl | 4-Cl | 5-OCH₃ |
| 2-430 | CF₃ | H | 3-CN | 4-Cl | 5-OCH₃ |
| 2-431 | CF₃ | H | 3-CH₃ | 4-Cl | 5-OCH₃ |
| 2-432 | CF₃ | H | 3-CF₃ | 4-Cl | 5-OCH₃ |
| 2-433 | CF₃ | H | 3-OCH₃ | 4-Cl | 5-OCH₃ |
| 2-434 | CF₃ | H | 3-OCF₃ | 4-Cl | 5-OCH₃ |
| 2-435 | CF₃ | H | 3-F | 4-Cl | 5-OCF₃ |
| 2-436 | CF₃ | H | 3-Cl | 4-Cl | 5-OCF₃ |
| 2-437 | CF₃ | H | 3-CN | 4-Cl | 5-OCF₃ |
| 2-438 | CF₃ | H | 3-CH₃ | 4-Cl | 5-OCF₃ |
| 2-439 | CF₃ | H | 3-CF₃ | 4-Cl | 5-OCF₃ |
| 2-440 | CF₃ | H | 3-OCH₃ | 4-Cl | 5-OCF₃ |
| 2-441 | CF₃ | H | 3-OCF₃ | 4-Cl | 5-OCF₃ |
| 2-442 | CF₃ | H | 3-F | 4-CN | 5-F |
| 2-443 | CF₃ | H | 3-Cl | 4-CN | 5-F |
| 2-444 | CF₃ | H | 3-CN | 4-CN | 5-F |
| 2-445 | CF₃ | H | 3-CH₃ | 4-CN | 5-F |
| 2-446 | CF₃ | H | 3-CF₃ | 4-CN | 5-F |
| 2-447 | CF₃ | H | 3-OCH₃ | 4-CN | 5-F |
| 2-448 | CF₃ | H | 3-OCF₃ | 4-CN | 5-F |
| 2-449 | CF₃ | H | 3-F | 4-CN | 5-Cl |
| 2-450 | CF₃ | H | 3-Cl | 4-CN | 5-Cl |
| 2-451 | CF₃ | H | 3-CN | 4-CN | 5-Cl |
| 2-452 | CF₃ | H | 3-CH₃ | 4-CN | 5-Cl |
| 2-453 | CF₃ | H | 3-CF₃ | 4-CN | 5-Cl |
| 2-454 | CF₃ | H | 3-OCH₃ | 4-CN | 5-Cl |
| 2-455 | CF₃ | H | 3-OCF₃ | 4-CN | 5-Cl |
| 2-456 | CF₃ | H | 3-F | 4-CN | 5-CN |
| 2-457 | CF₃ | H | 3-Cl | 4-CN | 5-CN |
| 2-458 | CF₃ | H | 3-CN | 4-CN | 5-CN |
| 2-459 | CF₃ | H | 3-CH₃ | 4-CN | 5-CN |
| 2-460 | CF₃ | H | 3-CF₃ | 4-CN | 5-CN |
| 2-461 | CF₃ | H | 3-OCH₃ | 4-CN | 5-CN |
| 2-462 | CF₃ | H | 3-OCF₃ | 4-CN | 5-CN |
| 2-463 | CF₃ | H | 3-F | 4-CN | 5-CH₃ |
| 2-464 | CF₃ | H | 3-Cl | 4-CN | 5-CH₃ |

TABLE 2-continued (Formulae Ia to Ij)

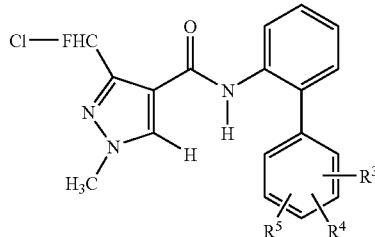

Ij

| Compound | m.p. [° C.] |
|---|---|
| Ij-344 | 154-157 |

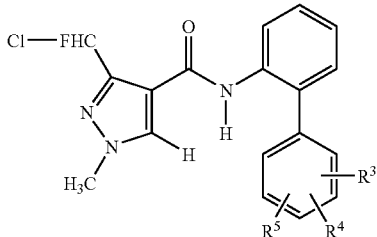

Ij

| Compound | m.p. [° C.] |
|---|---|
| Ij-344 | 154-157 |

| No. | R¹ | R² | R³ | R⁴ | R⁵ |
|---|---|---|---|---|---|
| 2-465 | CF₃ | H | 3-CN | 4-CN | 5-CH₃ |
| 2-466 | CF₃ | H | 3-CH₃ | 4-CN | 5-CH₃ |
| 2-467 | CF₃ | H | 3-CF₃ | 4-CN | 5-CH₃ |
| 2-468 | CF₃ | H | 3-OCH₃ | 4-CN | 5-CH₃ |
| 2-469 | CF₃ | H | 3-OCF₃ | 4-CN | 5-CH₃ |
| 2-470 | CF₃ | H | 3-F | 4-CN | 5-CF₃ |
| 2-471 | CF₃ | H | 3-Cl | 4-CN | 5-CF₃ |
| 2-472 | CF₃ | H | 3-CN | 4-CN | 5-CF₃ |
| 2-473 | CF₃ | H | 3-CH₃ | 4-CN | 5-CF₃ |
| 2-474 | CF₃ | H | 3-CF₃ | 4-CN | 5-CF₃ |
| 2-475 | CF₃ | H | 3-OCH₃ | 4-CN | 5-CF₃ |
| 2-576 | CF₃ | H | 3-OCF₃ | 4-CN | 5-CF₃ |
| 2-477 | CF₃ | H | 3-F | 4-CN | 5-OCH₃ |
| 2-478 | CF₃ | H | 3-Cl | 4-CN | 5-OCH₃ |
| 2-479 | CF₃ | H | 3-CN | 4-CN | 5-OCH₃ |
| 2-480 | CF₃ | H | 3-CH₃ | 4-CN | 5-OCH₃ |
| 2-481 | CF₃ | H | 3-CF₃ | 4-CN | 5-OCH₃ |
| 2-482 | CF₃ | H | 3-OCH₃ | 4-CN | 5-OCH₃ |
| 2-483 | CF₃ | H | 3-OCF₃ | 4-CN | 5-OCH₃ |
| 2-484 | CF₃ | H | 3-F | 4-CN | 5-OCF₃ |
| 2-485 | CF₃ | H | 3-Cl | 4-CN | 5-OCF₃ |
| 2-486 | CF₃ | H | 3-CN | 4-CN | 5-OCF₃ |
| 2-487 | CF₃ | H | 3-CH₃ | 4-CN | 5-OCF₃ |
| 2-488 | CF₃ | H | 3-CF₃ | 4-CN | 5-OCF₃ |
| 2-489 | CF₃ | H | 3-OCH₃ | 4-CN | 5-OCF₃ |
| 2-490 | CF₃ | H | 3-OCF₃ | 4-CN | 5-OCF₃ |
| 2-491 | CF₃ | H | 3-F | 4-CH₃ | 5-F |
| 2-492 | CF₃ | H | 3-Cl | 4-CH₃ | 5-F |
| 2-493 | CF₃ | H | 3-CN | 4-CH₃ | 5-F |
| 2-494 | CF₃ | H | 3-CH₃ | 4-CH₃ | 5-F |
| 2-495 | CF₃ | H | 3-CF₃ | 4-CH₃ | 5-F |
| 2-496 | CF₃ | H | 3-OCH₃ | 4-CH₃ | 5-F |
| 2-497 | CF₃ | H | 3-OCF₃ | 4-CH₃ | 5-F |
| 2-498 | CF₃ | H | 3-F | 4-CH₃ | 5-Cl |
| 2-499 | CF₃ | H | 3-Cl | 4-CH₃ | 5-Cl |
| 2-500 | CF₃ | H | 3-CN | 4-CH₃ | 5-Cl |
| 2-501 | CF₃ | H | 3-CH₃ | 4-CH₃ | 5-Cl |
| 2-502 | CF₃ | H | 3-CF₃ | 4-CH₃ | 5-Cl |
| 2-503 | CF₃ | H | 3-OCH₃ | 4-CH₃ | 5-Cl |
| 2-504 | CF₃ | H | 3-OCF₃ | 4-CH₃ | 5-Cl |
| 2-505 | CF₃ | H | 3-F | 4-CH₃ | 5-CN |
| 2-506 | CF₃ | H | 3-Cl | 4-CH₃ | 5-CN |
| 2-507 | CF₃ | H | 3-CN | 4-CH₃ | 5-CN |
| 2-508 | CF₃ | H | 3-CH₃ | 4-CH₃ | 5-CN |
| 2-509 | CF₃ | H | 3-CF₃ | 4-CH₃ | 5-CN |
| 2-510 | CF₃ | H | 3-OCH₃ | 4-CH₃ | 5-CN |
| 2-511 | CF₃ | H | 3-OCF₃ | 4-CH₃ | 5-CN |
| 2-512 | CF₃ | H | 3-F | 4-CH₃ | 5-CH₃ |
| 2-513 | CF₃ | H | 3-Cl | 4-CH₃ | 5-CH₃ |
| 2-514 | CF₃ | H | 3-CN | 4-CH₃ | 5-CH₃ |
| 2-515 | CF₃ | H | 3-CH₃ | 4-CH₃ | 5-CH₃ |
| 2-516 | CF₃ | H | 3-CF₃ | 4-CH₃ | 5-CH₃ |
| 2-517 | CF₃ | H | 3-OCH₃ | 4-CH₃ | 5-CH₃ |
| 2-518 | CF₃ | H | 3-OCF₃ | 4-CH₃ | 5-CH₃ |
| 2-519 | CF₃ | H | 3-F | 4-CH₃ | 5-CF₃ |
| 2-520 | CF₃ | H | 3-Cl | 4-CH₃ | 5-CF₃ |
| 2-521 | CF₃ | H | 3-CN | 4-CH₃ | 5-CF₃ |
| 2-522 | CF₃ | H | 3-CH₃ | 4-CH₃ | 5-CF₃ |
| 2-523 | CF₃ | H | 3-CF₃ | 4-CH₃ | 5-CF₃ |
| 2-524 | CF₃ | H | 3-OCH₃ | 4-CH₃ | 5-CF₃ |
| 2-525 | CF₃ | H | 3-OCF₃ | 4-CH₃ | 5-CF₃ |
| 2-526 | CF₃ | H | 3-F | 4-CH₃ | 5-OCH₃ |
| 2-527 | CF₃ | H | 3-Cl | 4-CH₃ | 5-OCH₃ |
| 2-528 | CF₃ | H | 3-CN | 4-CH₃ | 5-OCH₃ |
| 2-529 | CF₃ | H | 3-CH₃ | 4-CH₃ | 5-OCH₃ |
| 2-530 | CF₃ | H | 3-CF₃ | 4-CH₃ | 5-OCH₃ |
| 2-531 | CF₃ | H | 3-OCH₃ | 4-CH₃ | 5-OCH₃ |
| 2-532 | CF₃ | H | 3-OCF₃ | 4-CH₃ | 5-OCH₃ |
| 2-533 | CF₃ | H | 3-F | 4-CH₃ | 5-OCF₃ |
| 2-534 | CF₃ | H | 3-Cl | 4-CH₃ | 5-OCF₃ |
| 2-535 | CF₃ | H | 3-CN | 4-CH₃ | 5-OCF₃ |
| 2-536 | CF₃ | H | 3-CH₃ | 4-CH₃ | 5-OCF₃ |
| 2-537 | CF₃ | H | 3-CF₃ | 4-CH₃ | 5-OCF₃ |
| 2-538 | CF₃ | H | 3-OCH₃ | 4-CH₃ | 5-OCF₃ |
| 2-539 | CF₃ | H | 3-OCF₃ | 4-CH₃ | 5-OCF₃ |
| 2-540 | CF₃ | H | 3-F | 4-CF₃ | 5-F |
| 2-541 | CF₃ | H | 3-Cl | 4-CF₃ | 5-F |
| 2-542 | CF₃ | H | 3-CN | 4-CF₃ | 5-F |
| 2-543 | CF₃ | H | 3-CH₃ | 4-CF₃ | 5-F |
| 2-544 | CF₃ | H | 3-CF₃ | 4-CF₃ | 5-F |
| 2-545 | CF₃ | H | 3-OCH₃ | 4-CF₃ | 5-F |
| 2-546 | CF₃ | H | 3-OCF₃ | 4-CF₃ | 5-F |
| 2-547 | CF₃ | H | 3-F | 4-CF₃ | 5-Cl |
| 2-548 | CF₃ | H | 3-Cl | 4-CF₃ | 5-Cl |
| 2-549 | CF₃ | H | 3-CN | 4-CF₃ | 5-Cl |
| 2-550 | CF₃ | H | 3-CH₃ | 4-CF₃ | 5-Cl |
| 2-551 | CF₃ | H | 3-CF₃ | 4-CF₃ | 5-Cl |
| 2-552 | CF₃ | H | 3-OCH₃ | 4-CF₃ | 5-Cl |
| 2-553 | CF₃ | H | 3-OCF₃ | 4-CF₃ | 5-Cl |
| 2-554 | CF₃ | H | 3-F | 4-CF₃ | 5-CN |
| 2-555 | CF₃ | H | 3-Cl | 4-CF₃ | 5-CN |
| 2-556 | CF₃ | H | 3-CN | 4-CF₃ | 5-CN |
| 2-557 | CF₃ | H | 3-CH₃ | 4-CF₃ | 5-CN |
| 2-558 | CF₃ | H | 3-CF₃ | 4-CF₃ | 5-CN |
| 2-559 | CF₃ | H | 3-OCH₃ | 4-CF₃ | 5-CN |
| 2-560 | CF₃ | H | 3-OCF₃ | 4-CF₃ | 5-CN |
| 2-561 | CF₃ | H | 3-F | 4-CF₃ | 5-CH₃ |
| 2-562 | CF₃ | H | 3-Cl | 4-CF₃ | 5-CH₃ |
| 2-563 | CF₃ | H | 3-CN | 4-CF₃ | 5-CH₃ |
| 2-564 | CF₃ | H | 3-CH₃ | 4-CF₃ | 5-CH₃ |
| 2-565 | CF₃ | H | 3-CF₃ | 4-CF₃ | 5-CH₃ |
| 2-566 | CF₃ | H | 3-OCH₃ | 4-CF₃ | 5-CH₃ |
| 2-567 | CF₃ | H | 3-CN | 4-CF₃ | 5-CN |
| 2-568 | CF₃ | H | 3-F | 4-CF₃ | 5-CF₃ |
| 2-569 | CF₃ | H | 3-Cl | 4-CF₃ | 5-CF₃ |
| 2-570 | CF₃ | H | 3-CN | 4-CF₃ | 5-CF₃ |
| 2-571 | CF₃ | H | 3-CH₃ | 4-CF₃ | 5-CF₃ |
| 2-572 | CF₃ | H | 3-CF₃ | 4-CF₃ | 5-CF₃ |
| 2-573 | CF₃ | H | 3-OCH₃ | 4-CF₃ | 5-CF₃ |
| 2-574 | CF₃ | H | 3-OCF₃ | 4-CF₃ | 5-CF₃ |
| 2-575 | CF₃ | H | 3-F | 4-CF₃ | 5-OCH₃ |
| 2-576 | CF₃ | H | 3-Cl | 4-CF₃ | 5-OCH₃ |
| 2-577 | CF₃ | H | 3-CN | 4-CF₃ | 5-OCH₃ |
| 2-578 | CF₃ | H | 3-CH₃ | 4-CF₃ | 5-OCH₃ |
| 2-579 | CF₃ | H | 3-CF₃ | 4-CF₃ | 5-OCH₃ |
| 2-580 | CF₃ | H | 3-OCH₃ | 4-CF₃ | 5-OCH₃ |

TABLE 2-continued (Formulae Ia to Ij)

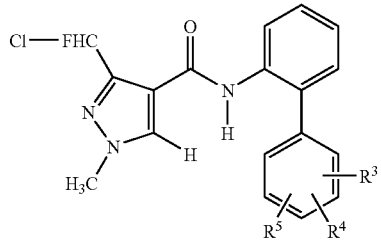

Ij

| Compound | m.p. [° C.] |
|---|---|
| Ij-344 | 154-157 |

| No. | R¹ | R² | R³ | R⁴ | R⁵ |
|---|---|---|---|---|---|
| 2-581 | CF₃ | H | 3-OCF₃ | 4-CF₃ | 5-OCH₃ |
| 2-582 | CF₃ | H | 3-F | 4-CF₃ | 5-OCF₃ |
| 2-583 | CF₃ | H | 3-Cl | 4-CF₃ | 5-OCF₃ |
| 2-584 | CF₃ | H | 3-CN | 4-CF₃ | 5-OCF₃ |
| 2-585 | CF₃ | H | 3-CH₃ | 4-CF₃ | 5-OCF₃ |
| 2-586 | CF₃ | H | 3-CF₃ | 4-CF₃ | 5-OCF₃ |
| 2-587 | CF₃ | H | 3-OCH₃ | 4-CF₃ | 5-OCF₃ |
| 2-588 | CF₃ | H | 3-OCF₃ | 4-CF₃ | 5-OCF₃ |
| 2-589 | CF₃ | H | 3-F | 4-OCH₃ | 5-F |
| 2-590 | CF₃ | H | 3-Cl | 4-OCH₃ | 5-F |
| 2-591 | CF₃ | H | 3-CN | 4-OCH₃ | 5-F |
| 2-592 | CF₃ | H | 3-CH₃ | 4-OCH₃ | 5-F |
| 2-593 | CF₃ | H | 3-CF₃ | 4-OCH₃ | 5-F |
| 2-594 | CF₃ | H | 3-OCH₃ | 4-OCH₃ | 5-F |
| 2-595 | CF₃ | H | 3-CF₃ | 4-OCH₃ | 5-F |
| 2-596 | CF₃ | H | 3-F | 4-OCH₃ | 5-Cl |
| 2-597 | CF₃ | H | 3-Cl | 4-OCH₃ | 5-Cl |
| 2-598 | CF₃ | H | 3-CN | 4-OCH₃ | 5-Cl |
| 2-599 | CF₃ | H | 3-CH₃ | 4-OCH₃ | 5-Cl |
| 2-600 | CF₃ | H | 3-CF₃ | 4-OCH₃ | 5-Cl |
| 2-601 | CF₃ | H | 3-OCH₃ | 4-OCH₃ | 5-Cl |
| 2-602 | CF₃ | H | 3-OCF₃ | 4-OCH₃ | 5-Cl |
| 2-603 | CF₃ | H | 3-F | 4-OCH₃ | 5-CN |
| 2-604 | CF₃ | H | 3-Cl | 4-OCH₃ | 5-CN |
| 2-605 | CF₃ | H | 3-CN | 4-OCH₃ | 5-CN |
| 2-606 | CF₃ | H | 3-CH₃ | 4-OCH₃ | 5-CN |
| 2-607 | CF₃ | H | 3-CF₃ | 4-OCH₃ | 5-CN |
| 2-608 | CF₃ | H | 3-OCH₃ | 4-OCH₃ | 5-CN |
| 2-609 | CF₃ | H | 3-OCF₃ | 4-OCH₃ | 5-CN |
| 2-610 | CF₃ | H | 3-F | 4-OCH₃ | 5-CH₃ |
| 2-611 | CF₃ | H | 3-Cl | 4-OCH₃ | 5-CH₃ |
| 2-612 | CF₃ | H | 3-CN | 4-OCH₃ | 5-CH₃ |
| 2-613 | CF₃ | H | 3-CH₃ | 4-OCH₃ | 5-CH₃ |
| 2-614 | CF₃ | H | 3-CF₃ | 4-OCH₃ | 5-CH₃ |
| 2-615 | CF₃ | H | 3-OCH₃ | 4-OCH₃ | 5-CH₃ |
| 2-616 | CF₃ | H | 3-OCF₃ | 4-OCH₃ | 5-CH₃ |
| 2-617 | CF₃ | H | 3-F | 4-OCH₃ | 5-CF₃ |
| 2-618 | CF₃ | H | 3-Cl | 4-OCH₃ | 5-CF₃ |
| 2-619 | CF₃ | H | 3-CN | 4-OCH₃ | 5-CF₃ |
| 2-620 | CF₃ | H | 3-CH₃ | 4-OCH₃ | 5-CF₃ |
| 2-621 | CF₃ | H | 3-CF₃ | 4-OCH₃ | 5-CF₃ |
| 2-622 | CF₃ | H | 3-OCH₃ | 4-OCH₃ | 5-CF₃ |
| 2-623 | CF₃ | H | 3-OCF₃ | 4-OCH₃ | 5-CF₃ |
| 2-624 | CF₃ | H | 3-F | 4-OCH₃ | 5-OCH₃ |
| 2-625 | CF₃ | H | 3-Cl | 4-OCH₃ | 5-OCH₃ |
| 2-626 | CF₃ | H | 3-CN | 4-OCH₃ | 5-OCH₃ |
| 2-627 | CF₃ | H | 3-CH₃ | 4-OCH₃ | 5-OCH₃ |
| 2-628 | CF₃ | H | 3-CF₃ | 4-OCH₃ | 5-OCH₃ |
| 2-629 | CF₃ | H | 3-OCH₃ | 4-OCH₃ | 5-OCH₃ |
| 2-630 | CF₃ | H | 3-OCF₃ | 4-OCH₃ | 5-OCH₃ |
| 2-631 | CF₃ | H | 3-F | 4-OCH₃ | 5-OCF₃ |
| 2-632 | CF₃ | H | 3-Cl | 4-OCH₃ | 5-OCF₃ |
| 2-633 | CF₃ | H | 3-CN | 4-OCH₃ | 5-OCF₃ |
| 2-634 | CF₃ | H | 3-CH₃ | 4-OCH₃ | 5-OCF₃ |
| 2-635 | CF₃ | H | 3-CF₃ | 4-OCH₃ | 5-OCF₃ |
| 2-636 | CF₃ | H | 3-OCH₃ | 4-OCH₃ | 5-OCF₃ |
| 2-637 | CF₃ | H | 3-OCF₃ | 4-OCH₃ | 5-OCF₃ |
| 2-638 | CF₃ | H | 3-F | 4-OCF₃ | 5-F |
| 2-639 | CF₃ | H | 3-Cl | 4-OCF₃ | 5-F |
| 2-640 | CF₃ | H | 3-CN | 4-OCF₃ | 5-F |
| 2-641 | CF₃ | H | 3-CH₃ | 4-OCF₃ | 5-F |
| 2-642 | CF₃ | H | 3-CF₃ | 4-OCF₃ | 5-F |
| 2-643 | CF₃ | H | 3-OCH₃ | 4-OCF₃ | 5-F |
| 2-644 | CF₃ | H | 3-OCF₃ | 4-OCF₃ | 5-F |
| 2-645 | CF₃ | H | 3-F | 4-OCF₃ | 5-Cl |
| 2-646 | CF₃ | H | 3-Cl | 4-OCF₃ | 5-Cl |
| 2-647 | CF₃ | H | 3-CN | 4-OCF₃ | 5-Cl |
| 2-648 | CF₃ | H | 3-CH₃ | 4-OCF₃ | 5-Cl |
| 2-649 | CF₃ | H | 3-CF₃ | 4-OCF₃ | 5-Cl |
| 2-650 | CF₃ | H | 3-OCH₃ | 4-OCF₃ | 5-Cl |
| 2-651 | CF₃ | H | 3-OCF₃ | 4-OCF₃ | 5-Cl |
| 2-652 | CF₃ | H | 3-F | 4-OCF₃ | 5-CN |
| 2-653 | CF₃ | H | 3-Cl | 4-OCF₃ | 5-CN |
| 2-654 | CF₃ | H | 3-CN | 4-OCF₃ | 5-CN |
| 2-655 | CF₃ | H | 3-CH₃ | 4-OCF₃ | 5-CN |
| 2-656 | CF₃ | H | 3-CF₃ | 4-OCF₃ | 5-CN |
| 2-657 | CF₃ | H | 3-OCH₃ | 4-OCF₃ | 5-CN |
| 2-658 | CF₃ | H | 3-OCF₃ | 4-OCF₃ | 5-CN |
| 2-659 | CF₃ | H | 3-F | 4-OCF₃ | 5-CH₃ |
| 2-660 | CF₃ | H | 3-Cl | 4-OCF₃ | 5-CH₃ |
| 2-661 | CF₃ | H | 3-CN | 4-OCF₃ | 5-CH₃ |
| 2-662 | CF₃ | H | 3-CH₃ | 4-OCF₃ | 5-CH₃ |
| 2-663 | CF₃ | H | 3-CF3 | 4-OCF₃ | 5-CH₃ |
| 2-664 | CF₃ | H | 3-OCH₃ | 4-OCF₃ | 5-CH₃ |
| 2-665 | CF₃ | H | 3-OCF₃ | 4-OCF₃ | 5-CH₃ |
| 2-666 | CF₃ | H | 3-F | 4-OCF₃ | 5-CF₃ |
| 2-667 | CF₃ | H | 3-Cl | 4-OCF₃ | 5-CF₃ |
| 2-668 | CF₃ | H | 3-CN | 4-OCF₃ | 5-CF₃ |
| 2-669 | CF₃ | H | 3-CH₃ | 4-OCF₃ | 5-CF₃ |
| 2-670 | CF₃ | H | 3-CF₃ | 4-OCF₃ | 5-CF₃ |
| 2-671 | CF₃ | H | 3-OCH₃ | 4-OCF₃ | 5-CF₃ |
| 2-672 | CF₃ | H | 3-OCF₃ | 4-OCF₃ | 5-CF₃ |
| 2-673 | CF₃ | H | 3-F | 4-OCF₃ | 5-OCH₃ |
| 2-674 | CF₃ | H | 3-Cl | 4-OCF₃ | 5-OCH₃ |
| 2-675 | CF₃ | H | 3-CN | 4-OCF₃ | 5-OCH₃ |
| 2-676 | CF₃ | H | 3-CH₃ | 4-OCF₃ | 5-OCH₃ |
| 2-677 | CF₃ | H | 3-CF₃ | 4-OCF₃ | 5-OCH₃ |
| 2-678 | CF₃ | H | 3-OCH₃ | 4-OCF₃ | 5-OCH₃ |
| 2-679 | CF₃ | H | 3-OCF₃ | 4-OCF₃ | 5-OCH₃ |
| 2-680 | CF₃ | H | 3-F | 4-OCF₃ | 5-OCF₃ |
| 2-681 | CF₃ | H | 3-Cl | 4-OCF₃ | 5-OCF₃ |
| 2-682 | CF₃ | H | 3-CN | 4-OCF₃ | 5-OCF₃ |
| 2-683 | CF₃ | H | 3-CH₃ | 4-OCF₃ | 5-OCF₃ |
| 2-684 | CF₃ | H | 3-CF₃ | 4-OCF₃ | 5-OCF₃ |
| 2-685 | CF₃ | H | 3-OCH₃ | 4-OCF₃ | 5-OCF₃ |
| 2-686 | CF₃ | H | 3-OCF₃ | 4-OCF₃ | 5-OCF₃ |
| 2-687 | CF₃ | H | 2-F | 4-F | 5-F |
| 2-688 | CF₃ | H | 2-F | 4-F | 5-Cl |
| 2-689 | CF₃ | H | 2-F | 4-F | 5-CN |
| 2-690 | CF₃ | H | 2-F | 4-F | 5-CH₃ |
| 2-691 | CF₃ | H | 2-F | 4-F | 4-CF₃ |
| 2-692 | CF₃ | H | 2-F | 4-F | 5-OCH₃ |
| 2-693 | CF₃ | H | 2-F | 4-F | 5-OCF₃ |
| 2-694 | CF₃ | H | 2-Cl | 4-F | 5-F |
| 2-695 | CF₃ | H | 2-Cl | 4-F | 5-Cl |
| 2-696 | CF₃ | H | 2-Cl | 4-F | 5-CN |

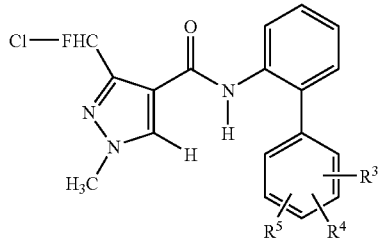

TABLE 2-continued (Formulae Ia to Ij)

Ij

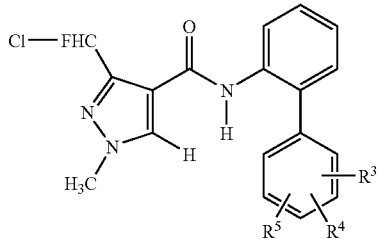

| Compound | m.p. [° C.] |
|---|---|
| Ij-344 | 154-157 |

| No. | R¹ | R² | R³ | R⁴ | R⁵ |
|---|---|---|---|---|---|
| 2-697 | CF₃ | H | 2-Cl | 4-F | 5-CH₃ |
| 2-698 | CF₃ | H | 2-Cl | 4-F | 5-CF₃ |
| 2-699 | CF₃ | H | 2-Cl | 4-F | 5-OCH₃ |
| 2-700 | CF₃ | H | 2-Cl | 4-F | 5-OCF₃ |
| 2-701 | CF₃ | H | 2-CN | 4-F | 5-F |
| 2-702 | CF₃ | H | 2-CN | 4-F | 5-Cl |
| 2-703 | CF₃ | H | 2-CN | 4-F | 5-CN |
| 2-704 | CF₃ | H | 2-CN | 4-F | 5-CH₃ |
| 2-705 | CF₃ | H | 2-CN | 4-F | 5-CF₃ |
| 2-706 | CF₃ | H | 2-CN | 4-F | 5-OCH₃ |
| 2-707 | CF₃ | H | 2-CN | 4-F | 5-OCF₃ |
| 2-708 | CF₃ | H | 2-CH₃ | 4-F | 5-F |
| 2-709 | CF₃ | H | 2-CH₃ | 4-F | 5-Cl |
| 2-710 | CF₃ | H | 2-CH₃ | 4-F | 5-CN |
| 2-711 | CF₃ | H | 2-CH₃ | 4-F | 5-CH₃ |
| 2-712 | CF₃ | H | 2-CH₃ | 4-F | 5-CF₃ |
| 2-713 | CF₃ | H | 2-CH₃ | 4-F | 5-OCH₃ |
| 2-714 | CF₃ | H | 2-CH₃ | 4-F | 5-OCF₃ |
| 2-715 | CF₃ | H | 2-CF₃ | 4-F | 5-F |
| 2-716 | CF₃ | H | 2-CF₃ | 4-F | 5-Cl |
| 2-717 | CF₃ | H | 2-CF₃ | 4-F | 5-CN |
| 2-718 | CF₃ | H | 2-CF₃ | 4-F | 5-CH₃ |
| 2-719 | CF₃ | H | 2-CF₃ | 4-F | 5-CF₃ |
| 2-720 | CF₃ | H | 2-CF₃ | 4-F | 5-OCH₃ |
| 2-721 | CF₃ | H | 2-CF₃ | 4-F | 5-OCF₃ |
| 2-722 | CF₃ | H | 2-OCH₃ | 4-F | 5-F |
| 2-723 | CF₃ | H | 2-OCH₃ | 4-F | 5-Cl |
| 2-724 | CF₃ | H | 2-OCH₃ | 4-F | 5-CN |
| 2-725 | CF₃ | H | 2-OCH₃ | 4-F | 5-CH₃ |
| 2-726 | CF₃ | H | 2-OCH₃ | 4-F | 5-CF₃ |
| 2-727 | CF₃ | H | 2-OCH₃ | 4-F | 5-OCH₃ |
| 2-728 | CF₃ | H | 2-OCH₃ | 4-F | 5-OCF₃ |
| 2-729 | CF₃ | H | 2-OCF₃ | 4-F | 5-F |
| 2-730 | CF₃ | H | 2-OCF₃ | 4-F | 5-Cl |
| 2-731 | CF₃ | H | 2-OCF₃ | 4-F | 5-CN |
| 2-732 | CF₃ | H | 2-OCF₃ | 4-F | 5-CH₃ |
| 2-733 | CF₃ | H | 2-OCF₃ | 4-F | 5-CF₃ |
| 2-734 | CF₃ | H | 2-OCF₃ | 4-F | 5-OCH₃ |
| 2-735 | CF₃ | H | 2-OCF₃ | 4-F | 5-OCF₃ |
| 2-736 | CF₃ | H | 2-F | 4-Cl | 5-F |
| 2-737 | CF₃ | H | 2-F | 4-Cl | 5-Cl |
| 2-738 | CF₃ | H | 2-F | 4-Cl | 5-CN |
| 2-739 | CF₃ | H | 2-F | 4-Cl | 5-CH₃ |
| 2-740 | CF₃ | H | 2-F | 4-Cl | 5-CF₃ |
| 2-741 | CF₃ | H | 2-F | 4-Cl | 5-OCH₃ |
| 2-742 | CF₃ | H | 2-F | 4-Cl | 5-OCF₃ |
| 2-743 | CF₃ | H | 2-Cl | 4-Cl | 5-F |
| 2-744 | CF₃ | H | 2-Cl | 4-Cl | 5-Cl |
| 2-745 | CF₃ | H | 2-Cl | 4-Cl | 5-CN |
| 2-746 | CF₃ | H | 2-Cl | 4-Cl | 5-CH₃ |
| 2-747 | CF₃ | H | 2-Cl | 4-Cl | 5-CF₃ |
| 2-748 | CF₃ | H | 2-Cl | 4-Cl | 5-OCH₃ |
| 2-749 | CF₃ | H | 2-Cl | 4-Cl | 5-OCF₃ |
| 2-750 | CF₃ | H | 2-CN | 4-Cl | 5-F |
| 2-751 | CF₃ | H | 2-CN | 4-Cl | 5-Cl |
| 2-752 | CF₃ | H | 2-CN | 4-Cl | 5-CN |
| 2-753 | CF₃ | H | 2-CN | 4-Cl | 5-CH₃ |
| 2-754 | CF₃ | H | 2-CN | 4-Cl | 5-CF₃ |
| 2-755 | CF₃ | H | 2-CN | 4-Cl | 5-OCH₃ |
| 2-756 | CF₃ | H | 2-CN | 4-Cl | 5-OCF₃ |
| 2-757 | CF₃ | H | 2-CH₃ | 4-Cl | 5-F |
| 2-758 | CF₃ | H | 2-CH₃ | 4-Cl | 5-Cl |
| 2-759 | CF₃ | H | 2-CH₃ | 4-Cl | 5-CN |
| 2-760 | CF₃ | H | 2-CH₃ | 4-Cl | 5-CH₃ |
| 2-761 | CF₃ | H | 2-CH₃ | 4-Cl | 5-CF₃ |
| 2-762 | CF₃ | H | 2-CH₃ | 4-Cl | 5-OCH₃ |
| 2-763 | CF₃ | H | 2-CH₃ | 4-Cl | 5-OCF₃ |
| 2-764 | CF₃ | H | 2-CF₃ | 4-Cl | 5-F |
| 2-765 | CF₃ | H | 2-CF₃ | 4-Cl | 5-Cl |
| 2-766 | CF₃ | H | 2-CF₃ | 4-Cl | 5-CN |
| 2-767 | CF₃ | H | 2-CF₃ | 4-Cl | 5-CH₃ |
| 2-768 | CF₃ | H | 2-CF₃ | 4-Cl | 5-CF₃ |
| 2-769 | CF₃ | H | 2-CF₃ | 4-Cl | 5-OCH₃ |
| 2-770 | CF₃ | H | 2-CF₃ | 4-Cl | 5-OCF₃ |
| 2-771 | CF₃ | H | 2-OCH₃ | 4-Cl | 5-F |
| 2-772 | CF₃ | H | 2-OCH₃ | 4-Cl | 5-Cl |
| 2-773 | CF₃ | H | 2-OCH₃ | 4-Cl | 5-CN |
| 2-774 | CF₃ | H | 2-OCH₃ | 4-Cl | 5-CH₃ |
| 2-775 | CF₃ | H | 2-OCH₃ | 4-Cl | 5-CF₃ |
| 2-776 | CF₃ | H | 2-OCH₃ | 4-Cl | 5-OCH₃ |
| 2-777 | CF₃ | H | 2-OCH₃ | 4-Cl | 5-OCF₃ |
| 2-778 | CF₃ | H | 2-OCF₃ | 4-Cl | 5-F |
| 2-779 | CF₃ | H | 2-OCF₃ | 4-Cl | 5-Cl |
| 2-780 | CF₃ | H | 2-OCF₃ | 4-Cl | 5-CN |
| 2-781 | CF₃ | H | 2-OCF₃ | 4-Cl | 5-CH₃ |
| 2-782 | CF₃ | H | 2-OCF₃ | 4-Cl | 5-CF₃ |
| 2-783 | CF₃ | H | 2-OCF₃ | 4-Cl | 5-OCH₃ |
| 2-784 | CF₃ | H | 2-OCF₃ | 4-Cl | 5-OCF₃ |
| 2-785 | CF₃ | H | 2-F | 4-CN | 5-F |
| 2-786 | CF₃ | H | 2-F | 4-CN | 5-Cl |
| 2-787 | CF₃ | H | 2-F | 4-CN | 5-CN |
| 2-788 | CF₃ | H | 2-F | 4-CN | 5-CH₃ |
| 2-789 | CF₃ | H | 2-F | 4-CN | 5-CF₃ |
| 2-790 | CF₃ | H | 2-F | 4-CN | 5-OCH₃ |
| 2-791 | CF₃ | H | 2-F | 4-CN | 5-OCF₃ |
| 2-792 | CF₃ | H | 2-Cl | 4-CN | 5-F |
| 2-793 | CF₃ | H | 2-Cl | 4-CN | 5-Cl |
| 2-794 | CF₃ | H | 2-Cl | 4-CN | 5-CN |
| 2-795 | CF₃ | H | 2-Cl | 4-CN | 5-CH₃ |
| 2-796 | CF₃ | H | 2-Cl | 4-CN | 5-CF₃ |
| 2-797 | CF₃ | H | 2-Cl | 4-CN | 5-OCH₃ |
| 2-798 | CF₃ | H | 2-Cl | 4-CN | 5-OCF₃ |
| 2-799 | CF₃ | H | 2-CN | 4-CN | 5-F |
| 2-800 | CF₃ | H | 2-CN | 4-CN | 5-Cl |
| 2-801 | CF₃ | H | 2-CN | 4-CN | 5-CN |
| 2-802 | CF₃ | H | 2-CN | 4-CN | 5-CH₃ |
| 2-803 | CF₃ | H | 2-CN | 4-CN | 5-CF₃ |
| 2-804 | CF₃ | H | 2-CN | 4-CN | 5-OCH₃ |
| 2-805 | CF₃ | H | 2-CN | 4-CN | 5-OCF₃ |
| 2-806 | CF₃ | H | 2-CH₃ | 4-CN | 5-F |
| 2-807 | CF₃ | H | 2-CH₃ | 4-CN | 5-Cl |
| 2-808 | CF₃ | H | 2-CH₃ | 4-CN | 5-CN |
| 2-809 | CF₃ | H | 2-CH₃ | 4-CN | 5-CH₃ |
| 2-810 | CF₃ | H | 2-CH₃ | 4-CN | 5-CF₃ |
| 2-811 | CF₃ | H | 2-CH₃ | 4-CN | 5-OCH₃ |
| 2-812 | CF₃ | H | 2-CH₃ | 4-CN | 5-OCF₃ |

TABLE 2-continued (Formulae Ia to Ij)

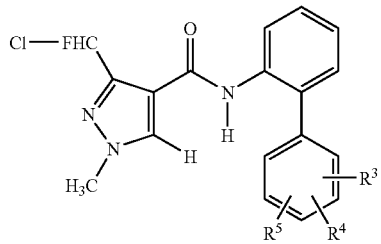

Ij

| Compound | m.p. [° C.] |
|---|---|
| Ij-344 | 154-157 |

| No. | R¹ | R² | R³ | R⁴ | R⁵ |
|---|---|---|---|---|---|
| 2-813 | CF₃ | H | 2-CF₃ | 4-CN | 5-F |
| 2-814 | CF₃ | H | 2-CF₃ | 4-CN | 5-Cl |
| 2-815 | CF₃ | H | 2-CF₃ | 4-CN | 5-CN |
| 2-816 | CF₃ | H | 2-CF₃ | 4-CN | 5-CH₃ |
| 2-817 | CF₃ | H | 2-CF₃ | 4-CN | 5-OCH₃ |
| 2-818 | CF₃ | H | 2-CF₃ | 4-CN | 5-OCH₃ |
| 2-819 | CF₃ | H | 2-CF₃ | 4-CN | 5-OCF₃ |
| 2-820 | CF₃ | H | 2-OCH₃ | 4-CN | 5-F |
| 2-821 | CF₃ | H | 2-OCH₃ | 4-CN | 5-Cl |
| 2-822 | CF₃ | H | 2-OCH₃ | 4-CN | 5-CN |
| 2-823 | CF₃ | H | 2-OCH₃ | 4-CN | 5-CH₃ |
| 2-824 | CF₃ | H | 2-OCH₃ | 4-CN | 5-CF₃ |
| 2-825 | CF₃ | H | 2-OCH₃ | 4-CN | 5-OCH₃ |
| 2-826 | CF₃ | H | 2-OCH₃ | 4-CN | 5-OCF₃ |
| 2-827 | CF₃ | H | 2-OCF₃ | 4-CN | 5-F |
| 2-828 | CF₃ | H | 2-OCF₃ | 4-CN | 5-Cl |
| 2-829 | CF₃ | H | 2-OCF₃ | 4-CN | 5-CN |
| 2-830 | CF₃ | H | 2-OCF₃ | 4-CN | 5-CH₃ |
| 2-831 | CF₃ | H | 2-OCF₃ | 4-CN | 5-CF₃ |
| 2-832 | CF₃ | H | 2-OCF₃ | 4-CN | 5-OCH₃ |
| 2-833 | CF₃ | H | 2-OCF₃ | 4-CN | 5-OCF₃ |
| 2-834 | CF₃ | H | 2-F | 4-CH₃ | 5-F |
| 2-835 | CF₃ | H | 2-F | 4-CH₃ | 5-Cl |
| 2-836 | CF₃ | H | 2-F | 4-CH₃ | 5-CN |
| 2-837 | CF₃ | H | 2-F | 4-CH₃ | 5-CH₃ |
| 2-838 | CF₃ | H | 2-F | 4-CH₃ | 5-CF₃ |
| 2-839 | CF₃ | H | 2-F | 4-CH₃ | 5-OCH₃ |
| 2-840 | CF₃ | H | 2-F | 4-CH₃ | 5-OCF₃ |
| 2-841 | CF₃ | H | 2-Cl | 4-CH₃ | 5-F |
| 2-842 | CF₃ | H | 2-Cl | 4-CH₃ | 5-Cl |
| 2-843 | CF₃ | H | 2-Cl | 4-CH₃ | 5-CN |
| 2-844 | CF₃ | H | 2-Cl | 4-CH₃ | 5-CH₃ |
| 2-845 | CF₃ | H | 2-Cl | 4-CH₃ | 5-CF₃ |
| 2-846 | CF₃ | H | 2-Cl | 4-CH₃ | 5-OCH₃ |
| 2-847 | CF₃ | H | 2-Cl | 4-CH₃ | 5-OCF₃ |
| 2-848 | CF₃ | H | 2-CN | 4-CH₃ | 5-F |
| 2-849 | CF₃ | H | 2-CN | 4-CH₃ | 5-Cl |
| 2-850 | CF₃ | H | 2-CN | 4-CH₃ | 5-CN |
| 2-851 | CF₃ | H | 2-CN | 4-CH₃ | 5-CH₃ |
| 2-852 | CF₃ | H | 2-CN | 4-CH₃ | 4-CF₃ |
| 2-853 | CF₃ | H | 2-CN | 4-CH₃ | 5-OCH₃ |
| 2-854 | CF₃ | H | 2-CN | 4-CH₃ | 5-OCF₃ |
| 2-855 | CF₃ | H | 2-CH₃ | 4-CH₃ | 5-F |
| 2-856 | CF₃ | H | 2-CH₃ | 4-CH₃ | 5-Cl |
| 2-857 | CF₃ | H | 2-CH₃ | 4-CH₃ | 5-CN |
| 2-858 | CF₃ | H | 2-CH₃ | 4-CH₃ | 5-CH₃ |
| 2-859 | CF₃ | H | 2-CH₃ | 4-CH₃ | 5-CF₃ |
| 2-860 | CF₃ | H | 2-CH₃ | 4-CH₃ | 5-OCH₃ |
| 2-861 | CF₃ | H | 2-CH₃ | 4-CH₃ | 5-OCF₃ |
| 2-862 | CF₃ | H | 2-CF₃ | 4-CH₃ | 5-F |
| 2-863 | CF₃ | H | 2-CF₃ | 4-CH₃ | 5-Cl |
| 2-864 | CF₃ | H | 2-CF₃ | 4-CH₃ | 5-CN |
| 2-865 | CF₃ | H | 2-CF₃ | 4-CH₃ | 5-CH₃ |
| 2-866 | CF₃ | H | 2-CF₃ | 4-CH₃ | 5-CF₃ |
| 2-867 | CF₃ | H | 2-CF₃ | 4-CH₃ | 5-OCH₃ |
| 2-868 | CF₃ | H | 2-CF₃ | 4-CH₃ | 5-OCF₃ |
| 2-869 | CF₃ | H | 2-OCH₃ | 4-CH₃ | 5-F |
| 2-870 | CF₃ | H | 2-OCH₃ | 4-CH₃ | 5-Cl |
| 2-871 | CF₃ | H | 2-OCH₃ | 4-CH₃ | 5-CN |
| 2-872 | CF₃ | H | 2-OCH₃ | 4-CH₃ | 5-CH₃ |
| 2-873 | CF₃ | H | 2-OCH₃ | 4-CH₃ | 5-CF₃ |
| 2-874 | CF₃ | H | 2-OCH₃ | 4-CH₃ | 5-OCH₃ |
| 2-875 | CF₃ | H | 2-OCH₃ | 4-CH₃ | 5-OCF₃ |
| 2-876 | CF₃ | H | 2-OCF₃ | 4-CH₃ | 5-F |
| 2-877 | CF₃ | H | 2-OCF₃ | 4-CH₃ | 5-Cl |
| 2-878 | CF₃ | H | 2-OCF₃ | 4-CH₃ | 5-CN |
| 2-879 | CF₃ | H | 2-OCF₃ | 4-CH₃ | 5-CH₃ |
| 2-880 | CF₃ | H | 2-OCF₃ | 4-CH₃ | 5-CF₃ |
| 2-881 | CF₃ | H | 2-OCF₃ | 4-CH₃ | 5-OCH₃ |
| 2-882 | CF₃ | H | 2-OCF₃ | 4-CH₃ | 5-OCF₃ |
| 2-883 | CF₃ | H | 2-F | 4-CF₃ | 5-F |
| 2-884 | CF₃ | H | 2-F | 4-CF₃ | 5-Cl |
| 2-885 | CF₃ | H | 2-F | 4-CF₃ | 5-CN |
| 2-886 | CF₃ | H | 2-F | 4-CF₃ | 5-CH₃ |
| 2-887 | CF₃ | H | 2-F | 4-CF₃ | 5-CF₃ |
| 2-888 | CF₃ | H | 2-F | 4-CF₃ | 5-OCH₃ |
| 2-889 | CF₃ | H | 2-F | 4-CF₃ | 5-OCF₃ |
| 2-890 | CF₃ | H | 2-Cl | 4-CF₃ | 5-F |
| 2-891 | CF₃ | H | 2-Cl | 4-CF₃ | 5-Cl |
| 2-892 | CF₃ | H | 2-Cl | 4-CF₃ | 5-CN |
| 2-893 | CF₃ | H | 2-Cl | 4-CF₃ | 5-CH₃ |
| 2-894 | CF₃ | H | 2-Cl | 4-CF₃ | 5-CF₃ |
| 2-895 | CF₃ | H | 2-Cl | 4-CF₃ | 5-OCH₃ |
| 2-896 | CF₃ | H | 2-Cl | 4-CF₃ | 5-OCF₃ |
| 2-897 | CF₃ | H | 2-CN | 4-CF₃ | 5-F |
| 2-898 | CF₃ | H | 2-CN | 4-CF₃ | 5-Cl |
| 2-899 | CF₃ | H | 2-CN | 4-CF₃ | 5-CN |
| 2-900 | CF₃ | H | 2-CN | 4-CF₃ | 5-CH₃ |
| 2-901 | CF₃ | H | 2-CN | 4-CF₃ | 5-CF₃ |
| 2-902 | CF₃ | H | 2-CN | 4-CF₃ | 5-OCH₃ |
| 2-903 | CF₃ | H | 2-CN | 4-CF₃ | 5-OCF₃ |
| 2-904 | CF₃ | H | 2-CH₃ | 4-CF₃ | 5-F |
| 2-905 | CF₃ | H | 2-CH₃ | 4-CF₃ | 5-Cl |
| 2-906 | CF₃ | H | 2-CH₃ | 4-CF₃ | 5-CN |
| 2-907 | CF₃ | H | 2-CH₃ | 4-CF₃ | 5-CH₃ |
| 2-908 | CF₃ | H | 2-CH₃ | 4-CF₃ | 5-CF₃ |
| 2-909 | CF₃ | H | 2-CH₃ | 4-CF₃ | 5-OCH₃ |
| 2-910 | CF₃ | H | 2-CH₃ | 4-CF₃ | 5-OCF₃ |
| 2-911 | CF₃ | H | 2-CF₃ | 4-CF₃ | 5-F |
| 2-912 | CF₃ | H | 2-CF₃ | 4-CF₃ | 5-Cl |
| 2-913 | CF₃ | H | 2-CF₃ | 4-CF₃ | 5-CN |
| 2-914 | CF₃ | H | 2-CF₃ | 4-CF₃ | 5-CH₃ |
| 2-915 | CF₃ | H | 2-CF₃ | 4-CF₃ | 5-CF₃ |
| 2-916 | CF₃ | H | 2-CF₃ | 4-CF₃ | 5-OCH₃ |
| 2-917 | CF₃ | H | 2-CF₃ | 4-CF₃ | 5-OCF₂ |
| 2-918 | CF₃ | H | 2-OCH₃ | 4-CF₃ | 5-F |
| 2-919 | CF₃ | H | 2-OCH₃ | 4-CF₃ | 5-Cl |
| 2-920 | CF₃ | H | 2-OCH₃ | 4-CF₃ | 5-CN |
| 2-921 | CF₃ | H | 2-OCH₃ | 4-CF₃ | 5-CH₃ |
| 2-922 | CF₃ | H | 2-OCH₃ | 4-CF₃ | 5-CF₃ |
| 2-923 | CF₃ | H | 2-OCH₃ | 4-CF₃ | 5-OCH₃ |
| 2-924 | CF₃ | H | 2-OCH₃ | 4-CF₃ | 5-OCF₃ |
| 2-925 | CF₃ | H | 2-OCF₃ | 4-CF₃ | 5-F |
| 2-926 | CF₃ | H | 2-OCF₃ | 4-CF₃ | 5-Cl |
| 2-927 | CF₃ | H | 2-OCF₃ | 4-CF₃ | 5-CN |
| 2-928 | CF₃ | H | 2-OCF₃ | 4-CF₃ | 5-CH₃ |

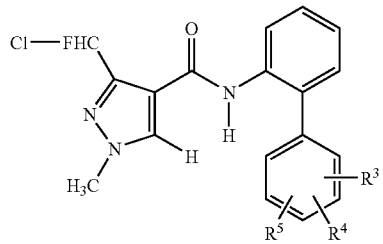

TABLE 2-continued (Formulae Ia to Ij)

Ij

| Compound | m.p. [° C.] |
|---|---|
| Ij-344 | 154-157 |

| No. | R¹ | R² | R³ | R⁴ | R⁵ |
|---|---|---|---|---|---|
| 2-929 | CF₃ | H | 2-OCF₃ | 4-CF₃ | 5-CF₃ |
| 2-930 | CF₃ | H | 2-OCF₃ | 4-CF₃ | 5-OCH₃ |
| 2-931 | CF₃ | H | 2-OCF₃ | 4-CF₃ | 5-OCF₃ |
| 2-932 | CF₃ | H | 2-F | 4-OCH₃ | 5-F |
| 2-933 | CF₃ | H | 2-F | 4-OCH₃ | 5-Cl |
| 2-934 | CF₃ | H | 2-F | 4-OCH₃ | 5-CN |
| 2-935 | CF₃ | H | 2-F | 4-OCH₃ | 5-CH₃ |
| 2-936 | CF₃ | H | 2-F | 4-OCH₃ | 5-CF₃ |
| 2-937 | CF₃ | H | 2-F | 4-OCH₃ | 5-OCH₃ |
| 2-938 | CF₃ | H | 2-F | 4-OCH₃ | 5-OCF₃ |
| 2-939 | CF₃ | H | 2-Cl | 4-OCH₃ | 5-F |
| 2-940 | CF₃ | H | 2-Cl | 4-OCH₃ | 5-Cl |
| 2-941 | CF₃ | H | 2-Cl | 4-OCH₃ | 5-CN |
| 2-942 | CF₃ | H | 2-Cl | 4-OCH₃ | 5-CH₃ |
| 2-943 | CF₃ | H | 2-Cl | 4-OCH₃ | 5-CF₃ |
| 2-944 | CF₃ | H | 2-Cl | 4-OCH₃ | 5-OCH₃ |
| 2-945 | CF₃ | H | 2-Cl | 4-OCH₃ | 5-OCF₃ |
| 2-946 | CF₃ | H | 2-CN | 4-OCH₃ | 5-F |
| 2-947 | CF₃ | H | 2-CN | 4-OCH₃ | 5-Cl |
| 2-948 | CF₃ | H | 2-CN | 4-OCH₃ | 5-CN |
| 2-949 | CF₃ | H | 2-CN | 4-OCH₃ | 5-CH₃ |
| 2-950 | CF₃ | H | 2-CN | 4-OCH₃ | 5-CF₃ |
| 2-951 | CF₃ | H | 2-CN | 4-OCH₃ | 5-OCH₃ |
| 2-952 | CF₃ | H | 2-CN | 4-OCH₃ | 5-OCF₃ |
| 2-953 | CF₃ | H | 2-CH₃ | 4-OCH₃ | 5-F |
| 2-954 | CF₃ | H | 2-CH₃ | 4-OCH₃ | 5-Cl |
| 2-955 | CF₃ | H | 2-CH₃ | 4-OCH₃ | 5-CN |
| 2-956 | CF₃ | H | 2-CH₃ | 4-OCH₃ | 5-CH₃ |
| 2-957 | CF₃ | H | 2-CH₃ | 4-OCH₃ | 5-CF₃ |
| 2-958 | CF₃ | H | 2-CH₃ | 4-OCH₃ | 5-OCH₃ |
| 2-959 | CF₃ | H | 2-CH₃ | 4-OCH₃ | 5-OCF₃ |
| 2-960 | CF₃ | H | 2-CF₃ | 4-OCH₃ | 5-F |
| 2-961 | CF₃ | H | 2-CF₃ | 4-OCH₃ | 5-Cl |
| 2-962 | CF₃ | H | 2-CF₃ | 4-OCH₃ | 5-CN |
| 2-963 | CF₃ | H | 2-CF₃ | 4-OCH₃ | 5-CH₃ |
| 2-964 | CF₃ | H | 2-CF₃ | 4-OCH₃ | 5-CF₃ |
| 2-965 | CF₃ | H | 2-CF₃ | 4-OCH₃ | 5-OCH₃ |
| 2-966 | CF₃ | H | 2-CF₃ | 4-OCH₃ | 5-OCF₃ |
| 2-967 | CF₃ | H | 2-OCH | 4-OCH₃ | 5-F |
| 2-968 | CF₃ | H | 2-OCH₃ | 4-OCH₃ | 5-Cl |
| 2-969 | CF₃ | H | 2-OCH₃ | 4-OCH₃ | 5-CN |
| 2-970 | CF₃ | H | 2-OCH₃ | 4-OCH₃ | 5-CH₃ |
| 2-971 | CF₃ | H | 2-OCH₃ | 4-OCH₃ | 5-CF₃ |
| 2-972 | CF₃ | H | 2-OCH₃ | 4-OCH₃ | 5-OCH₃ |
| 2-973 | CF₃ | H | 2-OCH₃ | 4-OCH₃ | 5-OCF₃ |
| 2-974 | CF₃ | H | 2-OCF₃ | 4-OCH₃ | 5-F |
| 2-975 | CF₃ | H | 2-OCF₃ | 4-OCH₃ | 5-Cl |
| 2-976 | CF₃ | H | 2-OCF₃ | 4-OCH₃ | 5-CN |
| 2-977 | CF₃ | H | 2-OCF₃ | 4-OCH₃ | 5-CH₃ |
| 2-978 | CF₃ | H | 2-OCF₃ | 4-OCH₃ | 5-CF₃ |
| 2-979 | CF₃ | H | 2-OCF₃ | 4-OCH₃ | 5-OCH₃ |
| 2-980 | CF₃ | H | 2-OCF₃ | 4-OCH₃ | 5-OCF₃ |
| 2-981 | CF₃ | H | 2-F | 4-OCF₃ | 5-F |
| 2-982 | CF₃ | H | 2-F | 4-OCF₃ | 5-Cl |
| 2-983 | CF₃ | H | 2-F | 4-OCF₃ | 5-CN |
| 2-984 | CF₃ | H | 2-F | 4-OCF₃ | 5-CH₃ |
| 2-985 | CF₃ | H | 2-F | 4-OCF₃ | 5-CF₃ |
| 2-986 | CF₃ | H | 2-F | 4-OCF₃ | 5-OCH₃ |
| 2-987 | CF₃ | H | 2-F | 4-OCF₃ | 5-OCF₃ |
| 2-988 | CF₃ | H | 2-Cl | 4-OCF₃ | 5-F |
| 2-989 | CF₃ | H | 2-Cl | 4-OCF₃ | 5-Cl |
| 2-990 | CF₃ | H | 2-Cl | 4-OCF₃ | 5-CN |
| 2-991 | CF₃ | H | 2-Cl | 4-OCF₃ | 5-CH₃ |
| 2-992 | CF₃ | H | 2-Cl | 4-OCF₃ | 5-CF₃ |
| 2-993 | CF₃ | H | 2-Cl | 4-OCF₃ | 5-OCH₃ |
| 2-994 | CF₃ | H | 2-Cl | 4-OCF₃ | 5-OCF₃ |
| 2-995 | CF₃ | H | 2-CN | 4-OCF₃ | 5-F |
| 2-996 | CF₃ | H | 2-CN | 4-OCF₃ | 5-Cl |
| 2-997 | CF₃ | H | 2-CN | 4-OCF₃ | 5-CN |
| 2-998 | CF₃ | H | 2-CN | 4-OCF₃ | 5-CH₃ |
| 2-999 | CF₃ | H | 2-CN | 4-OCF₃ | 5-CF₃ |
| 2-1000 | CF₃ | H | 2-CN | 4-OCF₃ | 5-OCH₃ |
| 2-1001 | CF₃ | H | 2-CN | 4-OCF₃ | 5-OCF₃ |
| 2-1002 | CF₃ | H | 2-CH₃ | 4-OCF₃ | 5-F |
| 2-1003 | CF₃ | H | 2-CH₃ | 4-OCF₃ | 5-Cl |
| 2-1004 | CF₃ | H | 2-CH₃ | 4-OCF₃ | 5-CN |
| 2-1005 | CF₃ | H | 2-CH₃ | 4-OCF₃ | 5-CH₃ |
| 2-1006 | CF₃ | H | 2-CH₃ | 4-OCF₃ | 5-CF₃ |
| 2-1007 | CF₃ | H | 2-CH₃ | 4-OCF₃ | 5-OCH₃ |
| 2-1008 | CF₃ | H | 2-CH₃ | 4-OCF₃ | 5-OCF₃ |
| 2-1009 | CF₃ | H | 2-CF₃ | 4-OCF₃ | 5-F |
| 2-1010 | CF₃ | H | 2-CF₃ | 4-OCF₃ | 5-Cl |
| 2-1011 | CF₃ | H | 2-CF₃ | 4-OCF₃ | 5-CN |
| 2-1012 | CF₃ | H | 2-CF₃ | 4-OCF₃ | 5-CH₃ |
| 2-1013 | CF₃ | H | 2-CF₃ | 4-OCF₃ | 5-CF₃ |
| 2-1014 | CF₃ | H | 2-CF₃ | 4-OCF₃ | 5-OCH₃ |
| 2-1015 | CF₃ | H | 2-CF₃ | 4-OCF₃ | 5-OCF₃ |
| 2-1016 | CF₃ | H | 2-OCH₃ | 4-OCF₃ | 5-F |
| 2-1017 | CF₃ | H | 2-OCH₃ | 4-OCF₃ | 5-Cl |
| 2-1018 | CF₃ | H | 2-OCH₃ | 4-OCF₃ | 5-CN |
| 2-1019 | CF₃ | H | 2-OCH₃ | 4-OCF₃ | 5-CH₃ |
| 2-1020 | CF₃ | H | 2-OCH₃ | 4-OCF₃ | 5-CF₃ |
| 2-1021 | CF₃ | H | 2-OCH₃ | 4-OCF₃ | 5-OCH₃ |
| 2-1022 | CF₃ | H | 2-OCH₃ | 4-OCF₃ | 5-OCF₃ |
| 2-1023 | CF₃ | H | 2-OCF₃ | 4-OCF₃ | 5-F |
| 2-1024 | CF₃ | H | 2-OCF₃ | 4-OCF₃ | 5-Cl |
| 2-1025 | CF₃ | H | 2-OCF₃ | 4-OCF₃ | 5-CN |
| 2-1026 | CF₃ | H | 2-OCF₃ | 4-OCF₃ | 5-CH₃ |
| 2-1027 | CF₃ | H | 2-OCF₃ | 4-OCF₃ | 5-CF₃ |
| 2-1028 | CF₃ | H | 2-OCF₃ | 4-OCF₃ | 5-OCH₃ |
| 2-1029 | CF₃ | H | 2-OCF₃ | 4-OCF₃ | 5-OCF₃ |

Alternatively to or in combination with at least one compound 2-1 to 2-1029, it is also possible to use at least one compound Ib-1 to Ib-1029, Ic-1 to Ic-1029, Id-1 to Id-1029, Ie-1 to Ie-1029, If-1 to If-1029, Ig-1 to Ig-1029, Ih-1 to Ih-1029 or Ij-1 to Ij-1029 in the preferred methods according to the invention for controlling phytopathogenic harmful fungi. In addition, methods according to the invention are used for preparing the inventive compositions and seed comprising at least one compound 2-1 to 2-1029.

As component A, preferred embodiments of the mixtures according to the invention comprise at least one, preferably one, compound selected from Table 3:

TABLE 3

| No. | Compound |
|---|---|
| 3-1 | N-(2'-fluoro-4'-chloro-5'-methoxybiphenyl-2-yl)-3-trifluoromethyl-1-methyl-1H-pyrazole-4-carboxamide |
| 3-2 | N-(2'-fluoro-4'-chloro-5'-methylbiphenyl-2-yl)-3-trifluoromethyl-1-methyl-1H-pyrazole-4-carboxamide |
| 3-3 | N-(3',4',5'-trifluorobiphenyl-2-yl)-3-trifluoromethyl-1-methyl-1H-pyrazole-4-carboxamide |
| 3-4 | N-(2',4',5'-trifluorobiphenyl-2-yl)-3-trifluoromethyl-1-methyl-1H-pyrazole-4-carboxamide |
| 3-5 | N-(2',4',5'-trifluorobiphenyl-2-yl)-3-trifluoromethyl-1-methyl-1H-pyrazole-4-carboxamide |
| 3-6 | N-(2'-fluoro-4'-chloro-5'-methoxybiphenyl-2-yl)-3-difluoromethyl-1-methyl-1H-pyrazole-4-carboxamide |
| 3-7 | N-(2',3',4'-trifluorobiphenyl-2-yl)-3-trifluoromethyl-1-methyl-1H-pyrazole-4-carboxamide |
| 3-8 | N-(2'-fluoro-4'-chloro-5'-methylbiphenyl-2-yl)-3-difluoromethyl-1-methyl-1H-pyrazole-4-carboxamide |
| 3-9 | N-(3',4',5'-trifluorobiphenyl-2-yl)-3-difluoromethyl-1-methyl-1H-pyrazole-4-carboxamide |
| 3-10 | N-(2',4',5'-trifluorobiphenyl-2-yl)-3-difluoromethyl-1-methyl-1H-pyrazole-4-carboxamide |
| 3-11 | N-(3',4',5'-trifluorobiphenyl-2-yl)-3-fluoromethyl-1-methyl-1H-pyrazole-4-carboxamide |
| 3-12 | N-(3',4',5'-trifluorobiphenyl-2-yl)-3-chlorodifluoromethyl-1-methyl-1H-pyrazole-4-carboxamide |
| 3-13 | N-(3',4',5'-trifluorobiphenyl-2-yl)-3-chlorofluoromethyl-1-methyl-1H-pyrazole-4-carboxamide |
| 3-14 | N-(2',3',4'-trifluorobiphenyl-2-yl)-3-fluoromethyl-1-methyl-1H-pyrazole-4-carboxamide |
| 3-15 | N-(2',4',5'-trifluorobiphenyl-2-yl)-3-fluoromethyl-1-methyl-1H-pyrazole-4-carboxamide |

The mixtures according to the invention comprise, as components B, at least one azolopyrimidinylamine of the formula II, or the latter is used in the methods according to the invention.

With a view to the intended use of the compounds of the formula II, particular preference is given to the following meanings of the substituents, in each case on their own or in combination:

Especially suitable for the mixtures according to the invention are compounds of the formula II in which $E^1$ is straight-chain or branched $C_3$-$C_{12}$-alkyl or phenyl which may be substituted by one to three halogen or $C_1$-$C_4$-alkyl groups.

In one embodiment of the compounds of the formula II, the aliphatic chains in $E^1$ and $E^2$ or in $E^1$ or $E^2$ are not substituted by $R^a$.

A preferred embodiment relates to compounds of the formula II in which $E^1$ is straight-chain or branched $C_5$-$C_{10}$-alkyl, in particular ethyl, 3,5,5-trimethylhexyl, n-heptyl, n-octyl, n-nonyl or n-decyl.

A further embodiment relates to compounds of the formula II in which $E^1$ is phenyl which is unsubstituted or substituted by one to four radicals $R^b$.

Preferred compounds of the formula II are those in which $E^1$ is a substituted phenyl group which corresponds to a group G

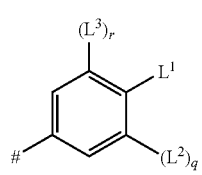

G in which $L^1$ to $L^3$ are halogen, cyano, hydroxyl, mercapto, nitro, $NR^AR^B$, $C_1$-$C_{10}$-alkyl, $C_1$-$C_6$-haloalkyl, $C_2$-$C_6$-alkenyl, $C_2$-$C_6$-alkynyl or $C_1$-$C_6$-alkoxy; r and q independently of one another may be 0 or 1 sein, where $NR^AR^B$ is as defined in formula II and # denotes the bond to the azolopyrimidine skeleton.

In a further embodiment of the compounds of the formula II, $L^1$ is halogen, cyano, hydroxyl, mercapto, nitro, $NR^AR^B$, $C_1$-$C_6$-alkyl, halomethyl and $C_1$-$C_2$-alkoxy, preferably halogen, cyano, $C_1$-$C_6$-alkyl, halomethyl or $C_1$-$C_2$-alkoxy.

In a further embodiment of the compounds of the formula II, q is 0 or $L^2$ is one of the groups mentioned above and q is 1.

In a further embodiment of the compounds of the formula II, r is 0 or $L^3$ is halogen, cyano, hydroxyl, mercapto, nitro, $NR^AR^B$, $C_1$-$C_6$-alkyl, halomethyl or $C_1$-$C_2$-alkoxy and r is 1. Preferably, r is 0.

Preference is given to compounds of the formula II in which $E^2$ is straight-chain or branched $C_1$-$C_{12}$-alkyl, $C_1$-$C_4$-alkoxy-$C_1$-$C_4$-alkyl or $C_1$-$C_4$-haloalkyl.

In a particularly preferred embodiment of the compounds of the formula II, $E^2$ is methyl, ethyl, n-propyl, n-octyl, trifluoromethyl or methoxymethyl, in particular methyl, ethyl, trifluoromethyl or methoxymethyl.

Preference is furthermore given to compounds of the formula II in which $E^3$ is hydrogen.

In a further embodiment of the compounds of the formula II, $E^3$ is amino.

One embodiment of the compounds of the formula II relates to those in which A is N. These compounds correspond to formula IIa in which the variables are as defined for formula II:

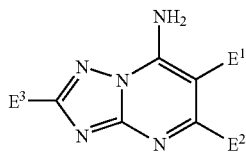

Another embodiment of the compounds of the formula II relates to those in which A is CH. These compounds correspond to formula IIb in which the variables are as defined for formula II:

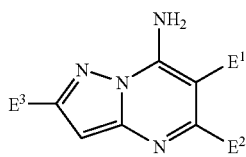

In a further embodiment of preferred compounds II, the sum of the carbon atoms in the carbon radicals of $E^1$ and $E^2$ is not more than 12.

In particular with a view to their intended use, preference is given to the compounds II compiled in the tables below. Moreover, the groups mentioned for a substituent in the tables are per se, independently of the combination in which they are mentioned, a particularly preferred embodiment of the substituent in question.

Table 4

Compounds of the formula IIa in which the combination of $E^1$, $E^2$ and $E^3$ for a compound corresponds in each case to one row of Table 6 (compounds 4a-1 to 4a-298)

Table 5

Compounds of the formula IIb in which the combination of $E^1$, $E^2$ and $E^3$ for a compound corresponds in each case to one row of Table 6 (compounds 5b-1 to 5b-298)

TABLE 6

| No. | $E^1$ | $E^2$ | $E^3$ |
|---|---|---|---|
| 6-1 | $C_6H_5$ | $CH_3$ | H |
| 6-2 | 2-Cl—$C_6H_4$ | $CH_3$ | H |
| 6-3 | 3-Cl—$C_6H_4$ | $CH_3$ | H |
| 6-4 | 4-Cl—$C_6H_4$ | $CH_3$ | H |
| 6-5 | 2-F—$C_6H_4$ | $CH_3$ | H |
| 6-6 | 3-F—$C_6H_4$ | $CH_3$ | H |
| 6-7 | 4-F—$C_6H_4$ | $CH_3$ | H |
| 6-8 | 2,4-$Cl_2$—$C_6H_3$ | $CH_3$ | H |
| 6-9 | 3,4-$Cl_2$—$C_6H_3$ | $CH_3$ | H |
| 6-10 | 2,4-$F_2$—$C_6H_3$ | $CH_3$ | H |
| 6-11 | 3,4-$F_2$—$C_6H_3$ | $CH_3$ | H |
| 6-12 | 4-$CH_3$—$C_6H_4$ | $CH_3$ | H |
| 6-13 | 4-$CH_2CH_3$—$C_6H_4$ | $CH_3$ | H |
| 6-14 | 4-$CH_2CH_2CH_3$—$C_6H_4$ | $CH_3$ | H |
| 6-15 | 4-$CH(CH_3)_2$—$C_6H_4$ | $CH_3$ | H |
| 6-16 | 4-$CH_2CH_2CH_2CH_3$—$C_6H_4$ | $CH_3$ | H |
| 6-17 | 4-$C(CH_3)CH_2CH_3$—$C_6H_4$ | $CH_3$ | H |
| 6-18 | 4-$C(CH_3)_3$—$C_6H_4$ | $CH_3$ | H |
| 6-19 | $CH_2CH_2CH_2CH_3$ | $CH_3$ | H |
| 6-20 | $CH_2CH_2CH_2CH_2CH_3$ | $CH_3$ | H |
| 6-21 | $CH_2CH_2CH_2CH_2CH_2CH_3$ | $CH_3$ | H |
| 6-22 | $CH_2CH(CH_3)CH_2CH_2CH_3$ | $CH_3$ | H |
| 6-23 | $CH_2CH(CH_2CH_3)_2$ | $CH_3$ | H |
| 6-24 | $CH_2CH_2CH_2CH_2CH_2CH_2CH_3$ | $CH_3$ | H |
| 6-25 | $CH_2CH_2CH_2CH_2CH_2CH_2CH_2CH_3$ | $CH_3$ | H |
| 6-26 | $CH_2CH_2CH_2CH_2CH_2CH_2CH_2CH_2CH_3$ | $CH_3$ | H |
| 6-27 | $CH_2CH_2CH_2CH_2CH_2CH_2CH_2CH_2CH_2CH_3$ | $CH_3$ | H |
| 6-28 | $CH_2CH_2CH(CH_3)CH_2CH(CH_3)_3$ | $CH_3$ | H |
| 6-29 | $CH_2CH_2CH_2CH_3$ | $CH_3$ | $NH_2$ |
| 6-30 | $CH_2CH_2CH_2CH_2CH_3$ | $CH_3$ | $NH_2$ |
| 6-31 | $CH_2CH_2CH_2CH_2CH_2CH_3$ | $CH_3$ | $NH_2$ |
| 6-32 | $CH_2CH(CH_3)CH_2CH_2CH_3$ | $CH_3$ | $NH_2$ |
| 6-33 | $CH_2CH(CH_2CH_3)_2$ | $CH_3$ | $NH_2$ |
| 6-34 | $CH_2CH_2CH_2CH_2CH_2CH_2CH_3$ | $CH_3$ | $NH_2$ |
| 6-35 | $CH_2CH_2CH_2CH_2CH_2CH_2CH_2CH_3$ | $CH_3$ | $NH_2$ |
| 6-36 | $CH_2CH_2CH_2CH_2CH_2CH_2CH_2CH_2CH_3$ | $CH_3$ | $NH_2$ |
| 6-37 | $CH_2CH_2CH_2CH_2CH_2CH_2CH_2CH_2CH_2CH_3$ | $CH_3$ | $NH_2$ |
| 6-38 | $CH_2CH_2CH(CH_3)CH_2CH(CH_3)_3$ | $CH_3$ | $NH_2$ |
| 6-39 | $CH_2CH_2CH_2CH_3$ | $CH_3$ | $CH_3$ |
| 6-40 | $CH_2CH_2CH_2CH_2CH_3$ | $CH_3$ | $CH_3$ |
| 6-41 | $CH_2CH_2CH_2CH_2CH_2CH_3$ | $CH_3$ | $CH_3$ |
| 6-42 | $CH_2CH(CH_3)CH_2CH_2CH_3$ | $CH_3$ | $CH_3$ |
| 6-43 | $CH_2CH(CH_2CH_3)_2$ | $CH_3$ | $CH_3$ |
| 6-44 | $CH_2CH_2CH_2CH_2CH_2CH_2CH_3$ | $CH_3$ | $CH_3$ |
| 6-45 | $CH_2CH_2CH_2CH_2CH_2CH_2CH_2CH_3$ | $CH_3$ | $CH_3$ |
| 6-46 | $CH_2CH_2CH_2CH_2CH_2CH_2CH_2CH_2CH_3$ | $CH_3$ | $CH_3$ |
| 6-47 | $CH_2CH_2CH_2CH_2CH_2CH_2CH_2CH_2CH_2CH_3$ | $CH_3$ | $CH_3$ |
| 6-48 | $CH_2CH_2CH(CH_3)CH_2CH(CH_3)_3$ | $CH_3$ | $CH_3$ |
| 6-49 | $(CH_2)_3$—O—$CH_3$ | $CH_3$ | H |
| 6-50 | $(CH_2)_3$—O—$CH_2CH_3$ | $CH_3$ | H |
| 6-51 | $(CH_2)_3$—O—$CH_2CH_2CH_3$ | $CH_3$ | H |

TABLE 6-continued

| No. | E¹ | E² | E³ |
|---|---|---|---|
| 6-52 | (CH$_2$)$_3$—O—CH$_2$CH$_2$CH$_2$CH$_3$ | CH$_3$ | H |
| 6-53 | (CH$_2$)$_3$—O—CH$_2$CH$_2$CH$_2$CH$_2$CH$_3$ | CH$_3$ | H |
| 6-54 | (CH$_2$)$_3$—O—CH$_2$CH$_2$CH$_2$CH$_2$CH$_2$CH$_3$ | CH$_3$ | H |
| 6-55 | (CH$_2$)$_3$—O—CH$_2$CH$_2$CH$_2$CH$_2$CH$_2$CH$_2$CH$_3$ | CH$_3$ | H |
| 6-56 | (CH$_2$)$_3$—O—CH$_2$CH$_2$CH$_2$CH$_2$CH$_2$CH$_2$CH$_2$CH$_3$ | CH$_3$ | H |
| 6-57 | (CH$_2$)$_3$—O—CH$_2$CH$_2$CH$_2$CH$_2$CH$_2$CH$_2$CH$_2$CH$_2$CH$_3$ | CH$_3$ | H |
| 6-58 | (CH$_2$)$_3$—O—CH(CH$_3$)$_2$ | CH$_3$ | H |
| 6-59 | (CH$_2$)$_3$—O—C(CH$_3$)$_3$ | CH$_3$ | H |
| 6-60 | (CH$_2$)$_3$—O—CH$_2$C(CH$_3$)$_3$ | CH$_3$ | H |
| 6-61 | (CH$_2$)$_3$—O—CH(CH$_3$)CH$_2$C(CH$_3$)$_3$ | CH$_3$ | H |
| 6-62 | (CH$_2$)$_3$—O—CH(CH$_2$CH$_3$)CH$_2$C(CH$_3$)$_3$ | CH$_3$ | H |
| 6-63 | (CH$_2$)$_3$—O—CH$_2$CH(CH$_3$)CH$_2$CH(CH$_3$)$_2$ | CH$_3$ | H |
| 6-64 | (CH$_2$)$_3$—O—CH$_2$CH(CH$_2$CH$_3$)CH$_2$CH$_2$CH$_3$ | CH$_3$ | H |
| 6-65 | (CH$_2$)$_3$—O—CH$_2$CH$_2$CH(CH$_3$)CH$_2$CH(CH$_3$)$_2$ | CH$_3$ | H |
| 6-66 | (CH$_2$)$_3$—O—CH$_2$CH$_2$CH(CH$_3$)CH$_2$C(CH$_3$)$_3$ | CH$_3$ | H |
| 6-67 | (CH$_2$)$_3$—O—CH$_2$CH$_2$CH(CH$_3$)CH$_2$CH$_2$CH(CH$_3$)$_2$ | CH$_3$ | H |
| 6-68 | (CH$_2$)$_3$—O—CH$_2$CH$_2$CH(CH$_3$)CH$_2$CH$_2$CH$_2$CH(CH$_3$)$_2$ | CH$_3$ | H |
| 6-69 | (CH$_2$)$_3$—O—CH$_3$ | CH$_3$ | CH$_3$ |
| 6-70 | (CH$_2$)$_3$—O—CH$_2$CH$_3$ | CH$_3$ | CH$_3$ |
| 6-71 | (CH$_2$)$_3$—O—CH$_2$CH$_2$CH$_3$ | CH$_3$ | CH$_3$ |
| 6-72 | (CH$_2$)$_3$—O—CH$_2$CH$_2$CH$_2$CH$_3$ | CH$_3$ | CH$_3$ |
| 6-73 | (CH$_2$)$_3$—O—CH$_2$CH$_2$CH$_2$CH$_2$CH$_3$ | CH$_3$ | CH$_3$ |
| 6-74 | (CH$_2$)$_3$—O—CH$_2$CH$_2$CH$_2$CH$_2$CH$_2$CH$_3$ | CH$_3$ | CH$_3$ |
| 6-75 | (CH$_2$)$_3$—O—CH$_2$CH$_2$CH$_2$CH$_2$CH$_2$CH$_2$CH$_3$ | CH$_3$ | CH$_3$ |
| 6-76 | (CH$_2$)$_3$—O—CH$_2$CH$_2$CH$_2$CH$_2$CH$_2$CH$_2$CH$_2$CH$_3$ | CH$_3$ | CH$_3$ |
| 6-77 | (CH$_2$)$_3$—O—CH$_2$CH$_2$CH$_2$CH$_2$CH$_2$CH$_2$CH$_2$CH$_2$CH$_3$ | CH$_3$ | CH$_3$ |
| 6-78 | (CH$_2$)$_3$—O—CH(CH$_3$)$_2$ | CH$_3$ | CH$_3$ |
| 6-79 | (CH$_2$)$_3$—O—C(CH$_3$)$_3$ | CH$_3$ | CH$_3$ |
| 6-80 | (CH$_2$)$_3$—O—CH$_2$C(CH$_3$)$_3$ | CH$_3$ | CH$_3$ |
| 6-81 | (CH$_2$)$_3$—O—CH(CH$_3$)CH$_2$C(CH$_3$)$_3$ | CH$_3$ | CH$_3$ |
| 6-82 | (CH$_2$)$_3$—O—CH(CH$_2$CH$_3$)CH$_2$C(CH$_3$)$_3$ | CH$_3$ | CH$_3$ |
| 6-83 | (CH$_2$)$_3$—O—CH$_2$CH(CH$_3$)CH$_2$CH(CH$_3$)$_2$ | CH$_3$ | CH$_3$ |
| 6-84 | (CH$_2$)$_3$—O—CH$_2$CH(CH$_2$CH$_3$)CH$_2$CH$_2$CH$_3$ | CH$_3$ | CH$_3$ |
| 6-85 | (CH$_2$)$_3$—O—CH$_2$CH$_2$CH(CH$_3$)CH$_2$CH(CH$_3$)$_2$ | CH$_3$ | CH$_3$ |
| 6-86 | (CH$_2$)$_3$—O—CH$_2$CH$_2$CH(CH$_3$)CH$_2$C(CH$_3$)$_3$ | CH$_3$ | CH$_3$ |
| 6-87 | (CH$_2$)$_3$—O—CH$_2$CH$_2$CH(CH$_3$)CH$_2$CH$_2$CH(CH$_3$)$_2$ | CH$_3$ | CH$_3$ |
| 6-88 | (CH$_2$)$_3$—O—CH$_2$CH$_2$CH(CH$_3$)CH$_2$CH$_2$CH$_2$CH(CH$_3$)$_2$ | CH$_3$ | CH$_3$ |
| 6-89 | CH$_2$—C$_6$H$_5$ | CF$_3$ | H |
| 6-90 | CH$_2$-(4-Cl—C$_6$H$_4$) | CF$_3$ | H |
| 6-91 | CH$_2$CH$_2$CH$_3$ | CF$_3$ | H |
| 6-92 | CH$_2$CH$_2$CH$_2$CH$_3$ | CF$_3$ | H |
| 6-93 | CH$_2$CH$_2$CH$_2$CH$_2$CH$_3$ | CF$_3$ | H |
| 6-94 | CH$_2$CH$_2$CH$_2$CH$_2$CH$_2$CH$_3$ | CF$_3$ | H |
| 6-95 | CH$_2$CH(CH$_3$)CH$_2$CH$_2$CH$_3$ | CF$_3$ | H |
| 6-96 | CH$_2$CH(CH$_2$CH$_3$)$_2$ | CF$_3$ | H |
| 6-97 | CH$_2$CH$_2$CH$_2$CH$_2$CH$_2$CH$_2$CH$_3$ | CF$_3$ | H |
| 6-98 | CH$_2$CH$_2$CH$_2$CH$_2$CH$_2$CH$_2$CH$_2$CH$_3$ | CF$_3$ | H |
| 6-99 | CH$_2$CH$_2$CH$_2$CH$_2$CH$_2$CH$_2$CH$_2$CH$_2$CH$_3$ | CF$_3$ | H |
| 6-100 | CH$_2$CH$_2$CH$_2$CH$_2$CH$_2$CH$_2$CH$_2$CH$_2$CH$_2$CH$_3$ | CF$_3$ | H |
| 6-101 | CH$_2$CH$_2$CH(CH$_3$)CH$_2$CH(CH$_3$)$_3$ | CF$_3$ | H |
| 6-102 | cyclo-C$_5$H$_9$ | CF$_3$ | H |
| 6-103 | cyclo-C$_6$H$_{11}$ | CF$_3$ | H |
| 6-104 | CH$_2$CH$_2$CH$_3$ | CH$_2$CH$_3$ | H |
| 6-105 | CH$_2$CH$_2$CH$_2$CH$_3$ | CH$_2$CH$_3$ | H |
| 6-106 | CH$_2$CH$_2$CH$_2$CH$_2$CH$_3$ | CH$_2$CH$_3$ | H |
| 6-107 | CH$_2$CH(CH$_3$)CH$_2$CH$_3$ | CH$_2$CH$_3$ | H |
| 6-108 | CH$_2$CH(CH$_2$CH$_3$)$_2$ | CH$_2$CH$_3$ | H |
| 6-109 | CH$_2$CH$_2$CH$_2$CH$_2$CH$_2$CH$_3$ | CH$_2$CH$_3$ | H |
| 6-110 | CH$_2$CH$_2$CH$_2$CH$_2$CH$_2$CH$_2$CH$_3$ | CH$_2$CH$_3$ | H |
| 6-111 | CH$_2$CH$_2$CH$_2$CH$_2$CH$_2$CH$_2$CH$_2$CH$_3$ | CH$_2$CH$_3$ | H |
| 6-112 | CH$_2$CH$_2$CH$_2$CH$_2$CH$_2$CH$_2$CH$_2$CH$_2$CH$_3$ | CH$_2$CH$_3$ | H |
| 6-113 | CH$_2$CH$_2$CH(CH$_3$)CH$_2$CH(CH$_3$)$_3$ | CH$_2$CH$_3$ | H |
| 6-114 | CH$_2$CH$_2$CH$_2$CH$_3$ | CH$_2$CH$_3$ | NH$_2$ |
| 6-115 | CH$_2$CH$_2$CH$_2$CH$_2$CH$_3$ | CH$_2$CH$_3$ | NH$_2$ |
| 6-116 | CH$_2$CH$_2$CH$_2$CH$_2$CH$_2$CH$_3$ | CH$_2$CH$_3$ | NH$_2$ |
| 6-117 | CH$_2$CH(CH$_3$)CH$_2$CH$_2$CH$_3$ | CH$_2$CH$_3$ | NH$_2$ |
| 6-118 | CH$_2$CH(CH$_2$CH$_3$)$_2$ | CH$_2$CH$_3$ | NH$_2$ |
| 6-119 | CH$_2$CH$_2$CH$_2$CH$_2$CH$_2$CH$_2$CH$_3$ | CH$_2$CH$_3$ | NH$_2$ |
| 6-120 | CH$_2$CH$_2$CH$_2$CH$_2$CH$_2$CH$_2$CH$_2$CH$_3$ | CH$_2$CH$_3$ | NH$_2$ |
| 6-121 | CH$_2$CH$_2$CH$_2$CH$_2$CH$_2$CH$_2$CH$_2$CH$_2$CH$_3$ | CH$_2$CH$_3$ | NH$_2$ |
| 6-122 | CH$_2$CH$_2$CH$_2$CH$_2$CH$_2$CH$_2$CH$_2$CH$_2$CH$_2$CH$_3$ | CH$_2$CH$_3$ | NH$_2$ |
| 6-123 | CH$_2$CH$_2$CH(CH$_3$)CH$_2$CH(CH$_3$)$_3$ | CH$_2$CH$_3$ | NH$_2$ |
| 6-124 | CH$_2$CH$_2$CH$_2$CH$_3$ | CH$_2$CH$_3$ | CH$_3$ |
| 6-125 | CH$_2$CH$_2$CH$_2$CH$_2$CH$_3$ | CH$_2$CH$_3$ | CH$_3$ |
| 6-126 | CH$_2$CH$_2$CH$_2$CH$_2$CH$_2$CH$_3$ | CH$_2$CH$_3$ | CH$_3$ |
| 6-127 | CH$_2$CH(CH$_3$)CH$_2$CH$_2$CH$_3$ | CH$_2$CH$_3$ | CH$_3$ |
| 6-128 | CH$_2$CH(CH$_2$CH$_3$)$_2$ | CH$_2$CH$_3$ | CH$_3$ |
| 6-129 | CH$_2$CH$_2$CH$_2$CH$_2$CH$_2$CH$_2$CH$_3$ | CH$_2$CH$_3$ | CH$_3$ |

TABLE 6-continued

| No. | E$^1$ | E$^2$ | E$^3$ |
|---|---|---|---|
| 6-130 | CH$_2$CH$_2$CH$_2$CH$_2$CH$_2$CH$_2$CH$_2$CH$_3$ | CH$_2$CH$_3$ | CH$_3$ |
| 6-131 | CH$_2$CH$_2$CH$_2$CH$_2$CH$_2$CH$_2$CH$_2$CH$_2$CH$_3$ | CH$_2$CH$_3$ | CH$_3$ |
| 6-132 | CH$_2$CH$_2$CH$_2$CH$_2$CH$_2$CH$_2$CH$_2$CH$_2$CH$_2$CH$_3$ | CH$_2$CH$_3$ | CH$_3$ |
| 6-133 | CH$_2$CH$_2$CH(CH$_3$)CH$_2$CH(CH$_3$)$_3$ | CH$_2$CH$_3$ | CH$_3$ |
| 6-134 | (CH$_2$)$_3$—O—CH$_3$ | CH$_2$CH$_3$ | H |
| 6-135 | (CH$_2$)$_3$—O—CH$_2$CH$_3$ | CH$_2$CH$_3$ | H |
| 6-136 | (CH$_2$)$_3$—O—CH$_2$CH$_2$CH$_3$ | CH$_2$CH$_3$ | H |
| 6-137 | (CH$_2$)$_3$—O—CH$_2$CH$_2$CH$_2$CH$_3$ | CH$_2$CH$_3$ | H |
| 6-138 | (CH$_2$)$_3$—O—CH$_2$CH$_2$CH$_2$CH$_2$CH$_3$ | CH$_2$CH$_3$ | H |
| 6-139 | (CH$_2$)$_3$—O—CH$_2$CH$_2$CH$_2$CH$_2$CH$_2$CH$_3$ | CH$_2$CH$_3$ | H |
| 6-140 | (CH$_2$)$_3$—O—CH$_2$CH$_2$CH$_2$CH$_2$CH$_2$CH$_2$CH$_3$ | CH$_2$CH$_3$ | H |
| 6-141 | (CH$_2$)$_3$—O—CH$_2$CH$_2$CH$_2$CH$_2$CH$_2$CH$_2$CH$_2$CH$_3$ | CH$_2$CH$_3$ | H |
| 6-142 | (CH$_2$)$_3$—O—CH$_2$CH$_2$CH$_2$CH$_2$CH$_2$CH$_2$CH$_2$CH$_2$CH$_3$ | CH$_2$CH$_3$ | H |
| 6-143 | (CH$_2$)$_3$—O—CH(CH$_3$)$_2$ | CH$_2$CH$_3$ | H |
| 6-144 | (CH$_2$)$_3$—O—C(CH$_3$)$_3$ | CH$_2$CH$_3$ | H |
| 6-145 | (CH$_2$)$_3$—O—CH$_2$C(CH$_3$)$_3$ | CH$_2$CH$_3$ | H |
| 6-146 | (CH$_2$)$_3$—O—CH(CH$_3$)CH$_2$C(CH$_3$)$_3$ | CH$_2$CH$_3$ | H |
| 6-147 | (CH$_2$)$_3$—O—CH(CH$_2$CH$_3$)CH$_2$C(CH$_3$)$_3$ | CH$_2$CH$_3$ | H |
| 6-148 | (CH$_2$)$_3$—O—CH$_2$CH(CH$_3$)CH$_2$CH(CH$_3$)$_2$ | CH$_2$CH$_3$ | H |
| 6-149 | (CH$_2$)$_3$—O—CH$_2$CH(CH$_2$CH$_3$)CH$_2$CH$_2$CH$_3$ | CH$_2$CH$_3$ | H |
| 6-150 | (CH$_2$)$_3$—O—CH$_2$CH$_2$CH(CH$_3$)CH$_2$CH(CH$_3$)$_2$ | CH$_2$CH$_3$ | H |
| 6-151 | (CH$_2$)$_3$—O—CH$_2$CH$_2$CH(CH$_3$)CH$_2$C(CH$_3$)$_3$ | CH$_2$CH$_3$ | H |
| 6-152 | (CH$_2$)$_3$—O—CH$_2$CH$_2$CH(CH$_3$)CH$_2$CH$_2$CH(CH$_3$)$_2$ | CH$_2$CH$_3$ | H |
| 6-153 | (CH$_2$)$_3$—O—CH$_2$CH$_2$CH(CH$_3$)CH$_2$CH$_2$CH$_2$CH(CH$_3$)$_2$ | CH$_2$CH$_3$ | H |
| 6-154 | (CH$_2$)$_3$—O—CH$_3$ | CH$_2$CH$_3$ | CH$_3$ |
| 6-155 | (CH$_2$)$_3$—O—CH$_2$CH$_3$ | CH$_2$CH$_3$ | CH$_3$ |
| 6-156 | (CH$_2$)$_3$—O—CH$_2$CH$_2$CH$_3$ | CH$_2$CH$_3$ | CH$_3$ |
| 6-157 | (CH$_2$)$_3$—O—CH$_2$CH$_2$CH$_2$CH$_3$ | CH$_2$CH$_3$ | CH$_3$ |
| 6-158 | (CH$_2$)$_3$—O—CH$_2$CH$_2$CH$_2$CH$_2$CH$_3$ | CH$_2$CH$_3$ | CH$_3$ |
| 6-159 | (CH$_2$)$_3$—O—CH$_2$CH$_2$CH$_2$CH$_2$CH$_2$CH$_3$ | CH$_2$CH$_3$ | CH$_3$ |
| 6-160 | (CH$_2$)$_3$—O—CH$_2$CH$_2$CH$_2$CH$_2$CH$_2$CH$_2$CH$_3$ | CH$_2$CH$_3$ | CH$_3$ |
| 6-161 | (CH$_2$)$_3$—O—CH$_2$CH$_2$CH$_2$CH$_2$CH$_2$CH$_2$CH$_2$CH$_3$ | CH$_2$CH$_3$ | CH$_3$ |
| 6-162 | (CH$_2$)$_3$—O—CH$_2$CH$_2$CH$_2$CH$_2$CH$_2$CH$_2$CH$_2$CH$_2$CH$_3$ | CH$_2$CH$_3$ | CH$_3$ |
| 6-163 | (CH$_2$)$_3$—O—CH(CH$_3$)$_2$ | CH$_2$CH$_3$ | CH$_3$ |
| 6-164 | (CH$_2$)$_3$—O—C(CH$_3$)$_3$ | CH$_2$CH$_3$ | CH$_3$ |
| 6-165 | (CH$_2$)$_3$—O—CH$_2$C(CH$_3$)$_3$ | CH$_2$CH$_3$ | CH$_3$ |
| 6-166 | (CH$_2$)$_3$—O—CH(CH$_3$)CH$_2$C(CH$_3$)$_3$ | CH$_2$CH$_3$ | CH$_3$ |
| 6-167 | (CH$_2$)$_3$—O—CH(CH$_2$CH$_3$)CH$_2$C(CH$_3$)$_3$ | CH$_2$CH$_3$ | CH$_3$ |
| 6-168 | (CH$_2$)$_3$—O—CH$_2$CH(CH$_3$)CH$_2$CH(CH$_3$)$_2$ | CH$_2$CH$_3$ | CH$_3$ |
| 6-169 | (CH$_2$)$_3$—O—CH$_2$CH(CH$_2$CH$_3$)CH$_2$CH$_2$CH$_3$ | CH$_2$CH$_3$ | CH$_3$ |
| 6-170 | (CH$_2$)$_3$—O—CH$_2$CH$_2$CH(CH$_3$)CH$_2$CH(CH$_3$)$_2$ | CH$_2$CH$_3$ | CH$_3$ |
| 6-171 | (CH$_2$)$_3$—O—CH$_2$CH$_2$CH(CH$_3$)CH$_2$C(CH$_3$)$_3$ | CH$_2$CH$_3$ | CH$_3$ |
| 6-172 | (CH$_2$)$_3$—O—CH$_2$CH$_2$CH(CH$_3$)CH$_2$CH$_2$CH(CH$_3$)$_2$ | CH$_2$CH$_3$ | CH$_3$ |
| 6-173 | (CH$_2$)$_3$—O—CH$_2$CH$_2$CH(CH$_3$)CH$_2$CH$_2$CH$_2$CH(CH$_3$)$_2$ | CH$_2$CH$_3$ | CH$_3$ |
| 6-174 | CH$_2$CH$_2$CH$_3$ | CH$_2$CH$_2$CH$_3$ | H |
| 6-175 | CH$_2$CH$_2$CH$_2$CH$_3$ | CH$_2$CH$_2$CH$_3$ | H |
| 6-176 | CH$_2$CH$_2$CH$_2$CH$_2$CH$_3$ | CH$_2$CH$_2$CH$_3$ | H |
| 6-177 | CH$_2$CH(CH$_3$)CH$_2$CH$_3$ | CH$_2$CH$_2$CH$_3$ | H |
| 6-178 | CH$_2$CH(CH$_2$CH$_3$)$_2$ | CH$_2$CH$_2$CH$_3$ | H |
| 6-179 | CH$_2$CH$_2$CH$_2$CH$_2$CH$_2$CH$_3$ | CH$_2$CH$_2$CH$_3$ | H |
| 6-180 | CH$_2$CH$_2$CH$_2$CH$_2$CH$_2$CH$_2$CH$_3$ | CH$_2$CH$_2$CH$_3$ | H |
| 6-181 | CH$_2$CH$_2$CH$_2$CH$_2$CH$_2$CH$_2$CH$_2$CH$_3$ | CH$_2$CH$_2$CH$_3$ | H |
| 6-182 | CH$_2$CH$_2$CH$_2$CH$_2$CH$_2$CH$_2$CH$_2$CH$_2$CH$_3$ | CH$_2$CH$_2$CH$_3$ | H |
| 6-183 | CH$_2$CH$_2$CH(CH$_3$)CH$_2$CH(CH$_3$)$_3$ | CH$_2$CH$_2$CH$_3$ | H |
| 6-184 | CH$_2$—O—CH$_2$CH$_2$CH$_3$ | CH$_2$CH$_2$CH$_3$ | H |
| 6-185 | CH$_2$—O—CH$_2$CH$_2$CH$_2$CH$_3$ | CH$_2$CH$_2$CH$_3$ | H |
| 6-186 | CH$_2$—O—CH$_2$CH$_2$CH$_2$CH$_2$CH$_3$ | CH$_2$CH$_2$CH$_3$ | H |
| 6-187 | CH$_2$—O—CH$_2$CH$_2$CH$_2$CH$_2$CH$_2$CH$_3$ | CH$_2$CH$_2$CH$_3$ | H |
| 6-188 | CH$_2$—O—CH$_2$CH$_2$CH$_2$CH$_2$CH$_2$CH$_2$CH$_3$ | CH$_2$CH$_2$CH$_3$ | H |
| 6-189 | CH$_2$—O—CH$_2$CH$_2$CH$_2$CH$_2$CH$_2$CH$_2$CH$_2$CH$_3$ | CH$_2$CH$_2$CH$_3$ | H |
| 6-190 | CH$_2$—O—C(CH$_3$)$_3$ | CH$_2$CH$_2$CH$_3$ | H |
| 6-191 | CH$_2$—O—CH$_2$C(CH$_3$)$_3$ | CH$_2$CH$_2$CH$_3$ | H |
| 6-192 | CH$_2$—O—CH(CH$_3$)CH$_2$C(CH$_3$)$_3$ | CH$_2$CH$_2$CH$_3$ | H |
| 6-193 | CH$_2$—O—CH(CH$_2$CH$_3$)CH$_2$C(CH$_3$)$_3$ | CH$_2$CH$_2$CH$_3$ | H |
| 6-194 | CH$_2$—O—CH$_2$CH(CH$_3$)CH$_2$CH(CH$_3$)$_2$ | CH$_2$CH$_2$CH$_3$ | H |
| 6-195 | CH$_2$—O—CH$_2$CH(CH$_2$CH$_3$)CH$_2$CH$_2$CH$_3$ | CH$_2$CH$_2$CH$_3$ | H |
| 6-196 | CH$_2$—O—CH$_2$CH$_2$CH(CH$_3$)CH$_2$CH(CH$_3$)$_2$ | CH$_2$CH$_2$CH$_3$ | H |
| 6-197 | CH$_2$—O—CH$_2$CH$_2$CH(CH$_3$)CH$_2$C(CH$_3$)$_3$ | CH$_2$CH$_2$CH$_3$ | H |
| 6-198 | CH$_2$—O—CH$_2$CH$_2$CH(CH$_3$)CH$_2$CH$_2$CH(CH$_3$)$_2$ | CH$_2$CH$_2$CH$_3$ | H |
| 6-199 | CH$_2$—O—CH$_2$CH$_2$CH(CH$_3$)CH$_2$CH$_2$CH$_2$CH(CH$_3$)$_2$ | CH$_2$CH$_2$CH$_3$ | H |
| 6-200 | (CH$_2$)$_2$—O—CH$_2$CH$_3$ | CH$_2$CH$_2$CH$_3$ | H |
| 6-201 | (CH$_2$)$_2$—O—CH$_2$CH$_2$CH$_3$ | CH$_2$CH$_2$CH$_3$ | H |
| 6-202 | (CH$_2$)$_2$—O—CH$_2$CH$_2$CH$_2$CH$_3$ | CH$_2$CH$_2$CH$_3$ | H |
| 6-203 | (CH$_2$)$_2$—O—CH$_2$CH$_2$CH$_2$CH$_2$CH$_3$ | CH$_2$CH$_2$CH$_3$ | H |
| 6-204 | (CH$_2$)$_2$—O—CH$_2$CH$_2$CH$_2$CH$_2$CH$_2$CH$_3$ | CH$_2$CH$_2$CH$_3$ | H |
| 6-205 | (CH$_2$)$_2$—O—CH$_2$CH$_2$CH$_2$CH$_2$CH$_2$CH$_2$CH$_3$ | CH$_2$CH$_2$CH$_3$ | H |
| 6-206 | (CH$_2$)$_2$—O—CH$_2$CH$_2$CH$_2$CH$_2$CH$_2$CH$_2$CH$_2$CH$_3$ | CH$_2$CH$_2$CH$_3$ | H |
| 6-207 | (CH$_2$)$_2$—O—CH(CH$_3$)$_2$ | CH$_2$CH$_2$CH$_3$ | H |

TABLE 6-continued

| No. | E¹ | E² | E³ |
|---|---|---|---|
| 6-208 | (CH$_2$)$_2$—O—C(CH$_3$)$_3$ | CH$_2$CH$_2$CH$_3$ | H |
| 6-209 | (CH$_2$)$_2$—O—CH$_2$C(CH$_3$)$_3$ | CH$_2$CH$_2$CH$_3$ | H |
| 6-210 | (CH$_2$)$_2$—O—CH(CH$_3$)CH$_2$C(CH$_3$)$_3$ | CH$_2$CH$_2$CH$_3$ | H |
| 6-211 | (CH$_2$)$_2$—O—CH(CH$_2$CH$_3$)CH$_2$C(CH$_3$)$_3$ | CH$_2$CH$_2$CH$_3$ | H |
| 6-212 | (CH$_2$)$_2$—O—CH$_2$CH(CH$_3$)CH$_2$CH(CH$_3$)$_2$ | CH$_2$CH$_2$CH$_3$ | H |
| 6-213 | (CH$_2$)$_2$—O—CH$_2$CH(CH$_2$CH$_3$)CH$_2$CH$_2$CH$_3$ | CH$_2$CH$_2$CH$_3$ | H |
| 6-214 | (CH$_2$)$_2$—O—CH$_2$CH$_2$CH(CH$_3$)CH$_2$CH(CH$_3$)$_2$ | CH$_2$CH$_2$CH$_3$ | H |
| 6-215 | (CH$_2$)$_2$—O—CH$_2$CH$_2$CH(CH$_3$)CH$_2$C(CH$_3$)$_3$ | CH$_2$CH$_2$CH$_3$ | H |
| 6-216 | (CH$_2$)$_2$—O—CH$_2$CH$_2$CH(CH$_3$)CH$_2$CH$_2$CH(CH$_3$)$_2$ | CH$_2$CH$_2$CH$_3$ | H |
| 6-217 | (CH$_2$)$_2$—O—CH$_2$CH$_2$CH(CH$_3$)CH$_2$CH$_2$CH$_2$CH(CH$_3$)$_2$ | CH$_2$CH$_2$CH$_3$ | H |
| 6-218 | (CH$_2$)$_3$—O—CH$_3$ | CH$_2$CH$_2$CH$_3$ | H |
| 6-219 | (CH$_2$)$_3$—O—CH$_2$CH$_3$ | CH$_2$CH$_2$CH$_3$ | H |
| 6-220 | (CH$_2$)$_3$—O—CH$_2$CH$_2$CH$_3$ | CH$_2$CH$_2$CH$_3$ | H |
| 6-221 | (CH$_2$)$_3$—O—CH$_2$CH$_2$CH$_2$CH$_3$ | CH$_2$CH$_2$CH$_3$ | H |
| 6-222 | (CH$_2$)$_3$—O—CH$_2$CH$_2$CH$_2$CH$_2$CH$_3$ | CH$_2$CH$_2$CH$_3$ | H |
| 6-223 | (CH$_2$)$_3$—O—CH$_2$CH$_2$CH$_2$CH$_2$CH$_2$CH$_3$ | CH$_2$CH$_2$CH$_3$ | H |
| 6-224 | (CH$_2$)$_3$—O—CH$_2$CH$_2$CH$_2$CH$_2$CH$_2$CH$_2$CH$_3$ | CH$_2$CH$_2$CH$_3$ | H |
| 6-225 | (CH$_2$)$_3$—O—CH$_2$CH$_2$CH$_2$CH$_2$CH$_2$CH$_2$CH$_2$CH$_3$ | CH$_2$CH$_2$CH$_3$ | H |
| 6-226 | (CH$_2$)$_3$—O—CH$_2$CH$_2$CH$_2$CH$_2$CH$_2$CH$_2$CH$_2$CH$_2$CH$_3$ | CH$_2$CH$_2$CH$_3$ | H |
| 6-227 | (CH$_2$)$_3$—O—CH(CH$_3$)$_2$ | CH$_2$CH$_2$CH$_3$ | H |
| 6-228 | (CH$_2$)$_3$—O—C(CH$_3$)$_3$ | CH$_2$CH$_2$CH$_3$ | H |
| 6-229 | (CH$_2$)$_3$—O—CH$_2$C(CH$_3$)$_3$ | CH$_2$CH$_2$CH$_3$ | H |
| 6-230 | (CH$_2$)$_3$—O—CH(CH$_3$)CH$_2$C(CH$_3$)$_3$ | CH$_2$CH$_2$CH$_3$ | H |
| 6-231 | (CH$_2$)$_3$—O—CH(CH$_2$CH$_3$)CH$_2$C(CH$_3$)$_3$ | CH$_2$CH$_2$CH$_3$ | H |
| 6-232 | (CH$_2$)$_3$—O—CH$_2$CH(CH$_3$)CH$_2$CH(CH$_3$)$_2$ | CH$_2$CH$_2$CH$_3$ | H |
| 6-233 | (CH$_2$)$_3$—O—CH$_2$CH(CH$_2$CH$_3$)CH$_2$CH$_2$CH$_3$ | CH$_2$CH$_2$CH$_3$ | H |
| 6-234 | (CH$_2$)$_3$—O—CH$_2$CH$_2$CH(CH$_3$)CH$_2$CH(CH$_3$)$_2$ | CH$_2$CH$_2$CH$_3$ | H |
| 6-235 | (CH$_2$)$_3$—O—CH$_2$CH$_2$CH(CH$_3$)CH$_2$C(CH$_3$)$_3$ | CH$_2$CH$_2$CH$_3$ | H |
| 6-236 | (CH$_2$)$_3$—O—CH$_2$CH$_2$CH(CH$_3$)CH$_2$CH$_2$CH(CH$_3$)$_2$ | CH$_2$CH$_2$CH$_3$ | H |
| 6-237 | (CH$_2$)$_3$—O—CH$_2$CH$_2$CH(CH$_3$)CH$_2$CH$_2$CH$_2$CH(CH$_3$)$_2$ | CH$_2$CH$_2$CH$_3$ | H |
| 6-238 | CH$_2$CH$_2$CH$_3$ | CH$_2$OCH$_3$ | H |
| 6-239 | CH$_2$CH$_2$CH$_2$CH$_3$ | CH$_2$OCH$_3$ | H |
| 6-240 | CH$_2$CH$_2$CH$_2$CH$_2$CH$_3$ | CH$_2$OCH$_3$ | H |
| 6-241 | CH$_2$CH$_2$CH$_2$CH$_2$CH$_2$CH$_3$ | CH$_2$OCH$_3$ | H |
| 6-242 | CH$_2$CH(CH$_3$)CH$_2$CH$_2$CH$_3$ | CH$_2$OCH$_3$ | H |
| 6-243 | CH$_2$CH(CH$_3$)$_2$ | CH$_2$OCH$_3$ | H |
| 6-244 | CH$_2$CH$_2$CH$_2$CH$_2$CH$_2$CH$_2$CH$_3$ | CH$_2$OCH$_3$ | H |
| 6-245 | CH$_2$CH$_2$CH$_2$CH$_2$CH$_2$CH$_2$CH$_2$CH$_3$ | CH$_2$OCH$_3$ | H |
| 6-246 | CH$_2$CH$_2$CH$_2$CH$_2$CH$_2$CH$_2$CH$_2$CH$_2$CH$_3$ | CH$_2$OCH$_3$ | H |
| 6-247 | CH$_2$CH$_2$CH$_2$CH$_2$CH$_2$CH$_2$CH$_2$CH$_2$CH$_2$CH$_3$ | CH$_2$OCH$_3$ | H |
| 6-248 | CH$_2$CH$_2$CH(CH$_3$)CH$_2$CH(CH$_3$)$_3$ | CH$_2$OCH$_3$ | H |
| 6-249 | (CH$_2$)$_3$—O—CH$_3$ | CH$_2$OCH$_3$ | H |
| 6-250 | (CH$_2$)$_3$—O—CH$_2$CH$_3$ | CH$_2$OCH$_3$ | H |
| 6-251 | (CH$_2$)$_3$—O—CH$_2$CH$_2$CH$_3$ | CH$_2$OCH$_3$ | H |
| 6-252 | (CH$_2$)$_3$—O—CH$_2$CH$_2$CH$_2$CH$_3$ | CH$_2$OCH$_3$ | H |
| 6-253 | (CH$_2$)$_3$—O—CH$_2$CH$_2$CH$_2$CH$_2$CH$_3$ | CH$_2$OCH$_3$ | H |
| 6-254 | (CH$_2$)$_3$—O—CH$_2$CH$_2$CH$_2$CH$_2$CH$_2$CH$_3$ | CH$_2$OCH$_3$ | H |
| 6-255 | (CH$_2$)$_3$—O—CH$_2$CH$_2$CH$_2$CH$_2$CH$_2$CH$_2$CH$_3$ | CH$_2$OCH$_3$ | H |
| 6-256 | (CH$_2$)$_3$—O—CH$_2$CH$_2$CH$_2$CH$_2$CH$_2$CH$_2$CH$_2$CH$_3$ | CH$_2$OCH$_3$ | H |
| 6-257 | (CH$_2$)$_3$—O—CH$_2$CH$_2$CH$_2$CH$_2$CH$_2$CH$_2$CH$_2$CH$_2$CH$_3$ | CH$_2$OCH$_3$ | H |
| 6-258 | (CH$_2$)$_3$—O—CH(CH$_3$)$_2$ | CH$_2$OCH$_3$ | H |
| 6-259 | (CH$_2$)$_3$—O—C(CH$_3$)$_3$ | CH$_2$OCH$_3$ | H |
| 6-260 | (CH$_2$)$_3$—O—CH$_2$C(CH$_3$)$_3$ | CH$_2$OCH$_3$ | H |
| 6-261 | (CH$_2$)$_3$—O—CH(CH$_3$)CH$_2$C(CH$_3$)$_3$ | CH$_2$OCH$_3$ | H |
| 6-262 | (CH$_2$)$_3$—O—CH(CH$_2$CH$_3$)CH$_2$C(CH$_3$)$_3$ | CH$_2$OCH$_3$ | H |
| 6-263 | (CH$_2$)$_3$—O—CH$_2$CH(CH$_3$)CH$_2$CH(CH$_3$)$_2$ | CH$_2$OCH$_3$ | H |
| 6-264 | (CH$_2$)$_3$—O—CH$_2$CH(CH$_2$CH$_3$)CH$_2$CH$_2$CH$_3$ | CH$_2$OCH$_3$ | H |
| 6-265 | (CH$_2$)$_3$—O—CH$_2$CH$_2$CH(CH$_3$)CH$_2$CH(CH$_3$)$_2$ | CH$_2$OCH$_3$ | H |
| 6-266 | (CH$_2$)$_3$—O—CH$_2$CH$_2$CH(CH$_3$)CH$_2$C(CH$_3$)$_3$ | CH$_2$OCH$_3$ | H |
| 6-267 | (CH$_2$)$_3$—O—CH$_2$CH$_2$CH(CH$_3$)CH$_2$CH$_2$CH(CH$_3$)$_2$ | CH$_2$OCH$_3$ | H |
| 6-268 | (CH$_2$)$_3$—O—CH$_2$CH$_2$CH(CH$_3$)CH$_2$CH$_2$CH$_2$CH(CH$_3$)$_2$ | CH$_2$OCH$_3$ | H |
| 6-269 | CH$_3$ | (CH$_2$)$_3$CH$_3$ | H |
| 6-270 | CH$_2$CH$_3$ | (CH$_2$)$_3$CH$_3$ | H |
| 6-271 | CH$_2$CH$_2$CH$_3$ | (CH$_2$)$_3$CH$_3$ | H |
| 6-272 | CH$_2$CH$_2$CH$_2$CH$_3$ | (CH$_2$)$_3$CH$_3$ | H |
| 6-273 | CH$_2$CH$_2$CH$_2$CH$_2$CH$_3$ | (CH$_2$)$_3$CH$_3$ | H |
| 6-274 | CH$_3$ | (CH$_2$)$_4$CH$_3$ | H |
| 6-275 | CH$_2$CH$_3$ | (CH$_2$)$_4$CH$_3$ | H |
| 6-276 | CH$_2$CH$_2$CH$_3$ | (CH$_2$)$_4$CH$_3$ | H |
| 6-277 | CH$_2$CH$_2$CH$_2$CH$_3$ | (CH$_2$)$_4$CH$_3$ | H |
| 6-278 | CH$_2$CH$_2$CH$_2$CH$_2$CH$_3$ | (CH$_2$)$_4$CH$_3$ | H |
| 6-279 | CH$_3$ | (CH$_2$)$_5$CH$_3$ | H |
| 6-280 | CH$_2$CH$_3$ | (CH$_2$)$_5$CH$_3$ | H |
| 6-281 | CH$_2$CH$_2$CH$_3$ | (CH$_2$)$_5$CH$_3$ | H |
| 6-282 | CH$_2$CH$_2$CH$_2$CH$_3$ | (CH$_2$)$_5$CH$_3$ | H |
| 6-283 | CH$_2$CH$_2$CH$_2$CH$_2$CH$_3$ | (CH$_2$)$_5$CH$_3$ | H |
| 6-284 | CH$_3$ | (CH$_2$)$_6$CH$_3$ | H |
| 6-285 | CH$_2$CH$_3$ | (CH$_2$)$_6$CH$_3$ | H |

TABLE 6-continued

| No. | E$^1$ | E$^2$ | E$^3$ |
|---|---|---|---|
| 6-286 | CH$_2$CH$_2$CH$_3$ | (CH$_2$)$_6$CH$_3$ | H |
| 6-287 | CH$_2$CH$_2$CH$_3$ | (CH$_2$)$_6$CH$_3$ | H |
| 6-288 | CH$_2$CH$_2$CH$_2$CH$_2$CH$_3$ | (CH$_2$)$_6$CH$_3$ | H |
| 6-289 | CH$_3$ | (CH$_2$)$_7$CH$_3$ | H |
| 6-290 | CH$_2$CH$_3$ | (CH$_2$)$_7$CH$_3$ | H |
| 6-291 | CH$_2$CH$_2$CH$_3$ | (CH$_2$)$_7$CH$_3$ | H |
| 6-292 | CH$_2$CH$_2$CH$_2$CH$_3$ | (CH$_2$)$_7$CH$_3$ | H |
| 6-293 | CH$_2$CH$_2$CH$_2$CH$_2$CH$_3$ | (CH$_2$)$_7$CH$_3$ | H |
| 6-294 | CH$_3$ | (CH$_2$)$_8$CH$_3$ | H |
| 6-295 | CH$_2$CH$_3$ | (CH$_2$)$_8$CH$_3$ | H |
| 6-296 | CH$_2$CH$_2$CH$_3$ | (CH$_2$)$_8$CH$_3$ | H |
| 6-297 | CH$_2$CH$_2$CH$_2$CH$_3$ | (CH$_2$)$_8$CH$_3$ | H |
| 6-298 | CH$_2$CH$_2$CH$_2$CH$_2$CH$_3$ | (CH$_2$)$_8$CH$_3$ | H |

Alternatively to or in combination with at least one compound 4a-1 to 4a-298, it is also possible to use at least one compound 5b-1 to 5b-298 in the preferred methods according to the invention for controlling phytopathogenic harmful fungi. In addition, methods according to the invention are used for preparing the inventive compositions and seed comprising at least one compound of Tables 4 or 5.

As component B, preferred embodiments of the mixtures according to the invention comprise at least one, preferably one, compound of formula II selected from Table 7:

TABLE 7

| No. | Compound |
|---|---|
| 7-1 | 6-(3,4-dichlorophenyl)-5-methyl-[1,2,4]triazolo[1,5-a]pyrimidin-7-ylamine |
| 7-2 | 6-(4-tert-butylphenyl)-5-methyl-[1,2,4]triazolo[1,5-a]pyrimidin-7-ylamine |
| 7-3 | 5-methyl-6-(3,5,5-trimethylhexyl)-[1,2,4]triazolo[1,5-a]pyrimidin-7-ylamine |
| 7-4 | 5-methyl-6-octyl-[1,2,4]triazolo[1,5-a]pyrimidin-7-ylamine |
| 7-5 | 5-ethyl-6-octyl-[1,2,4]triazolo[1,5-a]pyrimidin-2,7-diamine |
| 7-6 | 6-ethyl-5-octyl-[1,2,4]triazolo[1,5-a]pyrimidin-7-ylamine |
| 7-7 | 5-ethyl-6-octyl-[1,2,4]triazolo[1,5-a]pyrimidin-7-ylamine |
| 7-8 | 5-ethyl-6-(3,5,5-trimethylhexyl)-[1,2,4]triazolo[1,5-a]pyrimidin-7-ylamine |
| 7-9 | 6-octyl-5-propyl-[1,2,4]triazolo[1,5-a]pyrimidin-7-ylamine |
| 7-10 | 5-methoxymethyl-6-octyl-[1,2,4]triazolo[1,5-a]pyrimidin-7-ylamine |
| 7-11 | 6-octyl-5-trifluoromethyl-[1,2,4]triazolo[1,5-a]pyrimidin-7-ylamine |
| 7-12 | 5-trifluoromethyl-6-(3,5,5-trimethylhexyl)-[1,2,4]triazolo[1,5-a]pyrimidin-7-ylamine |

According to a further preferred embodiment, the mixtures according to the invention comprise, as component A, at least one compound I, selected from Table 3, and as component B at least one compound II, selected from Table 7. Preferred mixtures according to the invention comprise in each case one compound I and one compound II (binary combination) as components A and B. These binary combinations are listed in Table 8 below:

TABLE 8

| Binary combination | Compound I | Compound II |
|---|---|---|
| 8-1 | 3-1 | 7-1 |
| 8-2 | 3-1 | 7-2 |
| 8-3 | 3-1 | 7-3 |
| 8-4 | 3-1 | 7-4 |
| 8-5 | 3-1 | 7-5 |
| 8-6 | 3-1 | 7-6 |
| 8-7 | 3-1 | 7-7 |
| 8-8 | 3-1 | 7-8 |
| 8-9 | 3-1 | 7-9 |
| 8-10 | 3-1 | 7-10 |
| 8-11 | 3-1 | 7-11 |
| 8-12 | 3-1 | 7-12 |
| 8-13 | 3-2 | 7-1 |
| 8-14 | 3-2 | 7-2 |
| 8-15 | 3-2 | 7-3 |
| 8-16 | 3-2 | 7-4 |
| 8-17 | 3-2 | 7-5 |
| 8-18 | 3-2 | 7-6 |
| 8-19 | 3-2 | 7-7 |
| 8-20 | 3-2 | 7-8 |
| 8-21 | 3-2 | 7-9 |
| 8-22 | 3-2 | 7-10 |
| 8-23 | 3-2 | 7-11 |
| 8-24 | 3-2 | 7-12 |
| 8-25 | 3-3 | 7-1 |
| 8-26 | 3-3 | 7-2 |
| 8-27 | 3-3 | 7-3 |
| 8-28 | 3-3 | 7-4 |
| 8-29 | 3-3 | 7-5 |
| 8-30 | 3-3 | 7-6 |
| 8-31 | 3-3 | 7-7 |
| 8-32 | 3-3 | 7-8 |
| 8-33 | 3-3 | 7-9 |
| 8-34 | 3-3 | 7-10 |
| 8-35 | 3-3 | 7-11 |
| 8-36 | 3-3 | 7-12 |
| 8-37 | 3-4 | 7-1 |
| 8-38 | 3-4 | 7-2 |
| 8-39 | 3-4 | 7-3 |
| 8-40 | 3-4 | 7-4 |
| 8-41 | 3-4 | 7-5 |
| 8-42 | 3-4 | 7-6 |
| 8-43 | 3-4 | 7-7 |
| 8-44 | 3-4 | 7-8 |
| 8-45 | 3-4 | 7-9 |
| 8-46 | 3-4 | 7-10 |
| 8-47 | 3-4 | 7-11 |
| 8-48 | 3-4 | 7-12 |
| 8-49 | 3-5 | 7-1 |
| 8-50 | 3-5 | 7-2 |
| 8-51 | 3-5 | 7-3 |
| 8-52 | 3-5 | 7-4 |
| 8-53 | 3-5 | 7-5 |
| 8-54 | 3-5 | 7-6 |
| 8-55 | 3-5 | 7-7 |
| 8-56 | 3-5 | 7-8 |
| 8-57 | 3-5 | 7-9 |
| 8-58 | 3-5 | 7-10 |
| 8-59 | 3-5 | 7-11 |
| 8-60 | 3-5 | 7-12 |
| 8-61 | 3-6 | 7-1 |
| 8-62 | 3-6 | 7-2 |
| 8-63 | 3-6 | 7-3 |
| 8-64 | 3-6 | 7-4 |

TABLE 8-continued

| Binary combination | Compound I | Compound II |
|---|---|---|
| 8-65 | 3-6 | 7-5 |
| 8-66 | 3-6 | 7-6 |
| 8-67 | 3-6 | 7-7 |
| 8-68 | 3-6 | 7-8 |
| 8-69 | 3-6 | 7-9 |
| 8-70 | 3-6 | 7-10 |
| 8-71 | 3-6 | 7-11 |
| 8-72 | 3-6 | 7-12 |
| 8-73 | 3-7 | 7-1 |
| 8-74 | 3-7 | 7-2 |
| 8-75 | 3-7 | 7-3 |
| 8-76 | 3-7 | 7-4 |
| 8-77 | 3-7 | 7-5 |
| 8-78 | 3-7 | 7-6 |
| 8-79 | 3-7 | 7-7 |
| 8-80 | 3-7 | 7-8 |
| 8-81 | 3-7 | 7-9 |
| 8-82 | 3-7 | 7-10 |
| 8-83 | 3-7 | 7-11 |
| 8-84 | 3-7 | 7-12 |
| 8-85 | 3-8 | 7-1 |
| 8-86 | 3-8 | 7-2 |
| 8-87 | 3-8 | 7-3 |
| 8-88 | 3-8 | 7-4 |
| 8-89 | 3-8 | 7-5 |
| 8-90 | 3-8 | 7-6 |
| 8-91 | 3-8 | 7-7 |
| 8-92 | 3-8 | 7-8 |
| 8-93 | 3-8 | 7-9 |
| 8-94 | 3-8 | 7-10 |
| 8-95 | 3-8 | 7-11 |
| 8-96 | 3-8 | 7-12 |
| 8-97 | 3-9 | 7-1 |
| 8-98 | 3-9 | 7-2 |
| 8-99 | 3-9 | 7-3 |
| 8-100 | 3-9 | 7-4 |
| 8-101 | 3-9 | 7-5 |
| 8-102 | 3-9 | 7-6 |
| 8-103 | 3-9 | 7-7 |
| 8-104 | 3-9 | 7-8 |
| 8-105 | 3-9 | 7-9 |
| 8-106 | 3-9 | 7-10 |
| 8-107 | 3-9 | 7-11 |
| 8-108 | 3-9 | 7-12 |
| 8-109 | 3-10 | 7-1 |
| 8-110 | 3-10 | 7-2 |
| 8-111 | 3-10 | 7-3 |
| 8-112 | 3-10 | 7-4 |
| 8-113 | 3-10 | 7-5 |
| 8-114 | 3-10 | 7-6 |
| 8-115 | 3-10 | 7-7 |
| 8-116 | 3-10 | 7-8 |
| 8-117 | 3-10 | 7-9 |
| 8-118 | 3-10 | 7-10 |
| 8-119 | 3-10 | 7-11 |
| 8-120 | 3-10 | 7-12 |
| 8-121 | 3-11 | 7-1 |
| 8-122 | 3-11 | 7-2 |
| 8-123 | 3-11 | 7-3 |
| 8-124 | 3-11 | 7-4 |
| 8-125 | 3-11 | 7-5 |
| 8-126 | 3-11 | 7-6 |
| 8-127 | 3-11 | 7-7 |
| 8-128 | 3-11 | 7-8 |
| 8-129 | 3-11 | 7-9 |
| 8-130 | 3-11 | 7-10 |
| 8-131 | 3-11 | 7-11 |
| 8-132 | 3-11 | 7-12 |
| 8-133 | 3-12 | 7-1 |
| 8-134 | 3-12 | 7-2 |
| 8-135 | 3-12 | 7-3 |
| 8-136 | 3-12 | 7-4 |
| 8-137 | 3-12 | 7-5 |
| 8-138 | 3-12 | 7-6 |
| 8-139 | 3-12 | 7-7 |
| 8-140 | 3-12 | 7-8 |
| 8-141 | 3-12 | 7-9 |
| 8-142 | 3-12 | 7-10 |
| 8-143 | 3-12 | 7-11 |
| 8-144 | 3-12 | 7-12 |
| 8-145 | 3-13 | 7-1 |
| 8-146 | 3-13 | 7-2 |
| 8-147 | 3-13 | 7-3 |
| 8-148 | 3-13 | 7-4 |
| 8-149 | 3-13 | 7-5 |
| 8-150 | 3-13 | 7-6 |
| 8-151 | 3-13 | 7-7 |
| 8-152 | 3-13 | 7-8 |
| 8-153 | 3-13 | 7-9 |
| 8-154 | 3-13 | 7-10 |
| 8-155 | 3-13 | 7-11 |
| 8-156 | 3-13 | 7-12 |
| 8-157 | 3-14 | 7-1 |
| 8-158 | 3-14 | 7-2 |
| 8-159 | 3-14 | 7-3 |
| 8-160 | 3-14 | 7-4 |
| 8-161 | 3-14 | 7-5 |
| 8-162 | 3-14 | 7-6 |
| 8-163 | 3-14 | 7-7 |
| 8-164 | 3-14 | 7-8 |
| 8-165 | 3-14 | 7-9 |
| 8-166 | 3-14 | 7-10 |
| 8-167 | 3-14 | 7-11 |
| 8-168 | 3-14 | 7-12 |
| 8-169 | 3-15 | 7-1 |
| 8-170 | 3-15 | 7-2 |
| 8-171 | 3-15 | 7-3 |
| 8-172 | 3-15 | 7-4 |
| 8-173 | 3-15 | 7-5 |
| 8-174 | 3-15 | 7-6 |
| 8-175 | 3-15 | 7-7 |
| 8-176 | 3-15 | 7-8 |
| 8-177 | 3-15 | 7-9 |
| 8-178 | 3-15 | 7-10 |
| 8-179 | 3-15 | 7-11 |
| 8-180 | 3-15 | 7-12 |

In combination with at least one binary combination 8-1 to 8-180, it is also possibly to use at least one further active component C, selected from Table 9, in the preferred methods according to the invention for controlling phytopathogenic harmful fungi. In addition, methods according to the invention are used for preparing the inventive compositions and seed comprising at least one binary combination 8-1 to 8-180 and, as further active component C, at least one further active compound from Table 9.

According to a further preferred embodiment, the mixtures according to the invention comprise, as component A, at least one compound I, selected from Table 3, and as component B at least one compound II, selected from Table 7, and as further active component C at least one further active compound from Table 9.

TABLE 9

| Group of active compounds | Examples |
|---|---|
| azoles | bitertanol, bromuconazole, cyproconazole, difenoconazole, diniconazole, enilconazole, epoxiconazole, fluquinconazole, fenbuconazole, flusilazole, flutriafol, hexaconazole, imibenconazole, ipconazole, metconazole, myclobutanil, penconazole, propiconazole, prothioconazole, simeconazole, triadimefon, triadimenol, tebuconazole, tetraconazole, triticonazole, prochloraz, pefurazoate, imazalil, triflumizole, cyazofamid, benomyl, carbendazim, thiabendazole, fuberidazole, ethaboxam, etridiazole, hymexazole |
| strobilurins | azoxystrobin, dimoxystrobin, enestroburin, fluoxastrobin, kresoxim-methyl, metominostrobin, orysastrobin, picoxystrobin, pyraclostrobin, trifloxystrobin, or methyl (2-chloro-5-[1-(3-methylbenzyloxyimino)ethyl]benzyl)carbamate, methyl (2-chloro-5-[1-(6-methylpyridin-2-ylmethoxyimino)ethyl]benzyl)carbamate, methyl 2-(ortho-((2,5-dimethylphenyloxymethylene)phenyl)-3-methoxyacrylate |
| carboxamides | carboxin, benalaxyl, boscalid, fenhexamid, flutolanil, furametpyr, mepronil, metalaxyl, mefenoxam, ofurace, oxadixyl, oxycarboxin, penthiopyrad, thifluzamide, tiadinil, N-(4'-bromobiphenyl-2-yl)-4-difluoromethyl-2-methylthiazole-5-carboxamide, N-(4'-trifluoromethylbiphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide, N-(3',4'-dichloro-4-fluorobiphenyl-2-yl)-3-difluoromethyl-1-methyl-pyrazol-4-carboxamide, N-(3',4'-dichloro-5-fluorobiphenyl-2-yl)-3-difluoromethyl-1-methylpyrazole-4-carboxamide, 3,4-dichloro-N-(2-cyanophenyl)isothiazole-5-carboxamide, dimethomorph, flumorph, flumetover, fluopicolide (picobenzamide), zoxamide, carpropamid, diclocymet, mandipropamid, N-(2-{4-[3-(4-chlorophenyl)prop-2-ynyloxy]-3-methoxyphenyl}ethyl)-2-methanesulfonylamino-3-methylbutyramide, N-(2-{4-[3-(4-chlorophenyl)-prop-2-ynyloxy]-3-methoxyphenyl}ethyl)-2-ethanesulfonylamino-3-methylbutyramide |
| heterocyclic compound | fluazinam, pyrifenox, bupirimate, cyprodinii, fenarimol, ferimzone, mepanipyrim, nuarimol, pyrimethanil, triforine, fenpiclonil, fludioxonil, aldimorph, dodemorph, fenpropimorph, tridemorph, fenpropidin, iprodione, procymidone, vinclozolin, famoxadone, fenamidone, octhilinone, probenazole, amisulbrom, anilazine, diclomezine, pyroquilon, proquinazid, tricyclazole, 5-chloro-7-(4-methylpiperidin-1-yl)-6-(2,4,6-trifluorophenyl)-[1,2,4]triazolo[1,5-a]pyrimidine [AC1]; 2-butoxy-6-iodo-3-propylchromen-4-on, acibenzolar-S-methyl, captafol, captan, dazomet, folpet, fenoxanil, quinoxyfen, 3-[5-(4-chlorophenyl)-2,3-dimethylisoxazolidin-3-yl]pyridine |
| carbamates | mancozeb, maneb, metam, metiram, ferbam, propieb, thiram, zineb, ziram, diethofencarb, iprovalicarb, flubenthiavalicarb, propamocarb, methyl 3-(4-chlorophenyl)-3-(2-isopropoxycarbonylamino-3-methylbutyrylamino)propanate |
| other active compounds | guanidines: dodine, iminoctadine, guazatine antibiotics: kasugamycin streptomycin, polyoxins, validamycin A; nitrophenyl derivatives: binapacryl, dinocap, dinobuton, sulfur-containing heterocyclyl compounds: dithianon, isoprothiolane; organometal compounds: fentin salts, such as fentin acetate; organophosphorus compounds: edifenphos, iprobenfos, fosetyl, fosetyl-aluminum, phosphorous acid and its salts, pyrazophos, tolclofosmethyl; organochlorine compounds: chlorothalonil, dichlofluanid, flusulfamide, hexachlorobenzene, phthalide, pencycuron, quintozene, thiophanate-methyl, tolylfluanide; inorganic active compounds: sulfur or Cu salts, such as Bordeaux liquor, copper acetate, copper hydroxide, copper oxychloride or basic copper sulfate; growth-retarding substances: prohexadione and its salts, trinexapac-ethyl, chlormequat, mepiquat-chloride and diflufenzopyr; others: cyflufenamide, cymoxanil, dimethirimol, ethirimol, furalaxyl, metrafenone and spiroxamine, N-(cyclopropylmethoxyimino-(6-difluoromethoxy-2,3-difluorophenyl)methyl)-2-phenylacetamide, N'-(4-(4-chloro-3-trifluoromethylphenoxy)-2,5-dimethylphenyl)-N-ethyl-N-methyl formamidine, N'-(4-(4-fluoro-3-trifluoromethylphenoxy)-2,5-dimethylphenyl)-N-ethyl-N-methyl formamidine, N'-(2-methyl-5- |

TABLE 9-continued

| Group of active compounds | Examples |
|---|---|
| | trifluoromethyl-4-(3-trimethylsilanylpropoxy)phenyl)-N-ethyl-N-methyl formamidine and N'-(5-difluoromethyl-2-methyl-4-(3-trimethylsilanylpropoxy)phenyl)-N-ethyl-N-methyl formamidine; |
| organophosphates | acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon; |
| carbamates (II) | alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate; |
| pyrethroids | allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin; |
| arthropod growth regulators | a) chitin synthesis inhibitors: benzoylureas: chlorfluazuron, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) edysis antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat; |
| neonicotinoids | clothianidin, dinotefuran, imidacloprid, thiamethoxam, nitenpyram, acetamiprid, thiacloprid; the thozole derivative of the formula I'$^1$ |

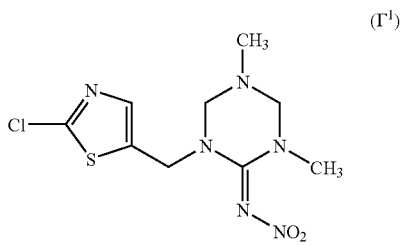

(I'$^1$)

| various | acetoprole, endosulfan, ethiprole, fipronil, vaniliprole, pyrafluprole, pyriprole, 5-amino-1-(2,6-dichloro-4-trifluoromethyl-phenyl)-4-trifluoromethanesulfinyl-1H-pyrazole-3-carbothion-amide; abamectin, emamectin, milbemectin, lepimectin, spinosad; fenazaquin, pyridaben, tebufenpyrad, tolfenpyrad, flufenerim; acequinocyl, fluacyprim, hydramethylnon; chlorfenapyr; cyhexatin, diafenthiuron, fenbutatin oxide, propargite; cyromazine; piperonyl butoxide; indoxacarb, metaflumizone, benclothiaz, bifenazate, cartap, flonicamid, pyridalyl, pymetrozine, sulfur, thiocyclam, flubendiamide, cyenopyrafen, flupyrazofos, cyflumetofen, amidoflumet, anthranilamides of the formula I'$^2$ |
|---|---|

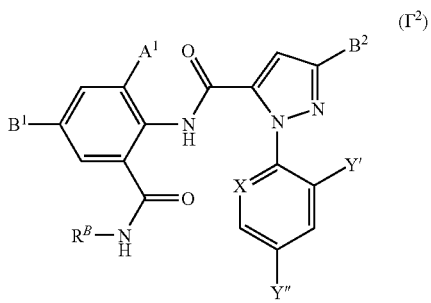

(I'$^2$)

TABLE 9-continued

| Group of active compounds | Examples |
|---|---|
| | in which $A^1$ is $CH_3$, Cl, Br, I; X is C—H, C—Cl, C—F or N; Y' is F, Cl or Br; Y" is hydrogen, F, Cl, $CF_3$; $B^1$ is hydrogen, Cl, Br, I, CN; $B^2$ is Cl, Br, $CF_3$, $OCH_2CF_3$, $OCF_2H$ and $R^B$ is hydrogen, $CH_3$ or $CH(CH_3)_2$;<br>$CF_2HCF_2CF_2CF_2CH_2C(CN)_2CH_2CH_2CF_3$;<br>$CF_3(CH_2)_2C(CN)_2CH_2(CF_2)_5CF_2H$;<br>$CF_3(CH_2)_2C(CN)_2(CH_2)_2C(CF_3)_2F$;<br>$CF_3(CH_2)_2C(CN)_2(CH_2)_2(CF_2)_3CF_3$;<br>$CF_2H(CF_2)_3CH_2C(CN)_2CH_2(CF_2)_3CF_2H$;<br>$CF_3(CH_2)_2C(CN)_2CH_2(CF_2)_3CF_3$;<br>$CF_3(CF_2)_2CH_2C(CN)_2CH_2(CF_2)_3CF_2H$; and<br>$CF_3CF_2CH_2C(CN)_2CH_2(CF_2)_3CF_2H$ |

Suitable phosphorous acid salts are, for example, Mn, Zn, Fe, Cu or $NH_4$ salts. The salts can be present as phosphites or hydrogen phosphites or as hydrates thereof.

Ternary mixtures according to the invention comprise in each case one compound I (as component A), one compound II (as component B) and a further component C. In one embodiment the ternary mixtures according to the invention comprise a fungicidal active compound as component C. In another embodiment they comprise an active compound against animal pests as component C. A number of ternary combinations are listed in Table 10 below:

TABLE 10

| No. | Binary combination | Active compound |
|---|---|---|
| 10-1 | 8-1 | epoxiconazole |
| 10-2 | 8-2 | epoxiconazole |
| 10-3 | 8-3 | epoxiconazole |
| 10-4 | 8-4 | epoxiconazole |
| 10-5 | 8-5 | epoxiconazole |
| 10-6 | 8-6 | epoxiconazole |
| 10-7 | 8-7 | epoxiconazole |
| 10-8 | 8-8 | epoxiconazole |
| 10-9 | 8-9 | epoxiconazole |
| 10-10 | 8-10 | epoxiconazole |
| 10-11 | 8-11 | epoxiconazole |
| 10-12 | 8-12 | epoxiconazole |
| 10-13 | 8-13 | epoxiconazole |
| 10-14 | 8-14 | epoxiconazole |
| 10-15 | 8-15 | epoxiconazole |
| 10-16 | 8-16 | epoxiconazole |
| 10-17 | 8-17 | epoxiconazole |
| 10-18 | 8-18 | epoxiconazole |
| 10-19 | 8-19 | epoxiconazole |
| 10-20 | 8-20 | epoxiconazole |
| 10-21 | 8-21 | epoxiconazole |
| 10-22 | 8-22 | epoxiconazole |
| 10-23 | 8-23 | epoxiconazole |
| 10-24 | 8-24 | epoxiconazole |
| 10-25 | 8-25 | epoxiconazole |
| 10-26 | 8-26 | epoxiconazole |
| 10-27 | 8-27 | epoxiconazole |
| 10-28 | 8-28 | epoxiconazole |
| 10-29 | 8-29 | epoxiconazole |
| 10-30 | 8-30 | epoxiconazole |
| 10-31 | 8-31 | epoxiconazole |
| 10-32 | 8-32 | epoxiconazole |
| 10-33 | 8-33 | epoxiconazole |
| 10-34 | 8-34 | epoxiconazole |
| 10-35 | 8-35 | epoxiconazole |
| 10-36 | 8-36 | epoxiconazole |
| 10-37 | 8-37 | epoxiconazole |
| 10-38 | 8-38 | epoxiconazole |
| 10-39 | 8-39 | epoxiconazole |
| 10-40 | 8-40 | epoxiconazole |
| 10-41 | 8-41 | epoxiconazole |
| 10-42 | 8-42 | epoxiconazole |
| 10-43 | 8-43 | epoxiconazole |
| 10-44 | 8-44 | epoxiconazole |
| 10-45 | 8-45 | epoxiconazole |
| 10-46 | 8-46 | epoxiconazole |
| 10-47 | 8-47 | epoxiconazole |
| 10-48 | 8-48 | epoxiconazole |
| 10-49 | 8-49 | epoxiconazole |
| 10-50 | 8-50 | epoxiconazole |
| 10-51 | 8-51 | epoxiconazole |
| 10-52 | 8-52 | epoxiconazole |
| 10-53 | 8-53 | epoxiconazole |
| 10-54 | 8-54 | epoxiconazole |
| 10-55 | 8-55 | epoxiconazole |
| 10-56 | 8-56 | epoxiconazole |
| 10-57 | 8-57 | epoxiconazole |
| 10-58 | 8-58 | epoxiconazole |
| 10-59 | 8-59 | epoxiconazole |
| 10-60 | 8-60 | epoxiconazole |
| 10-61 | 8-61 | epoxiconazole |
| 10-62 | 8-62 | epoxiconazole |
| 10-63 | 8-63 | epoxiconazole |
| 10-64 | 8-64 | epoxiconazole |
| 10-65 | 8-65 | epoxiconazole |
| 10-66 | 8-66 | epoxiconazole |
| 10-67 | 8-67 | epoxiconazole |
| 10-68 | 8-68 | epoxiconazole |
| 10-69 | 8-69 | epoxiconazole |
| 10-70 | 8-70 | epoxiconazole |
| 10-71 | 8-71 | epoxiconazole |
| 10-72 | 8-72 | epoxiconazole |
| 10-73 | 8-73 | epoxiconazole |
| 10-74 | 8-74 | epoxiconazole |
| 10-75 | 8-75 | epoxiconazole |
| 10-76 | 8-76 | epoxiconazole |
| 10-77 | 8-77 | epoxiconazole |
| 10-78 | 8-78 | epoxiconazole |
| 10-79 | 8-79 | epoxiconazole |
| 10-80 | 8-80 | epoxiconazole |
| 10-81 | 8-81 | epoxiconazole |
| 10-82 | 8-82 | epoxiconazole |
| 10-83 | 8-83 | epoxiconazole |
| 10-84 | 8-84 | epoxiconazole |
| 10-85 | 8-85 | epoxiconazole |
| 10-86 | 8-86 | epoxiconazole |
| 10-87 | 8-87 | epoxiconazole |
| 10-88 | 8-88 | epoxiconazole |
| 10-89 | 8-89 | epoxiconazole |
| 10-90 | 8-90 | epoxiconazole |
| 10-91 | 8-91 | epoxiconazole |
| 10-92 | 8-92 | epoxiconazole |
| 10-93 | 8-93 | epoxiconazole |
| 10-94 | 8-94 | epoxiconazole |
| 10-95 | 8-95 | epoxiconazole |
| 10-96 | 8-96 | epoxiconazole |
| 10-97 | 8-97 | epoxiconazole |
| 10-98 | 8-98 | epoxiconazole |

TABLE 10-continued

| No. | Binary combination | Active compound |
|---|---|---|
| 10-99 | 8-99 | epoxiconazole |
| 10-100 | 8-100 | epoxiconazole |
| 10-101 | 8-101 | epoxiconazole |
| 10-102 | 8-102 | epoxiconazole |
| 10-103 | 8-103 | epoxiconazole |
| 10-104 | 8-104 | epoxiconazole |
| 10-105 | 8-105 | epoxiconazole |
| 10-106 | 8-106 | epoxiconazole |
| 10-107 | 8-107 | epoxiconazole |
| 10-108 | 8-108 | epoxiconazole |
| 10-109 | 8-109 | epoxiconazole |
| 10-110 | 8-110 | epoxiconazole |
| 10-111 | 8-111 | epoxiconazole |
| 10-112 | 8-112 | epoxiconazole |
| 10-113 | 8-113 | epoxiconazole |
| 10-114 | 8-114 | epoxiconazole |
| 10-115 | 8-115 | epoxiconazole |
| 10-116 | 8-116 | epoxiconazole |
| 10-117 | 8-117 | epoxiconazole |
| 10-118 | 8-118 | epoxiconazole |
| 10-119 | 8-119 | epoxiconazole |
| 10-120 | 8-120 | epoxiconazole |
| 10-121 | 8-121 | epoxiconazole |
| 10-122 | 8-122 | epoxiconazole |
| 10-123 | 8-123 | epoxiconazole |
| 10-124 | 8-124 | epoxiconazole |
| 10-125 | 8-125 | epoxiconazole |
| 10-126 | 8-126 | epoxiconazole |
| 10-127 | 8-127 | epoxiconazole |
| 10-128 | 8-128 | epoxiconazole |
| 10-129 | 8-129 | epoxiconazole |
| 10-130 | 8-130 | epoxiconazole |
| 10-131 | 8-131 | epoxiconazole |
| 10-132 | 8-132 | epoxiconazole |
| 10-133 | 8-133 | epoxiconazole |
| 10-134 | 8-134 | epoxiconazole |
| 10-135 | 8-135 | epoxiconazole |
| 10-136 | 8-136 | epoxiconazole |
| 10-137 | 8-137 | epoxiconazole |
| 10-138 | 8-138 | epoxiconazole |
| 10-139 | 8-139 | epoxiconazole |
| 10-140 | 8-140 | epoxiconazole |
| 10-141 | 8-141 | epoxiconazole |
| 10-142 | 8-142 | epoxiconazole |
| 10-143 | 8-143 | epoxiconazole |
| 10-144 | 8-144 | epoxiconazole |
| 10-145 | 8-145 | epoxiconazole |
| 10-146 | 8-146 | epoxiconazole |
| 10-147 | 8-147 | epoxiconazole |
| 10-148 | 8-148 | epoxiconazole |
| 10-149 | 8-149 | epoxiconazole |
| 10-150 | 8-150 | epoxiconazole |
| 10-151 | 8-151 | epoxiconazole |
| 10-152 | 8-152 | epoxiconazole |
| 10-153 | 8-153 | epoxiconazole |
| 10-154 | 8-154 | epoxiconazole |
| 10-155 | 8-155 | epoxiconazole |
| 10-156 | 8-156 | epoxiconazole |
| 10-157 | 8-157 | epoxiconazole |
| 10-158 | 8-158 | epoxiconazole |
| 10-159 | 8-159 | epoxiconazole |
| 10-160 | 8-160 | epoxiconazole |
| 10-161 | 8-161 | epoxiconazole |
| 10-162 | 8-162 | epoxiconazole |
| 10-163 | 8-163 | epoxiconazole |
| 10-164 | 8-164 | epoxiconazole |
| 10-165 | 8-165 | epoxiconazole |
| 10-166 | 8-166 | epoxiconazole |
| 10-167 | 8-167 | epoxiconazole |
| 10-168 | 8-168 | epoxiconazole |
| 10-169 | 8-169 | epoxiconazole |
| 10-170 | 8-170 | epoxiconazole |
| 10-171 | 8-171 | epoxiconazole |
| 10-172 | 8-172 | epoxiconazole |
| 10-173 | 8-173 | epoxiconazole |
| 10-174 | 8-174 | epoxiconazole |
| 10-175 | 8-175 | epoxiconazole |
| 10-176 | 8-176 | epoxiconazole |
| 10-177 | 8-177 | epoxiconazole |
| 10-178 | 8-178 | epoxiconazole |
| 10-179 | 8-179 | epoxiconazole |
| 10-180 | 8-180 | epoxiconazole |
| 10-181 | 8-1 | metconazole |
| 10-182 | 8-2 | metconazole |
| 10-183 | 8-3 | metconazole |
| 10-184 | 8-4 | metconazole |
| 10-185 | 8-5 | metconazole |
| 10-186 | 8-6 | metconazole |
| 10-187 | 8-7 | metconazole |
| 10-188 | 8-8 | metconazole |
| 10-189 | 8-9 | metconazole |
| 10-190 | 8-10 | metconazole |
| 10-191 | 8-11 | metconazole |
| 10-192 | 8-12 | metconazole |
| 10-193 | 8-13 | metconazole |
| 10-194 | 8-14 | metconazole |
| 10-195 | 8-15 | metconazole |
| 10-196 | 8-16 | metconazole |
| 10-197 | 8-17 | metconazole |
| 10-198 | 8-18 | metconazole |
| 10-199 | 8-19 | metconazole |
| 10-200 | 8-20 | metconazole |
| 10-201 | 8-21 | metconazole |
| 10-202 | 8-22 | metconazole |
| 10-203 | 8-23 | metconazole |
| 10-204 | 8-24 | metconazole |
| 10-205 | 8-25 | metconazole |
| 10-206 | 8-26 | metconazole |
| 10-207 | 8-27 | metconazole |
| 10-208 | 8-28 | metconazole |
| 10-209 | 8-29 | metconazole |
| 10-210 | 8-30 | metconazole |
| 10-211 | 8-31 | metconazole |
| 10-212 | 8-32 | metconazole |
| 10-213 | 8-33 | metconazole |
| 10-214 | 8-34 | metconazole |
| 10-215 | 8-35 | metconazole |
| 10-216 | 8-36 | metconazole |
| 10-217 | 8-37 | metconazole |
| 10-218 | 8-38 | metconazole |
| 10-219 | 8-39 | metconazole |
| 10-220 | 8-40 | metconazole |
| 10-221 | 8-41 | metconazole |
| 10-222 | 8-42 | metconazole |
| 10-223 | 8-43 | metconazole |
| 10-224 | 8-44 | metconazole |
| 10-225 | 8-45 | metconazole |
| 10-226 | 8-46 | metconazole |
| 10-227 | 8-47 | metconazole |
| 10-228 | 8-48 | metconazole |
| 10-229 | 8-49 | metconazole |
| 10-230 | 8-50 | metconazole |
| 10-231 | 8-51 | metconazole |
| 10-232 | 8-52 | metconazole |
| 10-233 | 8-53 | metconazole |
| 10-234 | 8-54 | metconazole |
| 10-235 | 8-55 | metconazole |
| 10-236 | 8-56 | metconazole |
| 10-237 | 8-57 | metconazole |
| 10-238 | 8-58 | metconazole |
| 10-239 | 8-59 | metconazole |
| 10-240 | 8-60 | metconazole |
| 10-241 | 8-61 | metconazole |
| 10-242 | 8-62 | metconazole |
| 10-243 | 8-63 | metconazole |
| 10-244 | 8-64 | metconazole |
| 10-245 | 8-65 | metconazole |
| 10-246 | 8-66 | metconazole |
| 10-247 | 8-67 | metconazole |
| 10-248 | 8-68 | metconazole |
| 10-249 | 8-69 | metconazole |
| 10-250 | 8-70 | metconazole |
| 10-251 | 8-71 | metconazole |
| 10-252 | 8-72 | metconazole |

TABLE 10-continued

| No. | Binary combination | Active compound |
|---|---|---|
| 10-253 | 8-73 | metconazole |
| 10-254 | 8-74 | metconazole |
| 10-255 | 8-75 | metconazole |
| 10-256 | 8-76 | metconazole |
| 10-257 | 8-77 | metconazole |
| 10-258 | 8-78 | metconazole |
| 10-259 | 8-79 | metconazole |
| 10-260 | 8-80 | metconazole |
| 10-261 | 8-81 | metconazole |
| 10-262 | 8-82 | metconazole |
| 10-263 | 8-83 | metconazole |
| 10-264 | 8-84 | metconazole |
| 10-265 | 8-85 | metconazole |
| 10-266 | 8-86 | metconazole |
| 10-267 | 8-87 | metconazole |
| 10-268 | 8-88 | metconazole |
| 10-269 | 8-89 | metconazole |
| 10-270 | 8-90 | metconazole |
| 10-271 | 8-91 | metconazole |
| 10-272 | 8-92 | metconazole |
| 10-273 | 8-93 | metconazole |
| 10-274 | 8-94 | metconazole |
| 10-275 | 8-95 | metconazole |
| 10-276 | 8-96 | metconazole |
| 10-277 | 8-97 | metconazole |
| 10-278 | 8-98 | metconazole |
| 10-279 | 8-99 | metconazole |
| 10-280 | 8-100 | metconazole |
| 10-281 | 8-101 | metconazole |
| 10-282 | 8-102 | metconazole |
| 10-283 | 8-103 | metconazole |
| 10-284 | 8-104 | metconazole |
| 10-285 | 8-105 | metconazole |
| 10-286 | 8-106 | metconazole |
| 10-287 | 8-107 | metconazole |
| 10-288 | 8-108 | metconazole |
| 10-289 | 8-109 | metconazole |
| 10-290 | 8-110 | metconazole |
| 10-291 | 8-111 | metconazole |
| 10-292 | 8-112 | metconazole |
| 10-293 | 8-113 | metconazole |
| 10-294 | 8-114 | metconazole |
| 10-295 | 8-115 | metconazole |
| 10-296 | 8-116 | metconazole |
| 10-297 | 8-117 | metconazole |
| 10-298 | 8-118 | metconazole |
| 10-299 | 8-119 | metconazole |
| 10-300 | 8-120 | metconazole |
| 10-301 | 8-121 | metconazole |
| 10-302 | 8-122 | metconazole |
| 10-303 | 8-123 | metconazole |
| 10-304 | 8-124 | metconazole |
| 10-305 | 8-125 | metconazole |
| 10-306 | 8-126 | metconazole |
| 10-307 | 8-127 | metconazole |
| 10-308 | 8-128 | metconazole |
| 10-309 | 8-129 | metconazole |
| 10-310 | 8-130 | metconazole |
| 10-311 | 8-131 | metconazole |
| 10-312 | 8-132 | metconazole |
| 10-313 | 8-133 | metconazole |
| 10-314 | 8-134 | metconazole |
| 10-315 | 8-135 | metconazole |
| 10-316 | 8-136 | metconazole |
| 10-317 | 8-137 | metconazole |
| 10-318 | 8-138 | metconazole |
| 10-319 | 8-139 | metconazole |
| 10-320 | 8-140 | metconazole |
| 10-321 | 8-141 | metconazole |
| 10-322 | 8-142 | metconazole |
| 10-323 | 8-143 | metconazole |
| 10-324 | 8-144 | metconazole |
| 10-325 | 8-145 | metconazole |
| 10-326 | 8-146 | metconazole |
| 10-327 | 8-147 | metconazole |
| 10-328 | 8-148 | metconazole |
| 10-329 | 8-149 | metconazole |
| 10-330 | 8-150 | metconazole |
| 10-331 | 8-151 | metconazole |
| 10-332 | 8-152 | metconazole |
| 10-333 | 8-153 | metconazole |
| 10-334 | 8-154 | metconazole |
| 10-335 | 8-155 | metconazole |
| 10-336 | 8-156 | metconazole |
| 10-337 | 8-157 | metconazole |
| 10-338 | 8-158 | metconazole |
| 10-339 | 8-159 | metconazole |
| 10-340 | 8-160 | metconazole |
| 10-341 | 8-161 | metconazole |
| 10-342 | 8-162 | metconazole |
| 10-343 | 8-163 | metconazole |
| 10-344 | 8-164 | metconazole |
| 10-345 | 8-165 | metconazole |
| 10-346 | 8-166 | metconazole |
| 10-347 | 8-167 | metconazole |
| 10-348 | 8-168 | metconazole |
| 10-349 | 8-169 | metconazole |
| 10-350 | 8-170 | metconazole |
| 10-351 | 8-171 | metconazole |
| 10-352 | 8-172 | metconazole |
| 10-353 | 8-173 | metconazole |
| 10-354 | 8-174 | metconazole |
| 10-355 | 8-175 | metconazole |
| 10-356 | 8-176 | metconazole |
| 10-357 | 8-177 | metconazole |
| 10-358 | 8-178 | metconazole |
| 10-359 | 8-179 | metconazole |
| 10-360 | 8-180 | metconazole |
| 10-361 | 8-1 | tebuconazole |
| 10-362 | 8-2 | tebuconazole |
| 10-363 | 8-3 | tebuconazole |
| 10-364 | 8-4 | tebuconazole |
| 10-365 | 8-5 | tebuconazole |
| 10-366 | 8-6 | tebuconazole |
| 10-367 | 8-7 | tebuconazole |
| 10-368 | 8-8 | tebuconazole |
| 10-369 | 8-9 | tebuconazole |
| 10-370 | 8-10 | tebuconazole |
| 10-371 | 8-11 | tebuconazole |
| 10-372 | 8-12 | tebuconazole |
| 10-373 | 8-13 | tebuconazole |
| 10-374 | 8-14 | tebuconazole |
| 10-375 | 8-15 | tebuconazole |
| 10-376 | 8-16 | tebuconazole |
| 10-377 | 8-17 | tebuconazole |
| 10-378 | 8-18 | tebuconazole |
| 10-379 | 8-19 | tebuconazole |
| 10-380 | 8-20 | tebuconazole |
| 10-381 | 8-21 | tebuconazole |
| 10-382 | 8-22 | tebuconazole |
| 10-383 | 8-23 | tebuconazole |
| 10-384 | 8-24 | tebuconazole |
| 10-385 | 8-25 | tebuconazole |
| 10-386 | 8-26 | tebuconazole |
| 10-387 | 8-27 | tebuconazole |
| 10-388 | 8-28 | tebuconazole |
| 10-389 | 8-29 | tebuconazole |
| 10-390 | 8-30 | tebuconazole |
| 10-391 | 8-31 | tebuconazole |
| 10-392 | 8-32 | tebuconazole |
| 10-393 | 8-33 | tebuconazole |
| 10-394 | 8-34 | tebuconazole |
| 10-395 | 8-35 | tebuconazole |
| 10-396 | 8-36 | tebuconazole |
| 10-397 | 8-37 | tebuconazole |
| 10-398 | 8-38 | tebuconazole |
| 10-399 | 8-39 | tebuconazole |
| 10-400 | 8-40 | tebuconazole |
| 10-401 | 8-41 | tebuconazole |
| 10-402 | 8-42 | tebuconazole |
| 10-403 | 8-43 | tebuconazole |
| 10-404 | 8-44 | tebuconazole |
| 10-405 | 8-45 | tebuconazole |
| 10-406 | 8-46 | tebuconazole |

TABLE 10-continued

| No. | Binary combination | Active compound |
|---|---|---|
| 10-407 | 8-47 | tebuconazole |
| 10-408 | 8-48 | tebuconazole |
| 10-409 | 8-49 | tebuconazole |
| 10-410 | 8-50 | tebuconazole |
| 10-411 | 8-51 | tebuconazole |
| 10-412 | 8-52 | tebuconazole |
| 10-413 | 8-53 | tebuconazole |
| 10-414 | 8-54 | tebuconazole |
| 10-415 | 8-55 | tebuconazole |
| 10-416 | 8-56 | tebuconazole |
| 10-417 | 8-57 | tebuconazole |
| 10-418 | 8-58 | tebuconazole |
| 10-419 | 8-59 | tebuconazole |
| 10-420 | 8-60 | tebuconazole |
| 10-421 | 8-61 | tebuconazole |
| 10-422 | 8-62 | tebuconazole |
| 10-423 | 8-63 | tebuconazole |
| 10-424 | 8-64 | tebuconazole |
| 10-425 | 8-65 | tebuconazole |
| 10-426 | 8-66 | tebuconazole |
| 10-427 | 8-67 | tebuconazole |
| 10-428 | 8-68 | tebuconazole |
| 10-429 | 8-69 | tebuconazole |
| 10-430 | 8-70 | tebuconazole |
| 10-431 | 8-71 | tebuconazole |
| 10-432 | 8-72 | tebuconazole |
| 10-433 | 8-73 | tebuconazole |
| 10-434 | 8-74 | tebuconazole |
| 10-435 | 8-75 | tebuconazole |
| 10-436 | 8-76 | tebuconazole |
| 10-437 | 8-77 | tebuconazole |
| 10-438 | 8-78 | tebuconazole |
| 10-439 | 8-79 | tebuconazole |
| 10-440 | 8-80 | tebuconazole |
| 10-441 | 8-81 | tebuconazole |
| 10-442 | 8-82 | tebuconazole |
| 10-443 | 8-83 | tebuconazole |
| 10-444 | 8-84 | tebuconazole |
| 10-445 | 8-85 | tebuconazole |
| 10-446 | 8-86 | tebuconazole |
| 10-447 | 8-87 | tebuconazole |
| 10-448 | 8-88 | tebuconazole |
| 10-449 | 8-89 | tebuconazole |
| 10-450 | 8-90 | tebuconazole |
| 10-451 | 8-91 | tebuconazole |
| 10-452 | 8-92 | tebuconazole |
| 10-453 | 8-93 | tebuconazole |
| 10-454 | 8-94 | tebuconazole |
| 10-455 | 8-95 | tebuconazole |
| 10-456 | 8-96 | tebuconazole |
| 10-457 | 8-97 | tebuconazole |
| 10-458 | 8-98 | tebuconazole |
| 10-459 | 8-99 | tebuconazole |
| 10-460 | 8-100 | tebuconazole |
| 10-461 | 8-101 | tebuconazole |
| 10-462 | 8-102 | tebuconazole |
| 10-463 | 8-103 | tebuconazole |
| 10-464 | 8-104 | tebuconazole |
| 10-465 | 8-105 | tebuconazole |
| 10-466 | 8-106 | tebuconazole |
| 10-467 | 8-107 | tebuconazole |
| 10-468 | 8-108 | tebuconazole |
| 10-469 | 8-109 | tebuconazole |
| 10-470 | 8-110 | tebuconazole |
| 10-471 | 8-111 | tebuconazole |
| 10-472 | 8-112 | tebuconazole |
| 10-473 | 8-113 | tebuconazole |
| 10-474 | 8-114 | tebuconazole |
| 10-475 | 8-115 | tebuconazole |
| 10-476 | 8-116 | tebuconazole |
| 10-477 | 8-117 | tebuconazole |
| 10-478 | 8-118 | tebuconazole |
| 10-479 | 8-119 | tebuconazole |
| 10-480 | 8-120 | tebuconazole |
| 10-481 | 8-121 | tebuconazole |
| 10-482 | 8-122 | tebuconazole |
| 10-483 | 8-123 | tebuconazole |
| 10-484 | 8-124 | tebuconazole |
| 10-485 | 8-125 | tebuconazole |
| 10-486 | 8-126 | tebuconazole |
| 10-487 | 8-127 | tebuconazole |
| 10-488 | 8-128 | tebuconazole |
| 10-489 | 8-129 | tebuconazole |
| 10-490 | 8-130 | tebuconazole |
| 10-491 | 8-131 | tebuconazole |
| 10-492 | 8-132 | tebuconazole |
| 10-493 | 8-133 | tebuconazole |
| 10-494 | 8-134 | tebuconazole |
| 10-495 | 8-135 | tebuconazole |
| 10-496 | 8-136 | tebuconazole |
| 10-497 | 8-137 | tebuconazole |
| 10-498 | 8-138 | tebuconazole |
| 10-499 | 8-139 | tebuconazole |
| 10-500 | 8-140 | tebuconazole |
| 10-501 | 8-141 | tebuconazole |
| 10-502 | 8-142 | tebuconazole |
| 10-503 | 8-143 | tebuconazole |
| 10-504 | 8-144 | tebuconazole |
| 10-505 | 8-145 | tebuconazole |
| 10-506 | 8-146 | tebuconazole |
| 10-507 | 8-147 | tebuconazole |
| 10-508 | 8-148 | tebuconazole |
| 10-509 | 8-149 | tebuconazole |
| 10-510 | 8-150 | tebuconazole |
| 10-511 | 8-151 | tebuconazole |
| 10-512 | 8-152 | tebuconazole |
| 10-513 | 8-153 | tebuconazole |
| 10-514 | 8-154 | tebuconazole |
| 10-515 | 8-155 | tebuconazole |
| 10-516 | 8-156 | tebuconazole |
| 10-517 | 8-157 | tebuconazole |
| 10-518 | 8-158 | tebuconazole |
| 10-519 | 8-159 | tebuconazole |
| 10-520 | 8-160 | tebuconazole |
| 10-521 | 8-161 | tebuconazole |
| 10-522 | 8-162 | tebuconazole |
| 10-523 | 8-163 | tebuconazole |
| 10-524 | 8-164 | tebuconazole |
| 10-525 | 8-165 | tebuconazole |
| 10-526 | 8-166 | tebuconazole |
| 10-527 | 8-167 | tebuconazole |
| 10-528 | 8-168 | tebuconazole |
| 10-529 | 8-169 | tebuconazole |
| 10-530 | 8-170 | tebuconazole |
| 10-531 | 8-171 | tebuconazole |
| 10-532 | 8-172 | tebuconazole |
| 10-533 | 8-173 | tebuconazole |
| 10-534 | 8-174 | tebuconazole |
| 10-535 | 8-175 | tebuconazole |
| 10-536 | 8-176 | tebuconazole |
| 10-537 | 8-177 | tebuconazole |
| 10-538 | 8-178 | tebuconazole |
| 10-539 | 8-179 | tebuconazole |
| 10-540 | 8-180 | tebuconazole |
| 10-541 | 8-1 | fluquinconazole |
| 10-542 | 8-2 | fluquinconazole |
| 10-543 | 8-3 | fluquinconazole |
| 10-544 | 8-4 | fluquinconazole |
| 10-545 | 8-5 | fluquinconazole |
| 10-546 | 8-6 | fluquinconazole |
| 10-547 | 8-7 | fluquinconazole |
| 10-548 | 8-8 | fluquinconazole |
| 10-549 | 8-9 | fluquinconazole |
| 10-550 | 8-10 | fluquinconazole |
| 10-551 | 8-11 | fluquinconazole |
| 10-552 | 8-12 | fluquinconazole |
| 10-553 | 8-13 | fluquinconazole |
| 10-554 | 8-14 | fluquinconazole |
| 10-555 | 8-15 | fluquinconazole |
| 10-556 | 8-16 | fluquinconazole |
| 10-557 | 8-17 | fluquinconazole |
| 10-558 | 8-18 | fluquinconazole |
| 10-559 | 8-19 | fluquinconazole |
| 10-560 | 8-20 | fluquinconazole |

TABLE 10-continued

| No. | Binary combination | Active compound |
|---|---|---|
| 10-561 | 8-21 | fluquinconazole |
| 10-562 | 8-22 | fluquinconazole |
| 10-563 | 8-23 | fluquinconazole |
| 10-564 | 8-24 | fluquinconazole |
| 10-565 | 8-25 | fluquinconazole |
| 10-566 | 8-26 | fluquinconazole |
| 10-567 | 8-27 | fluquinconazole |
| 10-568 | 8-28 | fluquinconazole |
| 10-569 | 8-29 | fluquinconazole |
| 10-570 | 8-30 | fluquinconazole |
| 10-571 | 8-31 | fluquinconazole |
| 10-572 | 8-32 | fluquinconazole |
| 10-573 | 8-33 | fluquinconazole |
| 10-574 | 8-34 | fluquinconazole |
| 10-575 | 8-35 | fluquinconazole |
| 10-576 | 8-36 | fluquinconazole |
| 10-577 | 8-37 | fluquinconazole |
| 10-578 | 8-38 | fluquinconazole |
| 10-579 | 8-39 | fluquinconazole |
| 10-580 | 8-40 | fluquinconazole |
| 10-581 | 8-41 | fluquinconazole |
| 10-582 | 8-42 | fluquinconazole |
| 10-583 | 8-43 | fluquinconazole |
| 10-584 | 8-44 | fluquinconazole |
| 10-585 | 8-45 | fluquinconazole |
| 10-586 | 8-46 | fluquinconazole |
| 10-587 | 8-47 | fluquinconazole |
| 10-588 | 8-48 | fluquinconazole |
| 10-589 | 8-49 | fluquinconazole |
| 10-590 | 8-50 | fluquinconazole |
| 10-591 | 8-51 | fluquinconazole |
| 10-592 | 8-52 | fluquinconazole |
| 10-593 | 8-53 | fluquinconazole |
| 10-594 | 8-54 | fluquinconazole |
| 10-595 | 8-55 | fluquinconazole |
| 10-596 | 8-56 | fluquinconazole |
| 10-597 | 8-57 | fluquinconazole |
| 10-598 | 8-58 | fluquinconazole |
| 10-599 | 8-59 | fluquinconazole |
| 10-600 | 8-60 | fluquinconazole |
| 10-601 | 8-61 | fluquinconazole |
| 10-602 | 8-62 | fluquinconazole |
| 10-603 | 8-63 | fluquinconazole |
| 10-604 | 8-64 | fluquinconazole |
| 10-605 | 8-65 | fluquinconazole |
| 10-606 | 8-66 | fluquinconazole |
| 10-607 | 8-67 | fluquinconazole |
| 10-608 | 8-68 | fluquinconazole |
| 10-609 | 8-69 | fluquinconazole |
| 10-610 | 8-70 | fluquinconazole |
| 10-611 | 8-71 | fluquinconazole |
| 10-612 | 8-72 | fluquinconazole |
| 10-613 | 8-73 | fluquinconazole |
| 10-614 | 8-74 | fluquinconazole |
| 10-615 | 8-75 | fluquinconazole |
| 10-616 | 8-76 | fluquinconazole |
| 10-617 | 8-77 | fluquinconazole |
| 10-618 | 8-78 | fluquinconazole |
| 10-619 | 8-79 | fluquinconazole |
| 10-620 | 8-80 | fluquinconazole |
| 10-621 | 8-81 | fluquinconazole |
| 10-622 | 8-82 | fluquinconazole |
| 10-623 | 8-83 | fluquinconazole |
| 10-624 | 8-84 | fluquinconazole |
| 10-625 | 8-85 | fluquinconazole |
| 10-626 | 8-86 | fluquinconazole |
| 10-627 | 8-87 | fluquinconazole |
| 10-628 | 8-88 | fluquinconazole |
| 10-629 | 8-89 | fluquinconazole |
| 10-630 | 8-90 | fluquinconazole |
| 10-631 | 8-91 | fluquinconazole |
| 10-632 | 8-92 | fluquinconazole |
| 10-633 | 8-93 | fluquinconazole |
| 10-634 | 8-94 | fluquinconazole |
| 10-635 | 8-95 | fluquinconazole |
| 10-636 | 8-96 | fluquinconazole |
| 10-637 | 8-97 | fluquinconazole |
| 10-638 | 8-98 | fluquinconazole |
| 10-639 | 8-99 | fluquinconazole |
| 10-640 | 8-100 | fluquinconazole |
| 10-641 | 8-101 | fluquinconazole |
| 10-642 | 8-102 | fluquinconazole |
| 10-643 | 8-103 | fluquinconazole |
| 10-644 | 8-104 | fluquinconazole |
| 10-645 | 8-105 | fluquinconazole |
| 10-646 | 8-106 | fluquinconazole |
| 10-647 | 8-107 | fluquinconazole |
| 10-648 | 8-108 | fluquinconazole |
| 10-649 | 8-109 | fluquinconazole |
| 10-650 | 8-110 | fluquinconazole |
| 10-651 | 8-111 | fluquinconazole |
| 10-652 | 8-112 | fluquinconazole |
| 10-653 | 8-113 | fluquinconazole |
| 10-654 | 8-114 | fluquinconazole |
| 10-655 | 8-115 | fluquinconazole |
| 10-656 | 8-116 | fluquinconazole |
| 10-657 | 8-117 | fluquinconazole |
| 10-658 | 8-118 | fluquinconazole |
| 10-659 | 8-119 | fluquinconazole |
| 10-660 | 8-120 | fluquinconazole |
| 10-661 | 8-121 | fluquinconazole |
| 10-662 | 8-122 | fluquinconazole |
| 10-663 | 8-123 | fluquinconazole |
| 10-664 | 8-124 | fluquinconazole |
| 10-665 | 8-125 | fluquinconazole |
| 10-666 | 8-126 | fluquinconazole |
| 10-667 | 8-127 | fluquinconazole |
| 10-668 | 8-128 | fluquinconazole |
| 10-669 | 8-129 | fluquinconazole |
| 10-670 | 8-130 | fluquinconazole |
| 10-671 | 8-131 | fluquinconazole |
| 10-672 | 8-132 | fluquinconazole |
| 10-673 | 8-133 | fluquinconazole |
| 10-674 | 8-134 | fluquinconazole |
| 10-675 | 8-135 | fluquinconazole |
| 10-676 | 8-136 | fluquinconazole |
| 10-677 | 8-137 | fluquinconazole |
| 10-678 | 8-138 | fluquinconazole |
| 10-679 | 8-139 | fluquinconazole |
| 10-680 | 8-140 | fluquinconazole |
| 10-681 | 8-141 | fluquinconazole |
| 10-682 | 8-142 | fluquinconazole |
| 10-683 | 8-143 | fluquinconazole |
| 10-684 | 8-144 | fluquinconazole |
| 10-685 | 8-145 | fluquinconazole |
| 10-686 | 8-146 | fluquinconazole |
| 10-687 | 8-147 | fluquinconazole |
| 10-688 | 8-148 | fluquinconazole |
| 10-689 | 8-149 | fluquinconazole |
| 10-690 | 8-150 | fluquinconazole |
| 10-691 | 8-151 | fluquinconazole |
| 10-692 | 8-152 | fluquinconazole |
| 10-693 | 8-153 | fluquinconazole |
| 10-694 | 8-154 | fluquinconazole |
| 10-695 | 8-155 | fluquinconazole |
| 10-696 | 8-156 | fluquinconazole |
| 10-697 | 8-157 | fluquinconazole |
| 10-698 | 8-158 | fluquinconazole |
| 10-699 | 8-159 | fluquinconazole |
| 10-700 | 8-160 | fluquinconazole |
| 10-701 | 8-161 | fluquinconazole |
| 10-702 | 8-162 | fluquinconazole |
| 10-703 | 8-163 | fluquinconazole |
| 10-704 | 8-164 | fluquinconazole |
| 10-705 | 8-165 | fluquinconazole |
| 10-706 | 8-166 | fluquinconazole |
| 10-707 | 8-167 | fluquinconazole |
| 10-708 | 8-168 | fluquinconazole |
| 10-709 | 8-169 | fluquinconazole |
| 10-710 | 8-170 | fluquinconazole |
| 10-711 | 8-171 | fluquinconazole |
| 10-712 | 8-172 | fluquinconazole |
| 10-713 | 8-173 | fluquinconazole |
| 10-714 | 8-174 | fluquinconazole |

TABLE 10-continued

| No. | Binary combination | Active compound |
|---|---|---|
| 10-715 | 8-175 | fluquinconazole |
| 10-716 | 8-176 | fluquinconazole |
| 10-717 | 8-177 | fluquinconazole |
| 10-718 | 8-178 | fluquinconazole |
| 10-719 | 8-179 | fluquinconazole |
| 10-720 | 8-180 | fluquinconazole |
| 10-721 | 8-1 | flutriafol |
| 10-722 | 8-2 | flutriafol |
| 10-723 | 8-3 | flutriafol |
| 10-724 | 8-4 | flutriafol |
| 10-725 | 8-5 | flutriafol |
| 10-726 | 8-6 | flutriafol |
| 10-727 | 8-7 | flutriafol |
| 10-728 | 8-8 | flutriafol |
| 10-729 | 8-9 | flutriafol |
| 10-730 | 8-10 | flutriafol |
| 10-731 | 8-11 | flutriafol |
| 10-732 | 8-12 | flutriafol |
| 10-733 | 8-13 | flutriafol |
| 10-734 | 8-14 | flutriafol |
| 10-735 | 8-15 | flutriafol |
| 10-736 | 8-16 | flutriafol |
| 10-737 | 8-17 | flutriafol |
| 10-738 | 8-18 | flutriafol |
| 10-739 | 8-19 | flutriafol |
| 10-740 | 8-20 | flutriafol |
| 10-741 | 8-21 | flutriafol |
| 10-742 | 8-22 | flutriafol |
| 10-743 | 8-23 | flutriafol |
| 10-744 | 8-24 | flutriafol |
| 10-745 | 8-25 | flutriafol |
| 10-746 | 8-26 | flutriafol |
| 10-747 | 8-27 | flutriafol |
| 10-748 | 8-28 | flutriafol |
| 10-749 | 8-29 | flutriafol |
| 10-750 | 8-30 | flutriafol |
| 10-751 | 8-31 | flutriafol |
| 10-752 | 8-32 | flutriafol |
| 10-753 | 8-33 | flutriafol |
| 10-754 | 8-34 | flutriafol |
| 10-755 | 8-35 | flutriafol |
| 10-756 | 8-36 | flutriafol |
| 10-757 | 8-37 | flutriafol |
| 10-758 | 8-38 | flutriafol |
| 10-759 | 8-39 | flutriafol |
| 10-760 | 8-40 | flutriafol |
| 10-761 | 8-41 | flutriafol |
| 10-762 | 8-42 | flutriafol |
| 10-763 | 8-43 | flutriafol |
| 10-764 | 8-44 | flutriafol |
| 10-765 | 8-45 | flutriafol |
| 10-766 | 8-46 | flutriafol |
| 10-767 | 8-47 | flutriafol |
| 10-768 | 8-48 | flutriafol |
| 10-769 | 8-49 | flutriafol |
| 10-770 | 8-50 | flutriafol |
| 10-771 | 8-51 | flutriafol |
| 10-772 | 8-52 | flutriafol |
| 10-773 | 8-53 | flutriafol |
| 10-774 | 8-54 | flutriafol |
| 10-775 | 8-55 | flutriafol |
| 10-776 | 8-56 | flutriafol |
| 10-777 | 8-57 | flutriafol |
| 10-778 | 8-58 | flutriafol |
| 10-779 | 8-59 | flutriafol |
| 10-780 | 8-60 | flutriafol |
| 10-781 | 8-61 | flutriafol |
| 10-782 | 8-62 | flutriafol |
| 10-783 | 8-63 | flutriafol |
| 10-784 | 8-64 | flutriafol |
| 10-785 | 8-65 | flutriafol |
| 10-786 | 8-66 | flutriafol |
| 10-787 | 8-67 | flutriafol |
| 10-788 | 8-68 | flutriafol |
| 10-789 | 8-69 | flutriafol |
| 10-790 | 8-70 | flutriafol |
| 10-791 | 8-71 | flutriafol |
| 10-792 | 8-72 | flutriafol |
| 10-793 | 8-73 | flutriafol |
| 10-794 | 8-74 | flutriafol |
| 10-795 | 8-75 | flutriafol |
| 10-796 | 8-76 | flutriafol |
| 10-797 | 8-77 | flutriafol |
| 10-798 | 8-78 | flutriafol |
| 10-799 | 8-79 | flutriafol |
| 10-800 | 8-80 | flutriafol |
| 10-801 | 8-81 | flutriafol |
| 10-802 | 8-82 | flutriafol |
| 10-803 | 8-83 | flutriafol |
| 10-804 | 8-84 | flutriafol |
| 10-805 | 8-85 | flutriafol |
| 10-806 | 8-86 | flutriafol |
| 10-807 | 8-87 | flutriafol |
| 10-808 | 8-88 | flutriafol |
| 10-809 | 8-89 | flutriafol |
| 10-810 | 8-90 | flutriafol |
| 10-811 | 8-91 | flutriafol |
| 10-812 | 8-92 | flutriafol |
| 10-813 | 8-93 | flutriafol |
| 10-814 | 8-94 | flutriafol |
| 10-815 | 8-95 | flutriafol |
| 10-816 | 8-96 | flutriafol |
| 10-817 | 8-97 | flutriafol |
| 10-818 | 8-98 | flutriafol |
| 10-819 | 8-99 | flutriafol |
| 10-820 | 8-100 | flutriafol |
| 10-821 | 8-101 | flutriafol |
| 10-822 | 8-102 | flutriafol |
| 10-823 | 8-103 | flutriafol |
| 10-824 | 8-104 | flutriafol |
| 10-825 | 8-105 | flutriafol |
| 10-826 | 8-106 | flutriafol |
| 10-827 | 8-107 | flutriafol |
| 10-828 | 8-108 | flutriafol |
| 10-829 | 8-109 | flutriafol |
| 10-830 | 8-110 | flutriafol |
| 10-831 | 8-111 | flutriafol |
| 10-832 | 8-112 | flutriafol |
| 10-833 | 8-113 | flutriafol |
| 10-834 | 8-114 | flutriafol |
| 10-835 | 8-115 | flutriafol |
| 10-836 | 8-116 | flutriafol |
| 10-837 | 8-117 | flutriafol |
| 10-838 | 8-118 | flutriafol |
| 10-839 | 8-119 | flutriafol |
| 10-840 | 8-120 | flutriafol |
| 10-841 | 8-121 | flutriafol |
| 10-842 | 8-122 | flutriafol |
| 10-843 | 8-123 | flutriafol |
| 10-844 | 8-124 | flutriafol |
| 10-845 | 8-125 | flutriafol |
| 10-846 | 8-126 | flutriafol |
| 10-847 | 8-127 | flutriafol |
| 10-848 | 8-128 | flutriafol |
| 10-849 | 8-129 | flutriafol |
| 10-850 | 8-130 | flutriafol |
| 10-851 | 8-131 | flutriafol |
| 10-852 | 8-132 | flutriafol |
| 10-853 | 8-133 | flutriafol |
| 10-854 | 8-134 | flutriafol |
| 10-855 | 8-135 | flutriafol |
| 10-856 | 8-136 | flutriafol |
| 10-857 | 8-137 | flutriafol |
| 10-858 | 8-138 | flutriafol |
| 10-859 | 8-139 | flutriafol |
| 10-860 | 8-140 | flutriafol |
| 10-861 | 8-141 | flutriafol |
| 10-862 | 8-142 | flutriafol |
| 10-863 | 8-143 | flutriafol |
| 10-864 | 8-144 | flutriafol |
| 10-865 | 8-145 | flutriafol |
| 10-866 | 8-146 | flutriafol |
| 10-867 | 8-147 | flutriafol |
| 10-868 | 8-148 | flutriafol |

TABLE 10-continued

| No. | Binary combination | Active compound |
|---|---|---|
| 10-869 | 8-149 | flutriafol |
| 10-870 | 8-150 | flutriafol |
| 10-871 | 8-151 | flutriafol |
| 10-872 | 8-152 | flutriafol |
| 10-873 | 8-153 | flutriafol |
| 10-874 | 8-154 | flutriafol |
| 10-875 | 8-155 | flutriafol |
| 10-876 | 8-156 | flutriafol |
| 10-877 | 8-157 | flutriafol |
| 10-878 | 8-158 | flutriafol |
| 10-879 | 8-159 | flutriafol |
| 10-880 | 8-160 | flutriafol |
| 10-881 | 8-161 | flutriafol |
| 10-882 | 8-162 | flutriafol |
| 10-883 | 8-163 | flutriafol |
| 10-884 | 8-164 | flutriafol |
| 10-885 | 8-165 | flutriafol |
| 10-886 | 8-166 | flutriafol |
| 10-887 | 8-167 | flutriafol |
| 10-888 | 8-168 | flutriafol |
| 10-889 | 8-169 | flutriafol |
| 10-890 | 8-170 | flutriafol |
| 10-891 | 8-171 | flutriafol |
| 10-892 | 8-172 | flutriafol |
| 10-893 | 8-173 | flutriafol |
| 10-894 | 8-174 | flutriafol |
| 10-895 | 8-175 | flutriafol |
| 10-896 | 8-176 | flutriafol |
| 10-897 | 8-177 | flutriafol |
| 10-898 | 8-178 | flutriafol |
| 10-899 | 8-179 | flutriafol |
| 10-900 | 8-180 | flutriafol |
| 10-901 | 8-1 | triticonazole |
| 10-902 | 8-2 | triticonazole |
| 10-903 | 8-3 | triticonazole |
| 10-904 | 8-4 | triticonazole |
| 10-905 | 8-5 | triticonazole |
| 10-906 | 8-6 | triticonazole |
| 10-907 | 8-7 | triticonazole |
| 10-908 | 8-8 | triticonazole |
| 10-909 | 8-9 | triticonazole |
| 10-910 | 8-10 | triticonazole |
| 10-911 | 8-11 | triticonazole |
| 10-912 | 8-12 | triticonazole |
| 10-913 | 8-13 | triticonazole |
| 10-914 | 8-14 | triticonazole |
| 10-915 | 8-15 | triticonazole |
| 10-916 | 8-16 | triticonazole |
| 10-917 | 8-17 | triticonazole |
| 10-918 | 8-18 | triticonazole |
| 10-919 | 8-19 | triticonazole |
| 10-920 | 8-20 | triticonazole |
| 10-921 | 8-21 | triticonazole |
| 10-922 | 8-22 | triticonazole |
| 10-923 | 8-23 | triticonazole |
| 10-924 | 8-24 | triticonazole |
| 10-925 | 8-25 | triticonazole |
| 10-926 | 8-26 | triticonazole |
| 10-927 | 8-27 | triticonazole |
| 10-928 | 8-28 | triticonazole |
| 10-929 | 8-29 | triticonazole |
| 10-930 | 8-30 | triticonazole |
| 10-931 | 8-31 | triticonazole |
| 10-932 | 8-32 | triticonazole |
| 10-933 | 8-33 | triticonazole |
| 10-934 | 8-34 | triticonazole |
| 10-935 | 8-35 | triticonazole |
| 10-936 | 8-36 | triticonazole |
| 10-937 | 8-37 | triticonazole |
| 10-938 | 8-38 | triticonazole |
| 10-939 | 8-39 | triticonazole |
| 10-940 | 8-40 | triticonazole |
| 10-941 | 8-41 | triticonazole |
| 10-942 | 8-42 | triticonazole |
| 10-943 | 8-43 | triticonazole |
| 10-944 | 8-44 | triticonazole |
| 10-945 | 8-45 | triticonazole |
| 10-946 | 8-46 | triticonazole |
| 10-947 | 8-47 | triticonazole |
| 10-948 | 8-48 | triticonazole |
| 10-949 | 8-49 | triticonazole |
| 10-950 | 8-50 | triticonazole |
| 10-951 | 8-51 | triticonazole |
| 10-952 | 8-52 | triticonazole |
| 10-953 | 8-53 | triticonazole |
| 10-954 | 8-54 | triticonazole |
| 10-955 | 8-55 | triticonazole |
| 10-956 | 8-56 | triticonazole |
| 10-957 | 8-57 | triticonazole |
| 10-958 | 8-58 | triticonazole |
| 10-959 | 8-59 | triticonazole |
| 10-960 | 8-60 | triticonazole |
| 10-961 | 8-61 | triticonazole |
| 10-962 | 8-62 | triticonazole |
| 10-963 | 8-63 | triticonazole |
| 10-964 | 8-64 | triticonazole |
| 10-965 | 8-65 | triticonazole |
| 10-966 | 8-66 | triticonazole |
| 10-967 | 8-67 | triticonazole |
| 10-968 | 8-68 | triticonazole |
| 10-969 | 8-69 | triticonazole |
| 10-970 | 8-70 | triticonazole |
| 10-971 | 8-71 | triticonazole |
| 10-972 | 8-72 | triticonazole |
| 10-973 | 8-73 | triticonazole |
| 10-974 | 8-74 | triticonazole |
| 10-975 | 8-75 | triticonazole |
| 10-976 | 8-76 | triticonazole |
| 10-977 | 8-77 | triticonazole |
| 10-978 | 8-78 | triticonazole |
| 10-979 | 8-79 | triticonazole |
| 10-980 | 8-80 | triticonazole |
| 10-981 | 8-81 | triticonazole |
| 10-982 | 8-82 | triticonazole |
| 10-983 | 8-83 | triticonazole |
| 10-984 | 8-84 | triticonazole |
| 10-985 | 8-85 | triticonazole |
| 10-986 | 8-86 | triticonazole |
| 10-987 | 8-87 | triticonazole |
| 10-988 | 8-88 | triticonazole |
| 10-989 | 8-89 | triticonazole |
| 10-990 | 8-90 | triticonazole |
| 10-991 | 8-91 | triticonazole |
| 10-992 | 8-92 | triticonazole |
| 10-993 | 8-93 | triticonazole |
| 10-994 | 8-94 | triticonazole |
| 10-995 | 8-95 | triticonazole |
| 10-996 | 8-96 | triticonazole |
| 10-997 | 8-97 | triticonazole |
| 10-998 | 8-98 | triticonazole |
| 10-999 | 8-99 | triticonazole |
| 10-1000 | 8-100 | triticonazole |
| 10-1001 | 8-101 | triticonazole |
| 10-1002 | 8-102 | triticonazole |
| 10-1003 | 8-103 | triticonazole |
| 10-1004 | 8-104 | triticonazole |
| 10-1005 | 8-105 | triticonazole |
| 10-1006 | 8-106 | triticonazole |
| 10-1007 | 8-107 | triticonazole |
| 10-1008 | 8-108 | triticonazole |
| 10-1009 | 8-109 | triticonazole |
| 10-1010 | 8-110 | triticonazole |
| 10-1011 | 8-111 | triticonazole |
| 10-1012 | 8-112 | triticonazole |
| 10-1013 | 8-113 | triticonazole |
| 10-1014 | 8-114 | triticonazole |
| 10-1015 | 8-115 | triticonazole |
| 10-1016 | 8-116 | triticonazole |
| 10-1017 | 8-117 | triticonazole |
| 10-1018 | 8-118 | triticonazole |
| 10-1019 | 8-119 | triticonazole |
| 10-1020 | 8-120 | triticonazole |
| 10-1021 | 8-121 | triticonazole |
| 10-1022 | 8-122 | triticonazole |

TABLE 10-continued

| No. | Binary combination | Active compound |
|---|---|---|
| 10-1023 | 8-123 | triticonazole |
| 10-1024 | 8-124 | triticonazole |
| 10-1025 | 8-125 | triticonazole |
| 10-1026 | 8-126 | triticonazole |
| 10-1027 | 8-127 | triticonazole |
| 10-1028 | 8-128 | triticonazole |
| 10-1029 | 8-129 | triticonazole |
| 10-1030 | 8-130 | triticonazole |
| 10-1031 | 8-131 | triticonazole |
| 10-1032 | 8-132 | triticonazole |
| 10-1033 | 8-133 | triticonazole |
| 10-1034 | 8-134 | triticonazole |
| 10-1035 | 8-135 | triticonazole |
| 10-1036 | 8-136 | triticonazole |
| 10-1037 | 8-137 | triticonazole |
| 10-1038 | 8-138 | triticonazole |
| 10-1039 | 8-139 | triticonazole |
| 10-1040 | 8-140 | triticonazole |
| 10-1041 | 8-141 | triticonazole |
| 10-1042 | 8-142 | triticonazole |
| 10-1043 | 8-143 | triticonazole |
| 10-1044 | 8-144 | triticonazole |
| 10-1045 | 8-145 | triticonazole |
| 10-1046 | 8-146 | triticonazole |
| 10-1047 | 8-147 | triticonazole |
| 10-1048 | 8-148 | triticonazole |
| 10-1049 | 8-149 | triticonazole |
| 10-1050 | 8-150 | triticonazole |
| 10-1051 | 8-151 | triticonazole |
| 10-1052 | 8-152 | triticonazole |
| 10-1053 | 8-153 | triticonazole |
| 10-1054 | 8-154 | triticonazole |
| 10-1055 | 8-155 | triticonazole |
| 10-1056 | 8-156 | triticonazole |
| 10-1057 | 8-157 | triticonazole |
| 10-1058 | 8-158 | triticonazole |
| 10-1059 | 8-159 | triticonazole |
| 10-1060 | 8-160 | triticonazole |
| 10-1061 | 8-161 | triticonazole |
| 10-1062 | 8-162 | triticonazole |
| 10-1063 | 8-163 | triticonazole |
| 10-1064 | 8-164 | triticonazole |
| 10-1065 | 8-165 | triticonazole |
| 10-1066 | 8-166 | triticonazole |
| 10-1067 | 8-167 | triticonazole |
| 10-1068 | 8-168 | triticonazole |
| 10-1069 | 8-169 | triticonazole |
| 10-1070 | 8-170 | triticonazole |
| 10-1071 | 8-171 | triticonazole |
| 10-1072 | 8-172 | triticonazole |
| 10-1073 | 8-173 | triticonazole |
| 10-1074 | 8-174 | triticonazole |
| 10-1075 | 8-175 | triticonazole |
| 10-1076 | 8-176 | triticonazole |
| 10-1077 | 8-177 | triticonazole |
| 10-1078 | 8-178 | triticonazole |
| 10-1079 | 8-179 | triticonazole |
| 10-1080 | 8-180 | triticonazole |
| 10-1081 | 8-1 | prochloraz |
| 10-1082 | 8-2 | prochloraz |
| 10-1083 | 8-3 | prochloraz |
| 10-1084 | 8-4 | prochloraz |
| 10-1085 | 8-5 | prochloraz |
| 10-1086 | 8-6 | prochloraz |
| 10-1087 | 8-7 | prochloraz |
| 10-1088 | 8-8 | prochloraz |
| 10-1089 | 8-9 | prochloraz |
| 10-1090 | 8-10 | prochloraz |
| 10-1091 | 8-11 | prochloraz |
| 10-1092 | 8-12 | prochloraz |
| 10-1093 | 8-13 | prochloraz |
| 10-1094 | 8-14 | prochloraz |
| 10-1095 | 8-15 | prochloraz |
| 10-1096 | 8-16 | prochloraz |
| 10-1097 | 8-17 | prochloraz |
| 10-1098 | 8-18 | prochloraz |
| 10-1099 | 8-19 | prochloraz |
| 10-1100 | 8-20 | prochloraz |
| 10-1101 | 8-21 | prochloraz |
| 10-1102 | 8-22 | prochloraz |
| 10-1103 | 8-23 | prochloraz |
| 10-1104 | 8-24 | prochloraz |
| 10-1105 | 8-25 | prochloraz |
| 10-1106 | 8-26 | prochloraz |
| 10-1107 | 8-27 | prochloraz |
| 10-1108 | 8-28 | prochloraz |
| 10-1109 | 8-29 | prochloraz |
| 10-1110 | 8-30 | prochloraz |
| 10-1111 | 8-31 | prochloraz |
| 10-1112 | 8-32 | prochloraz |
| 10-1113 | 8-33 | prochloraz |
| 10-1114 | 8-34 | prochloraz |
| 10-1115 | 8-35 | prochloraz |
| 10-1116 | 8-36 | prochloraz |
| 10-1117 | 8-37 | prochloraz |
| 10-1118 | 8-38 | prochloraz |
| 10-1119 | 8-39 | prochloraz |
| 10-1120 | 8-40 | prochloraz |
| 10-1121 | 8-41 | prochloraz |
| 10-1122 | 8-42 | prochloraz |
| 10-1123 | 8-43 | prochloraz |
| 10-1124 | 8-44 | prochloraz |
| 10-1125 | 8-45 | prochloraz |
| 10-1126 | 8-46 | prochloraz |
| 10-1127 | 8-47 | prochloraz |
| 10-1128 | 8-48 | prochloraz |
| 10-1129 | 8-49 | prochloraz |
| 10-1130 | 8-50 | prochloraz |
| 10-1131 | 8-51 | prochloraz |
| 10-1132 | 8-52 | prochloraz |
| 10-1133 | 8-53 | prochloraz |
| 10-1134 | 8-54 | prochloraz |
| 10-1135 | 8-55 | prochloraz |
| 10-1136 | 8-56 | prochloraz |
| 10-1137 | 8-57 | prochloraz |
| 10-1138 | 8-58 | prochloraz |
| 10-1139 | 8-59 | prochloraz |
| 10-1140 | 8-60 | prochloraz |
| 10-1141 | 8-61 | prochloraz |
| 10-1142 | 8-62 | prochloraz |
| 10-1143 | 8-63 | prochloraz |
| 10-1144 | 8-64 | prochloraz |
| 10-1145 | 8-65 | prochloraz |
| 10-1146 | 8-66 | prochloraz |
| 10-1147 | 8-67 | prochloraz |
| 10-1148 | 8-68 | prochloraz |
| 10-1149 | 8-69 | prochloraz |
| 10-1150 | 8-70 | prochloraz |
| 10-1151 | 8-71 | prochloraz |
| 10-1152 | 8-72 | prochloraz |
| 10-1153 | 8-73 | prochloraz |
| 10-1154 | 8-74 | prochloraz |
| 10-1155 | 8-75 | prochloraz |
| 10-1156 | 8-76 | prochloraz |
| 10-1157 | 8-77 | prochloraz |
| 10-1158 | 8-78 | prochloraz |
| 10-1159 | 8-79 | prochloraz |
| 10-1160 | 8-80 | prochloraz |
| 10-1161 | 8-81 | prochloraz |
| 10-1162 | 8-82 | prochloraz |
| 10-1163 | 8-83 | prochloraz |
| 10-1164 | 8-84 | prochloraz |
| 10-1165 | 8-85 | prochloraz |
| 10-1166 | 8-86 | prochloraz |
| 10-1167 | 8-87 | prochloraz |
| 10-1168 | 8-88 | prochloraz |
| 10-1169 | 8-89 | prochloraz |
| 10-1170 | 8-90 | prochloraz |
| 10-1171 | 8-91 | prochloraz |
| 10-1172 | 8-92 | prochloraz |
| 10-1173 | 8-93 | prochloraz |
| 10-1174 | 8-94 | prochloraz |
| 10-1175 | 8-95 | prochloraz |
| 10-1176 | 8-96 | prochloraz |

TABLE 10-continued

| No. | Binary combination | Active compound |
|---|---|---|
| 10-1177 | 8-97 | prochloraz |
| 10-1178 | 8-98 | prochloraz |
| 10-1179 | 8-99 | prochloraz |
| 10-1180 | 8-100 | prochloraz |
| 10-1181 | 8-101 | prochloraz |
| 10-1182 | 8-102 | prochloraz |
| 10-1183 | 8-103 | prochloraz |
| 10-1184 | 8-104 | prochloraz |
| 10-1185 | 8-105 | prochloraz |
| 10-1186 | 8-106 | prochloraz |
| 10-1187 | 8-107 | prochloraz |
| 10-1188 | 8-108 | prochloraz |
| 10-1189 | 8-109 | prochloraz |
| 10-1190 | 8-110 | prochloraz |
| 10-1191 | 8-111 | prochloraz |
| 10-1192 | 8-112 | prochloraz |
| 10-1193 | 8-113 | prochloraz |
| 10-1194 | 8-114 | prochloraz |
| 10-1195 | 8-115 | prochloraz |
| 10-1196 | 8-116 | prochloraz |
| 10-1197 | 8-117 | prochloraz |
| 10-1198 | 8-118 | prochloraz |
| 10-1199 | 8-119 | prochloraz |
| 10-1200 | 8-120 | prochloraz |
| 10-1201 | 8-121 | prochloraz |
| 10-1202 | 8-122 | prochloraz |
| 10-1203 | 8-123 | prochloraz |
| 10-1204 | 8-124 | prochloraz |
| 10-1205 | 8-125 | prochloraz |
| 10-1206 | 8-126 | prochloraz |
| 10-1207 | 8-127 | prochloraz |
| 10-1208 | 8-128 | prochloraz |
| 10-1209 | 8-129 | prochloraz |
| 10-1210 | 8-130 | prochloraz |
| 10-1211 | 8-131 | prochloraz |
| 10-1212 | 8-132 | prochloraz |
| 10-1213 | 8-133 | prochloraz |
| 10-1214 | 8-134 | prochloraz |
| 10-1215 | 8-135 | prochloraz |
| 10-1216 | 8-136 | prochloraz |
| 10-1217 | 8-137 | prochloraz |
| 10-1218 | 8-138 | prochloraz |
| 10-1219 | 8-139 | prochloraz |
| 10-1220 | 8-140 | prochloraz |
| 10-1221 | 8-141 | prochloraz |
| 10-1222 | 8-142 | prochloraz |
| 10-1223 | 8-143 | prochloraz |
| 10-1224 | 8-144 | prochloraz |
| 10-1225 | 8-145 | prochloraz |
| 10-1226 | 8-146 | prochloraz |
| 10-1227 | 8-147 | prochloraz |
| 10-1228 | 8-148 | prochloraz |
| 10-1229 | 8-149 | prochloraz |
| 10-1230 | 8-150 | prochloraz |
| 10-1231 | 8-151 | prochloraz |
| 10-1232 | 8-152 | prochloraz |
| 10-1233 | 8-153 | prochloraz |
| 10-1234 | 8-154 | prochloraz |
| 10-1235 | 8-155 | prochloraz |
| 10-1236 | 8-156 | prochloraz |
| 10-1237 | 8-157 | prochloraz |
| 10-1238 | 8-158 | prochloraz |
| 10-1239 | 8-159 | prochloraz |
| 10-1240 | 8-160 | prochloraz |
| 10-1241 | 8-161 | prochloraz |
| 10-1242 | 8-162 | prochloraz |
| 10-1243 | 8-163 | prochloraz |
| 10-1244 | 8-164 | prochloraz |
| 10-1245 | 8-165 | prochloraz |
| 10-1246 | 8-166 | prochloraz |
| 10-1247 | 8-167 | prochloraz |
| 10-1248 | 8-168 | prochloraz |
| 10-1249 | 8-169 | prochloraz |
| 10-1250 | 8-170 | prochloraz |
| 10-1251 | 8-171 | prochloraz |
| 10-1252 | 8-172 | prochloraz |
| 10-1253 | 8-173 | prochloraz |
| 10-1254 | 8-174 | prochloraz |
| 10-1255 | 8-175 | prochloraz |
| 10-1256 | 8-176 | prochloraz |
| 10-1257 | 8-177 | prochloraz |
| 10-1258 | 8-178 | prochloraz |
| 10-1259 | 8-179 | prochloraz |
| 10-1260 | 8-180 | prochloraz |
| 10-1261 | 8-1 | carbendazim |
| 10-1262 | 8-2 | carbendazim |
| 10-1263 | 8-3 | carbendazim |
| 10-1264 | 8-4 | carbendazim |
| 10-1265 | 8-5 | carbendazim |
| 10-1266 | 8-6 | carbendazim |
| 10-1267 | 8-7 | carbendazim |
| 10-1268 | 8-8 | carbendazim |
| 10-1269 | 8-9 | carbendazim |
| 10-1270 | 8-10 | carbendazim |
| 10-1271 | 8-11 | carbendazim |
| 10-1272 | 8-12 | carbendazim |
| 10-1273 | 8-13 | carbendazim |
| 10-1274 | 8-14 | carbendazim |
| 10-1275 | 8-15 | carbendazim |
| 10-1276 | 8-16 | carbendazim |
| 10-1277 | 8-17 | carbendazim |
| 10-1278 | 8-18 | carbendazim |
| 10-1279 | 8-19 | carbendazim |
| 10-1280 | 8-20 | carbendazim |
| 10-1281 | 8-21 | carbendazim |
| 10-1282 | 8-22 | carbendazim |
| 10-1283 | 8-23 | carbendazim |
| 10-1284 | 8-24 | carbendazim |
| 10-1285 | 8-25 | carbendazim |
| 10-1286 | 8-26 | carbendazim |
| 10-1287 | 8-27 | carbendazim |
| 10-1288 | 8-28 | carbendazim |
| 10-1289 | 8-29 | carbendazim |
| 10-1290 | 8-30 | carbendazim |
| 10-1291 | 8-31 | carbendazim |
| 10-1292 | 8-32 | carbendazim |
| 10-1293 | 8-33 | carbendazim |
| 10-1294 | 8-34 | carbendazim |
| 10-1295 | 8-35 | carbendazim |
| 10-1296 | 8-36 | carbendazim |
| 10-1297 | 8-37 | carbendazim |
| 10-1298 | 8-38 | carbendazim |
| 10-1299 | 8-39 | carbendazim |
| 10-1300 | 8-40 | carbendazim |
| 10-1301 | 8-41 | carbendazim |
| 10-1302 | 8-42 | carbendazim |
| 10-1303 | 8-43 | carbendazim |
| 10-1304 | 8-44 | carbendazim |
| 10-1305 | 8-45 | carbendazim |
| 10-1306 | 8-46 | carbendazim |
| 10-1307 | 8-47 | carbendazim |
| 10-1308 | 8-48 | carbendazim |
| 10-1309 | 8-49 | carbendazim |
| 10-1310 | 8-50 | carbendazim |
| 10-1311 | 8-51 | carbendazim |
| 10-1312 | 8-52 | carbendazim |
| 10-1313 | 8-53 | carbendazim |
| 10-1314 | 8-54 | carbendazim |
| 10-1315 | 8-55 | carbendazim |
| 10-1316 | 8-56 | carbendazim |
| 10-1317 | 8-57 | carbendazim |
| 10-1318 | 8-58 | carbendazim |
| 10-1319 | 8-59 | carbendazim |
| 10-1320 | 8-60 | carbendazim |
| 10-1321 | 8-61 | carbendazim |
| 10-1322 | 8-62 | carbendazim |
| 10-1323 | 8-63 | carbendazim |
| 10-1324 | 8-64 | carbendazim |
| 10-1325 | 8-65 | carbendazim |
| 10-1326 | 8-66 | carbendazim |
| 10-1327 | 8-67 | carbendazim |
| 10-1328 | 8-68 | carbendazim |
| 10-1329 | 8-69 | carbendazim |
| 10-1330 | 8-70 | carbendazim |

TABLE 10-continued

| No. | Binary combination | Active compound |
|---|---|---|
| 10-1331 | 8-71 | carbendazim |
| 10-1332 | 8-72 | carbendazim |
| 10-1333 | 8-73 | carbendazim |
| 10-1334 | 8-74 | carbendazim |
| 10-1335 | 8-75 | carbendazim |
| 10-1336 | 8-76 | carbendazim |
| 10-1337 | 8-77 | carbendazim |
| 10-1338 | 8-78 | carbendazim |
| 10-1339 | 8-79 | carbendazim |
| 10-1340 | 8-80 | carbendazim |
| 10-1341 | 8-81 | carbendazim |
| 10-1342 | 8-82 | carbendazim |
| 10-1343 | 8-83 | carbendazim |
| 10-1344 | 8-84 | carbendazim |
| 10-1345 | 8-85 | carbendazim |
| 10-1346 | 8-86 | carbendazim |
| 10-1347 | 8-87 | carbendazim |
| 10-1348 | 8-88 | carbendazim |
| 10-1349 | 8-89 | carbendazim |
| 10-1350 | 8-90 | carbendazim |
| 10-1351 | 8-91 | carbendazim |
| 10-1352 | 8-92 | carbendazim |
| 10-1353 | 8-93 | carbendazim |
| 10-1354 | 8-94 | carbendazim |
| 10-1355 | 8-95 | carbendazim |
| 10-1356 | 8-96 | carbendazim |
| 10-1357 | 8-97 | carbendazim |
| 10-1358 | 8-98 | carbendazim |
| 10-1359 | 8-99 | carbendazim |
| 10-1360 | 8-100 | carbendazim |
| 10-1361 | 8-101 | carbendazim |
| 10-1362 | 8-102 | carbendazim |
| 10-1363 | 8-103 | carbendazim |
| 10-1364 | 8-104 | carbendazim |
| 10-1365 | 8-105 | carbendazim |
| 10-1366 | 8-106 | carbendazim |
| 10-1367 | 8-107 | carbendazim |
| 10-1368 | 8-108 | carbendazim |
| 10-1369 | 8-109 | carbendazim |
| 10-1370 | 8-110 | carbendazim |
| 10-1371 | 8-111 | carbendazim |
| 10-1372 | 8-112 | carbendazim |
| 10-1373 | 8-113 | carbendazim |
| 10-1374 | 8-114 | carbendazim |
| 10-1375 | 8-115 | carbendazim |
| 10-1376 | 8-116 | carbendazim |
| 10-1377 | 8-117 | carbendazim |
| 10-1378 | 8-118 | carbendazim |
| 10-1379 | 8-119 | carbendazim |
| 10-1380 | 8-120 | carbendazim |
| 10-1381 | 8-121 | carbendazim |
| 10-1382 | 8-122 | carbendazim |
| 10-1383 | 8-123 | carbendazim |
| 10-1384 | 8-124 | carbendazim |
| 10-1385 | 8-125 | carbendazim |
| 10-1386 | 8-126 | carbendazim |
| 10-1387 | 8-127 | carbendazim |
| 10-1388 | 8-128 | carbendazim |
| 10-1389 | 8-129 | carbendazim |
| 10-1390 | 8-130 | carbendazim |
| 10-1391 | 8-131 | carbendazim |
| 10-1392 | 8-132 | carbendazim |
| 10-1393 | 8-133 | carbendazim |
| 10-1394 | 8-134 | carbendazim |
| 10-1395 | 8-135 | carbendazim |
| 10-1396 | 8-136 | carbendazim |
| 10-1397 | 8-137 | carbendazim |
| 10-1398 | 8-138 | carbendazim |
| 10-1399 | 8-139 | carbendazim |
| 10-1400 | 8-140 | carbendazim |
| 10-1401 | 8-141 | carbendazim |
| 10-1402 | 8-142 | carbendazim |
| 10-1403 | 8-143 | carbendazim |
| 10-1404 | 8-144 | carbendazim |
| 10-1405 | 8-145 | carbendazim |
| 10-1406 | 8-146 | carbendazim |
| 10-1407 | 8-147 | carbendazim |
| 10-1408 | 8-148 | carbendazim |
| 10-1409 | 8-149 | carbendazim |
| 10-1410 | 8-150 | carbendazim |
| 10-1411 | 8-151 | carbendazim |
| 10-1412 | 8-152 | carbendazim |
| 10-1413 | 8-153 | carbendazim |
| 10-1414 | 8-154 | carbendazim |
| 10-1415 | 8-155 | carbendazim |
| 10-1416 | 8-156 | carbendazim |
| 10-1417 | 8-157 | carbendazim |
| 10-1418 | 8-158 | carbendazim |
| 10-1419 | 8-159 | carbendazim |
| 10-1420 | 8-160 | carbendazim |
| 10-1421 | 8-161 | carbendazim |
| 10-1422 | 8-162 | carbendazim |
| 10-1423 | 8-163 | carbendazim |
| 10-1424 | 8-164 | carbendazim |
| 10-1425 | 8-165 | carbendazim |
| 10-1426 | 8-166 | carbendazim |
| 10-1427 | 8-167 | carbendazim |
| 10-1428 | 8-168 | carbendazim |
| 10-1429 | 8-169 | carbendazim |
| 10-1430 | 8-170 | carbendazim |
| 10-1431 | 8-171 | carbendazim |
| 10-1432 | 8-172 | carbendazim |
| 10-1433 | 8-173 | carbendazim |
| 10-1434 | 8-174 | carbendazim |
| 10-1435 | 8-175 | carbendazim |
| 10-1436 | 8-176 | carbendazim |
| 10-1437 | 8-177 | carbendazim |
| 10-1438 | 8-178 | carbendazim |
| 10-1439 | 8-179 | carbendazim |
| 10-1440 | 8-180 | carbendazim |
| 10-1441 | 8-1 | kresoxim-methyl |
| 10-1442 | 8-2 | kresoxim-methyl |
| 10-1443 | 8-3 | kresoxim-methyl |
| 10-1444 | 8-4 | kresoxim-methyl |
| 10-1445 | 8-5 | kresoxim-methyl |
| 10-1446 | 8-6 | kresoxim-methyl |
| 10-1447 | 8-7 | kresoxim-methyl |
| 10-1448 | 8-8 | kresoxim-methyl |
| 10-1449 | 8-9 | kresoxim-methyl |
| 10-1450 | 8-10 | kresoxim-methyl |
| 10-1451 | 8-11 | kresoxim-methyl |
| 10-1452 | 8-12 | kresoxim-methyl |
| 10-1453 | 8-13 | kresoxim-methyl |
| 10-1454 | 8-14 | kresoxim-methyl |
| 10-1455 | 8-15 | kresoxim-methyl |
| 10-1456 | 8-16 | kresoxim-methyl |
| 10-1457 | 8-17 | kresoxim-methyl |
| 10-1458 | 8-18 | kresoxim-methyl |
| 10-1459 | 8-19 | kresoxim-methyl |
| 10-1460 | 8-20 | kresoxim-methyl |
| 10-1461 | 8-21 | kresoxim-methyl |
| 10-1462 | 8-22 | kresoxim-methyl |

TABLE 10-continued

| No. | Binary combination | Active compound |
|---|---|---|
| 10-1463 | 8-23 | kresoxim-methyl |
| 10-1464 | 8-24 | kresoxim-methyl |
| 10-1465 | 8-25 | kresoxim-methyl |
| 10-1466 | 8-26 | kresoxim-methyl |
| 10-1467 | 8-27 | kresoxim-methyl |
| 10-1468 | 8-28 | kresoxim-methyl |
| 10-1469 | 8-29 | kresoxim-methyl |
| 10-1470 | 8-30 | kresoxim-methyl |
| 10-1471 | 8-31 | kresoxim-methyl |
| 10-1472 | 8-32 | kresoxim-methyl |
| 10-1473 | 8-33 | kresoxim-methyl |
| 10-1474 | 8-34 | kresoxim-methyl |
| 10-1475 | 8-35 | kresoxim-methyl |
| 10-1476 | 8-36 | kresoxim-methyl |
| 10-1477 | 8-37 | kresoxim-methyl |
| 10-1478 | 8-38 | kresoxim-methyl |
| 10-1479 | 8-39 | kresoxim-methyl |
| 10-1480 | 8-40 | kresoxim-methyl |
| 10-1481 | 8-41 | kresoxim-methyl |
| 10-1482 | 8-42 | kresoxim-methyl |
| 10-1483 | 8-43 | kresoxim-methyl |
| 10-1484 | 8-44 | kresoxim-methyl |
| 10-1485 | 8-45 | kresoxim-methyl |
| 10-1486 | 8-46 | kresoxim-methyl |
| 10-1487 | 8-47 | kresoxim-methyl |
| 10-1488 | 8-48 | kresoxim-methyl |
| 10-1489 | 8-49 | kresoxim-methyl |
| 10-1490 | 8-50 | kresoxim-methyl |
| 10-1491 | 8-51 | kresoxim-methyl |
| 10-1492 | 8-52 | kresoxim-methyl |
| 10-1493 | 8-53 | kresoxim-methyl |
| 10-1494 | 8-54 | kresoxim-methyl |
| 10-1495 | 8-55 | kresoxim-methyl |
| 10-1496 | 8-56 | kresoxim-methyl |
| 10-1497 | 8-57 | kresoxim-methyl |
| 10-1498 | 8-58 | kresoxim-methyl |
| 10-1499 | 8-59 | kresoxim-methyl |
| 10-1500 | 8-60 | kresoxim-methyl |
| 10-1501 | 8-61 | kresoxim-methyl |
| 10-1502 | 8-62 | kresoxim-methyl |
| 10-1503 | 8-63 | kresoxim-methyl |
| 10-1504 | 8-64 | kresoxim-methyl |
| 10-1505 | 8-65 | kresoxim-methyl |
| 10-1506 | 8-66 | kresoxim-methyl |
| 10-1507 | 8-67 | kresoxim-methyl |
| 10-1508 | 8-68 | kresoxim-methyl |
| 10-1509 | 8-69 | kresoxim-methyl |
| 10-1510 | 8-70 | kresoxim-methyl |
| 10-1511 | 8-71 | kresoxim-methyl |
| 10-1512 | 8-72 | kresoxim-methyl |
| 10-1513 | 8-73 | kresoxim-methyl |
| 10-1514 | 8-74 | kresoxim-methyl |
| 10-1515 | 8-75 | kresoxim-methyl |
| 10-1516 | 8-76 | kresoxim-methyl |
| 10-1517 | 8-77 | kresoxim-methyl |
| 10-1518 | 8-78 | kresoxim-methyl |
| 10-1519 | 8-79 | kresoxim-methyl |
| 10-1520 | 8-80 | kresoxim-methyl |
| 10-1521 | 8-81 | kresoxim-methyl |
| 10-1522 | 8-82 | kresoxim-methyl |
| 10-1523 | 8-83 | kresoxim-methyl |
| 10-1524 | 8-84 | kresoxim-methyl |
| 10-1525 | 8-85 | kresoxim-methyl |
| 10-1526 | 8-86 | kresoxim-methyl |
| 10-1527 | 8-87 | kresoxim-methyl |
| 10-1528 | 8-88 | kresoxim-methyl |
| 10-1529 | 8-89 | kresoxim-methyl |
| 10-1530 | 8-90 | kresoxim-methyl |
| 10-1531 | 8-91 | kresoxim-methyl |
| 10-1532 | 8-92 | kresoxim-methyl |
| 10-1533 | 8-93 | kresoxim-methyl |
| 10-1534 | 8-94 | kresoxim-methyl |
| 10-1535 | 8-95 | kresoxim-methyl |
| 10-1536 | 8-96 | kresoxim-methyl |
| 10-1537 | 8-97 | kresoxim-methyl |
| 10-1538 | 8-98 | kresoxim-methyl |

TABLE 10-continued

| No. | Binary combination | Active compound |
|---|---|---|
| 10-1539 | 8-99 | kresoxim-methyl |
| 10-1540 | 8-100 | kresoxim-methyl |
| 10-1541 | 8-101 | kresoxim-methyl |
| 10-1542 | 8-102 | kresoxim-methyl |
| 10-1543 | 8-103 | kresoxim-methyl |
| 10-1544 | 8-104 | kresoxim-methyl |
| 10-1545 | 8-105 | kresoxim-methyl |
| 10-1546 | 8-106 | kresoxim-methyl |
| 10-1547 | 8-107 | kresoxim-methyl |
| 10-1548 | 8-108 | kresoxim-methyl |
| 10-1549 | 8-109 | kresoxim-methyl |
| 10-1550 | 8-110 | kresoxim-methyl |
| 10-1551 | 8-111 | kresoxim-methyl |
| 10-1552 | 8-112 | kresoxim-methyl |
| 10-1553 | 8-113 | kresoxim-methyl |
| 10-1554 | 8-114 | kresoxim-methyl |
| 10-1555 | 8-115 | kresoxim-methyl |
| 10-1556 | 8-116 | kresoxim-methyl |
| 10-1557 | 8-117 | kresoxim-methyl |
| 10-1558 | 8-118 | kresoxim-methyl |
| 10-1559 | 8-119 | kresoxim-methyl |
| 10-1560 | 8-120 | kresoxim-methyl |
| 10-1561 | 8-121 | kresoxim-methyl |
| 10-1562 | 8-122 | kresoxim-methyl |
| 10-1563 | 8-123 | kresoxim-methyl |
| 10-1564 | 8-124 | kresoxim-methyl |
| 10-1565 | 8-125 | kresoxim-methyl |
| 10-1566 | 8-126 | kresoxim-methyl |
| 10-1567 | 8-127 | kresoxim-methyl |
| 10-1568 | 8-128 | kresoxim-methyl |
| 10-1569 | 8-129 | kresoxim-methyl |
| 10-1570 | 8-130 | kresoxim-methyl |
| 10-1571 | 8-131 | kresoxim-methyl |
| 10-1572 | 8-132 | kresoxim-methyl |
| 10-1573 | 8-133 | kresoxim-methyl |
| 10-1574 | 8-134 | kresoxim-methyl |
| 10-1575 | 8-135 | kresoxim-methyl |
| 10-1576 | 8-136 | kresoxim-methyl |
| 10-1577 | 8-137 | kresoxim-methyl |
| 10-1578 | 8-138 | kresoxim-methyl |
| 10-1579 | 8-139 | kresoxim-methyl |
| 10-1580 | 8-140 | kresoxim-methyl |
| 10-1581 | 8-141 | kresoxim-methyl |
| 10-1582 | 8-142 | kresoxim-methyl |
| 10-1583 | 8-143 | kresoxim-methyl |
| 10-1584 | 8-144 | kresoxim-methyl |
| 10-1585 | 8-145 | kresoxim-methyl |
| 10-1586 | 8-146 | kresoxim-methyl |
| 10-1587 | 8-147 | kresoxim-methyl |
| 10-1588 | 8-148 | kresoxim-methyl |
| 10-1589 | 8-149 | kresoxim-methyl |
| 10-1590 | 8-150 | kresoxim-methyl |
| 10-1591 | 8-151 | kresoxim-methyl |
| 10-1592 | 8-152 | kresoxim-methyl |
| 10-1593 | 8-153 | kresoxim-methyl |
| 10-1594 | 8-154 | kresoxim-methyl |
| 10-1595 | 8-155 | kresoxim-methyl |
| 10-1596 | 8-156 | kresoxim-methyl |
| 10-1597 | 8-157 | kresoxim-methyl |
| 10-1598 | 8-158 | kresoxim-methyl |
| 10-1599 | 8-159 | kresoxim-methyl |
| 10-1600 | 8-160 | kresoxim-methyl |
| 10-1601 | 8-161 | kresoxim-methyl |
| 10-1602 | 8-162 | kresoxim-methyl |
| 10-1603 | 8-163 | kresoxim-methyl |
| 10-1604 | 8-164 | kresoxim-methyl |
| 10-1605 | 8-165 | kresoxim-methyl |
| 10-1606 | 8-166 | kresoxim-methyl |
| 10-1607 | 8-167 | kresoxim-methyl |
| 10-1608 | 8-168 | kresoxim-methyl |
| 10-1609 | 8-169 | kresoxim-methyl |
| 10-1610 | 8-170 | kresoxim-methyl |
| 10-1611 | 8-171 | kresoxim-methyl |
| 10-1612 | 8-172 | kresoxim-methyl |
| 10-1613 | 8-173 | kresoxim-methyl |
| 10-1614 | 8-174 | kresoxim-methyl |

TABLE 10-continued

| No. | Binary combination | Active compound |
|---|---|---|
| 10-1615 | 8-175 | kresoxim-methyl |
| 10-1616 | 8-176 | kresoxim-methyl |
| 10-1617 | 8-177 | kresoxim-methyl |
| 10-1618 | 8-178 | kresoxim-methyl |
| 10-1619 | 8-179 | kresoxim-methyl |
| 10-1620 | 8-180 | kresoxim-methyl |
| 10-1621 | 8-1 | pyraclostrobin |
| 10-1622 | 8-2 | pyraclostrobin |
| 10-1623 | 8-3 | pyraclostrobin |
| 10-1624 | 8-4 | pyraclostrobin |
| 10-1625 | 8-5 | pyraclostrobin |
| 10-1626 | 8-6 | pyraclostrobin |
| 10-1627 | 8-7 | pyraclostrobin |
| 10-1628 | 8-8 | pyraclostrobin |
| 10-1629 | 8-9 | pyraclostrobin |
| 10-1630 | 8-10 | pyraclostrobin |
| 10-1631 | 8-11 | pyraclostrobin |
| 10-1632 | 8-12 | pyraclostrobin |
| 10-1633 | 8-13 | pyraclostrobin |
| 10-1634 | 8-14 | pyraclostrobin |
| 10-1635 | 8-15 | pyraclostrobin |
| 10-1636 | 8-16 | pyraclostrobin |
| 10-1637 | 8-17 | pyraclostrobin |
| 10-1638 | 8-18 | pyraclostrobin |
| 10-1639 | 8-19 | pyraclostrobin |
| 10-1640 | 8-20 | pyraclostrobin |
| 10-1641 | 8-21 | pyraclostrobin |
| 10-1642 | 8-22 | pyraclostrobin |
| 10-1643 | 8-23 | pyraclostrobin |
| 10-1644 | 8-24 | pyraclostrobin |
| 10-1645 | 8-25 | pyraclostrobin |
| 10-1646 | 8-26 | pyraclostrobin |
| 10-1647 | 8-27 | pyraclostrobin |
| 10-1648 | 8-28 | pyraclostrobin |
| 10-1649 | 8-29 | pyraclostrobin |
| 10-1650 | 8-30 | pyraclostrobin |
| 10-1651 | 8-31 | pyraclostrobin |
| 10-1652 | 8-32 | pyraclostrobin |
| 10-1653 | 8-33 | pyraclostrobin |
| 10-1654 | 8-34 | pyraclostrobin |
| 10-1655 | 8-35 | pyraclostrobin |
| 10-1656 | 8-36 | pyraclostrobin |
| 10-1657 | 8-37 | pyraclostrobin |
| 10-1658 | 8-38 | pyraclostrobin |
| 10-1659 | 8-39 | pyraclostrobin |
| 10-1660 | 8-40 | pyraclostrobin |
| 10-1661 | 8-41 | pyraclostrobin |
| 10-1662 | 8-42 | pyraclostrobin |
| 10-1663 | 8-43 | pyraclostrobin |
| 10-1664 | 8-44 | pyraclostrobin |
| 10-1665 | 8-45 | pyraclostrobin |
| 10-1666 | 8-46 | pyraclostrobin |
| 10-1667 | 8-47 | pyraclostrobin |
| 10-1668 | 8-48 | pyraclostrobin |
| 10-1669 | 8-49 | pyraclostrobin |
| 10-1670 | 8-50 | pyraclostrobin |
| 10-1671 | 8-51 | pyraclostrobin |
| 10-1672 | 8-52 | pyraclostrobin |
| 10-1673 | 8-53 | pyraclostrobin |
| 10-1674 | 8-54 | pyraclostrobin |
| 10-1675 | 8-55 | pyraclostrobin |
| 10-1676 | 8-56 | pyraclostrobin |
| 10-1677 | 8-57 | pyraclostrobin |
| 10-1678 | 8-58 | pyraclostrobin |
| 10-1679 | 8-59 | pyraclostrobin |
| 10-1680 | 8-60 | pyraclostrobin |
| 10-1681 | 8-61 | pyraclostrobin |
| 10-1682 | 8-62 | pyraclostrobin |
| 10-1683 | 8-63 | pyraclostrobin |
| 10-1684 | 8-64 | pyraclostrobin |
| 10-1685 | 8-65 | pyraclostrobin |
| 10-1686 | 8-66 | pyraclostrobin |
| 10-1687 | 8-67 | pyraclostrobin |
| 10-1688 | 8-68 | pyraclostrobin |
| 10-1689 | 8-69 | pyraclostrobin |
| 10-1690 | 8-70 | pyraclostrobin |
| 10-1691 | 8-71 | pyraclostrobin |
| 10-1692 | 8-72 | pyraclostrobin |
| 10-1693 | 8-73 | pyraclostrobin |
| 10-1694 | 8-74 | pyraclostrobin |
| 10-1695 | 8-75 | pyraclostrobin |
| 10-1696 | 8-76 | pyraclostrobin |
| 10-1697 | 8-77 | pyraclostrobin |
| 10-1698 | 8-78 | pyraclostrobin |
| 10-1699 | 8-79 | pyraclostrobin |
| 10-1700 | 8-80 | pyraclostrobin |
| 10-1701 | 8-81 | pyraclostrobin |
| 10-1702 | 8-82 | pyraclostrobin |
| 10-1703 | 8-83 | pyraclostrobin |
| 10-1704 | 8-84 | pyraclostrobin |
| 10-1705 | 8-85 | pyraclostrobin |
| 10-1706 | 8-86 | pyraclostrobin |
| 10-1707 | 8-87 | pyraclostrobin |
| 10-1708 | 8-88 | pyraclostrobin |
| 10-1709 | 8-89 | pyraclostrobin |
| 10-1710 | 8-90 | pyraclostrobin |
| 10-1711 | 8-91 | pyraclostrobin |
| 10-1712 | 8-92 | pyraclostrobin |
| 10-1713 | 8-93 | pyraclostrobin |
| 10-1714 | 8-94 | pyraclostrobin |
| 10-1715 | 8-95 | pyraclostrobin |
| 10-1716 | 8-96 | pyraclostrobin |
| 10-1717 | 8-97 | pyraclostrobin |
| 10-1718 | 8-98 | pyraclostrobin |
| 10-1719 | 8-99 | pyraclostrobin |
| 10-1720 | 8-100 | pyraclostrobin |
| 10-1721 | 8-101 | pyraclostrobin |
| 10-1722 | 8-102 | pyraclostrobin |
| 10-1723 | 8-103 | pyraclostrobin |
| 10-1724 | 8-104 | pyraclostrobin |
| 10-1725 | 8-105 | pyraclostrobin |
| 10-1726 | 8-106 | pyraclostrobin |
| 10-1727 | 8-107 | pyraclostrobin |
| 10-1728 | 8-108 | pyraclostrobin |
| 10-1729 | 8-109 | pyraclostrobin |
| 10-1730 | 8-110 | pyraclostrobin |
| 10-1731 | 8-111 | pyraclostrobin |
| 10-1732 | 8-112 | pyraclostrobin |
| 10-1733 | 8-113 | pyraclostrobin |
| 10-1734 | 8-114 | pyraclostrobin |
| 10-1735 | 8-115 | pyraclostrobin |
| 10-1736 | 8-116 | pyraclostrobin |
| 10-1737 | 8-117 | pyraclostrobin |
| 10-1738 | 8-118 | pyraclostrobin |
| 10-1739 | 8-119 | pyraclostrobin |
| 10-1740 | 8-120 | pyraclostrobin |
| 10-1741 | 8-121 | pyraclostrobin |
| 10-1742 | 8-122 | pyraclostrobin |
| 10-1743 | 8-123 | pyraclostrobin |
| 10-1744 | 8-124 | pyraclostrobin |
| 10-1745 | 8-125 | pyraclostrobin |
| 10-1746 | 8-126 | pyraclostrobin |
| 10-1747 | 8-127 | pyraclostrobin |
| 10-1748 | 8-128 | pyraclostrobin |
| 10-1749 | 8-129 | pyraclostrobin |
| 10-1750 | 8-130 | pyraclostrobin |
| 10-1751 | 8-131 | pyraclostrobin |
| 10-1752 | 8-132 | pyraclostrobin |
| 10-1753 | 8-133 | pyraclostrobin |
| 10-1754 | 8-134 | pyraclostrobin |
| 10-1755 | 8-135 | pyraclostrobin |
| 10-1756 | 8-136 | pyraclostrobin |
| 10-1757 | 8-137 | pyraclostrobin |
| 10-1758 | 8-138 | pyraclostrobin |
| 10-1759 | 8-139 | pyraclostrobin |
| 10-1760 | 8-140 | pyraclostrobin |
| 10-1761 | 8-141 | pyraclostrobin |
| 10-1762 | 8-142 | pyraclostrobin |

TABLE 10-continued

| No. | Binary combination | Active compound |
|---|---|---|
| 10-1763 | 8-143 | pyraclostrobin |
| 10-1764 | 8-144 | pyraclostrobin |
| 10-1765 | 8-145 | pyraclostrobin |
| 10-1766 | 8-146 | pyraclostrobin |
| 10-1767 | 8-147 | pyraclostrobin |
| 10-1768 | 8-148 | pyraclostrobin |
| 10-1769 | 8-149 | pyraclostrobin |
| 10-1770 | 8-150 | pyraclostrobin |
| 10-1771 | 8-151 | pyraclostrobin |
| 10-1772 | 8-152 | pyraclostrobin |
| 10-1773 | 8-153 | pyraclostrobin |
| 10-1774 | 8-154 | pyraclostrobin |
| 10-1775 | 8-155 | pyraclostrobin |
| 10-1776 | 8-156 | pyraclostrobin |
| 10-1777 | 8-157 | pyraclostrobin |
| 10-1778 | 8-158 | pyraclostrobin |
| 10-1779 | 8-159 | pyraclostrobin |
| 10-1780 | 8-160 | pyraclostrobin |
| 10-1781 | 8-161 | pyraclostrobin |
| 10-1782 | 8-162 | pyraclostrobin |
| 10-1783 | 8-163 | pyraclostrobin |
| 10-1784 | 8-164 | pyraclostrobin |
| 10-1785 | 8-165 | pyraclostrobin |
| 10-1786 | 8-166 | pyraclostrobin |
| 10-1787 | 8-167 | pyraclostrobin |
| 10-1788 | 8-168 | pyraclostrobin |
| 10-1789 | 8-169 | pyraclostrobin |
| 10-1790 | 8-170 | pyraclostrobin |
| 10-1791 | 8-171 | pyraclostrobin |
| 10-1792 | 8-172 | pyraclostrobin |
| 10-1793 | 8-173 | pyraclostrobin |
| 10-1794 | 8-174 | pyraclostrobin |
| 10-1795 | 8-175 | pyraclostrobin |
| 10-1796 | 8-176 | pyraclostrobin |
| 10-1797 | 8-177 | pyraclostrobin |
| 10-1798 | 8-178 | pyraclostrobin |
| 10-1799 | 8-179 | pyraclostrobin |
| 10-1800 | 8-180 | pyraclostrobin |
| 10-1801 | 8-1 | orysastrobin |
| 10-1802 | 8-2 | orysastrobin |
| 10-1803 | 8-3 | orysastrobin |
| 10-1804 | 8-4 | orysastrobin |
| 10-1805 | 8-5 | orysastrobin |
| 10-1806 | 8-6 | orysastrobin |
| 10-1807 | 8-7 | orysastrobin |
| 10-1808 | 8-8 | orysastrobin |
| 10-1809 | 8-9 | orysastrobin |
| 10-1810 | 8-10 | orysastrobin |
| 10-1811 | 8-11 | orysastrobin |
| 10-1812 | 8-12 | orysastrobin |
| 10-1813 | 8-13 | orysastrobin |
| 10-1814 | 8-14 | orysastrobin |
| 10-1815 | 8-15 | orysastrobin |
| 10-1816 | 8-16 | orysastrobin |
| 10-1817 | 8-17 | orysastrobin |
| 10-1818 | 8-18 | orysastrobin |
| 10-1819 | 8-19 | orysastrobin |
| 10-1820 | 8-20 | orysastrobin |
| 10-1821 | 8-21 | orysastrobin |
| 10-1822 | 8-22 | orysastrobin |
| 10-1823 | 8-23 | orysastrobin |
| 10-1824 | 8-24 | orysastrobin |
| 10-1825 | 8-25 | orysastrobin |
| 10-1826 | 8-26 | orysastrobin |
| 10-1827 | 8-27 | orysastrobin |
| 10-1828 | 8-28 | orysastrobin |
| 10-1829 | 8-29 | orysastrobin |
| 10-1830 | 8-30 | orysastrobin |
| 10-1831 | 8-31 | orysastrobin |
| 10-1832 | 8-32 | orysastrobin |
| 10-1833 | 8-33 | orysastrobin |
| 10-1834 | 8-34 | orysastrobin |
| 10-1835 | 8-35 | orysastrobin |
| 10-1836 | 8-36 | orysastrobin |
| 10-1837 | 8-37 | orysastrobin |
| 10-1838 | 8-38 | orysastrobin |
| 10-1839 | 8-39 | orysastrobin |
| 10-1840 | 8-40 | orysastrobin |
| 10-1841 | 8-41 | orysastrobin |
| 10-1842 | 8-42 | orysastrobin |
| 10-1843 | 8-43 | orysastrobin |
| 10-1844 | 8-44 | orysastrobin |
| 10-1845 | 8-45 | orysastrobin |
| 10-1846 | 8-46 | orysastrobin |
| 10-1847 | 8-47 | orysastrobin |
| 10-1848 | 8-48 | orysastrobin |
| 10-1849 | 8-49 | orysastrobin |
| 10-1850 | 8-50 | orysastrobin |
| 10-1851 | 8-51 | orysastrobin |
| 10-1852 | 8-52 | orysastrobin |
| 10-1853 | 8-53 | orysastrobin |
| 10-1854 | 8-54 | orysastrobin |
| 10-1855 | 8-55 | orysastrobin |
| 10-1856 | 8-56 | orysastrobin |
| 10-1857 | 8-57 | orysastrobin |
| 10-1858 | 8-58 | orysastrobin |
| 10-1859 | 8-59 | orysastrobin |
| 10-1860 | 8-60 | orysastrobin |
| 10-1861 | 8-61 | orysastrobin |
| 10-1862 | 8-62 | orysastrobin |
| 10-1863 | 8-63 | orysastrobin |
| 10-1864 | 8-64 | orysastrobin |
| 10-1865 | 8-65 | orysastrobin |
| 10-1866 | 8-66 | orysastrobin |
| 10-1867 | 8-67 | orysastrobin |
| 10-1868 | 8-68 | orysastrobin |
| 10-1869 | 8-69 | orysastrobin |
| 10-1870 | 8-70 | orysastrobin |
| 10-1871 | 8-71 | orysastrobin |
| 10-1872 | 8-72 | orysastrobin |
| 10-1873 | 8-73 | orysastrobin |
| 10-1874 | 8-74 | orysastrobin |
| 10-1875 | 8-75 | orysastrobin |
| 10-1876 | 8-76 | orysastrobin |
| 10-1877 | 8-77 | orysastrobin |
| 10-1878 | 8-78 | orysastrobin |
| 10-1879 | 8-79 | orysastrobin |
| 10-1880 | 8-80 | orysastrobin |
| 10-1881 | 8-81 | orysastrobin |
| 10-1882 | 8-82 | orysastrobin |
| 10-1883 | 8-83 | orysastrobin |
| 10-1884 | 8-84 | orysastrobin |
| 10-1885 | 8-85 | orysastrobin |
| 10-1886 | 8-86 | orysastrobin |
| 10-1887 | 8-87 | orysastrobin |
| 10-1888 | 8-88 | orysastrobin |
| 10-1889 | 8-89 | orysastrobin |
| 10-1890 | 8-90 | orysastrobin |
| 10-1891 | 8-91 | orysastrobin |
| 10-1892 | 8-92 | orysastrobin |
| 10-1893 | 8-93 | orysastrobin |
| 10-1894 | 8-94 | orysastrobin |
| 10-1895 | 8-95 | orysastrobin |
| 10-1896 | 8-96 | orysastrobin |
| 10-1897 | 8-97 | orysastrobin |
| 10-1898 | 8-98 | orysastrobin |
| 10-1899 | 8-99 | orysastrobin |
| 10-1900 | 8-100 | orysastrobin |
| 10-1901 | 8-101 | orysastrobin |
| 10-1902 | 8-102 | orysastrobin |
| 10-1903 | 8-103 | orysastrobin |
| 10-1904 | 8-104 | orysastrobin |
| 10-1905 | 8-105 | orysastrobin |
| 10-1906 | 8-106 | orysastrobin |
| 10-1907 | 8-107 | orysastrobin |
| 10-1908 | 8-108 | orysastrobin |
| 10-1909 | 8-109 | orysastrobin |
| 10-1910 | 8-110 | orysastrobin |
| 10-1911 | 8-111 | orysastrobin |
| 10-1912 | 8-112 | orysastrobin |
| 10-1913 | 8-113 | orysastrobin |
| 10-1914 | 8-114 | orysastrobin |
| 10-1915 | 8-115 | orysastrobin |
| 10-1916 | 8-116 | orysastrobin |

TABLE 10-continued

| No. | Binary combination | Active compound |
|---|---|---|
| 10-1917 | 8-117 | orysastrobin |
| 10-1918 | 8-118 | orysastrobin |
| 10-1919 | 8-119 | orysastrobin |
| 10-1920 | 8-120 | orysastrobin |
| 10-1921 | 8-121 | orysastrobin |
| 10-1922 | 8-122 | orysastrobin |
| 10-1923 | 8-123 | orysastrobin |
| 10-1924 | 8-124 | orysastrobin |
| 10-1925 | 8-125 | orysastrobin |
| 10-1926 | 8-126 | orysastrobin |
| 10-1927 | 8-127 | orysastrobin |
| 10-1928 | 8-128 | orysastrobin |
| 10-1929 | 8-129 | orysastrobin |
| 10-1930 | 8-130 | orysastrobin |
| 10-1931 | 8-131 | orysastrobin |
| 10-1932 | 8-132 | orysastrobin |
| 10-1933 | 8-133 | orysastrobin |
| 10-1934 | 8-134 | orysastrobin |
| 10-1935 | 8-135 | orysastrobin |
| 10-1936 | 8-136 | orysastrobin |
| 10-1937 | 8-137 | orysastrobin |
| 10-1938 | 8-138 | orysastrobin |
| 10-1939 | 8-139 | orysastrobin |
| 10-1940 | 8-140 | orysastrobin |
| 10-1941 | 8-141 | orysastrobin |
| 10-1942 | 8-142 | orysastrobin |
| 10-1943 | 8-143 | orysastrobin |
| 10-1944 | 8-144 | orysastrobin |
| 10-1945 | 8-145 | orysastrobin |
| 10-1946 | 8-146 | orysastrobin |
| 10-1947 | 8-147 | orysastrobin |
| 10-1948 | 8-148 | orysastrobin |
| 10-1949 | 8-149 | orysastrobin |
| 10-1950 | 8-150 | orysastrobin |
| 10-1951 | 8-151 | orysastrobin |
| 10-1952 | 8-152 | orysastrobin |
| 10-1953 | 8-153 | orysastrobin |
| 10-1954 | 8-154 | orysastrobin |
| 10-1955 | 8-155 | orysastrobin |
| 10-1956 | 8-156 | orysastrobin |
| 10-1957 | 8-157 | orysastrobin |
| 10-1958 | 8-158 | orysastrobin |
| 10-1959 | 8-159 | orysastrobin |
| 10-1960 | 8-160 | orysastrobin |
| 10-1961 | 8-161 | orysastrobin |
| 10-1962 | 8-162 | orysastrobin |
| 10-1963 | 8-163 | orysastrobin |
| 10-1964 | 8-164 | orysastrobin |
| 10-1965 | 8-165 | orysastrobin |
| 10-1966 | 8-166 | orysastrobin |
| 10-1967 | 8-167 | orysastrobin |
| 10-1968 | 8-168 | orysastrobin |
| 10-1969 | 8-169 | orysastrobin |
| 10-1970 | 8-170 | orysastrobin |
| 10-1971 | 8-171 | orysastrobin |
| 10-1972 | 8-172 | orysastrobin |
| 10-1973 | 8-173 | orysastrobin |
| 10-1974 | 8-174 | orysastrobin |
| 10-1975 | 8-175 | orysastrobin |
| 10-1976 | 8-176 | orysastrobin |
| 10-1977 | 8-177 | orysastrobin |
| 10-1978 | 8-178 | orysastrobin |
| 10-1979 | 8-179 | orysastrobin |
| 10-1980 | 8-180 | orysastrobin |
| 10-1981 | 8-1 | dimethomorph |
| 10-1982 | 8-2 | dimethomorph |
| 10-1983 | 8-3 | dimethomorph |
| 10-1984 | 8-4 | dimethomorph |
| 10-1985 | 8-5 | dimethomorph |
| 10-1986 | 8-6 | dimethomorph |
| 10-1987 | 8-7 | dimethomorph |
| 10-1988 | 8-8 | dimethomorph |
| 10-1989 | 8-9 | dimethomorph |
| 10-1990 | 8-10 | dimethomorph |
| 10-1991 | 8-11 | dimethomorph |
| 10-1992 | 8-12 | dimethomorph |
| 10-1993 | 8-13 | dimethomorph |
| 10-1994 | 8-14 | dimethomorph |
| 10-1995 | 8-15 | dimethomorph |
| 10-1996 | 8-16 | dimethomorph |
| 10-1997 | 8-17 | dimethomorph |
| 10-1998 | 8-18 | dimethomorph |
| 10-1999 | 8-19 | dimethomorph |
| 10-2000 | 8-20 | dimethomorph |
| 10-2001 | 8-21 | dimethomorph |
| 10-2002 | 8-22 | dimethomorph |
| 10-2003 | 8-23 | dimethomorph |
| 10-2004 | 8-24 | dimethomorph |
| 10-2005 | 8-25 | dimethomorph |
| 10-2006 | 8-26 | dimethomorph |
| 10-2007 | 8-27 | dimethomorph |
| 10-2008 | 8-28 | dimethomorph |
| 10-2009 | 8-29 | dimethomorph |
| 10-2010 | 8-30 | dimethomorph |
| 10-2011 | 8-31 | dimethomorph |
| 10-2012 | 8-32 | dimethomorph |
| 10-2013 | 8-33 | dimethomorph |
| 10-2014 | 8-34 | dimethomorph |
| 10-2015 | 8-35 | dimethomorph |
| 10-2016 | 8-36 | dimethomorph |
| 10-2017 | 8-37 | dimethomorph |
| 10-2018 | 8-38 | dimethomorph |
| 10-2019 | 8-39 | dimethomorph |
| 10-2020 | 8-40 | dimethomorph |
| 10-2021 | 8-41 | dimethomorph |
| 10-2022 | 8-42 | dimethomorph |
| 10-2023 | 8-43 | dimethomorph |
| 10-2024 | 8-44 | dimethomorph |
| 10-2025 | 8-45 | dimethomorph |
| 10-2026 | 8-46 | dimethomorph |
| 10-2027 | 8-47 | dimethomorph |
| 10-2028 | 8-48 | dimethomorph |
| 10-2029 | 8-49 | dimethomorph |
| 10-2030 | 8-50 | dimethomorph |
| 10-2031 | 8-51 | dimethomorph |
| 10-2032 | 8-52 | dimethomorph |
| 10-2033 | 8-53 | dimethomorph |
| 10-2034 | 8-54 | dimethomorph |
| 10-2035 | 8-55 | dimethomorph |
| 10-2036 | 8-56 | dimethomorph |
| 10-2037 | 8-57 | dimethomorph |
| 10-2038 | 8-58 | dimethomorph |
| 10-2039 | 8-59 | dimethomorph |
| 10-2040 | 8-60 | dimethomorph |
| 10-2041 | 8-61 | dimethomorph |
| 10-2042 | 8-62 | dimethomorph |
| 10-2043 | 8-63 | dimethomorph |
| 10-2044 | 8-64 | dimethomorph |
| 10-2045 | 8-65 | dimethomorph |
| 10-2046 | 8-66 | dimethomorph |
| 10-2047 | 8-67 | dimethomorph |
| 10-2048 | 8-68 | dimethomorph |
| 10-2049 | 8-69 | dimethomorph |
| 10-2050 | 8-70 | dimethomorph |
| 10-2051 | 8-71 | dimethomorph |
| 10-2052 | 8-72 | dimethomorph |
| 10-2053 | 8-73 | dimethomorph |
| 10-2054 | 8-74 | dimethomorph |
| 10-2055 | 8-75 | dimethomorph |
| 10-2056 | 8-76 | dimethomorph |
| 10-2057 | 8-77 | dimethomorph |
| 10-2058 | 8-78 | dimethomorph |
| 10-2059 | 8-79 | dimethomorph |
| 10-2060 | 8-80 | dimethomorph |
| 10-2061 | 8-81 | dimethomorph |
| 10-2062 | 8-82 | dimethomorph |
| 10-2063 | 8-83 | dimethomorph |
| 10-2064 | 8-84 | dimethomorph |
| 10-2065 | 8-85 | dimethomorph |
| 10-2066 | 8-86 | dimethomorph |
| 10-2067 | 8-87 | dimethomorph |
| 10-2068 | 8-88 | dimethomorph |
| 10-2069 | 8-89 | dimethomorph |
| 10-2070 | 8-90 | dimethomorph |

TABLE 10-continued

| No. | Binary combination | Active compound |
|---|---|---|
| 10-2071 | 8-91 | dimethomorph |
| 10-2072 | 8-92 | dimethomorph |
| 10-2073 | 8-93 | dimethomorph |
| 10-2074 | 8-94 | dimethomorph |
| 10-2075 | 8-95 | dimethomorph |
| 10-2076 | 8-96 | dimethomorph |
| 10-2077 | 8-97 | dimethomorph |
| 10-2078 | 8-98 | dimethomorph |
| 10-2079 | 8-99 | dimethomorph |
| 10-2080 | 8-100 | dimethomorph |
| 10-2081 | 8-101 | dimethomorph |
| 10-2082 | 8-102 | dimethomorph |
| 10-2083 | 8-103 | dimethomorph |
| 10-2084 | 8-104 | dimethomorph |
| 10-2085 | 8-105 | dimethomorph |
| 10-2086 | 8-106 | dimethomorph |
| 10-2087 | 8-107 | dimethomorph |
| 10-2088 | 8-108 | dimethomorph |
| 10-2089 | 8-109 | dimethomorph |
| 10-2090 | 8-110 | dimethomorph |
| 10-2091 | 8-111 | dimethomorph |
| 10-2092 | 8-112 | dimethomorph |
| 10-2093 | 8-113 | dimethomorph |
| 10-2094 | 8-114 | dimethomorph |
| 10-2095 | 8-115 | dimethomorph |
| 10-2096 | 8-116 | dimethomorph |
| 10-2097 | 8-117 | dimethomorph |
| 10-2098 | 8-118 | dimethomorph |
| 10-2099 | 8-119 | dimethomorph |
| 10-2100 | 8-120 | dimethomorph |
| 10-2101 | 8-121 | dimethomorph |
| 10-2102 | 8-122 | dimethomorph |
| 10-2103 | 8-123 | dimethomorph |
| 10-2104 | 8-124 | dimethomorph |
| 10-2105 | 8-125 | dimethomorph |
| 10-2106 | 8-126 | dimethomorph |
| 10-2107 | 8-127 | dimethomorph |
| 10-2108 | 8-128 | dimethomorph |
| 10-2109 | 8-129 | dimethomorph |
| 10-2110 | 8-130 | dimethomorph |
| 10-2111 | 8-131 | dimethomorph |
| 10-2112 | 8-132 | dimethomorph |
| 10-2113 | 8-133 | dimethomorph |
| 10-2114 | 8-134 | dimethomorph |
| 10-2115 | 8-135 | dimethomorph |
| 10-2116 | 8-136 | dimethomorph |
| 10-2117 | 8-137 | dimethomorph |
| 10-2118 | 8-138 | dimethomorph |
| 10-2119 | 8-139 | dimethomorph |
| 10-2120 | 8-140 | dimethomorph |
| 10-2121 | 8-141 | dimethomorph |
| 10-2122 | 8-142 | dimethomorph |
| 10-2123 | 8-143 | dimethomorph |
| 10-2124 | 8-144 | dimethomorph |
| 10-2125 | 8-145 | dimethomorph |
| 10-2126 | 8-146 | dimethomorph |
| 10-2127 | 8-147 | dimethomorph |
| 10-2128 | 8-148 | dimethomorph |
| 10-2129 | 8-149 | dimethomorph |
| 10-2130 | 8-150 | dimethomorph |
| 10-2131 | 8-151 | dimethomorph |
| 10-2132 | 8-152 | dimethomorph |
| 10-2133 | 8-153 | dimethomorph |
| 10-2134 | 8-154 | dimethomorph |
| 10-2135 | 8-155 | dimethomorph |
| 10-2136 | 8-156 | dimethomorph |
| 10-2137 | 8-157 | dimethomorph |
| 10-2138 | 8-158 | dimethomorph |
| 10-2139 | 8-159 | dimethomorph |
| 10-2140 | 8-160 | dimethomorph |
| 10-2141 | 8-161 | dimethomorph |
| 10-2142 | 8-162 | dimethomorph |
| 10-2143 | 8-163 | dimethomorph |
| 10-2144 | 8-164 | dimethomorph |
| 10-2145 | 8-165 | dimethomorph |
| 10-2146 | 8-166 | dimethomorph |
| 10-2147 | 8-167 | dimethomorph |
| 10-2148 | 8-168 | dimethomorph |
| 10-2149 | 8-169 | dimethomorph |
| 10-2150 | 8-170 | dimethomorph |
| 10-2151 | 8-171 | dimethomorph |
| 10-2152 | 8-172 | dimethomorph |
| 10-2153 | 8-173 | dimethomorph |
| 10-2154 | 8-174 | dimethomorph |
| 10-2155 | 8-175 | dimethomorph |
| 10-2156 | 8-176 | dimethomorph |
| 10-2157 | 8-177 | dimethomorph |
| 10-2158 | 8-178 | dimethomorph |
| 10-2159 | 8-179 | dimethomorph |
| 10-2160 | 8-180 | dimethomorph |
| 10-2161 | 8-1 | pyrimethanil |
| 10-2162 | 8-2 | pyrimethanil |
| 10-2163 | 8-3 | pyrimethanil |
| 10-2164 | 8-4 | pyrimethanil |
| 10-2165 | 8-5 | pyrimethanil |
| 10-2166 | 8-6 | pyrimethanil |
| 10-2167 | 8-7 | pyrimethanil |
| 10-2168 | 8-8 | pyrimethanil |
| 10-2169 | 8-9 | pyrimethanil |
| 10-2170 | 8-10 | pyrimethanil |
| 10-2171 | 8-11 | pyrimethanil |
| 10-2172 | 8-12 | pyrimethanil |
| 10-2173 | 8-13 | pyrimethanil |
| 10-2174 | 8-14 | pyrimethanil |
| 10-2175 | 8-15 | pyrimethanil |
| 10-2176 | 8-16 | pyrimethanil |
| 10-2177 | 8-17 | pyrimethanil |
| 10-2178 | 8-18 | pyrimethanil |
| 10-2179 | 8-19 | pyrimethanil |
| 10-2180 | 8-20 | pyrimethanil |
| 10-2181 | 8-21 | pyrimethanil |
| 10-2182 | 8-22 | pyrimethanil |
| 10-2183 | 8-23 | pyrimethanil |
| 10-2184 | 8-24 | pyrimethanil |
| 10-2185 | 8-25 | pyrimethanil |
| 10-2186 | 8-26 | pyrimethanil |
| 10-2187 | 8-27 | pyrimethanil |
| 10-2188 | 8-28 | pyrimethanil |
| 10-2189 | 8-29 | pyrimethanil |
| 10-2190 | 8-30 | pyrimethanil |
| 10-2191 | 8-31 | pyrimethanil |
| 10-2192 | 8-32 | pyrimethanil |
| 10-2193 | 8-33 | pyrimethanil |
| 10-2194 | 8-34 | pyrimethanil |
| 10-2195 | 8-35 | pyrimethanil |
| 10-2196 | 8-36 | pyrimethanil |
| 10-2197 | 8-37 | pyrimethanil |
| 10-2198 | 8-38 | pyrimethanil |
| 10-2199 | 8-39 | pyrimethanil |
| 10-2200 | 8-40 | pyrimethanil |
| 10-2201 | 8-41 | pyrimethanil |
| 10-2202 | 8-42 | pyrimethanil |
| 10-2203 | 8-43 | pyrimethanil |
| 10-2204 | 8-44 | pyrimethanil |
| 10-2205 | 8-45 | pyrimethanil |
| 10-2206 | 8-46 | pyrimethanil |
| 10-2207 | 8-47 | pyrimethanil |
| 10-2208 | 8-48 | pyrimethanil |
| 10-2209 | 8-49 | pyrimethanil |
| 10-2210 | 8-50 | pyrimethanil |
| 10-2211 | 8-51 | pyrimethanil |
| 10-2212 | 8-52 | pyrimethanil |
| 10-2213 | 8-53 | pyrimethanil |
| 10-2214 | 8-54 | pyrimethanil |
| 10-2215 | 8-55 | pyrimethanil |
| 10-2216 | 8-56 | pyrimethanil |
| 10-2217 | 8-57 | pyrimethanil |
| 10-2218 | 8-58 | pyrimethanil |
| 10-2219 | 8-59 | pyrimethanil |
| 10-2220 | 8-60 | pyrimethanil |
| 10-2221 | 8-61 | pyrimethanil |
| 10-2222 | 8-62 | pyrimethanil |
| 10-2223 | 8-63 | pyrimethanil |
| 10-2224 | 8-64 | pyrimethanil |

TABLE 10-continued

| No. | Binary combination | Active compound |
|---|---|---|
| 10-2225 | 8-65 | pyrimethanil |
| 10-2226 | 8-66 | pyrimethanil |
| 10-2227 | 8-67 | pyrimethanil |
| 10-2228 | 8-68 | pyrimethanil |
| 10-2229 | 8-69 | pyrimethanil |
| 10-2230 | 8-70 | pyrimethanil |
| 10-2231 | 8-71 | pyrimethanil |
| 10-2232 | 8-72 | pyrimethanil |
| 10-2233 | 8-73 | pyrimethanil |
| 10-2234 | 8-74 | pyrimethanil |
| 10-2235 | 8-75 | pyrimethanil |
| 10-2236 | 8-76 | pyrimethanil |
| 10-2237 | 8-77 | pyrimethanil |
| 10-2238 | 8-78 | pyrimethanil |
| 10-2239 | 8-79 | pyrimethanil |
| 10-2240 | 8-80 | pyrimethanil |
| 10-2241 | 8-81 | pyrimethanil |
| 10-2242 | 8-82 | pyrimethanil |
| 10-2243 | 8-83 | pyrimethanil |
| 10-2244 | 8-84 | pyrimethanil |
| 10-2245 | 8-85 | pyrimethanil |
| 10-2246 | 8-86 | pyrimethanil |
| 10-2247 | 8-87 | pyrimethanil |
| 10-2248 | 8-88 | pyrimethanil |
| 10-2249 | 8-89 | pyrimethanil |
| 10-2250 | 8-90 | pyrimethanil |
| 10-2251 | 8-91 | pyrimethanil |
| 10-2252 | 8-92 | pyrimethanil |
| 10-2253 | 8-93 | pyrimethanil |
| 10-2254 | 8-94 | pyrimethanil |
| 10-2255 | 8-95 | pyrimethanil |
| 10-2256 | 8-96 | pyrimethanil |
| 10-2257 | 8-97 | pyrimethanil |
| 10-2258 | 8-98 | pyrimethanil |
| 10-2259 | 8-99 | pyrimethanil |
| 10-2260 | 8-100 | pyrimethanil |
| 10-2261 | 8-101 | pyrimethanil |
| 10-2262 | 8-102 | pyrimethanil |
| 10-2263 | 8-103 | pyrimethanil |
| 10-2264 | 8-104 | pyrimethanil |
| 10-2265 | 8-105 | pyrimethanil |
| 10-2266 | 8-106 | pyrimethanil |
| 10-2267 | 8-107 | pyrimethanil |
| 10-2268 | 8-108 | pyrimethanil |
| 10-2269 | 8-109 | pyrimethanil |
| 10-2270 | 8-110 | pyrimethanil |
| 10-2271 | 8-111 | pyrimethanil |
| 10-2272 | 8-112 | pyrimethanil |
| 10-2273 | 8-113 | pyrimethanil |
| 10-2274 | 8-114 | pyrimethanil |
| 10-2275 | 8-115 | pyrimethanil |
| 10-2276 | 8-116 | pyrimethanil |
| 10-2277 | 8-117 | pyrimethanil |
| 10-2278 | 8-118 | pyrimethanil |
| 10-2279 | 8-119 | pyrimethanil |
| 10-2280 | 8-120 | pyrimethanil |
| 10-2281 | 8-121 | pyrimethanil |
| 10-2282 | 8-122 | pyrimethanil |
| 10-2283 | 8-123 | pyrimethanil |
| 10-2284 | 8-124 | pyrimethanil |
| 10-2285 | 8-125 | pyrimethanil |
| 10-2286 | 8-126 | pyrimethanil |
| 10-2287 | 8-127 | pyrimethanil |
| 10-2288 | 8-128 | pyrimethanil |
| 10-2289 | 8-129 | pyrimethanil |
| 10-2290 | 8-130 | pyrimethanil |
| 10-2291 | 8-131 | pyrimethanil |
| 10-2292 | 8-132 | pyrimethanil |
| 10-2293 | 8-133 | pyrimethanil |
| 10-2294 | 8-134 | pyrimethanil |
| 10-2295 | 8-135 | pyrimethanil |
| 10-2296 | 8-136 | pyrimethanil |
| 10-2297 | 8-137 | pyrimethanil |
| 10-2298 | 8-138 | pyrimethanil |
| 10-2299 | 8-139 | pyrimethanil |
| 10-2300 | 8-140 | pyrimethanil |
| 10-2301 | 8-141 | pyrimethanil |
| 10-2302 | 8-142 | pyrimethanil |
| 10-2303 | 8-143 | pyrimethanil |
| 10-2304 | 8-144 | pyrimethanil |
| 10-2305 | 8-145 | pyrimethanil |
| 10-2306 | 8-146 | pyrimethanil |
| 10-2307 | 8-147 | pyrimethanil |
| 10-2308 | 8-148 | pyrimethanil |
| 10-2309 | 8-149 | pyrimethanil |
| 10-2310 | 8-150 | pyrimethanil |
| 10-2311 | 8-151 | pyrimethanil |
| 10-2312 | 8-152 | pyrimethanil |
| 10-2313 | 8-153 | pyrimethanil |
| 10-2314 | 8-154 | pyrimethanil |
| 10-2315 | 8-155 | pyrimethanil |
| 10-2316 | 8-156 | pyrimethanil |
| 10-2317 | 8-157 | pyrimethanil |
| 10-2318 | 8-158 | pyrimethanil |
| 10-2319 | 8-159 | pyrimethanil |
| 10-2320 | 8-160 | pyrimethanil |
| 10-2321 | 8-161 | pyrimethanil |
| 10-2322 | 8-162 | pyrimethanil |
| 10-2323 | 8-163 | pyrimethanil |
| 10-2324 | 8-164 | pyrimethanil |
| 10-2325 | 8-165 | pyrimethanil |
| 10-2326 | 8-166 | pyrimethanil |
| 10-2327 | 8-167 | pyrimethanil |
| 10-2328 | 8-168 | pyrimethanil |
| 10-2329 | 8-169 | pyrimethanil |
| 10-2330 | 8-170 | pyrimethanil |
| 10-2331 | 8-171 | pyrimethanil |
| 10-2332 | 8-172 | pyrimethanil |
| 10-2333 | 8-173 | pyrimethanil |
| 10-2334 | 8-174 | pyrimethanil |
| 10-2335 | 8-175 | pyrimethanil |
| 10-2336 | 8-176 | pyrimethanil |
| 10-2337 | 8-177 | pyrimethanil |
| 10-2338 | 8-178 | pyrimethanil |
| 10-2339 | 8-179 | pyrimethanil |
| 10-2340 | 8-180 | pyrimethanil |
| 10-2341 | 8-1 | AC1 |
| 10-2342 | 8-2 | AC1 |
| 10-2343 | 8-3 | AC1 |
| 10-2344 | 8-4 | AC1 |
| 10-2345 | 8-5 | AC1 |
| 10-2346 | 8-6 | AC1 |
| 10-2347 | 8-7 | AC1 |
| 10-2348 | 8-8 | AC1 |
| 10-2349 | 8-9 | AC1 |
| 10-2350 | 8-10 | AC1 |
| 10-2351 | 8-11 | AC1 |
| 10-2352 | 8-12 | AC1 |
| 10-2353 | 8-13 | AC1 |
| 10-2354 | 8-14 | AC1 |
| 10-2355 | 8-15 | AC1 |
| 10-2356 | 8-16 | AC1 |
| 10-2357 | 8-17 | AC1 |
| 10-2358 | 8-18 | AC1 |
| 10-2359 | 8-19 | AC1 |
| 10-2360 | 8-20 | AC1 |
| 10-2361 | 8-21 | AC1 |
| 10-2362 | 8-22 | AC1 |
| 10-2363 | 8-23 | AC1 |
| 10-2364 | 8-24 | AC1 |
| 10-2365 | 8-25 | AC1 |
| 10-2366 | 8-26 | AC1 |
| 10-2367 | 8-27 | AC1 |
| 10-2368 | 8-28 | AC1 |
| 10-2369 | 8-29 | AC1 |
| 10-2370 | 8-30 | AC1 |
| 10-2371 | 8-31 | AC1 |
| 10-2372 | 8-32 | AC1 |
| 10-2373 | 8-33 | AC1 |
| 10-2374 | 8-34 | AC1 |
| 10-2375 | 8-35 | AC1 |
| 10-2376 | 8-36 | AC1 |
| 10-2377 | 8-37 | AC1 |
| 10-2378 | 8-38 | AC1 |

TABLE 10-continued

| No. | Binary combination | Active compound |
|---|---|---|
| 10-2379 | 8-39 | AC1 |
| 10-2380 | 8-40 | AC1 |
| 10-2381 | 8-41 | AC1 |
| 10-2382 | 8-42 | AC1 |
| 10-2383 | 8-43 | AC1 |
| 10-2384 | 8-44 | AC1 |
| 10-2385 | 8-45 | AC1 |
| 10-2386 | 8-46 | AC1 |
| 10-2387 | 8-47 | AC1 |
| 10-2388 | 8-48 | AC1 |
| 10-2389 | 8-49 | AC1 |
| 10-2390 | 8-50 | AC1 |
| 10-2391 | 8-51 | AC1 |
| 10-2392 | 8-52 | AC1 |
| 10-2393 | 8-53 | AC1 |
| 10-2394 | 8-54 | AC1 |
| 10-2395 | 8-55 | AC1 |
| 10-2396 | 8-56 | AC1 |
| 10-2397 | 8-57 | AC1 |
| 10-2398 | 8-58 | AC1 |
| 10-2399 | 8-59 | AC1 |
| 10-2400 | 8-60 | AC1 |
| 10-2401 | 8-61 | AC1 |
| 10-2402 | 8-62 | AC1 |
| 10-2403 | 8-63 | AC1 |
| 10-2404 | 8-64 | AC1 |
| 10-2405 | 8-65 | AC1 |
| 10-2406 | 8-66 | AC1 |
| 10-2407 | 8-67 | AC1 |
| 10-2408 | 8-68 | AC1 |
| 10-2409 | 8-69 | AC1 |
| 10-2410 | 8-70 | AC1 |
| 10-2411 | 8-71 | AC1 |
| 10-2412 | 8-72 | AC1 |
| 10-2413 | 8-73 | AC1 |
| 10-2414 | 8-74 | AC1 |
| 10-2415 | 8-75 | AC1 |
| 10-2416 | 8-76 | AC1 |
| 10-2417 | 8-77 | AC1 |
| 10-2418 | 8-78 | AC1 |
| 10-2419 | 8-79 | AC1 |
| 10-2420 | 8-80 | AC1 |
| 10-2421 | 8-81 | AC1 |
| 10-2422 | 8-82 | AC1 |
| 10-2423 | 8-83 | AC1 |
| 10-2424 | 8-84 | AC1 |
| 10-2425 | 8-85 | AC1 |
| 10-2426 | 8-86 | AC1 |
| 10-2427 | 8-87 | AC1 |
| 10-2428 | 8-88 | AC1 |
| 10-2429 | 8-89 | AC1 |
| 10-2430 | 8-90 | AC1 |
| 10-2431 | 8-91 | AC1 |
| 10-2432 | 8-92 | AC1 |
| 10-2433 | 8-93 | AC1 |
| 10-2434 | 8-94 | AC1 |
| 10-2435 | 8-95 | AC1 |
| 10-2436 | 8-96 | AC1 |
| 10-2437 | 8-97 | AC1 |
| 10-2438 | 8-98 | AC1 |
| 10-2439 | 8-99 | AC1 |
| 10-2440 | 8-100 | AC1 |
| 10-2441 | 8-101 | AC1 |
| 10-2442 | 8-102 | AC1 |
| 10-2443 | 8-103 | AC1 |
| 10-2444 | 8-104 | AC1 |
| 10-2445 | 8-105 | AC1 |
| 10-2446 | 8-106 | AC1 |
| 10-2447 | 8-107 | AC1 |
| 10-2448 | 8-108 | AC1 |
| 10-2449 | 8-109 | AC1 |
| 10-2450 | 8-110 | AC1 |
| 10-2451 | 8-111 | AC1 |
| 10-2452 | 8-112 | AC1 |
| 10-2453 | 8-113 | AC1 |
| 10-2454 | 8-114 | AC1 |
| 10-2455 | 8-115 | AC1 |
| 10-2456 | 8-116 | AC1 |
| 10-2457 | 8-117 | AC1 |
| 10-2458 | 8-118 | AC1 |
| 10-2459 | 8-119 | AC1 |
| 10-2460 | 8-120 | AC1 |
| 10-2461 | 8-121 | AC1 |
| 10-2462 | 8-122 | AC1 |
| 10-2463 | 8-123 | AC1 |
| 10-2464 | 8-124 | AC1 |
| 10-2465 | 8-125 | AC1 |
| 10-2466 | 8-126 | AC1 |
| 10-2467 | 8-127 | AC1 |
| 10-2468 | 8-128 | AC1 |
| 10-2469 | 8-129 | AC1 |
| 10-2470 | 8-130 | AC1 |
| 10-2471 | 8-131 | AC1 |
| 10-2472 | 8-132 | AC1 |
| 10-2473 | 8-133 | AC1 |
| 10-2474 | 8-134 | AC1 |
| 10-2475 | 8-135 | AC1 |
| 10-2476 | 8-136 | AC1 |
| 10-2477 | 8-137 | AC1 |
| 10-2478 | 8-138 | AC1 |
| 10-2479 | 8-139 | AC1 |
| 10-2480 | 8-140 | AC1 |
| 10-2481 | 8-141 | AC1 |
| 10-2482 | 8-142 | AC1 |
| 10-2483 | 8-143 | AC1 |
| 10-2484 | 8-144 | AC1 |
| 10-2485 | 8-145 | AC1 |
| 10-2486 | 8-146 | AC1 |
| 10-2487 | 8-147 | AC1 |
| 10-2488 | 8-148 | AC1 |
| 10-2489 | 8-149 | AC1 |
| 10-2490 | 8-150 | AC1 |
| 10-2491 | 8-151 | AC1 |
| 10-2492 | 8-152 | AC1 |
| 10-2493 | 8-153 | AC1 |
| 10-2494 | 8-154 | AC1 |
| 10-2495 | 8-155 | AC1 |
| 10-2496 | 8-156 | AC1 |
| 10-2497 | 8-157 | AC1 |
| 10-2498 | 8-158 | AC1 |
| 10-2499 | 8-159 | AC1 |
| 10-2500 | 8-160 | AC1 |
| 10-2501 | 8-161 | AC1 |
| 10-2502 | 8-162 | AC1 |
| 10-2503 | 8-163 | AC1 |
| 10-2504 | 8-164 | AC1 |
| 10-2505 | 8-165 | AC1 |
| 10-2506 | 8-166 | AC1 |
| 10-2507 | 8-167 | AC1 |
| 10-2508 | 8-168 | AC1 |
| 10-2509 | 8-169 | AC1 |
| 10-2510 | 8-170 | AC1 |
| 10-2511 | 8-171 | AC1 |
| 10-2512 | 8-172 | AC1 |
| 10-2513 | 8-173 | AC1 |
| 10-2514 | 8-174 | AC1 |
| 10-2515 | 8-175 | AC1 |
| 10-2516 | 8-176 | AC1 |
| 10-2517 | 8-177 | AC1 |
| 10-2518 | 8-178 | AC1 |
| 10-2519 | 8-179 | AC1 |
| 10-2520 | 8-180 | AC1 |
| 10-2521 | 8-1 | dodemorph |
| 10-2522 | 8-2 | dodemorph |
| 10-2523 | 8-3 | dodemorph |
| 10-2524 | 8-4 | dodemorph |
| 10-2525 | 8-5 | dodemorph |
| 10-2526 | 8-6 | dodemorph |
| 10-2527 | 8-7 | dodemorph |
| 10-2528 | 8-8 | dodemorph |
| 10-2529 | 8-9 | dodemorph |
| 10-2530 | 8-10 | dodemorph |
| 10-2531 | 8-11 | dodemorph |
| 10-2532 | 8-12 | dodemorph |

TABLE 10-continued

| No. | Binary combination | Active compound |
|---|---|---|
| 10-2533 | 8-13 | dodemorph |
| 10-2534 | 8-14 | dodemorph |
| 10-2535 | 8-15 | dodemorph |
| 10-2536 | 8-16 | dodemorph |
| 10-2537 | 8-17 | dodemorph |
| 10-2538 | 8-18 | dodemorph |
| 10-2539 | 8-19 | dodemorph |
| 10-2540 | 8-20 | dodemorph |
| 10-2541 | 8-21 | dodemorph |
| 10-2542 | 8-22 | dodemorph |
| 10-2543 | 8-23 | dodemorph |
| 10-2544 | 8-24 | dodemorph |
| 10-2545 | 8-25 | dodemorph |
| 10-2546 | 8-26 | dodemorph |
| 10-2547 | 8-27 | dodemorph |
| 10-2548 | 8-28 | dodemorph |
| 10-2549 | 8-29 | dodemorph |
| 10-2550 | 8-30 | dodemorph |
| 10-2551 | 8-31 | dodemorph |
| 10-2552 | 8-32 | dodemorph |
| 10-2553 | 8-33 | dodemorph |
| 10-2554 | 8-34 | dodemorph |
| 10-2555 | 8-35 | dodemorph |
| 10-2556 | 8-36 | dodemorph |
| 10-2557 | 8-37 | dodemorph |
| 10-2558 | 8-38 | dodemorph |
| 10-2559 | 8-39 | dodemorph |
| 10-2560 | 8-40 | dodemorph |
| 10-2561 | 8-41 | dodemorph |
| 10-2562 | 8-42 | dodemorph |
| 10-2563 | 8-43 | dodemorph |
| 10-2564 | 8-44 | dodemorph |
| 10-2565 | 8-45 | dodemorph |
| 10-2566 | 8-46 | dodemorph |
| 10-2567 | 8-47 | dodemorph |
| 10-2568 | 8-48 | dodemorph |
| 10-2569 | 8-49 | dodemorph |
| 10-2570 | 8-50 | dodemorph |
| 10-2571 | 8-51 | dodemorph |
| 10-2572 | 8-52 | dodemorph |
| 10-2573 | 8-53 | dodemorph |
| 10-2574 | 8-54 | dodemorph |
| 10-2575 | 8-55 | dodemorph |
| 10-2576 | 8-56 | dodemorph |
| 10-2577 | 8-57 | dodemorph |
| 10-2578 | 8-58 | dodemorph |
| 10-2579 | 8-59 | dodemorph |
| 10-2580 | 8-60 | dodemorph |
| 10-2581 | 8-61 | dodemorph |
| 10-2582 | 8-62 | dodemorph |
| 10-2583 | 8-63 | dodemorph |
| 10-2584 | 8-64 | dodemorph |
| 10-2585 | 8-65 | dodemorph |
| 10-2586 | 8-66 | dodemorph |
| 10-2587 | 8-67 | dodemorph |
| 10-2588 | 8-68 | dodemorph |
| 10-2589 | 8-69 | dodemorph |
| 10-2590 | 8-70 | dodemorph |
| 10-2591 | 8-71 | dodemorph |
| 10-2592 | 8-72 | dodemorph |
| 10-2593 | 8-73 | dodemorph |
| 10-2594 | 8-74 | dodemorph |
| 10-2595 | 8-75 | dodemorph |
| 10-2596 | 8-76 | dodemorph |
| 10-2597 | 8-77 | dodemorph |
| 10-2598 | 8-78 | dodemorph |
| 10-2599 | 8-79 | dodemorph |
| 10-2600 | 8-80 | dodemorph |
| 10-2601 | 8-81 | dodemorph |
| 10-2602 | 8-82 | dodemorph |
| 10-2603 | 8-83 | dodemorph |
| 10-2604 | 8-84 | dodemorph |
| 10-2605 | 8-85 | dodemorph |
| 10-2606 | 8-86 | dodemorph |
| 10-2607 | 8-87 | dodemorph |
| 10-2608 | 8-88 | dodemorph |
| 10-2609 | 8-89 | dodemorph |
| 10-2610 | 8-90 | dodemorph |
| 10-2611 | 8-91 | dodemorph |
| 10-2612 | 8-92 | dodemorph |
| 10-2613 | 8-93 | dodemorph |
| 10-2614 | 8-94 | dodemorph |
| 10-2615 | 8-95 | dodemorph |
| 10-2616 | 8-96 | dodemorph |
| 10-2617 | 8-97 | dodemorph |
| 10-2618 | 8-98 | dodemorph |
| 10-2619 | 8-99 | dodemorph |
| 10-2620 | 8-100 | dodemorph |
| 10-2621 | 8-101 | dodemorph |
| 10-2622 | 8-102 | dodemorph |
| 10-2623 | 8-103 | dodemorph |
| 10-2624 | 8-104 | dodemorph |
| 10-2625 | 8-105 | dodemorph |
| 10-2626 | 8-106 | dodemorph |
| 10-2627 | 8-107 | dodemorph |
| 10-2628 | 8-108 | dodemorph |
| 10-2629 | 8-109 | dodemorph |
| 10-2630 | 8-110 | dodemorph |
| 10-2631 | 8-111 | dodemorph |
| 10-2632 | 8-112 | dodemorph |
| 10-2633 | 8-113 | dodemorph |
| 10-2634 | 8-114 | dodemorph |
| 10-2635 | 8-115 | dodemorph |
| 10-2636 | 8-116 | dodemorph |
| 10-2637 | 8-117 | dodemorph |
| 10-2638 | 8-118 | dodemorph |
| 10-2639 | 8-119 | dodemorph |
| 10-2640 | 8-120 | dodemorph |
| 10-2641 | 8-121 | dodemorph |
| 10-2642 | 8-122 | dodemorph |
| 10-2643 | 8-123 | dodemorph |
| 10-2644 | 8-124 | dodemorph |
| 10-2645 | 8-125 | dodemorph |
| 10-2646 | 8-126 | dodemorph |
| 10-2647 | 8-127 | dodemorph |
| 10-2648 | 8-128 | dodemorph |
| 10-2649 | 8-129 | dodemorph |
| 10-2650 | 8-130 | dodemorph |
| 10-2651 | 8-131 | dodemorph |
| 10-2652 | 8-132 | dodemorph |
| 10-2653 | 8-133 | dodemorph |
| 10-2654 | 8-134 | dodemorph |
| 10-2655 | 8-135 | dodemorph |
| 10-2656 | 8-136 | dodemorph |
| 10-2657 | 8-137 | dodemorph |
| 10-2658 | 8-138 | dodemorph |
| 10-2659 | 8-139 | dodemorph |
| 10-2660 | 8-140 | dodemorph |
| 10-2661 | 8-141 | dodemorph |
| 10-2662 | 8-142 | dodemorph |
| 10-2663 | 8-143 | dodemorph |
| 10-2664 | 8-144 | dodemorph |
| 10-2665 | 8-145 | dodemorph |
| 10-2666 | 8-146 | dodemorph |
| 10-2667 | 8-147 | dodemorph |
| 10-2668 | 8-148 | dodemorph |
| 10-2669 | 8-149 | dodemorph |
| 10-2670 | 8-150 | dodemorph |
| 10-2671 | 8-151 | dodemorph |
| 10-2672 | 8-152 | dodemorph |
| 10-2673 | 8-153 | dodemorph |
| 10-2674 | 8-154 | dodemorph |
| 10-2675 | 8-155 | dodemorph |
| 10-2676 | 8-156 | dodemorph |
| 10-2677 | 8-157 | dodemorph |
| 10-2678 | 8-158 | dodemorph |
| 10-2679 | 8-159 | dodemorph |
| 10-2680 | 8-160 | dodemorph |
| 10-2681 | 8-161 | dodemorph |
| 10-2682 | 8-162 | dodemorph |
| 10-2683 | 8-163 | dodemorph |
| 10-2684 | 8-164 | dodemorph |
| 10-2685 | 8-165 | dodemorph |
| 10-2686 | 8-166 | dodemorph |

TABLE 10-continued

| No. | Binary combination | Active compound |
|---|---|---|
| 10-2687 | 8-167 | dodemorph |
| 10-2688 | 8-168 | dodemorph |
| 10-2689 | 8-169 | dodemorph |
| 10-2690 | 8-170 | dodemorph |
| 10-2691 | 8-171 | dodemorph |
| 10-2692 | 8-172 | dodemorph |
| 10-2693 | 8-173 | dodemorph |
| 10-2694 | 8-174 | dodemorph |
| 10-2695 | 8-175 | dodemorph |
| 10-2696 | 8-176 | dodemorph |
| 10-2697 | 8-177 | dodemorph |
| 10-2698 | 8-178 | dodemorph |
| 10-2699 | 8-179 | dodemorph |
| 10-2700 | 8-180 | dodemorph |
| 10-2701 | 8-1 | fenpropimorph |
| 10-2702 | 8-2 | fenpropimorph |
| 10-2703 | 8-3 | fenpropimorph |
| 10-2704 | 8-4 | fenpropimorph |
| 10-2705 | 8-5 | fenpropimorph |
| 10-2706 | 8-6 | fenpropimorph |
| 10-2707 | 8-7 | fenpropimorph |
| 10-2708 | 8-8 | fenpropimorph |
| 10-2709 | 8-9 | fenpropimorph |
| 10-2710 | 8-10 | fenpropimorph |
| 10-2711 | 8-11 | fenpropimorph |
| 10-2712 | 8-12 | fenpropimorph |
| 10-2713 | 8-13 | fenpropimorph |
| 10-2714 | 8-14 | fenpropimorph |
| 10-2715 | 8-15 | fenpropimorph |
| 10-2716 | 8-16 | fenpropimorph |
| 10-2717 | 8-17 | fenpropimorph |
| 10-2718 | 8-18 | fenpropimorph |
| 10-2719 | 8-19 | fenpropimorph |
| 10-2720 | 8-20 | fenpropimorph |
| 10-2721 | 8-21 | fenpropimorph |
| 10-2722 | 8-22 | fenpropimorph |
| 10-2723 | 8-23 | fenpropimorph |
| 10-2724 | 8-24 | fenpropimorph |
| 10-2725 | 8-25 | fenpropimorph |
| 10-2726 | 8-26 | fenpropimorph |
| 10-2727 | 8-27 | fenpropimorph |
| 10-2728 | 8-28 | fenpropimorph |
| 10-2729 | 8-29 | fenpropimorph |
| 10-2730 | 8-30 | fenpropimorph |
| 10-2731 | 8-31 | fenpropimorph |
| 10-2732 | 8-32 | fenpropimorph |
| 10-2733 | 8-33 | fenpropimorph |
| 10-2734 | 8-34 | fenpropimorph |
| 10-2735 | 8-35 | fenpropimorph |
| 10-2736 | 8-36 | fenpropimorph |
| 10-2737 | 8-37 | fenpropimorph |
| 10-2738 | 8-38 | fenpropimorph |
| 10-2739 | 8-39 | fenpropimorph |
| 10-2740 | 8-40 | fenpropimorph |
| 10-2741 | 8-41 | fenpropimorph |
| 10-2742 | 8-42 | fenpropimorph |
| 10-2743 | 8-43 | fenpropimorph |
| 10-2744 | 8-44 | fenpropimorph |
| 10-2745 | 8-45 | fenpropimorph |
| 10-2746 | 8-46 | fenpropimorph |
| 10-2747 | 8-47 | fenpropimorph |
| 10-2748 | 8-48 | fenpropimorph |
| 10-2749 | 8-49 | fenpropimorph |
| 10-2750 | 8-50 | fenpropimorph |
| 10-2751 | 8-51 | fenpropimorph |
| 10-2752 | 8-52 | fenpropimorph |
| 10-2753 | 8-53 | fenpropimorph |
| 10-2754 | 8-54 | fenpropimorph |
| 10-2755 | 8-55 | fenpropimorph |
| 10-2756 | 8-56 | fenpropimorph |
| 10-2757 | 8-57 | fenpropimorph |
| 10-2758 | 8-58 | fenpropimorph |
| 10-2759 | 8-59 | fenpropimorph |
| 10-2760 | 8-60 | fenpropimorph |
| 10-2761 | 8-61 | fenpropimorph |
| 10-2762 | 8-62 | fenpropimorph |
| 10-2763 | 8-63 | fenpropimorph |
| 10-2764 | 8-64 | fenpropimorph |
| 10-2765 | 8-65 | fenpropimorph |
| 10-2766 | 8-66 | fenpropimorph |
| 10-2767 | 8-67 | fenpropimorph |
| 10-2768 | 8-68 | fenpropimorph |
| 10-2769 | 8-69 | fenpropimorph |
| 10-2770 | 8-70 | fenpropimorph |
| 10-2771 | 8-71 | fenpropimorph |
| 10-2772 | 8-72 | fenpropimorph |
| 10-2773 | 8-73 | fenpropimorph |
| 10-2774 | 8-74 | fenpropimorph |
| 10-2775 | 8-75 | fenpropimorph |
| 10-2776 | 8-76 | fenpropimorph |
| 10-2777 | 8-77 | fenpropimorph |
| 10-2778 | 8-78 | fenpropimorph |
| 10-2779 | 8-79 | fenpropimorph |
| 10-2780 | 8-80 | fenpropimorph |
| 10-2781 | 8-81 | fenpropimorph |
| 10-2782 | 8-82 | fenpropimorph |
| 10-2783 | 8-83 | fenpropimorph |
| 10-2784 | 8-84 | fenpropimorph |
| 10-2785 | 8-85 | fenpropimorph |
| 10-2786 | 8-86 | fenpropimorph |
| 10-2787 | 8-87 | fenpropimorph |
| 10-2788 | 8-88 | fenpropimorph |
| 10-2789 | 8-89 | fenpropimorph |
| 10-2790 | 8-90 | fenpropimorph |
| 10-2791 | 8-91 | fenpropimorph |
| 10-2792 | 8-92 | fenpropimorph |
| 10-2793 | 8-93 | fenpropimorph |
| 10-2794 | 8-94 | fenpropimorph |
| 10-2795 | 8-95 | fenpropimorph |
| 10-2796 | 8-96 | fenpropimorph |
| 10-2797 | 8-97 | fenpropimorph |
| 10-2798 | 8-98 | fenpropimorph |
| 10-2799 | 8-99 | fenpropimorph |
| 10-2800 | 8-100 | fenpropimorph |
| 10-2801 | 8-101 | fenpropimorph |
| 10-2802 | 8-102 | fenpropimorph |
| 10-2803 | 8-103 | fenpropimorph |
| 10-2804 | 8-104 | fenpropimorph |
| 10-2805 | 8-105 | fenpropimorph |
| 10-2806 | 8-106 | fenpropimorph |
| 10-2807 | 8-107 | fenpropimorph |
| 10-2808 | 8-108 | fenpropimorph |
| 10-2809 | 8-109 | fenpropimorph |
| 10-2810 | 8-110 | fenpropimorph |
| 10-2811 | 8-111 | fenpropimorph |
| 10-2812 | 8-112 | fenpropimorph |
| 10-2813 | 8-113 | fenpropimorph |
| 10-2814 | 8-114 | fenpropimorph |
| 10-2815 | 8-115 | fenpropimorph |
| 10-2816 | 8-116 | fenpropimorph |
| 10-2817 | 8-117 | fenpropimorph |
| 10-2818 | 8-118 | fenpropimorph |
| 10-2819 | 8-119 | fenpropimorph |
| 10-2820 | 8-120 | fenpropimorph |
| 10-2821 | 8-121 | fenpropimorph |
| 10-2822 | 8-122 | fenpropimorph |
| 10-2823 | 8-123 | fenpropimorph |
| 10-2824 | 8-124 | fenpropimorph |
| 10-2825 | 8-125 | fenpropimorph |
| 10-2826 | 8-126 | fenpropimorph |
| 10-2827 | 8-127 | fenpropimorph |
| 10-2828 | 8-128 | fenpropimorph |
| 10-2829 | 8-129 | fenpropimorph |
| 10-2830 | 8-130 | fenpropimorph |
| 10-2831 | 8-131 | fenpropimorph |
| 10-2832 | 8-132 | fenpropimorph |
| 10-2833 | 8-133 | fenpropimorph |
| 10-2834 | 8-134 | fenpropimorph |
| 10-2835 | 8-135 | fenpropimorph |
| 10-2836 | 8-136 | fenpropimorph |
| 10-2837 | 8-137 | fenpropimorph |
| 10-2838 | 8-138 | fenpropimorph |
| 10-2839 | 8-139 | fenpropimorph |
| 10-2840 | 8-140 | fenpropimorph |

TABLE 10-continued

| No. | Binary combination | Active compound |
|---|---|---|
| 10-2841 | 8-141 | fenpropimorph |
| 10-2842 | 8-142 | fenpropimorph |
| 10-2843 | 8-143 | fenpropimorph |
| 10-2844 | 8-144 | fenpropimorph |
| 10-2845 | 8-145 | fenpropimorph |
| 10-2846 | 8-146 | fenpropimorph |
| 10-2847 | 8-147 | fenpropimorph |
| 10-2848 | 8-148 | fenpropimorph |
| 10-2849 | 8-149 | fenpropimorph |
| 10-2850 | 8-150 | fenpropimorph |
| 10-2851 | 8-151 | fenpropimorph |
| 10-2852 | 8-152 | fenpropimorph |
| 10-2853 | 8-153 | fenpropimorph |
| 10-2854 | 8-154 | fenpropimorph |
| 10-2855 | 8-155 | fenpropimorph |
| 10-2856 | 8-156 | fenpropimorph |
| 10-2857 | 8-157 | fenpropimorph |
| 10-2858 | 8-158 | fenpropimorph |
| 10-2859 | 8-159 | fenpropimorph |
| 10-2860 | 8-160 | fenpropimorph |
| 10-2861 | 8-161 | fenpropimorph |
| 10-2862 | 8-162 | fenpropimorph |
| 10-2863 | 8-163 | fenpropimorph |
| 10-2864 | 8-164 | fenpropimorph |
| 10-2865 | 8-165 | fenpropimorph |
| 10-2866 | 8-166 | fenpropimorph |
| 10-2867 | 8-167 | fenpropimorph |
| 10-2868 | 8-168 | fenpropimorph |
| 10-2869 | 8-169 | fenpropimorph |
| 10-2870 | 8-170 | fenpropimorph |
| 10-2871 | 8-171 | fenpropimorph |
| 10-2872 | 8-172 | fenpropimorph |
| 10-2873 | 8-173 | fenpropimorph |
| 10-2874 | 8-174 | fenpropimorph |
| 10-2875 | 8-175 | fenpropimorph |
| 10-2876 | 8-176 | fenpropimorph |
| 10-2877 | 8-177 | fenpropimorph |
| 10-2878 | 8-178 | fenpropimorph |
| 10-2879 | 8-179 | fenpropimorph |
| 10-2880 | 8-180 | fenpropimorph |
| 10-2881 | 8-1 | tridemorph |
| 10-2882 | 8-2 | tridemorph |
| 10-2883 | 8-3 | tridemorph |
| 10-2884 | 8-4 | tridemorph |
| 10-2885 | 8-5 | tridemorph |
| 10-2886 | 8-6 | tridemorph |
| 10-2887 | 8-7 | tridemorph |
| 10-2888 | 8-8 | tridemorph |
| 10-2889 | 8-9 | tridemorph |
| 10-2890 | 8-10 | tridemorph |
| 10-2891 | 8-11 | tridemorph |
| 10-2892 | 8-12 | tridemorph |
| 10-2893 | 8-13 | tridemorph |
| 10-2894 | 8-14 | tridemorph |
| 10-2895 | 8-15 | tridemorph |
| 10-2896 | 8-16 | tridemorph |
| 10-2897 | 8-17 | tridemorph |
| 10-2898 | 8-18 | tridemorph |
| 10-2899 | 8-19 | tridemorph |
| 10-2900 | 8-20 | tridemorph |
| 10-2901 | 8-21 | tridemorph |
| 10-2902 | 8-22 | tridemorph |
| 10-2903 | 8-23 | tridemorph |
| 10-2904 | 8-24 | tridemorph |
| 10-2905 | 8-25 | tridemorph |
| 10-2906 | 8-26 | tridemorph |
| 10-2907 | 8-27 | tridemorph |
| 10-2908 | 8-28 | tridemorph |
| 10-2909 | 8-29 | tridemorph |
| 10-2910 | 8-30 | tridemorph |
| 10-2911 | 8-31 | tridemorph |
| 10-2912 | 8-32 | tridemorph |
| 10-2913 | 8-33 | tridemorph |
| 10-2914 | 8-34 | tridemorph |
| 10-2915 | 8-35 | tridemorph |
| 10-2916 | 8-36 | tridemorph |
| 10-2917 | 8-37 | tridemorph |
| 10-2918 | 8-38 | tridemorph |
| 10-2919 | 8-39 | tridemorph |
| 10-2920 | 8-40 | tridemorph |
| 10-2921 | 8-41 | tridemorph |
| 10-2922 | 8-42 | tridemorph |
| 10-2923 | 8-43 | tridemorph |
| 10-2924 | 8-44 | tridemorph |
| 10-2925 | 8-45 | tridemorph |
| 10-2926 | 8-46 | tridemorph |
| 10-2927 | 8-47 | tridemorph |
| 10-2928 | 8-48 | tridemorph |
| 10-2929 | 8-49 | tridemorph |
| 10-2930 | 8-50 | tridemorph |
| 10-2931 | 8-51 | tridemorph |
| 10-2932 | 8-52 | tridemorph |
| 10-2933 | 8-53 | tridemorph |
| 10-2934 | 8-54 | tridemorph |
| 10-2935 | 8-55 | tridemorph |
| 10-2936 | 8-56 | tridemorph |
| 10-2937 | 8-57 | tridemorph |
| 10-2938 | 8-58 | tridemorph |
| 10-2939 | 8-59 | tridemorph |
| 10-2940 | 8-60 | tridemorph |
| 10-2941 | 8-61 | tridemorph |
| 10-2942 | 8-62 | tridemorph |
| 10-2943 | 8-63 | tridemorph |
| 10-2944 | 8-64 | tridemorph |
| 10-2945 | 8-65 | tridemorph |
| 10-2946 | 8-66 | tridemorph |
| 10-2947 | 8-67 | tridemorph |
| 10-2948 | 8-68 | tridemorph |
| 10-2949 | 8-69 | tridemorph |
| 10-2950 | 8-70 | tridemorph |
| 10-2951 | 8-71 | tridemorph |
| 10-2952 | 8-72 | tridemorph |
| 10-2953 | 8-73 | tridemorph |
| 10-2954 | 8-74 | tridemorph |
| 10-2955 | 8-75 | tridemorph |
| 10-2956 | 8-76 | tridemorph |
| 10-2957 | 8-77 | tridemorph |
| 10-2958 | 8-78 | tridemorph |
| 10-2959 | 8-79 | tridemorph |
| 10-2960 | 8-80 | tridemorph |
| 10-2961 | 8-81 | tridemorph |
| 10-2962 | 8-82 | tridemorph |
| 10-2963 | 8-83 | tridemorph |
| 10-2964 | 8-84 | tridemorph |
| 10-2965 | 8-85 | tridemorph |
| 10-2966 | 8-86 | tridemorph |
| 10-2967 | 8-87 | tridemorph |
| 10-2968 | 8-88 | tridemorph |
| 10-2969 | 8-89 | tridemorph |
| 10-2970 | 8-90 | tridemorph |
| 10-2971 | 8-91 | tridemorph |
| 10-2972 | 8-92 | tridemorph |
| 10-2973 | 8-93 | tridemorph |
| 10-2974 | 8-94 | tridemorph |
| 10-2975 | 8-95 | tridemorph |
| 10-2976 | 8-96 | tridemorph |
| 10-2977 | 8-97 | tridemorph |
| 10-2978 | 8-98 | tridemorph |
| 10-2979 | 8-99 | tridemorph |
| 10-2980 | 8-100 | tridemorph |
| 10-2981 | 8-101 | tridemorph |
| 10-2982 | 8-102 | tridemorph |
| 10-2983 | 8-103 | tridemorph |
| 10-2984 | 8-104 | tridemorph |
| 10-2985 | 8-105 | tridemorph |
| 10-2986 | 8-106 | tridemorph |
| 10-2987 | 8-107 | tridemorph |
| 10-2988 | 8-108 | tridemorph |
| 10-2989 | 8-109 | tridemorph |
| 10-2990 | 8-110 | tridemorph |
| 10-2991 | 8-111 | tridemorph |
| 10-2992 | 8-112 | tridemorph |
| 10-2993 | 8-113 | tridemorph |
| 10-2994 | 8-114 | tridemorph |

TABLE 10-continued

| No. | Binary combination | Active compound |
|---|---|---|
| 10-2995 | 8-115 | tridemorph |
| 10-2996 | 8-116 | tridemorph |
| 10-2997 | 8-117 | tridemorph |
| 10-2998 | 8-118 | tridemorph |
| 10-2999 | 8-119 | tridemorph |
| 10-3000 | 8-120 | tridemorph |
| 10-3001 | 8-121 | tridemorph |
| 10-3002 | 8-122 | tridemorph |
| 10-3003 | 8-123 | tridemorph |
| 10-3004 | 8-124 | tridemorph |
| 10-3005 | 8-125 | tridemorph |
| 10-3006 | 8-126 | tridemorph |
| 10-3007 | 8-127 | tridemorph |
| 10-3008 | 8-128 | tridemorph |
| 10-3009 | 8-129 | tridemorph |
| 10-3010 | 8-130 | tridemorph |
| 10-3011 | 8-131 | tridemorph |
| 10-3012 | 8-132 | tridemorph |
| 10-3013 | 8-133 | tridemorph |
| 10-3014 | 8-134 | tridemorph |
| 10-3015 | 8-135 | tridemorph |
| 10-3016 | 8-136 | tridemorph |
| 10-3017 | 8-137 | tridemorph |
| 10-3018 | 8-138 | tridemorph |
| 10-3019 | 8-139 | tridemorph |
| 10-3020 | 8-140 | tridemorph |
| 10-3021 | 8-141 | tridemorph |
| 10-3022 | 8-142 | tridemorph |
| 10-3023 | 8-143 | tridemorph |
| 10-3024 | 8-144 | tridemorph |
| 10-3025 | 8-145 | tridemorph |
| 10-3026 | 8-146 | tridemorph |
| 10-3027 | 8-147 | tridemorph |
| 10-3028 | 8-148 | tridemorph |
| 10-3029 | 8-149 | tridemorph |
| 10-3030 | 8-150 | tridemorph |
| 10-3031 | 8-151 | tridemorph |
| 10-3032 | 8-152 | tridemorph |
| 10-3033 | 8-153 | tridemorph |
| 10-3034 | 8-154 | tridemorph |
| 10-3035 | 8-155 | tridemorph |
| 10-3036 | 8-156 | tridemorph |
| 10-3037 | 8-157 | tridemorph |
| 10-3038 | 8-158 | tridemorph |
| 10-3039 | 8-159 | tridemorph |
| 10-3040 | 8-160 | tridemorph |
| 10-3041 | 8-161 | tridemorph |
| 10-3042 | 8-162 | tridemorph |
| 10-3043 | 8-163 | tridemorph |
| 10-3044 | 8-164 | tridemorph |
| 10-3045 | 8-165 | tridemorph |
| 10-3046 | 8-166 | tridemorph |
| 10-3047 | 8-167 | tridemorph |
| 10-3048 | 8-168 | tridemorph |
| 10-3049 | 8-169 | tridemorph |
| 10-3050 | 8-170 | tridemorph |
| 10-3051 | 8-171 | tridemorph |
| 10-3052 | 8-172 | tridemorph |
| 10-3053 | 8-173 | tridemorph |
| 10-3054 | 8-174 | tridemorph |
| 10-3055 | 8-175 | tridemorph |
| 10-3056 | 8-176 | tridemorph |
| 10-3057 | 8-177 | tridemorph |
| 10-3058 | 8-178 | tridemorph |
| 10-3059 | 8-179 | tridemorph |
| 10-3060 | 8-180 | tridemorph |
| 10-3061 | 8-1 | iprodione |
| 10-3062 | 8-2 | iprodione |
| 10-3063 | 8-3 | iprodione |
| 10-3064 | 8-4 | iprodione |
| 10-3065 | 8-5 | iprodione |
| 10-3066 | 8-6 | iprodione |
| 10-3067 | 8-7 | iprodione |
| 10-3068 | 8-8 | iprodione |
| 10-3069 | 8-9 | iprodione |
| 10-3070 | 8-10 | iprodione |
| 10-3071 | 8-11 | iprodione |
| 10-3072 | 8-12 | iprodione |
| 10-3073 | 8-13 | iprodione |
| 10-3074 | 8-14 | iprodione |
| 10-3075 | 8-15 | iprodione |
| 10-3076 | 8-16 | iprodione |
| 10-3077 | 8-17 | iprodione |
| 10-3078 | 8-18 | iprodione |
| 10-3079 | 8-19 | iprodione |
| 10-3080 | 8-20 | iprodione |
| 10-3081 | 8-21 | iprodione |
| 10-3082 | 8-22 | iprodione |
| 10-3083 | 8-23 | iprodione |
| 10-3084 | 8-24 | iprodione |
| 10-3085 | 8-25 | iprodione |
| 10-3086 | 8-26 | iprodione |
| 10-3087 | 8-27 | iprodione |
| 10-3088 | 8-28 | iprodione |
| 10-3089 | 8-29 | iprodione |
| 10-3090 | 8-30 | iprodione |
| 10-3091 | 8-31 | iprodione |
| 10-3092 | 8-32 | iprodione |
| 10-3093 | 8-33 | iprodione |
| 10-3094 | 8-34 | iprodione |
| 10-3095 | 8-35 | iprodione |
| 10-3096 | 8-36 | iprodione |
| 10-3097 | 8-37 | iprodione |
| 10-3098 | 8-38 | iprodione |
| 10-3099 | 8-39 | iprodione |
| 10-3100 | 8-40 | iprodione |
| 10-3101 | 8-41 | iprodione |
| 10-3102 | 8-42 | iprodione |
| 10-3103 | 8-43 | iprodione |
| 10-3104 | 8-44 | iprodione |
| 10-3105 | 8-45 | iprodione |
| 10-3106 | 8-46 | iprodione |
| 10-3107 | 8-47 | iprodione |
| 10-3108 | 8-48 | iprodione |
| 10-3109 | 8-49 | iprodione |
| 10-3110 | 8-50 | iprodione |
| 10-3111 | 8-51 | iprodione |
| 10-3112 | 8-52 | iprodione |
| 10-3113 | 8-53 | iprodione |
| 10-3114 | 8-54 | iprodione |
| 10-3115 | 8-55 | iprodione |
| 10-3116 | 8-56 | iprodione |
| 10-3117 | 8-57 | iprodione |
| 10-3118 | 8-58 | iprodione |
| 10-3119 | 8-59 | iprodione |
| 10-3120 | 8-60 | iprodione |
| 10-3121 | 8-61 | iprodione |
| 10-3122 | 8-62 | iprodione |
| 10-3123 | 8-63 | iprodione |
| 10-3124 | 8-64 | iprodione |
| 10-3125 | 8-65 | iprodione |
| 10-3126 | 8-66 | iprodione |
| 10-3127 | 8-67 | iprodione |
| 10-3128 | 8-68 | iprodione |
| 10-3129 | 8-69 | iprodione |
| 10-3130 | 8-70 | iprodione |
| 10-3131 | 8-71 | iprodione |
| 10-3132 | 8-72 | iprodione |
| 10-3133 | 8-73 | iprodione |
| 10-3134 | 8-74 | iprodione |
| 10-3135 | 8-75 | iprodione |
| 10-3136 | 8-76 | iprodione |
| 10-3137 | 8-77 | iprodione |
| 10-3138 | 8-78 | iprodione |
| 10-3139 | 8-79 | iprodione |
| 10-3140 | 8-80 | iprodione |
| 10-3141 | 8-81 | iprodione |
| 10-3142 | 8-82 | iprodione |
| 10-3143 | 8-83 | iprodione |
| 10-3144 | 8-84 | iprodione |
| 10-3145 | 8-85 | iprodione |
| 10-3146 | 8-86 | iprodione |
| 10-3147 | 8-87 | iprodione |
| 10-3148 | 8-88 | iprodione |

TABLE 10-continued

| No. | Binary combination | Active compound |
|---|---|---|
| 10-3149 | 8-89 | iprodione |
| 10-3150 | 8-90 | iprodione |
| 10-3151 | 8-91 | iprodione |
| 10-3152 | 8-92 | iprodione |
| 10-3153 | 8-93 | iprodione |
| 10-3154 | 8-94 | iprodione |
| 10-3155 | 8-95 | iprodione |
| 10-3156 | 8-96 | iprodione |
| 10-3157 | 8-97 | iprodione |
| 10-3158 | 8-98 | iprodione |
| 10-3159 | 8-99 | iprodione |
| 10-3160 | 8-100 | iprodione |
| 10-3161 | 8-101 | iprodione |
| 10-3162 | 8-102 | iprodione |
| 10-3163 | 8-103 | iprodione |
| 10-3164 | 8-104 | iprodione |
| 10-3165 | 8-105 | iprodione |
| 10-3166 | 8-106 | iprodione |
| 10-3167 | 8-107 | iprodione |
| 10-3168 | 8-108 | iprodione |
| 10-3169 | 8-109 | iprodione |
| 10-3170 | 8-110 | iprodione |
| 10-3171 | 8-111 | iprodione |
| 10-3172 | 8-112 | iprodione |
| 10-3173 | 8-113 | iprodione |
| 10-3174 | 8-114 | iprodione |
| 10-3175 | 8-115 | iprodione |
| 10-3176 | 8-116 | iprodione |
| 10-3177 | 8-117 | iprodione |
| 10-3178 | 8-118 | iprodione |
| 10-3179 | 8-119 | iprodione |
| 10-3180 | 8-120 | iprodione |
| 10-3181 | 8-121 | iprodione |
| 10-3182 | 8-122 | iprodione |
| 10-3183 | 8-123 | iprodione |
| 10-3184 | 8-124 | iprodione |
| 10-3185 | 8-125 | iprodione |
| 10-3186 | 8-126 | iprodione |
| 10-3187 | 8-127 | iprodione |
| 10-3188 | 8-128 | iprodione |
| 10-3189 | 8-129 | iprodione |
| 10-3190 | 8-130 | iprodione |
| 10-3191 | 8-131 | iprodione |
| 10-3192 | 8-132 | iprodione |
| 10-3193 | 8-133 | iprodione |
| 10-3194 | 8-134 | iprodione |
| 10-3195 | 8-135 | iprodione |
| 10-3196 | 8-136 | iprodione |
| 10-3197 | 8-137 | iprodione |
| 10-3198 | 8-138 | iprodione |
| 10-3199 | 8-139 | iprodione |
| 10-3200 | 8-140 | iprodione |
| 10-3201 | 8-141 | iprodione |
| 10-3202 | 8-142 | iprodione |
| 10-3203 | 8-143 | iprodione |
| 10-3204 | 8-144 | iprodione |
| 10-3205 | 8-145 | iprodione |
| 10-3206 | 8-146 | iprodione |
| 10-3207 | 8-147 | iprodione |
| 10-3208 | 8-148 | iprodione |
| 10-3209 | 8-149 | iprodione |
| 10-3210 | 8-150 | iprodione |
| 10-3211 | 8-151 | iprodione |
| 10-3212 | 8-152 | iprodione |
| 10-3213 | 8-153 | iprodione |
| 10-3214 | 8-154 | iprodione |
| 10-3215 | 8-155 | iprodione |
| 10-3216 | 8-156 | iprodione |
| 10-3217 | 8-157 | iprodione |
| 10-3218 | 8-158 | iprodione |
| 10-3219 | 8-159 | iprodione |
| 10-3220 | 8-160 | iprodione |
| 10-3221 | 8-161 | iprodione |
| 10-3222 | 8-162 | iprodione |
| 10-3223 | 8-163 | iprodione |
| 10-3224 | 8-164 | iprodione |
| 10-3225 | 8-165 | iprodione |
| 10-3226 | 8-166 | iprodione |
| 10-3227 | 8-167 | iprodione |
| 10-3228 | 8-168 | iprodione |
| 10-3229 | 8-169 | iprodione |
| 10-3230 | 8-170 | iprodione |
| 10-3231 | 8-171 | iprodione |
| 10-3232 | 8-172 | iprodione |
| 10-3233 | 8-173 | iprodione |
| 10-3234 | 8-174 | iprodione |
| 10-3235 | 8-175 | iprodione |
| 10-3236 | 8-176 | iprodione |
| 10-3237 | 8-177 | iprodione |
| 10-3238 | 8-178 | iprodione |
| 10-3239 | 8-179 | iprodione |
| 10-3240 | 8-180 | iprodione |
| 10-3241 | 8-1 | vinclozolin |
| 10-3242 | 8-2 | vinclozolin |
| 10-3243 | 8-3 | vinclozolin |
| 10-3244 | 8-4 | vinclozolin |
| 10-3245 | 8-5 | vinclozolin |
| 10-3246 | 8-6 | vinclozolin |
| 10-3247 | 8-7 | vinclozolin |
| 10-3248 | 8-8 | vinclozolin |
| 10-3249 | 8-9 | vinclozolin |
| 10-3250 | 8-10 | vinclozolin |
| 10-3251 | 8-11 | vinclozolin |
| 10-3252 | 8-12 | vinclozolin |
| 10-3253 | 8-13 | vinclozolin |
| 10-3254 | 8-14 | vinclozolin |
| 10-3255 | 8-15 | vinclozolin |
| 10-3256 | 8-16 | vinclozolin |
| 10-3257 | 8-17 | vinclozolin |
| 10-3258 | 8-18 | vinclozolin |
| 10-3259 | 8-19 | vinclozolin |
| 10-3260 | 8-20 | vinclozolin |
| 10-3261 | 8-21 | vinclozolin |
| 10-3262 | 8-22 | vinclozolin |
| 10-3263 | 8-23 | vinclozolin |
| 10-3264 | 8-24 | vinclozolin |
| 10-3265 | 8-25 | vinclozolin |
| 10-3266 | 8-26 | vinclozolin |
| 10-3267 | 8-27 | vinclozolin |
| 10-3268 | 8-28 | vinclozolin |
| 10-3269 | 8-29 | vinclozolin |
| 10-3270 | 8-30 | vinclozolin |
| 10-3271 | 8-31 | vinclozolin |
| 10-3272 | 8-32 | vinclozolin |
| 10-3273 | 8-33 | vinclozolin |
| 10-3274 | 8-34 | vinclozolin |
| 10-3275 | 8-35 | vinclozolin |
| 10-3276 | 8-36 | vinclozolin |
| 10-3277 | 8-37 | vinclozolin |
| 10-3278 | 8-38 | vinclozolin |
| 10-3279 | 8-39 | vinclozolin |
| 10-3280 | 8-40 | vinclozolin |
| 10-3281 | 8-41 | vinclozolin |
| 10-3282 | 8-42 | vinclozolin |
| 10-3283 | 8-43 | vinclozolin |
| 10-3284 | 8-44 | vinclozolin |
| 10-3285 | 8-45 | vinclozolin |
| 10-3286 | 8-46 | vinclozolin |
| 10-3287 | 8-47 | vinclozolin |
| 10-3288 | 8-48 | vinclozolin |
| 10-3289 | 8-49 | vinclozolin |
| 10-3290 | 8-50 | vinclozolin |
| 10-3291 | 8-51 | vinclozolin |
| 10-3292 | 8-52 | vinclozolin |
| 10-3293 | 8-53 | vinclozolin |
| 10-3294 | 8-54 | vinclozolin |
| 10-3295 | 8-55 | vinclozolin |
| 10-3296 | 8-56 | vinclozolin |
| 10-3297 | 8-57 | vinclozolin |
| 10-3298 | 8-58 | vinclozolin |
| 10-3299 | 8-59 | vinclozolin |
| 10-3300 | 8-60 | vinclozolin |
| 10-3301 | 8-61 | vinclozolin |
| 10-3302 | 8-62 | vinclozolin |

TABLE 10-continued

| No. | Binary combination | Active compound |
|---|---|---|
| 10-3303 | 8-63 | vinclozolin |
| 10-3304 | 8-64 | vinclozolin |
| 10-3305 | 8-65 | vinclozolin |
| 10-3306 | 8-66 | vinclozolin |
| 10-3307 | 8-67 | vinclozolin |
| 10-3308 | 8-68 | vinclozolin |
| 10-3309 | 8-69 | vinclozolin |
| 10-3310 | 8-70 | vinclozolin |
| 10-3311 | 8-71 | vinclozolin |
| 10-3312 | 8-72 | vinclozolin |
| 10-3313 | 8-73 | vinclozolin |
| 10-3314 | 8-74 | vinclozolin |
| 10-3315 | 8-75 | vinclozolin |
| 10-3316 | 8-76 | vinclozolin |
| 10-3317 | 8-77 | vinclozolin |
| 10-3318 | 8-78 | vinclozolin |
| 10-3319 | 8-79 | vinclozolin |
| 10-3320 | 8-80 | vinclozolin |
| 10-3321 | 8-81 | vinclozolin |
| 10-3322 | 8-82 | vinclozolin |
| 10-3323 | 8-83 | vinclozolin |
| 10-3324 | 8-84 | vinclozolin |
| 10-3325 | 8-85 | vinclozolin |
| 10-3326 | 8-86 | vinclozolin |
| 10-3327 | 8-87 | vinclozolin |
| 10-3328 | 8-88 | vinclozolin |
| 10-3329 | 8-89 | vinclozolin |
| 10-3330 | 8-90 | vinclozolin |
| 10-3331 | 8-91 | vinclozolin |
| 10-3332 | 8-92 | vinclozolin |
| 10-3333 | 8-93 | vinclozolin |
| 10-3334 | 8-94 | vinclozolin |
| 10-3335 | 8-95 | vinclozolin |
| 10-3336 | 8-96 | vinclozolin |
| 10-3337 | 8-97 | vinclozolin |
| 10-3338 | 8-98 | vinclozolin |
| 10-3339 | 8-99 | vinclozolin |
| 10-3340 | 8-100 | vinclozolin |
| 10-3341 | 8-101 | vinclozolin |
| 10-3342 | 8-102 | vinclozolin |
| 10-3343 | 8-103 | vinclozolin |
| 10-3344 | 8-104 | vinclozolin |
| 10-3345 | 8-105 | vinclozolin |
| 10-3346 | 8-106 | vinclozolin |
| 10-3347 | 8-107 | vinclozolin |
| 10-3348 | 8-108 | vinclozolin |
| 10-3349 | 8-109 | vinclozolin |
| 10-3350 | 8-110 | vinclozolin |
| 10-3351 | 8-111 | vinclozolin |
| 10-3352 | 8-112 | vinclozolin |
| 10-3353 | 8-113 | vinclozolin |
| 10-3354 | 8-114 | vinclozolin |
| 10-3355 | 8-115 | vinclozolin |
| 10-3356 | 8-116 | vinclozolin |
| 10-3357 | 8-117 | vinclozolin |
| 10-3358 | 8-118 | vinclozolin |
| 10-3359 | 8-119 | vinclozolin |
| 10-3360 | 8-120 | vinclozolin |
| 10-3361 | 8-121 | vinclozolin |
| 10-3362 | 8-122 | vinclozolin |
| 10-3363 | 8-123 | vinclozolin |
| 10-3364 | 8-124 | vinclozolin |
| 10-3365 | 8-125 | vinclozolin |
| 10-3366 | 8-126 | vinclozolin |
| 10-3367 | 8-127 | vinclozolin |
| 10-3368 | 8-128 | vinclozolin |
| 10-3369 | 8-129 | vinclozolin |
| 10-3370 | 8-130 | vinclozolin |
| 10-3371 | 8-131 | vinclozolin |
| 10-3372 | 8-132 | vinclozolin |
| 10-3373 | 8-133 | vinclozolin |
| 10-3374 | 8-134 | vinclozolin |
| 10-3375 | 8-135 | vinclozolin |
| 10-3376 | 8-136 | vinclozolin |
| 10-3377 | 8-137 | vinclozolin |
| 10-3378 | 8-138 | vinclozolin |
| 10-3379 | 8-139 | vinclozolin |
| 10-3380 | 8-140 | vinclozolin |
| 10-3381 | 8-141 | vinclozolin |
| 10-3382 | 8-142 | vinclozolin |
| 10-3383 | 8-143 | vinclozolin |
| 10-3384 | 8-144 | vinclozolin |
| 10-3385 | 8-145 | vinclozolin |
| 10-3386 | 8-146 | vinclozolin |
| 10-3387 | 8-147 | vinclozolin |
| 10-3388 | 8-148 | vinclozolin |
| 10-3389 | 8-149 | vinclozolin |
| 10-3390 | 8-150 | vinclozolin |
| 10-3391 | 8-151 | vinclozolin |
| 10-3392 | 8-152 | vinclozolin |
| 10-3393 | 8-153 | vinclozolin |
| 10-3394 | 8-154 | vinclozolin |
| 10-3395 | 8-155 | vinclozolin |
| 10-3396 | 8-156 | vinclozolin |
| 10-3397 | 8-157 | vinclozolin |
| 10-3398 | 8-158 | vinclozolin |
| 10-3399 | 8-159 | vinclozolin |
| 10-3400 | 8-160 | vinclozolin |
| 10-3401 | 8-161 | vinclozolin |
| 10-3402 | 8-162 | vinclozolin |
| 10-3403 | 8-163 | vinclozolin |
| 10-3404 | 8-164 | vinclozolin |
| 10-3405 | 8-165 | vinclozolin |
| 10-3406 | 8-166 | vinclozolin |
| 10-3407 | 8-167 | vinclozolin |
| 10-3408 | 8-168 | vinclozolin |
| 10-3409 | 8-169 | vinclozolin |
| 10-3410 | 8-170 | vinclozolin |
| 10-3411 | 8-171 | vinclozolin |
| 10-3412 | 8-172 | vinclozolin |
| 10-3413 | 8-173 | vinclozolin |
| 10-3414 | 8-174 | vinclozolin |
| 10-3415 | 8-175 | vinclozolin |
| 10-3416 | 8-176 | vinclozolin |
| 10-3417 | 8-177 | vinclozolin |
| 10-3418 | 8-178 | vinclozolin |
| 10-3419 | 8-179 | vinclozolin |
| 10-3420 | 8-180 | vinclozolin |
| 10-3421 | 8-1 | mancozeb |
| 10-3422 | 8-2 | mancozeb |
| 10-3423 | 8-3 | mancozeb |
| 10-3424 | 8-4 | mancozeb |
| 10-3425 | 8-5 | mancozeb |
| 10-3426 | 8-6 | mancozeb |
| 10-3427 | 8-7 | mancozeb |
| 10-3428 | 8-8 | mancozeb |
| 10-3429 | 8-9 | mancozeb |
| 10-3430 | 8-10 | mancozeb |
| 10-3431 | 8-11 | mancozeb |
| 10-3432 | 8-12 | mancozeb |
| 10-3433 | 8-13 | mancozeb |
| 10-3434 | 8-14 | mancozeb |
| 10-3435 | 8-15 | mancozeb |
| 10-3436 | 8-16 | mancozeb |
| 10-3437 | 8-17 | mancozeb |
| 10-3438 | 8-18 | mancozeb |
| 10-3439 | 8-19 | mancozeb |
| 10-3440 | 8-20 | mancozeb |
| 10-3441 | 8-21 | mancozeb |
| 10-3442 | 8-22 | mancozeb |
| 10-3443 | 8-23 | mancozeb |
| 10-3444 | 8-24 | mancozeb |
| 10-3445 | 8-25 | mancozeb |
| 10-3446 | 8-26 | mancozeb |
| 10-3447 | 8-27 | mancozeb |
| 10-3448 | 8-28 | mancozeb |
| 10-3449 | 8-29 | mancozeb |
| 10-3450 | 8-30 | mancozeb |
| 10-3451 | 8-31 | mancozeb |
| 10-3452 | 8-32 | mancozeb |
| 10-3453 | 8-33 | mancozeb |
| 10-3454 | 8-34 | mancozeb |
| 10-3455 | 8-35 | mancozeb |
| 10-3456 | 8-36 | mancozeb |

TABLE 10-continued

| No. | Binary combination | Active compound |
|---|---|---|
| 10-3457 | 8-37 | mancozeb |
| 10-3458 | 8-38 | mancozeb |
| 10-3459 | 8-39 | mancozeb |
| 10-3460 | 8-40 | mancozeb |
| 10-3461 | 8-41 | mancozeb |
| 10-3462 | 8-42 | mancozeb |
| 10-3463 | 8-43 | mancozeb |
| 10-3464 | 8-44 | mancozeb |
| 10-3465 | 8-45 | mancozeb |
| 10-3466 | 8-46 | mancozeb |
| 10-3467 | 8-47 | mancozeb |
| 10-3468 | 8-48 | mancozeb |
| 10-3469 | 8-49 | mancozeb |
| 10-3470 | 8-50 | mancozeb |
| 10-3471 | 8-51 | mancozeb |
| 10-3472 | 8-52 | mancozeb |
| 10-3473 | 8-53 | mancozeb |
| 10-3474 | 8-54 | mancozeb |
| 10-3475 | 8-55 | mancozeb |
| 10-3476 | 8-56 | mancozeb |
| 10-3477 | 8-57 | mancozeb |
| 10-3478 | 8-58 | mancozeb |
| 10-3479 | 8-59 | mancozeb |
| 10-3480 | 8-60 | mancozeb |
| 10-3481 | 8-61 | mancozeb |
| 10-3482 | 8-62 | mancozeb |
| 10-3483 | 8-63 | mancozeb |
| 10-3484 | 8-64 | mancozeb |
| 10-3485 | 8-65 | mancozeb |
| 10-3486 | 8-66 | mancozeb |
| 10-3487 | 8-67 | mancozeb |
| 10-3488 | 8-68 | mancozeb |
| 10-3489 | 8-69 | mancozeb |
| 10-3490 | 8-70 | mancozeb |
| 10-3491 | 8-71 | mancozeb |
| 10-3492 | 8-72 | mancozeb |
| 10-3493 | 8-73 | mancozeb |
| 10-3494 | 8-74 | mancozeb |
| 10-3495 | 8-75 | mancozeb |
| 10-3496 | 8-76 | mancozeb |
| 10-3497 | 8-77 | mancozeb |
| 10-3498 | 8-78 | mancozeb |
| 10-3499 | 8-79 | mancozeb |
| 10-3500 | 8-80 | mancozeb |
| 10-3501 | 8-81 | mancozeb |
| 10-3502 | 8-82 | mancozeb |
| 10-3503 | 8-83 | mancozeb |
| 10-3504 | 8-84 | mancozeb |
| 10-3505 | 8-85 | mancozeb |
| 10-3506 | 8-86 | mancozeb |
| 10-3507 | 8-87 | mancozeb |
| 10-3508 | 8-88 | mancozeb |
| 10-3509 | 8-89 | mancozeb |
| 10-3510 | 8-90 | mancozeb |
| 10-3511 | 8-91 | mancozeb |
| 10-3512 | 8-92 | mancozeb |
| 10-3513 | 8-93 | mancozeb |
| 10-3514 | 8-94 | mancozeb |
| 10-3515 | 8-95 | mancozeb |
| 10-3516 | 8-96 | mancozeb |
| 10-3517 | 8-97 | mancozeb |
| 10-3518 | 8-98 | mancozeb |
| 10-3519 | 8-99 | mancozeb |
| 10-3520 | 8-100 | mancozeb |
| 10-3521 | 8-101 | mancozeb |
| 10-3522 | 8-102 | mancozeb |
| 10-3523 | 8-103 | mancozeb |
| 10-3524 | 8-104 | mancozeb |
| 10-3525 | 8-105 | mancozeb |
| 10-3526 | 8-106 | mancozeb |
| 10-3527 | 8-107 | mancozeb |
| 10-3528 | 8-108 | mancozeb |
| 10-3529 | 8-109 | mancozeb |
| 10-3530 | 8-110 | mancozeb |
| 10-3531 | 8-111 | mancozeb |
| 10-3532 | 8-112 | mancozeb |
| 10-3533 | 8-113 | mancozeb |
| 10-3534 | 8-114 | mancozeb |
| 10-3535 | 8-115 | mancozeb |
| 10-3536 | 8-116 | mancozeb |
| 10-3537 | 8-117 | mancozeb |
| 10-3538 | 8-118 | mancozeb |
| 10-3539 | 8-119 | mancozeb |
| 10-3540 | 8-120 | mancozeb |
| 10-3541 | 8-121 | mancozeb |
| 10-3542 | 8-122 | mancozeb |
| 10-3543 | 8-123 | mancozeb |
| 10-3544 | 8-124 | mancozeb |
| 10-3545 | 8-125 | mancozeb |
| 10-3546 | 8-126 | mancozeb |
| 10-3547 | 8-127 | mancozeb |
| 10-3548 | 8-128 | mancozeb |
| 10-3549 | 8-129 | mancozeb |
| 10-3550 | 8-130 | mancozeb |
| 10-3551 | 8-131 | mancozeb |
| 10-3552 | 8-132 | mancozeb |
| 10-3553 | 8-133 | mancozeb |
| 10-3554 | 8-134 | mancozeb |
| 10-3555 | 8-135 | mancozeb |
| 10-3556 | 8-136 | mancozeb |
| 10-3557 | 8-137 | mancozeb |
| 10-3558 | 8-138 | mancozeb |
| 10-3559 | 8-139 | mancozeb |
| 10-3560 | 8-140 | mancozeb |
| 10-3561 | 8-141 | mancozeb |
| 10-3562 | 8-142 | mancozeb |
| 10-3563 | 8-143 | mancozeb |
| 10-3564 | 8-144 | mancozeb |
| 10-3565 | 8-145 | mancozeb |
| 10-3566 | 8-146 | mancozeb |
| 10-3567 | 8-147 | mancozeb |
| 10-3568 | 8-148 | mancozeb |
| 10-3569 | 8-149 | mancozeb |
| 10-3570 | 8-150 | mancozeb |
| 10-3571 | 8-151 | mancozeb |
| 10-3572 | 8-152 | mancozeb |
| 10-3573 | 8-153 | mancozeb |
| 10-3574 | 8-154 | mancozeb |
| 10-3575 | 8-155 | mancozeb |
| 10-3576 | 8-156 | mancozeb |
| 10-3577 | 8-157 | mancozeb |
| 10-3578 | 8-158 | mancozeb |
| 10-3579 | 8-159 | mancozeb |
| 10-3580 | 8-160 | mancozeb |
| 10-3581 | 8-161 | mancozeb |
| 10-3582 | 8-162 | mancozeb |
| 10-3583 | 8-163 | mancozeb |
| 10-3584 | 8-164 | mancozeb |
| 10-3585 | 8-165 | mancozeb |
| 10-3586 | 8-166 | mancozeb |
| 10-3587 | 8-167 | mancozeb |
| 10-3588 | 8-168 | mancozeb |
| 10-3589 | 8-169 | mancozeb |
| 10-3590 | 8-170 | mancozeb |
| 10-3591 | 8-171 | mancozeb |
| 10-3592 | 8-172 | mancozeb |
| 10-3593 | 8-173 | mancozeb |
| 10-3594 | 8-174 | mancozeb |
| 10-3595 | 8-175 | mancozeb |
| 10-3596 | 8-176 | mancozeb |
| 10-3597 | 8-177 | mancozeb |
| 10-3598 | 8-178 | mancozeb |
| 10-3599 | 8-179 | mancozeb |
| 10-3600 | 8-180 | mancozeb |
| 10-3601 | 8-1 | metiram |
| 10-3602 | 8-2 | metiram |
| 10-3603 | 8-3 | metiram |
| 10-3604 | 8-4 | metiram |
| 10-3605 | 8-5 | metiram |
| 10-3606 | 8-6 | metiram |
| 10-3607 | 8-7 | metiram |
| 10-3608 | 8-8 | metiram |
| 10-3609 | 8-9 | metiram |
| 10-3610 | 8-10 | metiram |

TABLE 10-continued

| No. | Binary combination | Active compound |
|---|---|---|
| 10-3611 | 8-11 | metiram |
| 10-3612 | 8-12 | metiram |
| 10-3613 | 8-13 | metiram |
| 10-3614 | 8-14 | metiram |
| 10-3615 | 8-15 | metiram |
| 10-3616 | 8-16 | metiram |
| 10-3617 | 8-17 | metiram |
| 10-3618 | 8-18 | metiram |
| 10-3619 | 8-19 | metiram |
| 10-3620 | 8-20 | metiram |
| 10-3621 | 8-21 | metiram |
| 10-3622 | 8-22 | metiram |
| 10-3623 | 8-23 | metiram |
| 10-3624 | 8-24 | metiram |
| 10-3625 | 8-25 | metiram |
| 10-3626 | 8-26 | metiram |
| 10-3627 | 8-27 | metiram |
| 10-3628 | 8-28 | metiram |
| 10-3629 | 8-29 | metiram |
| 10-3630 | 8-30 | metiram |
| 10-3631 | 8-31 | metiram |
| 10-3632 | 8-32 | metiram |
| 10-3633 | 8-33 | metiram |
| 10-3634 | 8-34 | metiram |
| 10-3635 | 8-35 | metiram |
| 10-3636 | 8-36 | metiram |
| 10-3637 | 8-37 | metiram |
| 10-3638 | 8-38 | metiram |
| 10-3639 | 8-39 | metiram |
| 10-3640 | 8-40 | metiram |
| 10-3641 | 8-41 | metiram |
| 10-3642 | 8-42 | metiram |
| 10-3643 | 8-43 | metiram |
| 10-3644 | 8-44 | metiram |
| 10-3645 | 8-45 | metiram |
| 10-3646 | 8-46 | metiram |
| 10-3647 | 8-47 | metiram |
| 10-3648 | 8-48 | metiram |
| 10-3649 | 8-49 | metiram |
| 10-3650 | 8-50 | metiram |
| 10-3651 | 8-51 | metiram |
| 10-3652 | 8-52 | metiram |
| 10-3653 | 8-53 | metiram |
| 10-3654 | 8-54 | metiram |
| 10-3655 | 8-55 | metiram |
| 10-3656 | 8-56 | metiram |
| 10-3657 | 8-57 | metiram |
| 10-3658 | 8-58 | metiram |
| 10-3659 | 8-59 | metiram |
| 10-3660 | 8-60 | metiram |
| 10-3661 | 8-61 | metiram |
| 10-3662 | 8-62 | metiram |
| 10-3663 | 8-63 | metiram |
| 10-3664 | 8-64 | metiram |
| 10-3665 | 8-65 | metiram |
| 10-3666 | 8-66 | metiram |
| 10-3667 | 8-67 | metiram |
| 10-3668 | 8-68 | metiram |
| 10-3669 | 8-69 | metiram |
| 10-3670 | 8-70 | metiram |
| 10-3671 | 8-71 | metiram |
| 10-3672 | 8-72 | metiram |
| 10-3673 | 8-73 | metiram |
| 10-3674 | 8-74 | metiram |
| 10-3675 | 8-75 | metiram |
| 10-3676 | 8-76 | metiram |
| 10-3677 | 8-77 | metiram |
| 10-3678 | 8-78 | metiram |
| 10-3679 | 8-79 | metiram |
| 10-3680 | 8-80 | metiram |
| 10-3681 | 8-81 | metiram |
| 10-3682 | 8-82 | metiram |
| 10-3683 | 8-83 | metiram |
| 10-3684 | 8-84 | metiram |
| 10-3685 | 8-85 | metiram |
| 10-3686 | 8-86 | metiram |
| 10-3687 | 8-87 | metiram |
| 10-3688 | 8-88 | metiram |
| 10-3689 | 8-89 | metiram |
| 10-3690 | 8-90 | metiram |
| 10-3691 | 8-91 | metiram |
| 10-3692 | 8-92 | metiram |
| 10-3693 | 8-93 | metiram |
| 10-3694 | 8-94 | metiram |
| 10-3695 | 8-95 | metiram |
| 10-3696 | 8-96 | metiram |
| 10-3697 | 8-97 | metiram |
| 10-3698 | 8-98 | metiram |
| 10-3699 | 8-99 | metiram |
| 10-3700 | 8-100 | metiram |
| 10-3701 | 8-101 | metiram |
| 10-3702 | 8-102 | metiram |
| 10-3703 | 8-103 | metiram |
| 10-3704 | 8-104 | metiram |
| 10-3705 | 8-105 | metiram |
| 10-3706 | 8-106 | metiram |
| 10-3707 | 8-107 | metiram |
| 10-3708 | 8-108 | metiram |
| 10-3709 | 8-109 | metiram |
| 10-3710 | 8-110 | metiram |
| 10-3711 | 8-111 | metiram |
| 10-3712 | 8-112 | metiram |
| 10-3713 | 8-113 | metiram |
| 10-3714 | 8-114 | metiram |
| 10-3715 | 8-115 | metiram |
| 10-3716 | 8-116 | metiram |
| 10-3717 | 8-117 | metiram |
| 10-3718 | 8-118 | metiram |
| 10-3719 | 8-119 | metiram |
| 10-3720 | 8-120 | metiram |
| 10-3721 | 8-121 | metiram |
| 10-3722 | 8-122 | metiram |
| 10-3723 | 8-123 | metiram |
| 10-3724 | 8-124 | metiram |
| 10-3725 | 8-125 | metiram |
| 10-3726 | 8-126 | metiram |
| 10-3727 | 8-127 | metiram |
| 10-3728 | 8-128 | metiram |
| 10-3729 | 8-129 | metiram |
| 10-3730 | 8-130 | metiram |
| 10-3731 | 8-131 | metiram |
| 10-3732 | 8-132 | metiram |
| 10-3733 | 8-133 | metiram |
| 10-3734 | 8-134 | metiram |
| 10-3735 | 8-135 | metiram |
| 10-3736 | 8-136 | metiram |
| 10-3737 | 8-137 | metiram |
| 10-3738 | 8-138 | metiram |
| 10-3739 | 8-139 | metiram |
| 10-3740 | 8-140 | metiram |
| 10-3741 | 8-141 | metiram |
| 10-3742 | 8-142 | metiram |
| 10-3743 | 8-143 | metiram |
| 10-3744 | 8-144 | metiram |
| 10-3745 | 8-145 | metiram |
| 10-3746 | 8-146 | metiram |
| 10-3747 | 8-147 | metiram |
| 10-3748 | 8-148 | metiram |
| 10-3749 | 8-149 | metiram |
| 10-3750 | 8-150 | metiram |
| 10-3751 | 8-151 | metiram |
| 10-3752 | 8-152 | metiram |
| 10-3753 | 8-153 | metiram |
| 10-3754 | 8-154 | metiram |
| 10-3755 | 8-155 | metiram |
| 10-3756 | 8-156 | metiram |
| 10-3757 | 8-157 | metiram |
| 10-3758 | 8-158 | metiram |
| 10-3759 | 8-159 | metiram |
| 10-3760 | 8-160 | metiram |
| 10-3761 | 8-161 | metiram |
| 10-3762 | 8-162 | metiram |
| 10-3763 | 8-163 | metiram |
| 10-3764 | 8-164 | metiram |

TABLE 10-continued

| No. | Binary combination | Active compound |
|---|---|---|
| 10-3765 | 8-165 | metiram |
| 10-3766 | 8-166 | metiram |
| 10-3767 | 8-167 | metiram |
| 10-3768 | 8-168 | metiram |
| 10-3769 | 8-169 | metiram |
| 10-3770 | 8-170 | metiram |
| 10-3771 | 8-171 | metiram |
| 10-3772 | 8-172 | metiram |
| 10-3773 | 8-173 | metiram |
| 10-3774 | 8-174 | metiram |
| 10-3775 | 8-175 | metiram |
| 10-3776 | 8-176 | metiram |
| 10-3777 | 8-177 | metiram |
| 10-3778 | 8-178 | metiram |
| 10-3779 | 8-179 | metiram |
| 10-3780 | 8-180 | metiram |
| 10-3781 | 8-1 | chlorothalonil |
| 10-3782 | 8-2 | chlorothalonil |
| 10-3783 | 8-3 | chlorothalonil |
| 10-3784 | 8-4 | chlorothalonil |
| 10-3785 | 8-5 | chlorothalonil |
| 10-3786 | 8-6 | chlorothalonil |
| 10-3787 | 8-7 | chlorothalonil |
| 10-3788 | 8-8 | chlorothalonil |
| 10-3789 | 8-9 | chlorothalonil |
| 10-3790 | 8-10 | chlorothalonil |
| 10-3791 | 8-11 | chlorothalonil |
| 10-3792 | 8-12 | chlorothalonil |
| 10-3793 | 8-13 | chlorothalonil |
| 10-3794 | 8-14 | chlorothalonil |
| 10-3795 | 8-15 | chlorothalonil |
| 10-3796 | 8-16 | chlorothalonil |
| 10-3797 | 8-17 | chlorothalonil |
| 10-3798 | 8-18 | chlorothalonil |
| 10-3799 | 8-19 | chlorothalonil |
| 10-3800 | 8-20 | chlorothalonil |
| 10-3801 | 8-21 | chlorothalonil |
| 10-3802 | 8-22 | chlorothalonil |
| 10-3803 | 8-23 | chlorothalonil |
| 10-3804 | 8-24 | chlorothalonil |
| 10-3805 | 8-25 | chlorothalonil |
| 10-3806 | 8-26 | chlorothalonil |
| 10-3807 | 8-27 | chlorothalonil |
| 10-3808 | 8-28 | chlorothalonil |
| 10-3809 | 8-29 | chlorothalonil |
| 10-3810 | 8-30 | chlorothalonil |
| 10-3811 | 8-31 | chlorothalonil |
| 10-3812 | 8-32 | chlorothalonil |
| 10-3813 | 8-33 | chlorothalonil |
| 10-3814 | 8-34 | chlorothalonil |
| 10-3815 | 8-35 | chlorothalonil |
| 10-3816 | 8-36 | chlorothalonil |
| 10-3817 | 8-37 | chlorothalonil |
| 10-3818 | 8-38 | chlorothalonil |
| 10-3819 | 8-39 | chlorothalonil |
| 10-3820 | 8-40 | chlorothalonil |
| 10-3821 | 8-41 | chlorothalonil |
| 10-3822 | 8-42 | chlorothalonil |
| 10-3823 | 8-43 | chlorothalonil |
| 10-3824 | 8-44 | chlorothalonil |
| 10-3825 | 8-45 | chlorothalonil |
| 10-3826 | 8-46 | chlorothalonil |
| 10-3827 | 8-47 | chlorothalonil |
| 10-3828 | 8-48 | chlorothalonil |
| 10-3829 | 8-49 | chlorothalonil |
| 10-3830 | 8-50 | chlorothalonil |
| 10-3831 | 8-51 | chlorothalonil |
| 10-3832 | 8-52 | chlorothalonil |
| 10-3833 | 8-53 | chlorothalonil |
| 10-3834 | 8-54 | chlorothalonil |
| 10-3835 | 8-55 | chlorothalonil |
| 10-3836 | 8-56 | chlorothalonil |
| 10-3837 | 8-57 | chlorothalonil |
| 10-3838 | 8-58 | chlorothalonil |
| 10-3839 | 8-59 | chlorothalonil |
| 10-3840 | 8-60 | chlorothalonil |
| 10-3841 | 8-61 | chlorothalonil |
| 10-3842 | 8-62 | chlorothalonil |
| 10-3843 | 8-63 | chlorothalonil |
| 10-3844 | 8-64 | chlorothalonil |
| 10-3845 | 8-65 | chlorothalonil |
| 10-3846 | 8-66 | chlorothalonil |
| 10-3847 | 8-67 | chlorothalonil |
| 10-3848 | 8-68 | chlorothalonil |
| 10-3849 | 8-69 | chlorothalonil |
| 10-3850 | 8-70 | chlorothalonil |
| 10-3851 | 8-71 | chlorothalonil |
| 10-3852 | 8-72 | chlorothalonil |
| 10-3853 | 8-73 | chlorothalonil |
| 10-3854 | 8-74 | chlorothalonil |
| 10-3855 | 8-75 | chlorothalonil |
| 10-3856 | 8-76 | chlorothalonil |
| 10-3857 | 8-77 | chlorothalonil |
| 10-3858 | 8-78 | chlorothalonil |
| 10-3859 | 8-79 | chlorothalonil |
| 10-3860 | 8-80 | chlorothalonil |
| 10-3861 | 8-81 | chlorothalonil |
| 10-3862 | 8-82 | chlorothalonil |
| 10-3863 | 8-83 | chlorothalonil |
| 10-3864 | 8-84 | chlorothalonil |
| 10-3865 | 8-85 | chlorothalonil |
| 10-3866 | 8-86 | chlorothalonil |
| 10-3867 | 8-87 | chlorothalonil |
| 10-3868 | 8-88 | chlorothalonil |
| 10-3869 | 8-89 | chlorothalonil |
| 10-3870 | 8-90 | chlorothalonil |
| 10-3871 | 8-91 | chlorothalonil |
| 10-3872 | 8-92 | chlorothalonil |
| 10-3873 | 8-93 | chlorothalonil |
| 10-3874 | 8-94 | chlorothalonil |
| 10-3875 | 8-95 | chlorothalonil |
| 10-3876 | 8-96 | chlorothalonil |
| 10-3877 | 8-97 | chlorothalonil |
| 10-3878 | 8-98 | chlorothalonil |
| 10-3879 | 8-99 | chlorothalonil |
| 10-3880 | 8-100 | chlorothalonil |
| 10-3881 | 8-101 | chlorothalonil |
| 10-3882 | 8-102 | chlorothalonil |
| 10-3883 | 8-103 | chlorothalonil |
| 10-3884 | 8-104 | chlorothalonil |
| 10-3885 | 8-105 | chlorothalonil |
| 10-3886 | 8-106 | chlorothalonil |
| 10-3887 | 8-107 | chlorothalonil |
| 10-3888 | 8-108 | chlorothalonil |
| 10-3889 | 8-109 | chlorothalonil |
| 10-3890 | 8-110 | chlorothalonil |
| 10-3891 | 8-111 | chlorothalonil |
| 10-3892 | 8-112 | chlorothalonil |
| 10-3893 | 8-113 | chlorothalonil |
| 10-3894 | 8-114 | chlorothalonil |
| 10-3895 | 8-115 | chlorothalonil |
| 10-3896 | 8-116 | chlorothalonil |
| 10-3897 | 8-117 | chlorothalonil |
| 10-3898 | 8-118 | chlorothalonil |
| 10-3899 | 8-119 | chlorothalonil |
| 10-3900 | 8-120 | chlorothalonil |
| 10-3901 | 8-121 | chlorothalonil |
| 10-3902 | 8-122 | chlorothalonil |
| 10-3903 | 8-123 | chlorothalonil |
| 10-3904 | 8-124 | chlorothalonil |
| 10-3905 | 8-125 | chlorothalonil |
| 10-3906 | 8-126 | chlorothalonil |
| 10-3907 | 8-127 | chlorothalonil |
| 10-3908 | 8-128 | chlorothalonil |
| 10-3909 | 8-129 | chlorothalonil |
| 10-3910 | 8-130 | chlorothalonil |
| 10-3911 | 8-131 | chlorothalonil |
| 10-3912 | 8-132 | chlorothalonil |
| 10-3913 | 8-133 | chlorothalonil |
| 10-3914 | 8-134 | chlorothalonil |
| 10-3915 | 8-135 | chlorothalonil |
| 10-3916 | 8-136 | chlorothalonil |
| 10-3917 | 8-137 | chlorothalonil |
| 10-3918 | 8-138 | chlorothalonil |

TABLE 10-continued

| No. | Binary combination | Active compound |
|---|---|---|
| 10-3919 | 8-139 | chlorothalonil |
| 10-3920 | 8-140 | chlorothalonil |
| 10-3921 | 8-141 | chlorothalonil |
| 10-3922 | 8-142 | chlorothalonil |
| 10-3923 | 8-143 | chlorothalonil |
| 10-3924 | 8-144 | chlorothalonil |
| 10-3925 | 8-145 | chlorothalonil |
| 10-3926 | 8-146 | chlorothalonil |
| 10-3927 | 8-147 | chlorothalonil |
| 10-3928 | 8-148 | chlorothalonil |
| 10-3929 | 8-149 | chlorothalonil |
| 10-3930 | 8-150 | chlorothalonil |
| 10-3931 | 8-151 | chlorothalonil |
| 10-3932 | 8-152 | chlorothalonil |
| 10-3933 | 8-153 | chlorothalonil |
| 10-3934 | 8-154 | chlorothalonil |
| 10-3935 | 8-155 | chlorothalonil |
| 10-3936 | 8-156 | chlorothalonil |
| 10-3937 | 8-157 | chlorothalonil |
| 10-3938 | 8-158 | chlorothalonil |
| 10-3939 | 8-159 | chlorothalonil |
| 10-3940 | 8-160 | chlorothalonil |
| 10-3941 | 8-161 | chlorothalonil |
| 10-3942 | 8-162 | chlorothalonil |
| 10-3943 | 8-163 | chlorothalonil |
| 10-3944 | 8-164 | chlorothalonil |
| 10-3945 | 8-165 | chlorothalonil |
| 10-3946 | 8-166 | chlorothalonil |
| 10-3947 | 8-167 | chlorothalonil |
| 10-3948 | 8-168 | chlorothalonil |
| 10-3949 | 8-169 | chlorothalonil |
| 10-3950 | 8-170 | chlorothalonil |
| 10-3951 | 8-171 | chlorothalonil |
| 10-3952 | 8-172 | chlorothalonil |
| 10-3953 | 8-173 | chlorothalonil |
| 10-3954 | 8-174 | chlorothalonil |
| 10-3955 | 8-175 | chlorothalonil |
| 10-3956 | 8-176 | chlorothalonil |
| 10-3957 | 8-177 | chlorothalonil |
| 10-3958 | 8-178 | chlorothalonil |
| 10-3959 | 8-179 | chlorothalonil |
| 10-3960 | 8-180 | chlorothalonil |
| 10-3961 | 8-1 | metrafenone |
| 10-3962 | 8-2 | metrafenone |
| 10-3963 | 8-3 | metrafenone |
| 10-3964 | 8-4 | metrafenone |
| 10-3965 | 8-5 | metrafenone |
| 10-3966 | 8-6 | metrafenone |
| 10-3967 | 8-7 | metrafenone |
| 10-3968 | 8-8 | metrafenone |
| 10-3969 | 8-9 | metrafenone |
| 10-3970 | 8-10 | metrafenone |
| 10-3971 | 8-11 | metrafenone |
| 10-3972 | 8-12 | metrafenone |
| 10-3973 | 8-13 | metrafenone |
| 10-3974 | 8-14 | metrafenone |
| 10-3975 | 8-15 | metrafenone |
| 10-3976 | 8-16 | metrafenone |
| 10-3977 | 8-17 | metrafenone |
| 10-3978 | 8-18 | metrafenone |
| 10-3979 | 8-19 | metrafenone |
| 10-3980 | 8-20 | metrafenone |
| 10-3981 | 8-21 | metrafenone |
| 10-3982 | 8-22 | metrafenone |
| 10-3983 | 8-23 | metrafenone |
| 10-3984 | 8-24 | metrafenone |
| 10-3985 | 8-25 | metrafenone |
| 10-3986 | 8-26 | metrafenone |
| 10-3987 | 8-27 | metrafenone |
| 10-3988 | 8-28 | metrafenone |
| 10-3989 | 8-29 | metrafenone |
| 10-3990 | 8-30 | metrafenone |
| 10-3991 | 8-31 | metrafenone |
| 10-3992 | 8-32 | metrafenone |
| 10-3993 | 8-33 | metrafenone |
| 10-3994 | 8-34 | metrafenone |
| 10-3995 | 8-35 | metrafenone |
| 10-3996 | 8-36 | metrafenone |
| 10-3997 | 8-37 | metrafenone |
| 10-3998 | 8-38 | metrafenone |
| 10-3999 | 8-39 | metrafenone |
| 10-4000 | 8-40 | metrafenone |
| 10-4001 | 8-41 | metrafenone |
| 10-4002 | 8-42 | metrafenone |
| 10-4003 | 8-43 | metrafenone |
| 10-4004 | 8-44 | metrafenone |
| 10-4005 | 8-45 | metrafenone |
| 10-4006 | 8-46 | metrafenone |
| 10-4007 | 8-47 | metrafenone |
| 10-4008 | 8-48 | metrafenone |
| 10-4009 | 8-49 | metrafenone |
| 10-4010 | 8-50 | metrafenone |
| 10-4011 | 8-51 | metrafenone |
| 10-4012 | 8-52 | metrafenone |
| 10-4013 | 8-53 | metrafenone |
| 10-4014 | 8-54 | metrafenone |
| 10-4015 | 8-55 | metrafenone |
| 10-4016 | 8-56 | metrafenone |
| 10-4017 | 8-57 | metrafenone |
| 10-4018 | 8-58 | metrafenone |
| 10-4019 | 8-59 | metrafenone |
| 10-4020 | 8-60 | metrafenone |
| 10-4021 | 8-61 | metrafenone |
| 10-4022 | 8-62 | metrafenone |
| 10-4023 | 8-63 | metrafenone |
| 10-4024 | 8-64 | metrafenone |
| 10-4025 | 8-65 | metrafenone |
| 10-4026 | 8-66 | metrafenone |
| 10-4027 | 8-67 | metrafenone |
| 10-4028 | 8-68 | metrafenone |
| 10-4029 | 8-69 | metrafenone |
| 10-4030 | 8-70 | metrafenone |
| 10-4031 | 8-71 | metrafenone |
| 10-4032 | 8-72 | metrafenone |
| 10-4033 | 8-73 | metrafenone |
| 10-4034 | 8-74 | metrafenone |
| 10-4035 | 8-75 | metrafenone |
| 10-4036 | 8-76 | metrafenone |
| 10-4037 | 8-77 | metrafenone |
| 10-4038 | 8-78 | metrafenone |
| 10-4039 | 8-79 | metrafenone |
| 10-4040 | 8-80 | metrafenone |
| 10-4041 | 8-81 | metrafenone |
| 10-4042 | 8-82 | metrafenone |
| 10-4043 | 8-83 | metrafenone |
| 10-4044 | 8-84 | metrafenone |
| 10-4045 | 8-85 | metrafenone |
| 10-4046 | 8-86 | metrafenone |
| 10-4047 | 8-87 | metrafenone |
| 10-4048 | 8-88 | metrafenone |
| 10-4049 | 8-89 | metrafenone |
| 10-4050 | 8-90 | metrafenone |
| 10-4051 | 8-91 | metrafenone |
| 10-4052 | 8-92 | metrafenone |
| 10-4053 | 8-93 | metrafenone |
| 10-4054 | 8-94 | metrafenone |
| 10-4055 | 8-95 | metrafenone |
| 10-4056 | 8-96 | metrafenone |
| 10-4057 | 8-97 | metrafenone |
| 10-4058 | 8-98 | metrafenone |
| 10-4059 | 8-99 | metrafenone |
| 10-4060 | 8-100 | metrafenone |
| 10-4061 | 8-101 | metrafenone |
| 10-4062 | 8-102 | metrafenone |
| 10-4063 | 8-103 | metrafenone |
| 10-4064 | 8-104 | metrafenone |
| 10-4065 | 8-105 | metrafenone |
| 10-4066 | 8-106 | metrafenone |
| 10-4067 | 8-107 | metrafenone |
| 10-4068 | 8-108 | metrafenone |
| 10-4069 | 8-109 | metrafenone |
| 10-4070 | 8-110 | metrafenone |
| 10-4071 | 8-111 | metrafenone |
| 10-4072 | 8-112 | metrafenone |

TABLE 10-continued

| No. | Binary combination | Active compound |
|---|---|---|
| 10-4073 | 8-113 | metrafenone |
| 10-4074 | 8-114 | metrafenone |
| 10-4075 | 8-115 | metrafenone |
| 10-4076 | 8-116 | metrafenone |
| 10-4077 | 8-117 | metrafenone |
| 10-4078 | 8-118 | metrafenone |
| 10-4079 | 8-119 | metrafenone |
| 10-4080 | 8-120 | metrafenone |
| 10-4081 | 8-121 | metrafenone |
| 10-4082 | 8-122 | metrafenone |
| 10-4083 | 8-123 | metrafenone |
| 10-4084 | 8-124 | metrafenone |
| 10-4085 | 8-125 | metrafenone |
| 10-4086 | 8-126 | metrafenone |
| 10-4087 | 8-127 | metrafenone |
| 10-4088 | 8-128 | metrafenone |
| 10-4089 | 8-129 | metrafenone |
| 10-4090 | 8-130 | metrafenone |
| 10-4091 | 8-131 | metrafenone |
| 10-4092 | 8-132 | metrafenone |
| 10-4093 | 8-133 | metrafenone |
| 10-4094 | 8-134 | metrafenone |
| 10-4095 | 8-135 | metrafenone |
| 10-4096 | 8-136 | metrafenone |
| 10-4097 | 8-137 | metrafenone |
| 10-4098 | 8-138 | metrafenone |
| 10-4099 | 8-139 | metrafenone |
| 10-4100 | 8-140 | metrafenone |
| 10-4101 | 8-141 | metrafenone |
| 10-4102 | 8-142 | metrafenone |
| 10-4103 | 8-143 | metrafenone |
| 10-4104 | 8-144 | metrafenone |
| 10-4105 | 8-145 | metrafenone |
| 10-4106 | 8-146 | metrafenone |
| 10-4107 | 8-147 | metrafenone |
| 10-4108 | 8-148 | metrafenone |
| 10-4109 | 8-149 | metrafenone |
| 10-4110 | 8-150 | metrafenone |
| 10-4111 | 8-151 | metrafenone |
| 10-4112 | 8-152 | metrafenone |
| 10-4113 | 8-153 | metrafenone |
| 10-4114 | 8-154 | metrafenone |
| 10-4115 | 8-155 | metrafenone |
| 10-4116 | 8-156 | metrafenone |
| 10-4117 | 8-157 | metrafenone |
| 10-4118 | 8-158 | metrafenone |
| 10-4119 | 8-159 | metrafenone |
| 10-4120 | 8-160 | metrafenone |
| 10-4121 | 8-161 | metrafenone |
| 10-4122 | 8-162 | metrafenone |
| 10-4123 | 8-163 | metrafenone |
| 10-4124 | 8-164 | metrafenone |
| 10-4125 | 8-165 | metrafenone |
| 10-4126 | 8-166 | metrafenone |
| 10-4127 | 8-167 | metrafenone |
| 10-4128 | 8-168 | metrafenone |
| 10-4129 | 8-169 | metrafenone |
| 10-4130 | 8-170 | metrafenone |
| 10-4131 | 8-171 | metrafenone |
| 10-4132 | 8-172 | metrafenone |
| 10-4133 | 8-173 | metrafenone |
| 10-4134 | 8-174 | metrafenone |
| 10-4135 | 8-175 | metrafenone |
| 10-4136 | 8-176 | metrafenone |
| 10-4137 | 8-177 | metrafenone |
| 10-4138 | 8-178 | metrafenone |
| 10-4139 | 8-179 | metrafenone |
| 10-4140 | 8-180 | metrafenone |
| 10-4141 | 8-1 | $H_3PO_3$ |
| 10-4142 | 8-2 | $H_3PO_3$ |
| 10-4143 | 8-3 | $H_3PO_3$ |
| 10-4144 | 8-4 | $H_3PO_3$ |
| 10-4145 | 8-5 | $H_3PO_3$ |
| 10-4146 | 8-6 | $H_3PO_3$ |
| 10-4147 | 8-7 | $H_3PO_3$ |
| 10-4148 | 8-8 | $H_3PO_3$ |
| 10-4149 | 8-9 | $H_3PO_3$ |
| 10-4150 | 8-10 | $H_3PO_3$ |
| 10-4151 | 8-11 | $H_3PO_3$ |
| 10-4152 | 8-12 | $H_3PO_3$ |
| 10-4153 | 8-13 | $H_3PO_3$ |
| 10-4154 | 8-14 | $H_3PO_3$ |
| 10-4155 | 8-15 | $H_3PO_3$ |
| 10-4156 | 8-16 | $H_3PO_3$ |
| 10-4157 | 8-17 | $H_3PO_3$ |
| 10-4158 | 8-18 | $H_3PO_3$ |
| 10-4159 | 8-19 | $H_3PO_3$ |
| 10-4160 | 8-20 | $H_3PO_3$ |
| 10-4161 | 8-21 | $H_3PO_3$ |
| 10-4162 | 8-22 | $H_3PO_3$ |
| 10-4163 | 8-23 | $H_3PO_3$ |
| 10-4164 | 8-24 | $H_3PO_3$ |
| 10-4165 | 8-25 | $H_3PO_3$ |
| 10-4166 | 8-26 | $H_3PO_3$ |
| 10-4167 | 8-27 | $H_3PO_3$ |
| 10-4168 | 8-28 | $H_3PO_3$ |
| 10-4169 | 8-29 | $H_3PO_3$ |
| 10-4170 | 8-30 | $H_3PO_3$ |
| 10-4171 | 8-31 | $H_3PO_3$ |
| 10-4172 | 8-32 | $H_3PO_3$ |
| 10-4173 | 8-33 | $H_3PO_3$ |
| 10-4174 | 8-34 | $H_3PO_3$ |
| 10-4175 | 8-35 | $H_3PO_3$ |
| 10-4176 | 8-36 | $H_3PO_3$ |
| 10-4177 | 8-37 | $H_3PO_3$ |
| 10-4178 | 8-38 | $H_3PO_3$ |
| 10-4179 | 8-39 | $H_3PO_3$ |
| 10-4180 | 8-40 | $H_3PO_3$ |
| 10-4181 | 8-41 | $H_3PO_3$ |
| 10-4182 | 8-42 | $H_3PO_3$ |
| 10-4183 | 8-43 | $H_3PO_3$ |
| 10-4184 | 8-44 | $H_3PO_3$ |
| 10-4185 | 8-45 | $H_3PO_3$ |
| 10-4186 | 8-46 | $H_3PO_3$ |
| 10-4187 | 8-47 | $H_3PO_3$ |
| 10-4188 | 8-48 | $H_3PO_3$ |
| 10-4189 | 8-49 | $H_3PO_3$ |
| 10-4190 | 8-50 | $H_3PO_3$ |
| 10-4191 | 8-51 | $H_3PO_3$ |
| 10-4192 | 8-52 | $H_3PO_3$ |
| 10-4193 | 8-53 | $H_3PO_3$ |
| 10-4194 | 8-54 | $H_3PO_3$ |
| 10-4195 | 8-55 | $H_3PO_3$ |
| 10-4196 | 8-56 | $H_3PO_3$ |
| 10-4197 | 8-57 | $H_3PO_3$ |
| 10-4198 | 8-58 | $H_3PO_3$ |
| 10-4199 | 8-59 | $H_3PO_3$ |
| 10-4200 | 8-60 | $H_3PO_3$ |
| 10-4201 | 8-61 | $H_3PO_3$ |
| 10-4202 | 8-62 | $H_3PO_3$ |
| 10-4203 | 8-63 | $H_3PO_3$ |
| 10-4204 | 8-64 | $H_3PO_3$ |
| 10-4205 | 8-65 | $H_3PO_3$ |
| 10-4206 | 8-66 | $H_3PO_3$ |
| 10-4207 | 8-67 | $H_3PO_3$ |
| 10-4208 | 8-68 | $H_3PO_3$ |
| 10-4209 | 8-69 | $H_3PO_3$ |
| 10-4210 | 8-70 | $H_3PO_3$ |
| 10-4211 | 8-71 | $H_3PO_3$ |
| 10-4212 | 8-72 | $H_3PO_3$ |
| 10-4213 | 8-73 | $H_3PO_3$ |
| 10-4214 | 8-74 | $H_3PO_3$ |
| 10-4215 | 8-75 | $H_3PO_3$ |
| 10-4216 | 8-76 | $H_3PO_3$ |
| 10-4217 | 8-77 | $H_3PO_3$ |
| 10-4218 | 8-78 | $H_3PO_3$ |
| 10-4219 | 8-79 | $H_3PO_3$ |
| 10-4220 | 8-80 | $H_3PO_3$ |
| 10-4221 | 8-81 | $H_3PO_3$ |
| 10-4222 | 8-82 | $H_3PO_3$ |
| 10-4223 | 8-83 | $H_3PO_3$ |
| 10-4224 | 8-84 | $H_3PO_3$ |
| 10-4225 | 8-85 | $H_3PO_3$ |
| 10-4226 | 8-86 | $H_3PO_3$ |

TABLE 10-continued

| No. | Binary combination | Active compound |
|---|---|---|
| 10-4227 | 8-87 | $H_3PO_3$ |
| 10-4228 | 8-88 | $H_3PO_3$ |
| 10-4229 | 8-89 | $H_3PO_3$ |
| 10-4230 | 8-90 | $H_3PO_3$ |
| 10-4231 | 8-91 | $H_3PO_3$ |
| 10-4232 | 8-92 | $H_3PO_3$ |
| 10-4233 | 8-93 | $H_3PO_3$ |
| 10-4234 | 8-94 | $H_3PO_3$ |
| 10-4235 | 8-95 | $H_3PO_3$ |
| 10-4236 | 8-96 | $H_3PO_3$ |
| 10-4237 | 8-97 | $H_3PO_3$ |
| 10-4238 | 8-98 | $H_3PO_3$ |
| 10-4239 | 8-99 | $H_3PO_3$ |
| 10-4240 | 8-100 | $H_3PO_3$ |
| 10-4241 | 8-101 | $H_3PO_3$ |
| 10-4242 | 8-102 | $H_3PO_3$ |
| 10-4243 | 8-103 | $H_3PO_3$ |
| 10-4244 | 8-104 | $H_3PO_3$ |
| 10-4245 | 8-105 | $H_3PO_3$ |
| 10-4246 | 8-106 | $H_3PO_3$ |
| 10-4247 | 8-107 | $H_3PO_3$ |
| 10-4248 | 8-108 | $H_3PO_3$ |
| 10-4249 | 8-109 | $H_3PO_3$ |
| 10-4250 | 8-110 | $H_3PO_3$ |
| 10-4251 | 8-111 | $H_3PO_3$ |
| 10-4252 | 8-112 | $H_3PO_3$ |
| 10-4253 | 8-113 | $H_3PO_3$ |
| 10-4254 | 8-114 | $H_3PO_3$ |
| 10-4255 | 8-115 | $H_3PO_3$ |
| 10-4256 | 8-116 | $H_3PO_3$ |
| 10-4257 | 8-117 | $H_3PO_3$ |
| 10-4258 | 8-118 | $H_3PO_3$ |
| 10-4259 | 8-119 | $H_3PO_3$ |
| 10-4260 | 8-120 | $H_3PO_3$ |
| 10-4261 | 8-121 | $H_3PO_3$ |
| 10-4262 | 8-122 | $H_3PO_3$ |
| 10-4263 | 8-123 | $H_3PO_3$ |
| 10-4264 | 8-124 | $H_3PO_3$ |
| 10-4265 | 8-125 | $H_3PO_3$ |
| 10-4266 | 8-126 | $H_3PO_3$ |
| 10-4267 | 8-127 | $H_3PO_3$ |
| 10-4268 | 8-128 | $H_3PO_3$ |
| 10-4269 | 8-129 | $H_3PO_3$ |
| 10-4270 | 8-130 | $H_3PO_3$ |
| 10-4271 | 8-131 | $H_3PO_3$ |
| 10-4272 | 8-132 | $H_3PO_3$ |
| 10-4273 | 8-133 | $H_3PO_3$ |
| 10-4274 | 8-134 | $H_3PO_3$ |
| 10-4275 | 8-135 | $H_3PO_3$ |
| 10-4276 | 8-136 | $H_3PO_3$ |
| 10-4277 | 8-137 | $H_3PO_3$ |
| 10-4278 | 8-138 | $H_3PO_3$ |
| 10-4279 | 8-139 | $H_3PO_3$ |
| 10-4280 | 8-140 | $H_3PO_3$ |
| 10-4281 | 8-141 | $H_3PO_3$ |
| 10-4282 | 8-142 | $H_3PO_3$ |
| 10-4283 | 8-143 | $H_3PO_3$ |
| 10-4284 | 8-144 | $H_3PO_3$ |
| 10-4285 | 8-145 | $H_3PO_3$ |
| 10-4286 | 8-146 | $H_3PO_3$ |
| 10-4287 | 8-147 | $H_3PO_3$ |
| 10-4288 | 8-148 | $H_3PO_3$ |
| 10-4289 | 8-149 | $H_3PO_3$ |
| 10-4290 | 8-150 | $H_3PO_3$ |
| 10-4291 | 8-151 | $H_3PO_3$ |
| 10-4292 | 8-152 | $H_3PO_3$ |
| 10-4293 | 8-153 | $H_3PO_3$ |
| 10-4294 | 8-154 | $H_3PO_3$ |
| 10-4295 | 8-155 | $H_3PO_3$ |
| 10-4296 | 8-156 | $H_3PO_3$ |
| 10-4297 | 8-157 | $H_3PO_3$ |
| 10-4298 | 8-158 | $H_3PO_3$ |
| 10-4299 | 8-159 | $H_3PO_3$ |
| 10-4300 | 8-160 | $H_3PO_3$ |
| 10-4301 | 8-161 | $H_3PO_3$ |
| 10-4302 | 8-162 | $H_3PO_3$ |
| 10-4303 | 8-163 | $H_3PO_3$ |
| 10-4304 | 8-164 | $H_3PO_3$ |
| 10-4305 | 8-165 | $H_3PO_3$ |
| 10-4306 | 8-166 | $H_3PO_3$ |
| 10-4307 | 8-167 | $H_3PO_3$ |
| 10-4308 | 8-168 | $H_3PO_3$ |
| 10-4309 | 8-169 | $H_3PO_3$ |
| 10-4310 | 8-170 | $H_3PO_3$ |
| 10-4311 | 8-171 | $H_3PO_3$ |
| 10-4312 | 8-172 | $H_3PO_3$ |
| 10-4313 | 8-173 | $H_3PO_3$ |
| 10-4314 | 8-174 | $H_3PO_3$ |
| 10-4315 | 8-175 | $H_3PO_3$ |
| 10-4316 | 8-176 | $H_3PO_3$ |
| 10-4317 | 8-177 | $H_3PO_3$ |
| 10-4318 | 8-178 | $H_3PO_3$ |
| 10-4319 | 8-179 | $H_3PO_3$ |
| 10-4320 | 8-180 | $H_3PO_3$ |
| 10-4321 | 8-1 | dithianon |
| 10-4322 | 8-2 | dithianon |
| 10-4323 | 8-3 | dithianon |
| 10-4324 | 8-4 | dithianon |
| 10-4325 | 8-5 | dithianon |
| 10-4326 | 8-6 | dithianon |
| 10-4327 | 8-7 | dithianon |
| 10-4328 | 8-8 | dithianon |
| 10-4329 | 8-9 | dithianon |
| 10-4330 | 8-10 | dithianon |
| 10-4331 | 8-11 | dithianon |
| 10-4332 | 8-12 | dithianon |
| 10-4333 | 8-13 | dithianon |
| 10-4334 | 8-14 | dithianon |
| 10-4335 | 8-15 | dithianon |
| 10-4336 | 8-16 | dithianon |
| 10-4337 | 8-17 | dithianon |
| 10-4338 | 8-18 | dithianon |
| 10-4339 | 8-19 | dithianon |
| 10-4340 | 8-20 | dithianon |
| 10-4341 | 8-21 | dithianon |
| 10-4342 | 8-22 | dithianon |
| 10-4343 | 8-23 | dithianon |
| 10-4344 | 8-24 | dithianon |
| 10-4345 | 8-25 | dithianon |
| 10-4346 | 8-26 | dithianon |
| 10-4347 | 8-27 | dithianon |
| 10-4348 | 8-28 | dithianon |
| 10-4349 | 8-29 | dithianon |
| 10-4350 | 8-30 | dithianon |
| 10-4351 | 8-31 | dithianon |
| 10-4352 | 8-32 | dithianon |
| 10-4353 | 8-33 | dithianon |
| 10-4354 | 8-34 | dithianon |
| 10-4355 | 8-35 | dithianon |
| 10-4356 | 8-36 | dithianon |
| 10-4357 | 8-37 | dithianon |
| 10-4358 | 8-38 | dithianon |
| 10-4359 | 8-39 | dithianon |
| 10-4360 | 8-40 | dithianon |
| 10-4361 | 8-41 | dithianon |
| 10-4362 | 8-42 | dithianon |
| 10-4363 | 8-43 | dithianon |
| 10-4364 | 8-44 | dithianon |
| 10-4365 | 8-45 | dithianon |
| 10-4366 | 8-46 | dithianon |
| 10-4367 | 8-47 | dithianon |
| 10-4368 | 8-48 | dithianon |
| 10-4369 | 8-49 | dithianon |
| 10-4370 | 8-50 | dithianon |
| 10-4371 | 8-51 | dithianon |
| 10-4372 | 8-52 | dithianon |
| 10-4373 | 8-53 | dithianon |
| 10-4374 | 8-54 | dithianon |
| 10-4375 | 8-55 | dithianon |
| 10-4376 | 8-56 | dithianon |
| 10-4377 | 8-57 | dithianon |
| 10-4378 | 8-58 | dithianon |
| 10-4379 | 8-59 | dithianon |
| 10-4380 | 8-60 | dithianon |

TABLE 10-continued

| No. | Binary combination | Active compound |
|---|---|---|
| 10-4381 | 8-61 | dithianon |
| 10-4382 | 8-62 | dithianon |
| 10-4383 | 8-63 | dithianon |
| 10-4384 | 8-64 | dithianon |
| 10-4385 | 8-65 | dithianon |
| 10-4386 | 8-66 | dithianon |
| 10-4387 | 8-67 | dithianon |
| 10-4388 | 8-68 | dithianon |
| 10-4389 | 8-69 | dithianon |
| 10-4390 | 8-70 | dithianon |
| 10-4391 | 8-71 | dithianon |
| 10-4392 | 8-72 | dithianon |
| 10-4393 | 8-73 | dithianon |
| 10-4394 | 8-74 | dithianon |
| 10-4395 | 8-75 | dithianon |
| 10-4396 | 8-76 | dithianon |
| 10-4397 | 8-77 | dithianon |
| 10-4398 | 8-78 | dithianon |
| 10-4399 | 8-79 | dithianon |
| 10-4400 | 8-80 | dithianon |
| 10-4401 | 8-81 | dithianon |
| 10-4402 | 8-82 | dithianon |
| 10-4403 | 8-83 | dithianon |
| 10-4404 | 8-84 | dithianon |
| 10-4405 | 8-85 | dithianon |
| 10-4406 | 8-86 | dithianon |
| 10-4407 | 8-87 | dithianon |
| 10-4408 | 8-88 | dithianon |
| 10-4409 | 8-89 | dithianon |
| 10-4410 | 8-90 | dithianon |
| 10-4411 | 8-91 | dithianon |
| 10-4412 | 8-92 | dithianon |
| 10-4413 | 8-93 | dithianon |
| 10-4414 | 8-94 | dithianon |
| 10-4415 | 8-95 | dithianon |
| 10-4416 | 8-96 | dithianon |
| 10-4417 | 8-97 | dithianon |
| 10-4418 | 8-98 | dithianon |
| 10-4419 | 8-99 | dithianon |
| 10-4420 | 8-100 | dithianon |
| 10-4421 | 8-101 | dithianon |
| 10-4422 | 8-102 | dithianon |
| 10-4423 | 8-103 | dithianon |
| 10-4424 | 8-104 | dithianon |
| 10-4425 | 8-105 | dithianon |
| 10-4426 | 8-106 | dithianon |
| 10-4427 | 8-107 | dithianon |
| 10-4428 | 8-108 | dithianon |
| 10-4429 | 8-109 | dithianon |
| 10-4430 | 8-110 | dithianon |
| 10-4431 | 8-111 | dithianon |
| 10-4432 | 8-112 | dithianon |
| 10-4433 | 8-113 | dithianon |
| 10-4434 | 8-114 | dithianon |
| 10-4435 | 8-115 | dithianon |
| 10-4436 | 8-116 | dithianon |
| 10-4437 | 8-117 | dithianon |
| 10-4438 | 8-118 | dithianon |
| 10-4439 | 8-119 | dithianon |
| 10-4440 | 8-120 | dithianon |
| 10-4441 | 8-121 | dithianon |
| 10-4442 | 8-122 | dithianon |
| 10-4443 | 8-123 | dithianon |
| 10-4444 | 8-124 | dithianon |
| 10-4445 | 8-125 | dithianon |
| 10-4446 | 8-126 | dithianon |
| 10-4447 | 8-127 | dithianon |
| 10-4448 | 8-128 | dithianon |
| 10-4449 | 8-129 | dithianon |
| 10-4450 | 8-130 | dithianon |
| 10-4451 | 8-131 | dithianon |
| 10-4452 | 8-132 | dithianon |
| 10-4453 | 8-133 | dithianon |
| 10-4454 | 8-134 | dithianon |
| 10-4455 | 8-135 | dithianon |
| 10-4456 | 8-136 | dithianon |
| 10-4457 | 8-137 | dithianon |
| 10-4458 | 8-138 | dithianon |
| 10-4459 | 8-139 | dithianon |
| 10-4460 | 8-140 | dithianon |
| 10-4461 | 8-141 | dithianon |
| 10-4462 | 8-142 | dithianon |
| 10-4463 | 8-143 | dithianon |
| 10-4464 | 8-144 | dithianon |
| 10-4465 | 8-145 | dithianon |
| 10-4466 | 8-146 | dithianon |
| 10-4467 | 8-147 | dithianon |
| 10-4468 | 8-148 | dithianon |
| 10-4469 | 8-149 | dithianon |
| 10-4470 | 8-150 | dithianon |
| 10-4471 | 8-151 | dithianon |
| 10-4472 | 8-152 | dithianon |
| 10-4473 | 8-153 | dithianon |
| 10-4474 | 8-154 | dithianon |
| 10-4475 | 8-155 | dithianon |
| 10-4476 | 8-156 | dithianon |
| 10-4477 | 8-157 | dithianon |
| 10-4478 | 8-158 | dithianon |
| 10-4479 | 8-159 | dithianon |
| 10-4480 | 8-160 | dithianon |
| 10-4481 | 8-161 | dithianon |
| 10-4482 | 8-162 | dithianon |
| 10-4483 | 8-163 | dithianon |
| 10-4484 | 8-164 | dithianon |
| 10-4485 | 8-165 | dithianon |
| 10-4486 | 8-166 | dithianon |
| 10-4487 | 8-167 | dithianon |
| 10-4488 | 8-168 | dithianon |
| 10-4489 | 8-169 | dithianon |
| 10-4490 | 8-170 | dithianon |
| 10-4491 | 8-171 | dithianon |
| 10-4492 | 8-172 | dithianon |
| 10-4493 | 8-173 | dithianon |
| 10-4494 | 8-174 | dithianon |
| 10-4495 | 8-175 | dithianon |
| 10-4496 | 8-176 | dithianon |
| 10-4497 | 8-177 | dithianon |
| 10-4498 | 8-178 | dithianon |
| 10-4499 | 8-179 | dithianon |
| 10-4500 | 8-180 | dithianon |
| 10-4501 | 8-1 | Cu salts |
| 10-4502 | 8-2 | Cu salts |
| 10-4503 | 8-3 | Cu salts |
| 10-4504 | 8-4 | Cu salts |
| 10-4505 | 8-5 | Cu salts |
| 10-4506 | 8-6 | Cu salts |
| 10-4507 | 8-7 | Cu salts |
| 10-4508 | 8-8 | Cu salts |
| 10-4509 | 8-9 | Cu salts |
| 10-4510 | 8-10 | Cu salts |
| 10-4511 | 8-11 | Cu salts |
| 10-4512 | 8-12 | Cu salts |
| 10-4513 | 8-13 | Cu salts |
| 10-4514 | 8-14 | Cu salts |
| 10-4515 | 8-15 | Cu salts |
| 10-4516 | 8-16 | Cu salts |
| 10-4517 | 8-17 | Cu salts |
| 10-4518 | 8-18 | Cu salts |
| 10-4519 | 8-19 | Cu salts |
| 10-4520 | 8-20 | Cu salts |
| 10-4521 | 8-21 | Cu salts |
| 10-4522 | 8-22 | Cu salts |
| 10-4523 | 8-23 | Cu salts |
| 10-4524 | 8-24 | Cu salts |
| 10-4525 | 8-25 | Cu salts |
| 10-4526 | 8-26 | Cu salts |
| 10-4527 | 8-27 | Cu salts |
| 10-4528 | 8-28 | Cu salts |
| 10-4529 | 8-29 | Cu salts |
| 10-4530 | 8-30 | Cu salts |
| 10-4531 | 8-31 | Cu salts |
| 10-4532 | 8-32 | Cu salts |
| 10-4533 | 8-33 | Cu salts |
| 10-4534 | 8-34 | Cu salts |

TABLE 10-continued

| No. | Binary combination | Active compound |
|---|---|---|
| 10-4535 | 8-35 | Cu salts |
| 10-4536 | 8-36 | Cu salts |
| 10-4537 | 8-37 | Cu salts |
| 10-4538 | 8-38 | Cu salts |
| 10-4539 | 8-39 | Cu salts |
| 10-4540 | 8-40 | Cu salts |
| 10-4541 | 8-41 | Cu salts |
| 10-4542 | 8-42 | Cu salts |
| 10-4543 | 8-43 | Cu salts |
| 10-4544 | 8-44 | Cu salts |
| 10-4545 | 8-45 | Cu salts |
| 10-4546 | 8-46 | Cu salts |
| 10-4547 | 8-47 | Cu salts |
| 10-4548 | 8-48 | Cu salts |
| 10-4549 | 8-49 | Cu salts |
| 10-4550 | 8-50 | Cu salts |
| 10-4551 | 8-51 | Cu salts |
| 10-4552 | 8-52 | Cu salts |
| 10-4553 | 8-53 | Cu salts |
| 10-4554 | 8-54 | Cu salts |
| 10-4555 | 8-55 | Cu salts |
| 10-4556 | 8-56 | Cu salts |
| 10-4557 | 8-57 | Cu salts |
| 10-4558 | 8-58 | Cu salts |
| 10-4559 | 8-59 | Cu salts |
| 10-4560 | 8-60 | Cu salts |
| 10-4561 | 8-61 | Cu salts |
| 10-4562 | 8-62 | Cu salts |
| 10-4563 | 8-63 | Cu salts |
| 10-4564 | 8-64 | Cu salts |
| 10-4565 | 8-65 | Cu salts |
| 10-4566 | 8-66 | Cu salts |
| 10-4567 | 8-67 | Cu salts |
| 10-4568 | 8-68 | Cu salts |
| 10-4569 | 8-69 | Cu salts |
| 10-4570 | 8-70 | Cu salts |
| 10-4571 | 8-71 | Cu salts |
| 10-4572 | 8-72 | Cu salts |
| 10-4573 | 8-73 | Cu salts |
| 10-4574 | 8-74 | Cu salts |
| 10-4575 | 8-75 | Cu salts |
| 10-4576 | 8-76 | Cu salts |
| 10-4577 | 8-77 | Cu salts |
| 10-4578 | 8-78 | Cu salts |
| 10-4579 | 8-79 | Cu salts |
| 10-4580 | 8-80 | Cu salts |
| 10-4581 | 8-81 | Cu salts |
| 10-4582 | 8-82 | Cu salts |
| 10-4583 | 8-83 | Cu salts |
| 10-4584 | 8-84 | Cu salts |
| 10-4585 | 8-85 | Cu salts |
| 10-4586 | 8-86 | Cu salts |
| 10-4587 | 8-87 | Cu salts |
| 10-4588 | 8-88 | Cu salts |
| 10-4589 | 8-89 | Cu salts |
| 10-4590 | 8-90 | Cu salts |
| 10-4591 | 8-91 | Cu salts |
| 10-4592 | 8-92 | Cu salts |
| 10-4593 | 8-93 | Cu salts |
| 10-4594 | 8-94 | Cu salts |
| 10-4595 | 8-95 | Cu salts |
| 10-4596 | 8-96 | Cu salts |
| 10-4597 | 8-97 | Cu salts |
| 10-4598 | 8-98 | Cu salts |
| 10-4599 | 8-99 | Cu salts |
| 10-4600 | 8-100 | Cu salts |
| 10-4601 | 8-101 | Cu salts |
| 10-4602 | 8-102 | Cu salts |
| 10-4603 | 8-103 | Cu salts |
| 10-4604 | 8-104 | Cu salts |
| 10-4605 | 8-105 | Cu salts |
| 10-4606 | 8-106 | Cu salts |
| 10-4607 | 8-107 | Cu salts |
| 10-4608 | 8-108 | Cu salts |
| 10-4609 | 8-109 | Cu salts |
| 10-4610 | 8-110 | Cu salts |
| 10-4611 | 8-111 | Cu salts |
| 10-4612 | 8-112 | Cu salts |
| 10-4613 | 8-113 | Cu salts |
| 10-4614 | 8-114 | Cu salts |
| 10-4615 | 8-115 | Cu salts |
| 10-4616 | 8-116 | Cu salts |
| 10-4617 | 8-117 | Cu salts |
| 10-4618 | 8-118 | Cu salts |
| 10-4619 | 8-119 | Cu salts |
| 10-4620 | 8-120 | Cu salts |
| 10-4621 | 8-121 | Cu salts |
| 10-4622 | 8-122 | Cu salts |
| 10-4623 | 8-123 | Cu salts |
| 10-4624 | 8-124 | Cu salts |
| 10-4625 | 8-125 | Cu salts |
| 10-4626 | 8-126 | Cu salts |
| 10-4627 | 8-127 | Cu salts |
| 10-4628 | 8-128 | Cu salts |
| 10-4629 | 8-129 | Cu salts |
| 10-4630 | 8-130 | Cu salts |
| 10-4631 | 8-131 | Cu salts |
| 10-4632 | 8-132 | Cu salts |
| 10-4633 | 8-133 | Cu salts |
| 10-4634 | 8-134 | Cu salts |
| 10-4635 | 8-135 | Cu salts |
| 10-4636 | 8-136 | Cu salts |
| 10-4637 | 8-137 | Cu salts |
| 10-4638 | 8-138 | Cu salts |
| 10-4639 | 8-139 | Cu salts |
| 10-4640 | 8-140 | Cu salts |
| 10-4641 | 8-141 | Cu salts |
| 10-4642 | 8-142 | Cu salts |
| 10-4643 | 8-143 | Cu salts |
| 10-4644 | 8-144 | Cu salts |
| 10-4645 | 8-145 | Cu salts |
| 10-4646 | 8-146 | Cu salts |
| 10-4647 | 8-147 | Cu salts |
| 10-4648 | 8-148 | Cu salts |
| 10-4649 | 8-149 | Cu salts |
| 10-4650 | 8-150 | Cu salts |
| 10-4651 | 8-151 | Cu salts |
| 10-4652 | 8-152 | Cu salts |
| 10-4653 | 8-153 | Cu salts |
| 10-4654 | 8-154 | Cu salts |
| 10-4655 | 8-155 | Cu salts |
| 10-4656 | 8-156 | Cu salts |
| 10-4657 | 8-157 | Cu salts |
| 10-4658 | 8-158 | Cu salts |
| 10-4659 | 8-159 | Cu salts |
| 10-4660 | 8-160 | Cu salts |
| 10-4661 | 8-161 | Cu salts |
| 10-4662 | 8-162 | Cu salts |
| 10-4663 | 8-163 | Cu salts |
| 10-4664 | 8-164 | Cu salts |
| 10-4665 | 8-165 | Cu salts |
| 10-4666 | 8-166 | Cu salts |
| 10-4667 | 8-167 | Cu salts |
| 10-4668 | 8-168 | Cu salts |
| 10-4669 | 8-169 | Cu salts |
| 10-4670 | 8-170 | Cu salts |
| 10-4671 | 8-171 | Cu salts |
| 10-4672 | 8-172 | Cu salts |
| 10-4673 | 8-173 | Cu salts |
| 10-4674 | 8-174 | Cu salts |
| 10-4675 | 8-175 | Cu salts |
| 10-4676 | 8-176 | Cu salts |
| 10-4677 | 8-177 | Cu salts |
| 10-4678 | 8-178 | Cu salts |
| 10-4679 | 8-179 | Cu salts |
| 10-4680 | 8-180 | Cu salts |

The mixtures according to the invention, in particular those comprising a compound I and a compound II, are distinguished by an outstanding effectiveness against a broad spectrum of phytopathogenic fungi from the classes of the Ascomycetes, Basidiomycetes, Deuteromycetes and Peronosporomycetes (syn. Oomycetes). Some are systemically effective and they can be used in plant protection as foliar fungicides, as fungicides for seed dressing and as soil fungicides. In addition, they can also be used for treating seed.

They are particularly important in the control of a multitude of fungi on various cultivated plants, such as wheat, rye, barley, oats, rice, corn, grass, bananas, cotton, soybeans, coffee, sugar cane, vines, fruits and ornamental plants, and vegetables, such as cucumbers, beans, tomatoes, potatoes and cucurbits, and on the seeds of these plants. They may also be used in crops which are tolerant to insect or fungal attack by means of breeding, including genetic engineering methods.

The mixtures according to the invention are of particular importance for controlling *Botryosphaeria* species, *Cylindrocarpon* species, *Eutypa lata, Neonectria liriodendri* and *Stereum hirsutum*, which inter alia attack the wood or the roots of grapevines.

The mixtures according to the invention are especially suitable for controlling the following plant diseases:
*Alternaria* species on vegetables, oilseed rape, sugar beet, fruit, rice, soybeans, and also on potatoes (for example *A. solani* or *A. alternata*) and tomatoes (for example *A. solani* or *A. alternata*) and *Alternaria* ssp. (black head) on wheat,
*Aphanomyces* species on sugar beet and vegetables,
*Ascochyta* species on cereals and vegetables, for example *Ascochyta tritici* (leaf spot) on wheat,
*Bipolaris* and *Drechslera* species on corn, cereals, rice and corn (for example *D. maydis*),
*Blumeria graminis* (powdery mildew) on cereals (for example wheat or barley), *Botrytis cinerea* (gray mold) on strawberries, vegetables, flowers, grapevines and wheat (ear mold),
*Bremia lactucae* on lettuce,
*Cercospora* species on corn, rice, sugar beet and, for example, *Cercospora sojina* (leaf blotch) or *Cercospora kikuchii* (leaf blotch) on soybeans,
*Cladosporium herbarum* (black mold) on wheat,
*Cochliobolus* species on corn, cereals (for example *Cochliobolus sativus*) and rice (for example *Cochliobolus miyabeanus*),
*Colletotricum* species on cotton and, for example, *Colletotrichum truncatum* (antracnose) on soybeans,
*Corynespora cassiicola* (leaf blotch) on soybeans,
*Dematophora necatrix* (root/stem rot) on soybeans,
*Diaporthe phaseolorum* (stem disease) on soybeans,
*Drechslera* species, *Pyrenophora* species on corn, cereals, rice and lawn, on barley (for example *D. teres*) and on wheat (for example *D. tritici-repentis*),
Esca on grapevines, caused by *Phaeoacremonium chlamydosporium, Ph. Aleophilum,* and *Formitipora punctata* (syn. *Phellinus punctatus*),
*Elsinoe ampelina* on grapevines,
*Epicoccum* spp. (black head) on wheat,
*Exserohilum* species on corn,
*Erysiphe cichoracearum* and *Sphaerotheca fuliginea* on cucumbers,
*Fusarium* and *Verticillium* species on various plants: for example *F. graminearum* or *F. culmorum* (root rot) on cereals (for example wheat or barley) or, for example,
*F. oxysporum* on tomatoes and *Fusarium solani* (stem disease) on soybeans,
*Gaeumanomyces graminis* (take-all) on cereals (for example wheat or barley),
*Gibberella* species on cereals and rice (for example *Gibberella fujikuroi*),
*Glomerella cingulata* on grapevines and other plants,
Grainstaining complex on rice,
*Guignardia budwelli* on grapevines,
*Helminthosporium* species on corn and rice,
*Isariopsis clavispora* on grapevines,
*Macrophomina phaseolina* (root/stem rot) on soybeans,
*Michrodochium nivale* (pink snow mold) on cereals (for example wheat or barley),
*Microsphaera diffusa* (powdery mildew) on soybeans,
*Mycosphaerella* species on cereals, bananas and peanuts, such as, for example,
*M. graminicola* on wheat or *M. fijiensis* on bananas,
*Peronospora* species on cabbage (for example *P. brassicae*), bulbous plants (for example *P. destructor*) and, for example,
*Peronospora manshurica* (downy mildew) on soybeans,
*Phakopsara pachyrhizi* (soybean rust) and *Phakopsara meibomiae* (soybean rust) on soybeans,
*Phialophora gregata* (stem disease) on soybeans,
*Phomopsis* species on sunflowers, grapevines (for example *P. viticola*) and soybeans (for example *Phomopsis phaseoli*),
*Phytophthora* species on various plants, for example *P. capsici* on bell peppers,
*Phytophthora megasperma* (leaf/stem rot) on soybeans, *Phytophthora infestans* on potatoes and tomatoes,
*Plasmopara viticola* on grapevines,
*Podosphaera leucotricha* on apples,
*Pseudocercosporella herpotrichoides* (strawbreaker) on cereals (wheat or barley),
*Pseudoperonospora* on various plants, for example *P. cubensis* on cucumbers or *P. humili* on hops,
*Pseudopezicula tracheiphilai* on grapevines,
*Puccinia* species on various plants, for example *P. triticina, P. striformins, P. hordei* or *P. graminis* on cereals (for example wheat or barley) or on asparagus (for example *P. asparagi*),
*Pyricularia oryzae, Corticium sasakii, Sarocladium oryzae, S. attenuatum, Pyrenophora tritici-repentis* (leaf spot) on wheat or *Pyrenophora teres* (net blotch) on barley,
*Entyloma oryzae* on rice,
*Pyricularia grisea* on lawn and cereals,
*Pythium* spp. on lawn, rice, corn, cotton, oilseed rape, sunflowers, sugar beet, vegetables and other plants (for example *P. ultimum* or *P. aphanidermatum*),
*Ramularia collo-cygni* (physiological leaf spots) on barley,
*Rhizoctonia* species on cotton, rice, potatoes, lawn, corn, oilseed rape, potatoes, sugar beet, vegetables and on various other plants, for example *Rhizoctonia solani* (root/stem rot) on soybeans or *Rhizoctonia cerealis* (yellow patch) on wheat or barley,
*Rhynchosporium secalis* on barley (scald), rye and triticale,
*Sclerotinia* species on oilseed rape, sunflowers and, for example, *Sclerotinia sclerotiorum* (stem disease) or *Sclerotinia rolfsii* (stem disease) on soybeans,
*Septoria glycines* (brown spot) on soybeans,
*Septoria tritici* (leaf spot) and *Stagonospora nodorum* on wheat,
*Erysiphe* (syn. *Uncinula*) *necator* on grapevines,
*Setospaeria* species on corn and lawn,
*Sphacelotheca reilinia* on corn,
*Stagonospora nodorum* (glume blotch) on wheat,
*Thievaliopsis* species on soybeans and cotton,
*Tilletia* species on cereals,
*Typhula incarnata* (snow mold) on wheat or barley,
*Ustilago* species on cereals, corn (for example *U. maydis*) and sugar cane,
*Venturia* species (scab) on apples (for example *V. inaequalis*) and pears.

The mixtures according to the invention, in particular those comprising a compound I and a compound II, are particularly suitable for controlling harmful fungi from the class of the Peronosporomycetes (syn. Oomycetes), such as *Peronospora* species, *Phytophthora* species, *Plasmopara viticola* and *Pseudoperonospora* species, in particular those mentioned above.

The mixtures according to the invention, in particular those comprising a compound I and a compound II, are furthermore suitable for controlling harmful fungi in the protection of materials (for example wood, paper, paint dispersions, fibers or fabrics) and in the protection of stored products. In the protection of wood, particular attention is paid to the following harmful fungi: Ascomycetes, such as *Ophiostoma* spp., *Ceratocystis* spp., *Aureobasidium pullulans, Scierophoma* spp., *Chaetomium* spp., *Humicola* spp., *Petriella* spp., *Trichurus* spp.; Basidiomycetes, such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes, such as *Aspergillus* spp., *Cladosporium* spp., *Penicillium* spp., *Trichoderma* spp., *Alternaria* spp., *Paecilomyces* spp. and Zygomycetes, such as *Mucor* spp., additionally in the protection of materials the following yeasts: *Candida* spp. and *Saccharomyces cerevisae*.

The manner in which the mixtures according to the invention may be applied can be varied widely. Thus, the compounds I and the compounds II can be applied simultaneously, that is jointly or separately, or in succession, the order in the case of separate application generally not having any effect on the control results.

Usually, what is applied are mixtures of a compound I and a compound II. However, mixtures of a compound I and a compound II and a further component C against harmful fungi or against other pests such as insects, arachnids or nematodes or else herbicidally active compound or growth regulators or fertilizers may also offer particular advantages.

Suitable further components C in the above sense are in particular the active compounds mentioned in Table 9. Here, it is possible to use one or more of the active compounds mentioned.

Mixtures according to the invention consisting of three active compounds (ternary combinations) comprise, for example, a compound of the formula I, in particular N-(2'-fluoro-4'-chloro-5'-methylbiphenyl-2-yl)-1-methyl-3-trifluoromethyl-1H-pyrazole-4-carboxamide, N-(3',4',5'-trifluorobiphenyl-2-yl)-1-methyl-3-trifluoromethyl-1H-pyrazole-4-carboxamide, N-(3',4',5'-trifluorobiphenyl-2-yl)-1-methyl-3-difluoromethyl-1H-pyrazole-4-carboxamide, N-(2',4',5'-trifluorobiphenyl-2-yl)-1-methyl-3-difluoromethyl-1H-pyrazole-4-carboxamide or N-(3',4',5'-trifluorobiphenyl-2-yl)-3-chlorofluoromethyl-1-methyl-1H-pyrazole-4-carboxamide, a compound of the formula II, in particular 6-(3,4-dichlorophenyl)-5-methyl-[1,2,4]triazolo[1,5-a]pyrimidin-7-ylamine, 6-(4-tert-butylphenyl)-5-methyl-[1,2,4]triazolo[1,5-a]pyrimidin-7-ylamine, 5-methyl-6-(3,5,5-trimethylhexyl)-[1,2,4]triazolo[1,5-a]pyrimidin-7-ylamine, 5-methyl-6-octyl-[1,2,4]triazolo[1,5-a]pyrimidin-7-ylamine, 5-ethyl-6-octyl-[1,2,4]triazolo[1,5-a]pyrimidine-2,7-diamine, 6-ethyl-5-octyl-[1,2,4]triazolo[1,5-a]pyrimidin-7-ylamine, 5-ethyl-6-octyl-[1,2,4]triazolo[1,5-a]pyrimidin-7-ylamine, 5-ethyl-6-(3,5,5-trimethylhexyl)-[1,2,4]triazolo[1,5-a]pyrimidin-7-ylamine, 6-octyl-5-propyl-[1,2,4]triazolo[1,5-a]pyrimidin-7-ylamine, 5-methoxymethyl-6-octyl-[1,2,4]triazolo[1,5-a]pyrimidin-7-ylamine, 6-octyl-5-trifluoromethyl-[1,2,4]triazolo[1,5-a]pyrimidin-7-ylamine and 5-trifluoromethyl-6-(3,5,5-trimethyl-hexyl)-[1,2,4]triazolo[1,5-a]pyrimidin-7-ylamine, and an active compound of Table 9.

Compounds I and compounds II are usually empoyed in a weight ratio of from 100:1 to 1:100, preferably from 20:1 to 1:20, in particular from 10:1 to 1:10.

If the mixture according to the invention comprises a further component C, the latter is preferably employed in a ratio of from 20:1 to 1:20, based on the compound 1.

Depending on the nature of the compound and the desired effect, the application rates of the mixtures according to the invention are in the range of from 5 g/ha to 2000 g/ha, preferably from 50 to 900 g/ha, in particular from 50 to 750 g/ha.

The application rates for the compounds I and II and, if appropriate, the component C are in the range of from 1 to 1000 g/ha, preferably from 10 to 900 g/ha, in particular from 20 to 750 g/ha.

In the treatment of seed, for example by dusting, coating or drenching seed, application rates of mixture are generally from 1 to 1000 g/100 kg of seed, preferably from 1 to 750 g/100 kg, in particular from 5 to 500 g/100 kg of seed.

According to the invention, the method for controlling harmful fungi is carried out by separate or joint application of at least one compound I and at least one compound II by spraying or dusting the seeds, the plants or the soils before or after sowing of the plants or before or after emergence of the plants.

A further embodiment of the method according to the invention for controlling harmful fungi is carried out by application of a mixture according to the invention comprising in particular components A and B and also a further active compound of Table 9 as component C, by spraying or dusting the seeds, the plants or the soils before or after sowing of the plants or before or after emergence of the plants.

The mixtures according to the invention, in particular those comprising a compound I and a compound II, can be converted into the customary formulations, for example solutions, emulsions, suspensions, dusts, powders, pastes or granules. The use form depends on the particular intended purpose; in each case, it should ensure a fine and even distribution of the mixture according to the invention.

The formulations are prepared in a known manner, for example by extending the active compound with solvents and carriers or solvents or carriers, if desired using further auxiliaries such as emulsifiers and dispersants. Here, individual compounds may also have various functions. Solvents, carriers and auxiliaries suitable for this purpose are essentially:

water, aromatic solvents (for example Solvesso® products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used.

carriers such as ground natural minerals (for example kaolins, clays, talc, chalk) and ground synthetic minerals (for example highly disperse silica, silicates); emulsifiers such as nonionogenic and anionic emulsifiers (for example polyoxyethylene fatty alcohol ethers, alkylsulfonates and arylsulfonates) and dispersants such as lignosulfite waste liquors and methylcellulose.

The preparations according to the invention can be formulated in solid form or in liquid form. Depending on the embodiment, the preparations according to the invention may also comprise auxiliaries and/or carriers customary in crop protection compositions or in compositions for the protection of materials. The auxiliaries include in particular conventional surface-active substances and other additives and carriers customary in crop protection and in the protection of materials, which compounds may be solid or liquid. The surface-active substances include in particular surfactants, especially those having wetting agent properties. The other auxiliaries (additives) include in particular thickeners, antifoams, preservatives, antifreeze agents, stabilizers, anticaking agents or powder-flow aids and buffers.

Conventional surface-active substances which are suitable in principle are anionic, nonionic and amphoteric surfactants including polymer surfactants, and the molecular weight of the surfactants will typically not exceed a value of 2000 Dalton and in particular 1000 Dalton (number-average).

The anionic surfactants include, for example, carboxylates, in particular alkali metal, alkaline earth metal, and ammonium salts of fatty acids, for example potassium stearate, which are usually also referred to as soaps; acyl glutamates; sarcosinates, for example sodium lauroyl sarcosinate; taurates; methylcelluloses; alkyl phosphates, in particular alkyl esters of mono- and diphosphoric acid; sulfates, in particular alkyl sulfates and alkyl ether sulfates; sulfonates, furthermore alkyl sulfonates and alkylaryl sulfonates, in particular alkali metal, alkaline earth metal and ammonium salts of arylsulfonic acids and of alkyl-substituted arylsulfonic acids, alkylbenzenesulfonic acids, such as, for example, lignol and phenolsulfonic acid, naphthalene- and dibutyl-naphthalenesulfonic acids, or dodecylbenzenesulfonates, alkylnaphthalene-sulfonates, alkyl methyl ester sulfonates, condensates of sulfonated naphthalene and derivatives thereof with formaldehyde, condensates of naphthalene sulfonic acids, phenol- and/or phenolsulfonic acids with formaldehyde or with formaldehyde and urea, mono- or dialkyl sulfosuccinates; and also protein hydrolysates and lignosulfite waste liquors. The abovementioned sulfonic acids are advantageously used in the form of their neutral or, if appropriate, basic salts.

The nonionic surfactants include, for example:
fatty alcohol alkoxylates and oxoalcohol alkoxylates, in particular ethoxylates and propoxylates having degrees of alkoxylation of usually from 2 to 100 and in particular from 3 to 50, for example alkoxylates of $C_8$-$C_{30}$-alkanols or alk(adi)enols, for example of isotridecyl alcohol, lauryl alcohol, oleyl alcohol or stearyl alcohol, and their $C_1$-$C_4$-alkyl ethers and $C_1$-$C_4$-alkyl esters, for example their acetates;
alkoxylated animal and/or vegetable fats and/or oils, for example corn oil ethoxylates, castor oil ethoxylates, tallow fat ethoxylates,
glycerol esters, such as, for example, glycerol monostearate,
alkylphenol alkoxylates, such as, for example, ethoxylated isooctylphenol, octylphenol or nonylphenol, tributylphenol polyoxyethylene ether,
fatty amine alkoxylates, fatty acid amide alkoxylates and fatty acid diethanolamide alkoxylates, in particular their ethoxylates,
sugar surfactants, sorbitol esters, such as, for example, sorbitan fatty acid esters (sorbitan monooleate, sorbitan tristearate), polyoxyethylene sorbitan fatty acid esters, alkyl polyglycosides, N-alkylguconamides,
alkyl methyl sulfoxides,
alkyldimethylphosphine oxides, such as, for example, tetradecyldimethyl-phosphine oxide.

The amphoteric surfactants include, for example, sulfobetaines, carboxybetaines and alkyldimethylamine oxides, for example tetradecyldimethylamine oxide.

Other surfactants which may be mentioned here by way of example are perfluoro surfactants, silicone surfactants, phospholipids, such as, for example, lecithin or chemically modified lecithins, amino acid surfactants, for example N-lauroyl-glutamate.

Suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydro-naphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dustable products can be prepared by mixing or concomitantly grinding the active components A and B and, if present further actives with at least one solid carrier.

Granules, for example coated granules, impregnated granules and homogeneous granules, can be prepared by binding the active compounds to at least one solid carrier. Examples of solid carriers are mineral earths such as silica gels, silicates, talc, kaolin, altaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

The formulations of the mixtures according to the invention generally comprise from 0.01 to 95% by weight, preferably from 0.1 to 90% by weight, of the compounds I and II. Here, the active compounds are preferably employed in a purity of from 90% to 100%, preferably from 95% to 100%.

For the treatment of seed, the formulations in question give, after two-to-tenfold dilution, active compound concentrations of from 0.01 to 60% by weight, preferably from 0.1 to 40% by weight, in the ready-to-use preparations.

The following are examples of formulations:
1. Products for dilution with water
F1) Water-Soluble Concentrates (SL)
10 parts by weight of a mixture according to the invention are dissolved in 90 parts by weight of water or in a water-soluble solvent. As an alternative, wetters or other auxiliaries are added. The active compound dissolves upon dilution with water. In this way, a formulation having a content of 10% by weight of active compound is obtained.
F2) Dispersible Concentrates (DC)
20 parts by weight of a mixture according to the invention are dissolved in 70 parts by weight of cyclohexanone with addition of 10 parts by weight of a dispersant, for example polyvinylpyrrolidone. Dilution with water gives a dispersion. The formulation has an active compound content of 20% by weight.
F3) Emulsifiable Concentrates (EC)
15 parts by weight of a mixture according to the invention are dissolved in 75 parts by weight of xylene with addition of calcium dodecylbenzenesulfonate and castor oil ethoxylate (in each case 5 parts by weight). Dilution with water gives an emulsion. The formulation has an active compound content of 15% by weight.
F4) Emulsions (EW, EO)
25 parts by weight of a mixture according to the invention are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (Ultraturrax) and made into a homogeneous emulsion. Dilution with water gives an emulsion. The formulation has an active compound content of 25% by weight.

F5) Suspensions (SC, OD)

In an agitated ball mill, 20 parts by weight of a mixture according to the invention are comminuted with addition of 10 parts by weight of dispersants and wetters and 70 parts by weight of water or an organic solvent to give a fine active compound suspension. Dilution with water gives a stable suspension of the active compound. The formulation has an active compound content of 20% by weight.

F6) Water-Dispersible Granules and Water-Soluble Granules (WG, SG)

50 parts by weight of a mixture according to the invention are ground finely with addition of 50 parts by weight of dispersants and wetters and prepared as water-dispersible or water-soluble granules by means of technical appliances (for example extrusion, spray tower, fluidized bed). Dilution with water gives a stable dispersion or solution of the active compound. The formulation has an active compound content of 50% by weight.

F7) Water-Dispersible Powders and Water-Soluble Powders (WP, SP)

75 parts by weight of a mixture according to the invention are ground in a rotor-stator mill with addition of 25 parts by weight of dispersants, wetters and silica gel. Dilution with water gives a stable dispersion or solution of the active compound. The formulation has an active compound content of 75% by weight.

2. Products to be Applied Undiluted

F8) Dustable Powders (DP)

5 parts by weight of a mixture according to the invention are ground finely and mixed intimately with 95 parts by weight of finely divided kaolin. This gives a dustable product having an active compound content of 5% by weight.

F9) Granules (GR, FG, GG, MG)

0.5 part by weight of a mixture according to the invention is ground finely and associated with 99.5 parts by weight of carriers. Current methods are extrusion, spray-drying or the fluidized bed. This gives granules to be applied undiluted having an active compound content of 0.5% by weight.

F10) ULV Solutions (UL)

10 parts by weight of a mixture according to the invention are dissolved in 90 parts by weight of an organic solvent, for example xylene. This gives a product to be applied undiluted having an active compound content of 10% by weight.

For seed treatment, use is usually made of water-soluble concentrates (LS), suspensions (FS), dustable powders (DS), water-dispersible and water-soluble powders (WS, SS), emulsions (ES), emulsifiable concentrates (EC) and gel formulations (GF). These formulations can be applied to the seed in undiluted form or, preferably, diluted. Application can be carried out prior to sowing.

Preference is given to using formulations in suspensions for seed treatment. Usually, such formulations comprise from 1 to 800 g of active compound/l, from 1 to 200 g of surfactants/l, from 0 to 200 g of antifreeze agents/l, from 0 to 400 g of binder/l, from 0 to 200 g of colorants/l and solvents, preferably water.

Analogous formulations F1 to F10 of the mixtures according to the invention comprising compounds I and II or, if appropriate, a further active compound comprise the respective amount of the individual active compounds. They are usually mixed directly before application during dilution to the ready-to-use active compound concentration (tank mix).

The active compound concentrations in the ready-to-use preparations can be varied within relatively wide ranges. In general, they are from 0.0001 to 10%, preferably from 0.01 to 1%.

The active compounds can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds according to the invention.

Aqueous use forms can be prepared from emulsion concentrates, pastes or wettable powders (wettable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water.

The active components and, if appropriate, further active compounds may also be used successfully in the ultra-low-volume process (ULV), it being possible to apply formulations comprising over 95% by weight of active compound, or even to apply the active compound without additives.

Oils of various types, wetting agents, adjuvants, herbicides, other pesticides, or bactericides may be added to the active compounds, even, if appropriate, not until immediately prior to use (tank mix). These agents may be admixed with the compositions according to the invention in a weight ratio of from 1:100 to 100:1, preferably from 1:10 to 10:1.

Suitable adjuvants in this sense are in particular: organically modified polysiloxanes, for example Break Thru S 240®; alcohol alkoxylates, for example Atplus 245®, Atplus MBA 1303®, Plurafac LF 300® and Lutensol ON 30®; EO/PO block polymers, for example Pluronic RPE 2035® and Genapol B®; alcohol ethoxylates, for example Lutensol XP 80®; and sodium dioctylsulfosuccinate, for example Leophen RA®.

The mixtures according to the invention comprising the compounds I and II or the corresponding formulations are applied by treating the harmful fungi, the plants, seeds, soils, areas, materials or spaces to be kept free from them with a fungicidally effective amount of the mixture of the compounds of the invention. Application can be carried out before or after infection by the harmful fungi.

USE EXAMPLES

The fungicidal effect of the individual compounds and the mixtures according to the invention was demonstrated by the following tests.

The expected efficacies of active compound combinations were determined using Colby's formula (Colby, S. R. "Calculating synergistic and antagonistic responses of herbicide combinations", Weeds, 15, 20-22, 1967) and compared with the observed efficacies.

Colby's formula: $E = x + y - x \cdot y / 100$

E expected efficacy, expressed in % of the untreated control, when using the mixture of the active compounds A and B at the concentrations a and b;

x efficacy, expressed in % of the untreated control, when using the active compound A at the concentration a;

y efficacy, expressed in % of the untreated control, when using the active compound B at the concentration b.

Micro Tests

The active compounds were formulated separately as a stock solution having a concentration of 10 000 ppm in DMSO.

Use Example 1

Activity Against the Late Blight Pathogen *Phytophthora infestans* in the Microtiter Test The stock solution is pipetted onto a microtiter plate (MTP) and diluted to the stated active compound concentration using a pea juice-based aqueous nutrient medium for fungi. An aqueous zoospore suspension of *Phytophthora infestans* was then added. The plates were placed in a water vapor-saturated chamber at temperatures of 18° C. Using an absorption photometer, the MTPs were measured at 405 nm on day 7 after the inoculation.

The measured parameters were compared to the growth of the active compound-free control variant and the fungus- and active compound-free blank value to determine the relative growth in % of the pathogens in the individual active compounds.

| No. | Active compound/active compound combination | Conc. [ppm] | Ratio | Observed effect (%) | Effect calculated according to Colby (%) |
|---|---|---|---|---|---|
| 1 | 3-1 | 16 | | 4 | |
| | | 4 | | 0 | |
| | | 1 | | 0 | |
| 2 | 3-3 | 4 | | 0 | |
| | | 1 | | 0 | |
| | | 0.25 | | 0 | |
| 3 | 3-6 | 16 | | 18 | |
| | | 4 | | 3 | |
| | | 1 | | 0 | |
| 4 | 3-7 | 4 | | 4 | |
| | | 1 | | 1 | |
| 5 | 3-8 | 16 | | 20 | |
| | | 4 | | 10 | |
| 6 | 3-9 | 4 | | 9 | |
| 7 | 3-10 | 4 | | 6 | |
| | | 1 | | 1 | |
| 8 | 3-11 | 16 | | 9 | |
| | | 1 | | 7 | |
| 9 | 3-12 | 1 | | 11 | |
| 10 | 3-13 | 16 | | 4 | |
| | | 4 | | 4 | |
| | | 1 | | 1 | |
| 11 | 3-14 | 16 | | 18 | |
| | | 4 | | 11 | |
| | | 1 | | 3 | |
| 12 | 7-3 | 1 | | 31 | |
| 13 | 7-4 | 4 | | 45 | |
| 14 | 7-5 | 4 | | 73 | |
| | | 0.25 | | 27 | |
| 15 | 7-9 | 4 | | 58 | |
| | | 1 | | 20 | |
| 16 | 7-12 | 16 | | 66 | |
| 17 | 3-1 + 7-3 | 1 + 1 | 1:1 | 67 | 31 |
| 18 | 3-3 + 7-3 | 1 + 1 | 1:1 | 74 | 31 |
| 19 | 3-6 + 7-3 | 1 + 1 | 1:1 | 51 | 31 |
| 20 | 3-10 + 7-3 | 1 + 1 | 1:1 | 56 | 32 |
| 21 | 3-11 + 7-3 | 1 + 1 | 1:1 | 62 | 36 |
| 22 | 3-13 + 7-3 | 1 + 1 | 1:1 | 64 | 32 |
| 23 | 3-14 + 7-3 | 1 + 1 | 1:1 | 75 | 34 |

-continued

| No. | Active compound/active compound combination | Conc. [ppm] | Ratio | Observed effect (%) | Effect calculated according to Colby (%) |
|---|---|---|---|---|---|
| 24 | 3-1 + 7-4 | 4 + 4 | 1:1 | 98 | 45 |
| 25 | 3-3 + 7-4 | 4 + 4 | 1:1 | 80 | 45 |
| 26 | 3-6 + 7-4 | 4 + 4 | 1:1 | 88 | 46 |
| 27 | 3-7 + 7-4 | 4 + 4 | 1:1 | 84 | 47 |
| 28 | 3-8 + 7-4 | 4 + 4 | 1:1 | 75 | 50 |
| 29 | 3-9 + 7-4 | 4 + 4 | 1:1 | 76 | 49 |
| 30 | 3-10 + 7-4 | 4 + 4 | 1:1 | 68 | 48 |
| 31 | 3-12 + 7-4 | 4 + 4 | 1:1 | 74 | 47 |
| 32 | 3-13 + 7-4 | 4 + 4 | 1:1 | 75 | 47 |
| 33 | 3-14 + 7-4 | 4 + 4 | 1:1 | 82 | 51 |
| 34 | 3-1 + 7-5 | 4 + 4 | 1:1 | 94 | 73 |
| 35 | 3-3 + 7-5 | 0.25 + 0.25 | 1:1 | 26 | 0 |
| 36 | 3-14 + 7-5 | 4 + 4 | 1:1 | 97 | 76 |
| 37 | 3-1 + 7-9 | 4 + 4 | 1:1 | 85 | 58 |
| 38 | 3-3 + 7-9 | 1 + 1 | 1:1 | 89 | 20 |
| 39 | 3-6 + 7-9 | 1 + 1 | 1:1 | 81 | 20 |
| 40 | 3-7 + 7-9 | 1 + 1 | 1:1 | 57 | 21 |
| 41 | 3-8 + 7-9 | 4 + 4 | 1:1 | 87 | 62 |
| 42 | 3-10 + 7-9 | 1 + 1 | 1:1 | 56 | 32 |
| 43 | 3-12 + 7-9 | 1 + 1 | 1:1 | 48 | 29 |
| 44 | 3-13 + 7-9 | 1 + 1 | 1:1 | 53 | 21 |
| 45 | 3-14 + 7-9 | 1 + 1 | 1:1 | 48 | 23 |
| 46 | 3-1 + 7-12 | 16 + 16 | 1:1 | 35 | 7 |
| 47 | 3-6 + 7-12 | 16 + 16 | 1:1 | 100 | 72 |
| 48 | 3-8 + 7-12 | 16 + 16 | 1:1 | 100 | 72 |
| 49 | 3-11 + 7-12 | 16 + 16 | 1:1 | 100 | 69 |
| 50 | 3-12 + 7-12 | 16 + 16 | 1:1 | 100 | 68 |
| 51 | 3-13 + 7-12 | 16 + 16 | 1:1 | 100 | 67 |
| 52 | 3-14 + 7-12 | 16 + 16 | 1:1 | 100 | 72 |

Greenhouse

The active compounds were separately or jointly prepared as a stock solution comprising 25 mg of active compound which was made up to 10 ml using a mixture of acetone and/or dimethyl sulfoxide and the emulsifier Uniperol® EL (wetting agent having emulsifying and dispersing action based on ethoxylated alkylphenols) in a volume ratio of solvent/emulsifier of 99 to 1. The mixture was then made up with water to 100 ml. This stock solution was diluted with the solvent/emulsifier/water mixture described to the concentration of active compound stated below.

Use Example 2

Curative Activity Against Brown Rust of Wheat Caused by *Puccinia recondita*

Leaves of potted wheat seedlings were inoculated with a spore suspension of brown rust (*Puccinia recondita*). The pots were then placed in a chamber with high atmospheric humidity (90 to 95%) and 20 to 22° C. for 24 hours. During this time, the spores germinated and the germ tubes penetrated into the leaf tissue. The next day, the infected plants were sprayed to runoff point with the active compound solution described above at the active compound concentration stated below. After the spray coating had dried on, the test plants were cultivated in a greenhouse at temperatures between 20 and 22° C. and at 65 to 70% relative atmospheric humidity for 7 days. The extent of the rust fungus development on the leaves was then determined.

The visually determined percentages of infected leaf areas were converted into efficacies in % of the untreated control.

The efficacy (E) is calculated as follows using Abbot's formula:

Abbot's formula: $E = (1 - \alpha/\beta) \cdot 100$

α corresponds to the fungicidal infection of the treated plants in % and

β corresponds to the fungicidal infection of the untreated (control) plants in %

An efficacy of 0 means that the infection level of the treated plants corresponds to that of the untreated control plants; an efficacy of 100 means that the treated plants were not infected.

| No. | Active compound/ active compound combination | Conc. [ppm] | Ratio | Observed effect (%) | Effect calculated according to Colby (%) |
|---|---|---|---|---|---|
| 53 | — (control) | — | | 0 (90% infection) | |
| 54 | 3-9 | 0.25 | | 0 | |
| 55 | 7-5 | 1 | | 0 | |
| 56 | 7-6 | 1 | | 0 | |
| 57 | 7-8 | 1 | | 0 | |
| 58 | 3-9 + 7-5 | 0.25 + 1 | 1:4 | 67 | 0 |
| 59 | 3-9 + 7-6 | 0.25 + 1 | 1:4 | 72 | 0 |
| 60 | 3-9 + 7-8 | 0.25 + 1 | 1:4 | 44 | 0 |

Use Example 3

Protective Activity Against *Puccinia recondita* on Wheat (Brown Rust of Wheat)

Leaves of potted wheat seedlings were sprayed to runoff point with an aqueous suspension having the active compound concentration stated below. The next day, the treated plants were inoculated with a spore suspension of brown rust of wheat (*Puccinia recondita*). The plants were then placed in a chamber with high atmospheric humidity (90 to 95%) at 20 to 22° C. for 24 hours. During this time, the spores germinated and the germ tubes penetrated into the leaf tissue. The next day, the test plants were returned to the greenhouse and cultivated at temperatures between 20 and 22° C. and at 65 to 70% relative atmospheric humidity for a further 7 days. The extent of the rust fungus development on the leaves was then determined visually.

| No. | Active compound/ active compound combination | Conc. [ppm] | Ratio | Observed effect (%) | Effect calculated according to Colby (%) |
|---|---|---|---|---|---|
| 61 | — (control) | — | | 0 (80% infection) | |
| 62 | 3-9 | 0.25 | | 50 | |
| 63 | 7-1 | 1 | | 0 | |
| 64 | 3-9 + 7-1 | 0.25 + 1 | 1:4 | 88 | 50 |

Use Example 4

Activity Against Early Blight on Tomatoes Caused by *Alternaria solani*

Leaves of potted tomato plants are sprayed to runoff point with an aqueous suspension having the concentration of active compounds stated below. The next day, the leaves are infected with an aqueous spore suspension of *Alternaria solani* in a 2% biomalt solution having a density of 0.17×10⁶ spores/ml. The plants are then placed in a water vapor-saturated chamber at temperatures between 20 and 22° C. After 5 days, the disease on the untreated, but infected control plants had developed to such an extent that the infection could be determined visually in %.

Use Example 5

Activity Against Gray Mold on Bell Pepper Leaves Caused by *Botrytis cinerea*, 1 Day Protective Application Bell pepper seedlings of the cultivar "Neusiedler Ideal Elite" are, after 2-3 leaves are well developed, sprayed to runoff point with an aqueous suspension in the active compound concentration stated below. The next day, the treated plants are inoculated with a spore suspension of *Botrytis cinerea* which comprises $1.7 \times 10^6$ spores/ml in a 2% strength aqueous biomalt solution. The test plants are then placed in a dark climatized chamber at 22 to 24° C. and high atmospheric humidity. After 5 days, the extent of the fungal infection on the leaves can be determined visually in %.

The test results show that, by virtue of the synergism, the mixtures according to the invention are considerably more active than had been predicted using Colby's formula.

The invention claimed is:

1. A fungicidal mixture comprising:
A) at least one 1-methylpyrazol-4-ylcarboxanilide of the formula I

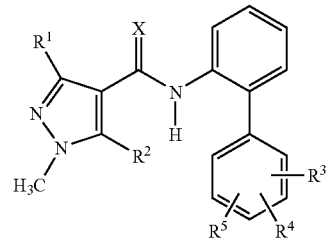

I in which the substituents have the following meanings:
X is oxygen or sulfur:
$R^1$ is $C_1$-$C_4$-alkyl or $C_1$-$C_4$-haloalkyl;
$R^2$ is hydrogen or halogen;
$R^3$, $R^4$ and $R^5$ independently of one another are cyano, nitro, halogen, $C_1$-$C_4$-alkyl, $C_1$-$C_4$-haloalkyl, $C_1$-$C_4$-alkoxy, $C_1$-$C_4$-haloalkoxy or $C_1$-$C_4$alkylthio;
and
B) at least one azolopyrimidinylamine of the formula II

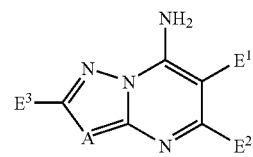

II in which the substituents have the following meaning:
$E^1$ is $C_3$-$C_{12}$-alkyl, $C_2$-$C_{12}$-alkenyl, $C_5$-$C_{12}$-alkoxyalkyl, $C_3$-$C_6$-cycloalkyl, phenyl or phenyl-$C_1$-$C_4$-alkyl;
$E^2$ is $C_1$-$C_{12}$-alkyl, $C_2$-$C_{12}$-alkenyl, $C_1$-$C_4$-haloalkyl or $C_1$-$C_4$-alkoxy-$C_1$-$C_4$-alkyl;

where the aliphatic chains in $E^1$ and/or $E^2$ may be substituted by one to four identical or different groups $R^a$:

$R^a$ is halogen, cyano, hydroxy, mercapto, $C_1$-$C_{10}$-alkyl, $C_1$-$C_{10}$-haloalkyl, $C_3$-$C_8$-cycloalkyl, $C_2$-$C_{10}$-alkenyl, $C_2$-$C_{10}$-alkynyl, $C_1$-$C_6$-alkoxy, $C_1$-$C_6$-alkylthio, $C_1$-$C_6$-alkoxy-$C_1$-$C_6$-alkyl or $NR^AR^B$;

$R^A$, $R^B$ independently of one another are hydrogen or $C_1$-$C_6$-alkyl;

where the cyclic groups in $E^1$ and/or $R^a$ may be substituted by one to four groups $R^b$:

$R^b$ is halogen, cyano, hydroxyl, mercapto, nitro, $NR^AR^B$, $C_1$-$C_{10}$-alkyl, $C_1$-$C_6$-haloalkyl, $C_2$-$C_6$-alkenyl, $C_2$-$C_6$-alkynyl or $C_1$-$C_6$-alkoxy;

$E^3$ is hydrogen, halogen, cyano, $NR^AR^B$, hydroxyl, mercapto, $C_1$-$C_6$-alkyl, $C_1$-$C_6$-haloalkyl, $C_3$-$C_8$-cycloalkyl, $C_1$-$C_6$-alkoxy, $C_1$-$C_6$-alkylthio, $C_3$-$C_8$-cycloalkoxy, $C_3$-$C_8$-cycloalkylthio, carboxyl, formyl, $C_1$-$C_{10}$-alkyl-carbonyl, $C_1$-$C_{10}$-alkoxycarbonyl, $C_2$-$C_{10}$-alkenyloxycarbonyl, $C_2$-$C_{10}$-alkynyloxycarbonyl, phenyl, phenoxy, phenylthio, benzyloxy, benzylthio or $C_1$-$C_6$-alkyl-$S(O)_m$;

m is 0, 1 or 2; and

A is CH or N;

in a synergistically effective amount.

2. The fungicidal mixture of claim 1, comprising component A and component B in a weight ratio of from 100:1 to 1:100.

3. The fungicidal mixture of claim 1 comprising, as component A, at least one 1-methylpyrazol-4-ylcarboxanilide of the formula I where $R^1$ is methyl or halomethyl; $R^2$ is hydrogen, fluorine or chlorine; and $R^3$, $R^4$ and $R^5$ are each halogen.

4. The fungicidal mixture of claim 1 comprising, as component A, at least one compound I selected from the group consisting of:

N-(2'-fluoro-4'-chloro-5'-methoxybiphenyl-2-yl)-3-trifluoromethyl-1-methyl-1H-pyrazole-4-carboxamide, N-(2'-fluoro-4'-chloro-5'-methylbiphenyl-2-yl)-3-trifluoromethyl-1-methyl-1H-pyrazole-4-carboxamide, N-(3',4',5'-trifluorobiphenyl-2-yl)-3-trifluoromethyl-1-methyl-1H-pyrazole-4-carboxamide, N-(2',4',5'-trifluorobiphenyl-2-yl)-3-trifluoromethyl-1-methyl-1H-pyrazole-4-carboxamide, N-(2',3',4'-trifluorobiphenyl-2-yl)-3-trifluoromethyl-1-methyl-1H-pyrazole-4-carboxamide, N-(2'-fluoro-4'-chloro-5'-methoxybiphenyl-2-yl)-3-difluoromethyl-1-methyl-1H-pyrazole-4-carboxamide, N-(2'-fluoro-4'-chloro-5'-methylbiphenyl-2-yl), 3-difluoromethyl-1-methyl-1H-pyrazole-4-carboxamide, N-(3',4',5'-trifluorobiphenyl-2-yl)-3-difluoromethyl-1-methyl-1H-pyrazole-4-carboxamide, N-(2',4',5'-trifluorobiphenyl-2-yl)-3-difluoromethyl-1-methyl-1H-pyrazole-4-carboxamide, N-(3',4',5'-trifluorobiphenyl-2-yl)-3-fluoromethyl-1-methyl-1H-pyrazole-4-carboxamide, N-(3',4',5'-trifluorobiphenyl-2-yl)-3-chlorodifluoromethyl-1-methyl-1H-pyrazole-4-carboxamide, N-(3',4',5'-trifluorobiphenyl-2-yl)-3-chlorofluoromethyl-1-methyl-1H-pyrazole-4-carboxamide, N-(2',3',4'-trifluorobiphenyl-2-yl)-3-fluoromethyl-1-methyl-1H-pyrazole-4-carboxamide and N-(2',4',5'-trifluorobiphenyl-2-yl)-3-fluoromethyl-1-methyl-1H-pyrazole-4-carboxamide.

5. The fungicidal mixture of claim 1 comprising, as component B, at least one compound of the formula IIa

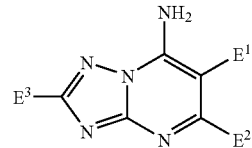

in which the substituents have the following meanings:

$E^1$ is $C_3$-$C_{12}$-alkyl, $C_5$-$C_{12}$-alkoxyalkyl, phenyl or phenyl-$C_1$-$C_4$-alkyl, where phenyl may be substituted by one to three groups $R^b$;

$E^2$ is $C_1$-$C_{12}$-alkyl, $C_1$-$C_4$-haloalkyl or $C_1$-$C_4$-alkoxy-$C_1$-$C_4$-alkyl;

$E^3$ is hydrogen or $NH_2$;

$R^b$ is halogen, cyano, hydroxyl, mercapto, nitro, $NR^AR^B$, $C_1$-$C_{10}$-alkyl, $C_1$-$C_6$-haloalkyl, $C_2$-$C_6$-alkenyl, $C_2$-$C_6$-alkynyl or $C_1$-$C_6$-alkoxy; wherein $R^A$, $R^B$ independently of one another are hydrogen or $C_1$-$C_6$-alkyl.

6. The fungicidal mixture of claim 1, comprising, as component B, at least one compound II selected from the group consisting of 6-(3,4-dichlorophenyl)-5-methyl-[1,2,4]triazolo[1,5-a]pyrimidin-7-ylamine, 6-(4-tert-butylphenyl)-5-methyl-[1,2,4]triazolo[1,5-a]pyrimidin-7-ylamine, 5-methyl-6-(3,5,5-trimethylhexyl)-[1,2,4]triazolo[1,5-a]pyrimidin-7-ylamine, 5-methyl-6-octyl-[1,2,4]triazolo[1,5-a]pyrimidin-7-ylamine, 6-methyl-5-octyl-[1,2,4]triazolo[1,5-a]pyrimidin-7-ylamine, 6-ethyl-5-octyl-[1,2,4]triazolo[1,5-a]pyrimidin-7-ylamine, 5-ethyl-6-octyl-[1,2,4]triazolo[1,5-a]pyrimidin-7-ylamine, 5-ethyl-6-(3,5,5-trimethylhexyl)-[1,2,4]triazolo[1,5-a]pyrimidin-7-ylamine, 6-octyl-5-propyl-[1,2,4]triazolo[1,5-a]pyrimidin-7-ylamine, 5-methoxymethyl-6-octyl-[1,2,4]triazolo[1,5-a]pyrimidin-7-ylamine, 6-octyl-5-trifluoromethyl-[1,2,4]triazolo[1,5-a]pyrimidin-7-ylamine and 5-trifluoromethyl-6-(3,5,5-trimethylhexyl)-[1,2,4]triazolo[1,5-a]pyrimidin-7-ylamine.

7. A fungicidal composition comprising at least one liquid or solid carrier and the mixture of claim 1.

8. A method for controlling phytopathogenic harmful fungi wherein the fungi, their habitat or the plants, the soil, seed, areas, materials or spaces to be protected against fungal attack are treated with a synergistically effective amount of the mixture of claim 1.

9. The method according of claim 8, wherein the compound I and the compound II or their mixtures are applied in an amount of from 5 g/ha to 2000 g/ha.

10. The method of claim 8, wherein the compound I and the compound II or their mixtures are applied in an amount of from 1 g to 1000 g per 100 kg of seed.

11. The method of claim 8, wherein harmful fungi from the class of the Oomycetes are controlled.

12. Seed comprising a mixture of claim 1 in an amount of from 1 g to 1000 g per 100 kg of seed.

13. A method for controlling phytopathogenic harmful fungi comprising treating the fungi, their habitat or the plants, the soil, seed, areas, materials or spaces to be protected against fungal attack with compound I

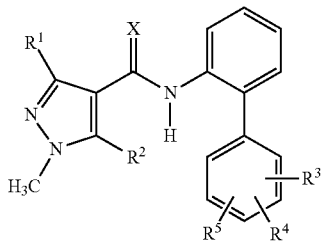

wherein:
X is oxygen or sulfur:
$R^1$ is $C_1$-$C_4$-alkyl or $C_1$-$C_4$-haloalkyl;
$R^2$ is hydrogen or halogen;
$R^3$, $R^4$ and $R^5$ independently of one another are cyano, nitro, halogen, $C_1$-$C_4$-alkyl, $C_1$-$C_4$-haloalkyl, $C_1$-$C_4$-alkoxy, $C_1$-$C_4$-haloalkoxy or $C_1$-$C_4$-alkylthio;
and compound II

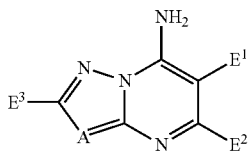

wherein:
$E^1$ is $C_3$-$C_{12}$-alkyl, $C_2$-$C_{12}$-alkenyl, $C_5$-$C_{12}$-alkoxyalkyl, $C_3$-$C_6$-cycloalkyl, phenyl or phenyl-$C_1$-$C_4$-alkyl;

$E^2$ is $C_1$-$C_{12}$-alkyl, $C_2$-$C_{12}$-alkenyl, $C_1$-$C_4$-haloalkyl or $C_1$-$C_4$-alkoxy-$C_1$-$C_4$-alkyl;
  where the aliphatic chains in $E^1$ and/or $E^2$ may be substituted by one to four identical or different groups $R^a$:
  $R^a$ is halogen, cyano, hydroxy, mercapto, $C_1$-$C_{10}$-haloalkyl, $C_3$-$C_8$-cycloalkyl, $C_2$-$C_{10}$-alkenyl, $C_2$-$C_{10}$-alkynyl, $C_1$-$C_6$-alkoxy, $C_1$-$C_6$-alkylthio, $C_1$-$C_6$-alkoxy-$C_1$-$C_6$-alkyl or $NR^A R^B$;
  $R^A$, $R^B$ independently of one another are hydrogen or $C_1$-$C_6$-alkyl;
  where the cyclic groups in $E^1$ and/or $R^a$ may be substituted by one to four groups $R^b$:
  $R^b$ is halogen, cyano, hydroxyl, mercapto, nitro, $NR^A R^B$, $C_1$-$C_{10}$-alkyl, $C_1$-$C_6$-haloalkyl, $C_2$-$C_6$-alkenyl, $C_2$-$C_6$-alkynyl or $C_1$-$C_6$-alkoxy;
$E^3$ is hydrogen, halogen, cyano, $NR^A R^B$, hydroxyl, mercapto, $C_1$-$C_6$-alkyl, $C_1$-$C_6$-haloalkyl, $C_3$-$C_8$-cycloalkyl, $C_1$-$C_6$-alkoxy, $C_1$-$C_6$-alkylthio, $C_3$-$C_8$-cycloalkoxy, $C_3$-$C_8$-cycloalkylthio, carboxyl, formyl, $C_1$-$C_{10}$-alkylcarbonyl, $C_1$-$C_{10}$-alkoxycarbonyl, $C_2$-$C_{10}$-alkenyloxycarbonyl, $C_2$-$C_{10}$-alkynyloxycarbonyl, phenyl, phenoxy, phenylthio, benzyloxy, benzylthio or $C_1$-$C_6$-alkyl-$S(O)_m$;
m is 0, 1 or 2; and
A is CH or N;
in a synergistically effective amount wherein compound I and compound II are applied simultaneously, that is jointly or separately, or in succession.

14. The method according of claim 13, wherein the compound I and the compound II or their mixtures are applied in an amount of from 5 g/ha to 2000 g/ha.

15. The method of claim 13, wherein the compound I and the compound II or their mixtures are applied in an amount of from 1 g to 1000 g per 100 kg of seed.

16. The method of claim 13, wherein harmful fungi from the class of the Oomycetes are controlled.

* * * * *

UNITED STATES PATENT AND TRADEMARK OFFICE
CERTIFICATE OF CORRECTION

| | |
|---|---|
| PATENT NO. | : 8,211,828 B2 |
| APPLICATION NO. | : 12/522209 |
| DATED | : July 3, 2012 |
| INVENTOR(S) | : Jochen Dietz et al. |

It is certified that error appears in the above-identified patent and that said Letters Patent is hereby corrected as shown below:

In claim 13, col. 124, line 5, after "mercapto," insert --$C_1$-$C_{10}$-alkyl,--.

Signed and Sealed this
Ninth Day of October, 2012

David J. Kappos
*Director of the United States Patent and Trademark Office*